(12) United States Patent
Gauvin et al.

(10) Patent No.: US 9,802,901 B2
(45) Date of Patent: *Oct. 31, 2017

(54) ANTIBACTERIAL 2H-INDAZOLE DERIVATIVES

(71) Applicant: Idorsia Pharmaceuticals Ltd, Allschwil (CH)

(72) Inventors: Jean-Christophe Gauvin, Allschwil (CH); Azely Mirre, Allschwil (CH); Etienne Ochala, Allschwil (CH); Jean-Philippe Surivet, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/021,649

(22) PCT Filed: Sep. 12, 2014

(86) PCT No.: PCT/IB2014/064458
§ 371 (c)(1),
(2) Date: Mar. 11, 2016

(87) PCT Pub. No.: WO2015/036964
PCT Pub. Date: Mar. 19, 2015

(65) Prior Publication Data
US 2016/0221959 A1    Aug. 4, 2016

(30) Foreign Application Priority Data

Sep. 13, 2013  (WO) ............... PCT/IB2013/058537

(51) Int. Cl.
| | | |
|---|---|---|
| C07D 231/56 | (2006.01) |
| C07D 403/10 | (2006.01) |
| C07D 401/06 | (2006.01) |
| C07D 405/06 | (2006.01) |
| C07D 403/06 | (2006.01) |
| C07F 9/6503 | (2006.01) |
| C07D 405/10 | (2006.01) |
| C07D 409/10 | (2006.01) |
| C07D 413/10 | (2006.01) |

(52) U.S. Cl.
CPC ......... *C07D 231/56* (2013.01); *C07D 401/06* (2013.01); *C07D 403/06* (2013.01); *C07D 403/10* (2013.01); *C07D 405/06* (2013.01); *C07D 405/10* (2013.01); *C07D 409/10* (2013.01); *C07D 413/10* (2013.01); *C07F 9/65038* (2013.01)

(58) Field of Classification Search
CPC .. C07D 231/56; C07D 405/06; C07D 405/10; C07D 403/10; C07D 409/10; C07D 401/06; C07D 403/06; C07D 413/10; C07F 9/65038
See application file for complete search history.

(56) References Cited

U.S. PATENT DOCUMENTS

| | | |
|---|---|---|
| 2012/0232083 A1 | 9/2012 | Reilly et al. |
| 2017/0081292 A1 | 3/2017 | Chapoux et al. |

FOREIGN PATENT DOCUMENTS

| | | |
|---|---|---|
| WO | WO 03/050132 A1 | 6/2003 |
| WO | WO 03/051797 A2 | 6/2003 |
| WO | WO 03/077914 A1 | 9/2003 |
| WO | WO 2005/103032 A2 | 11/2005 |
| WO | WO 2006/063281 A2 | 6/2006 |

(Continued)

OTHER PUBLICATIONS

U.S. Appl. No. 15/106,790, filed Jun. 20, 2016.
U.S. Appl. No. 15/123,184, filed Sep. 1, 2016.
Bellina et al., "Palladium Catalysts for the Suzuki Cross-Coupling Reaction: An Overview of Recent Advances," Synthesis (2004), pp. 2419• 2440.

(Continued)

*Primary Examiner* — Sarah Pihonak
*Assistant Examiner* — Jason A Deck
(74) *Attorney, Agent, or Firm* — Arent Fox LLP

(57) ABSTRACT

The invention relates to antibacterial compounds of formula I

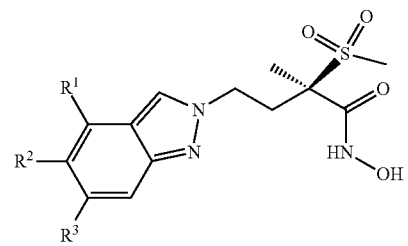

wherein $R^1$ is H or halogen; $R^2$ is alkynyloxy or the group M; $R^3$ is H or halogen; M is one of the groups

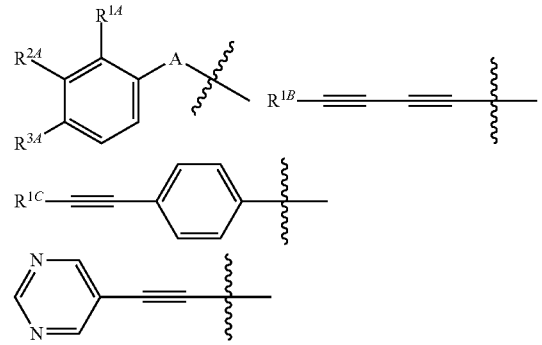

wherein A is a bond, $CH_2CH_2$, CH=CH or C≡C and $R^{1A}$, $R^{2A}$, $R^{3A}$, $R^{1B}$ and $R^{1C}$ are as defined in claim 1; and salts thereof.

16 Claims, No Drawings

(56) References Cited

FOREIGN PATENT DOCUMENTS

| WO | WO 2006/099972 A1 | 9/2006 |
|----|-------------------|--------|
| WO | WO 2008/154642 A2 | 12/2008 |
| WO | WO 2010/100475 A1 | 9/2010 |
| WO | WO 2010/135536 A2 | 11/2010 |
| WO | WO 2011/021209 A1 | 2/2011 |
| WO | WO 2011/045703 A2 | 4/2011 |
| WO | WO 2011/073845 A1 | 6/2011 |
| WO | WO 2012/037410 A2 | 3/2012 |
| WO | WO 2012/093809 A2 | 7/2012 |
| WO | WO 2012/120397 A1 | 9/2012 |
| WO | WO 2012/137094 A1 | 10/2012 |
| WO | WO 2012/137099 A1 | 10/2012 |
| WO | WO 2012/154204 A1 | 11/2012 |
| WO | WO 2013/170030 A1 | 11/2013 |
| WO | WO 2015/091741 A1 | 6/2015 |
| WO | WO 2015/132228 A1 | 9/2015 |

OTHER PUBLICATIONS

Benz, Comprehensive Organic Synthesis, B.M. Trost, I. Fleming, Eds; Pergamon Press: New York (1991), vol. 6, pp. 381-417.

Comprehensive Organic Transformations. A guide to Functional Group Preparations; 2nd Edition, R. C. Larock, Wiley-VC; New York, Chichester, Weinheim, Brisbane, Singapore, Toronto, 1999. Section nitriles, carboxylic acids and derivatives pp. 1941-1949.

Fu, "The Development of Versatile Methods for Palladium-Catalyzed Coupling Reactions of Aryl Electrophiles through the Use of P(t-BU)3 and PCy3 as Ligands," Acc. Chem. Res. (2008), 41, pp. 1555-1564.

Furst et al., "Synthesis of an Advanced Intermediate of the Jatrophane Diterpene PI-4: A Dibromide Coupling Approach," J. Org. Chem. (2013), 78(17), pp. 8748-8758.

Greene, Protective for the Carboxyl Group, Protecting Groups in Organic Synthesis, 3rd Ed (1999) pp. 369-453.

Greene, Protective Groups in Organic Synthesis, 3rd Ed (1999), pp. 1-3.

Handbook of Pharmaceutical Salts. Properties, Selection and Use., P. Heinrich Stahl, Camille G. Wermuth (Eds.), Wiley-VCH (2008) and 'Pharmaceutical Salts and Co crystals', Johan Wouters and Luc Quéré (Eds.), RSC Publishing (2012).

Kantchev et al., "Pd—N-Heterocyclic Carbene (NHC) Catalysts for Cross-Coupling Reactions," Aldrichimica Acta (2006), 39 pp. 97-111.

Knight et al., "A synthesis of •-tocopherol featuring benzyne trapping by an alcohol," Tetrahedron Lett. (2009), 50(26), pp. 3534-3537.

Marmer et al., "The preparation and Reactions of Novel o-Acylhydroxylamines," J. Org. Chem. (1972), 37, pp. 3520-3523.

Mauger et al., "Synthetic Applications of Buchwald's Phosphines in Palladium-Catalyzed Aromatic-Bond-Forming Reactions," Chem. Rev. (1995), vol. 95, pp. 2457-2483.

McAllister et al., "Heterocyclic methylsulfone hydroxamic acid LpxC inhibitors as Gram-negative antibacterial agents," Bioorg. & Med. Chem. Letters, 2012, 22 (22), pp. 6832-6838.

Methods for Dilution Antimicrobial Susceptibility Tests for Bacteria that Grow Aerobically, Approved standard, 7th ed., Clinical and Laboratory Standards Institute (CLSI) Document M7-A7, Wayne, PA, USA (2006)) pp. 1-64.

Miyaura et al., "Palladium-Catalyzed Cross-Coupling Reactions of Organoboron Compounds," Chem. Rev. (1995), 95, pp. 2457-2483.

Mohapatra et al., "The first asymmetric total syntheses of 3(1R,2R)- and 3((1S,2R)-2-(12-methyltridecyl)cyclopropyl)propanoic acid," Tetrahedron Lett. (2012), 53(49), pp. 6718 6720.

Perner et al., "Synthesis and biological evaluation of 6, 7-disubstituted 4-aminopyrido [2,3-d]pyrimidines as adenosine kinase inhibitors," Biorg. Med. Chem. Lett. (2005), 15, pp. 2803 2807.

Reddy et al., "Mild and efficient oxy-iodination of alkynes and phenols and potassium iodide and tert-butyl hydroperoxide," Tetrahedron Lett. (2010), 51, pp. 2170-2173.

Remington, The Science and Practice of Pharmacy, 21st Edition (2005), Part 5, "Pharmaceutical Manufacturing", published by Lippincott Williams & Wilkins, pp. 1-5.

Sakagami et al., "Synthesis, in vitro pharmacology, and pharmacokinetic profiles of 2-[1-amino-1-carboxy-2-(9H-xanthen-9-yl)-ethyl]-1-fluoro-cyclopropanecarboxylic acid and its 6-heptyl ester, a potent mGluR2 antagonist," Bioorg. Med. Chem. (2008), 16(8), pp. 4359 4366.

Sanford et al., "The Sanford Guide to Antimicrobial Therapy", 42nd Edition, Antimicrobial Therapy, Inc., 2012, pp. 1-4.

Sleveland et al., "Synthesis of Phenylboronic Acids in Continuous Flow by Means of a Multijet Oscillating Disc Reactor System Operating at Cryogenic Temperatures," Org. Process Res. Dev. (2012), 16, pp. 1121-1130.

Smith III, et al., "Spongipyran synthetic studies. Total synthesis of (+)-spongistatin 2," Tetrahedron (2009), 65(33), pp. 6470 6488.

Sonogashira, "Cross-coupling Reactions to sp Carbon Atoms," Metal-Catalyzed Reactions, Diederich, F., Stang, P.J., Eds.; Wiley VCH, New York (1998), pp. 203-229.

Tsuda et al., "Application of Modified Mosher's Method for Primary Alcohols with a Methyl Group at C2 Position," Chem. Pharm. Bull. (2003), 51, pp. 448-451.

Wang et al., "A very Concise and Stereoselective Synthesis of 3-Substituted cis-Hex-3-ene-1,5-diyne and Corresponding Epoxydiyne," J. Org. Chem. (2001), 66, pp. 2146-2148.

Co-pending U.S. Appl. No. 15/528,407, filed May 19, 2017.

U.S. Appl. No. 15/311,758, Chapoux et al., Antibacterial Quinazoline-4(3H)-One Derivatives, filed Jul. 16, 2016.

ANTIBACTERIAL 2H-INDAZOLE DERIVATIVES

CROSS REFERENCE TO RELATED APPLICATION

This application is a 35 U.S.C. 371 National Phase of International Patent Application No. PCT/IB2014/064458 filed Sep. 12, 2014, which claims priority to International Patent Application No. PCT/IB2013/058537 filed Sep. 13, 2013, the disclosure of these prior applications are hereby incorporated in their entirety by reference.

The present invention concerns antibacterial 2H-indazole derivatives, pharmaceutical compositions containing them and uses of these compounds in the manufacture of medicaments for the treatment of bacterial infections. These compounds are useful antimicrobial agents effective against a variety of human and veterinary pathogens, especially Gram-negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumoniae, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new target. In this respect, LpxC, which is an essential enzyme in the biosynthesis of lipopolysaccharides (a major constituent of the outer membrane of Gram-negative bacteria), has received some attention and several patent applications relating to LpxC inhibitors have been published recently.

For example, WO 2011/045703 describes antibacterial compounds of formula (A1)

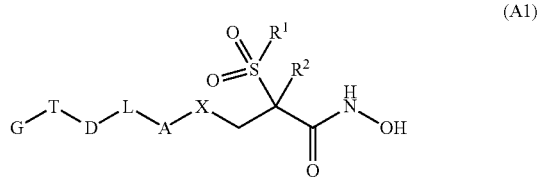

(A1)

wherein $R^1$ is $(C_1-C_3)$alkyl; $R^2$ is H or $(C_1-C_3)$alkyl; X is $CH_2$, O, NH, S or $SO_2$; A is an optionally substituted phenyl or a 6-membered heteroaryl group; L is absent or is S, SH, OH, —$(CH_2)_p$—O—$(CH_2)_n$—, —$(CH_2)_p$—O—$(CH_2)_z$—O—$(CH_2)_n$—, —S—$(CH_2)_z$— or —$(CH_2)_z$—S—; D is absent or is an optionally substituted group containing a carbocyclic or heterocyclic component with optionally a $(C_1-C_3)$alkyl chain appended; T is absent or is —$(CH_2)_z$—, —$(CH_2)_z$—O— or —O—$(CH_2)_p$—C(O)—$(CH_2)_n$—; G is absent or is an optionally substituted carbocyclic or heterocyclic group; and n and p are integers each ranging from 0 to 3 and z is an integer ranging from 1 to 3.

WO 2011/073845 and WO 2012/120397 describe antibacterial compounds with a structural formula similar to formula (A1), whereby the group corresponding to the group A of formula (A1) however respectively represents a pyridin-2-one or a fluoropyridin-2-one residue.

WO 2012/137094 describes antibacterial compounds of formulae (A2) and (A3)

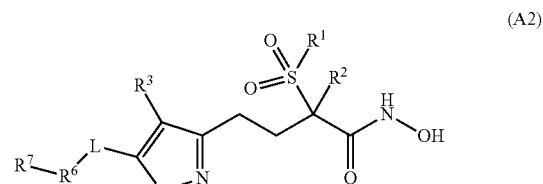

(A2)

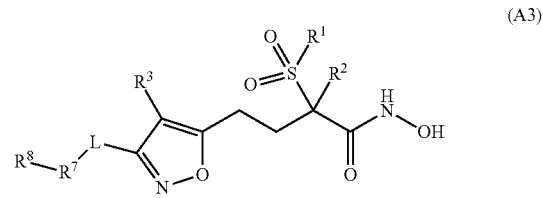

(A3)

wherein $R^1$ is $(C_1-C_3)$alkyl; $R^2$ is H or $(C_1-C_3)$alkyl; $R^3$ is H, $(C_1-C_3)$alkoxy, $(C_1-C_3)$alkyl, cyano, $(C_1-C_3)$haloalkoxy, $(C_1-C_3)$haloalkyl, halogen or hydroxy; L is a bond, —$(CH_2)_n$—, —$(CH_2)_nO(CH_2)_p$—, —$(CH_2)_nNR^4(CH_2)_p$—, —$(CH_2)_nSO_2NR^4(CH_2)_p$—, —$(CH_2)_nCONR^4(CH_2)_p$— or —$(CH_2)_nNR^4CO(CH_2)_p$—; $R^4$ and $R^5$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^6$ is $(C_1-C_6)$alkoxy$(C_1-C_6)$alkyl, $(C_1-C_6)$alkoxycarbonyl, $(C_1-C_6)$alkyl-$NR^4$—$(C_1-C_6)$alkyl, $(C_1-C_6)$alkylthio$(C_1-C_6)$alkyl, $(C_1-C_6)$alkylthiocarbonyl, $(C_6-C_{12})$aryl, $(C_6-C_{12})$aryloxy, $(C_6-C_{12})$arylthio, $(C_6-C_{12})$aryl-$NR^4$—, $(C_3-C_8)$cycloalkyl, $(C_3-C_8)$cycloalkyloxy, $(C_3-C_8)$cycloalkylthio, $(C_5-C_8)$cycloalkyl-$NR^4$—, $(C_5-C_{12})$hetero aryl, $(C_5-C_{12})$heteroaryloxy, $(C_5-C_{12})$heteroarylthio, $(C_5-C_{12})$heteroaryl-$NR^4$—, $(C_3-C_{13})$heterocyclyl, $(C_3-C_{13})$heterocyclyloxy, $(C_3-C_{13})$heterocyclylthio, $(C_3-C_{13})$heterocycle-$NR^4$—, hydroxy$(C_1-C_{10})$alkyl, mercapto$(C_1-C_6)$alkyl, $(NR^4R^5)$alkyl, or $(NR^4R^5)$carbonyl; and $R^7$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2012/137099 describes antibacterial compounds of formula (A4)

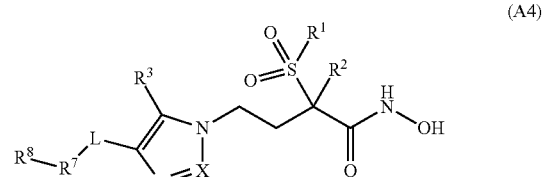

(A4)

wherein R¹ is (C₁-C₃)alkyl; R² is H or (C₁-C₃)alkyl; R³ is H or (C₁-C₃)alkyl; X is N or CR⁴; Y is N or CR⁴; R⁴ is H or (C₁-C₃)alkyl; L is a bond, (C₂-C₆)alkenylene, (C₁-C₆)alkylene, (C₂-C₆)alkynylene, —(CH₂)$_n$O(CH₂)$_p$—, —(CH₂)$_n$S(CH₂)$_p$—, —(CH₂)$_n$NR⁵(CH₂)$_p$—, —(CH₂)$_n$SO₂NR⁵(CH₂)$_p$—, —(CH₂)$_n$NR⁵SO₂(CH₂)$_p$—, —(CH₂)$_n$CONR⁵(CH₂)$_p$— or —(CH₂)$_n$NR⁵CO(CH₂)$_p$—; R⁵ and R⁶ are independently H, (C₁-C₆)alkyl, (C₁-C₆)alkylcarbonyl, (C₃-C₈)cycloalkyl, (C₃-C₈)cycloalkyl(C₁-C₆)alkyl or formyl; n is 0, 1, 2, 3 or 4; p is 0, 1, 2, 3 or 4; R⁷ is (C₂-C₆)alkenyl, (C₁-C₆)alkoxy, (C₁-C₆)alkoxy(C₁-C₆)alkyl, (C₁-C₆)alkoxycarbonyl, (C₁-C₆)alkyl, (C₁-C₆)alkylcarbonyl, (C₁-C₆)alkyl-NR⁵—C₁-C₆)alkyl, (C₁-C₆)alkylthio, (C₁-C₆)alkylthio(C₁-C₆)alkyl, (C₁-C₆)alkylthiocarbonyl, (C₂-C₆)alkynyl, (C₆-C₁₂)aryl, (C₆-C₁₂)aryloxy, (C₆-C₁₂)arylthio, (C₆-C₁₂)aryl-NR⁵—, cyano, cyano(C₁-C₆)alkyl, (C₅-C₈)cycloalkenyl, (C₃-C₈)cycloalkyl, (C₃-C₈)cycloalkyloxy, (C₃-C₈)cycloalkylthio, (C₅-C₈)cycloalkyl-NR⁵—(C₅-C₁₂)heteroaryl, (C₅-C₁₂)heteroaryl oxy, (C₅-C₁₂)heteroarylthio, (C₅-C₁₂)heteroaryl-NR⁵—, (C₃-C₁₃)heterocyclyl, (C₃-C₁₃)heterocyclyloxy, (C₃-C₁₃)heterocyclylthio, (C₃-C₁₃)heterocyclyl-NR⁵—, hydroxy(C₁-C₁₀)alkyl, mercapto(C₁-C₆)alkyl, (NR⁵R⁶)alkyl, or (NR⁵R⁶)carbonyl; and R⁸ is absent or is (C₆-C₁₂)aryl, (C₆-C₁₂)aryl(C₁-C₆)alkyl, (C₃-C₈)cycloalkyl, (C₃-C₈)cycloalkyl(C₁-C₆)alkyl, (C₅-C₁₂)heteroaryl, (C₅-C₁₂)heteroaryl(C₁-C₆)alkyl, (C₃-C₁₃)heterocyclyl or (C₃-C₁₃)heterocyclyl(C₁-C₆)alkyl.

The instant invention provides new antibacterial 2H-indazole derivatives, namely the compounds of formula I described herein.

Various embodiments of the invention are presented hereafter:

1) The invention relates to compounds of formula I

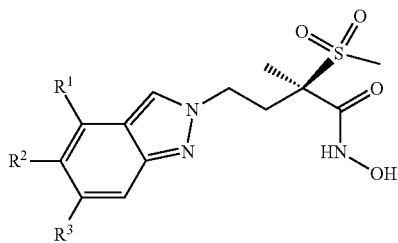

I wherein
R¹ represents H or halogen;
R² represents (C₃-C₄)alkynyloxy or the group M;
R³ represents H or halogen;
M is one of the groups M$^A$, M$^B$, M$^C$ and M$^D$ represented hereafter

M$^A$

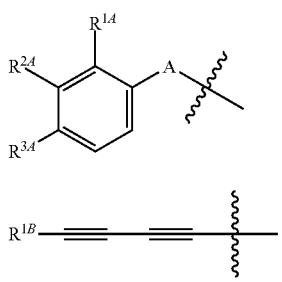

M$^B$

M$^C$

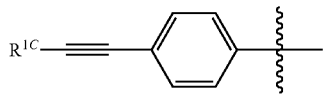

M$^D$

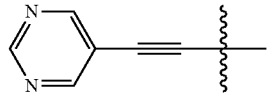

wherein A represents a bond, CH₂CH₂, CH=CH or C≡C;
R$^{1A}$ represents H or halogen;
R$^{2A}$ represents H, (C₁-C₃)alkoxy or halogen;
R$^{3A}$ represents H, (C₁-C₃)alkoxy, hydroxy(C₁-C₄)alkoxy, (C₁-C₃)alkoxy(C₂-C₃)alkoxy, dihydroxy(C₃-C₄)alkoxy, (C₁-C₃)thioalkoxy, trifluoromethoxy, amino, di(C₁-C₃)alkylamino, 2-hydroxyacetamido, hydroxy(C₁-C₄)alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy(C₁-C₃)alkyl)oxetan-3-yl, 3-aminooxetan-3-yl, 3-(di(C₁-C₃)alkylamino)oxetan-3-yl, 3-hydroxythietan-3-yl, morpholin-4-yl(C₂-C₃)alkoxy, morpholin-4-yl-(C₁-C₂)alkyl, oxazol-2-yl or [1,2,3]triazol-2-yl;
R$^{1B}$ represents 3-hydroxyoxetan-3-yl, 3-aminooxetan-3-yl, 3-hydroxythietan-3-yl, hydroxy(C₁-C₃)alkyl, dihydroxy(C₂-C₄)alkyl, amino(C₁-C₄)alkyl, (dimethylamino)methyl, 1-hydroxymethyl-cycloprop-1-yl, trans-2-(1,2-dihydroxyethyl)cycloprop-1-yl, 1-((phosphonooxy)methyl)cyclopropyl, 1-(((dimethylglycyl)oxy)methyl)cyclopropyl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, trans-2-aminomethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxy-oxetan-3-yl, 3-hydroxymethyl-oxetan-3-yl, 1-(2-hydroxy acetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, piperidin-4-yl, 1-(2-hydroxyacetyl)piperidin-4-yl, 1-(2-aminoacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl; and
R$^{1C}$ represents 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, 1-fluoro-2-(hydroxymethyl)cyclopropyl or 2-fluoro-2-(hydroxymethyl)cyclopropyl;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "(C$_x$-C$_y$)alkyl" (x and y each being an integer) refers to a straight or branched chain alkyl group containing x to y carbon atoms. For example, a (C₁-C₃)alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "dialkylamino", used alone or in combination, refers to an amino group wherein each hydrogen atom has been replaced by an alkyl group as defined before, whereby the alkyl groups may be the same or different. The term "di($C_x$-$C_y$)alkylamino" (x and y each being an integer) refers to a dialkylamino group as defined before wherein each alkyl group independently contains x to y carbon atoms. For example, a di($C_1$-$C_3$) alkylamino group is a dialkylamino group as defined before wherein each alkyl group independently contains from one to three carbon atoms. Representative examples of dialkylamino groups include dimethylamino, diethylamino, N-ethyl-N-methyl-amino and N-iso-propyl-N-methyl-amino. Preferred are dimethylamino and diethylamino. Most preferred is dimethylamino.

The term "hydroxyalkyl", used alone or in combination, refers to an alkyl group as defined before wherein one hydrogen atom has been replaced by a hydroxy group. The term "hydroxy($C_x$-$C_y$)alkyl" (x and y each being an integer) refers to a hydroxyalkyl group as defined before which contains x to y carbon atoms. For example, a hydroxy($C_1$-$C_4$)alkyl group is a hydroxyalkyl group as defined before which contains from one to four carbon atoms. Representative examples of hydroxyalkyl groups include hydroxymethyl, 2-hydroxyethyl, 2-hydroxypropyl and 3-hydroxypropyl. Preferred are hydroxymethyl and 2-hydroxyethyl. Most preferred is hydroxymethyl.

The term "dihydroxyalkyl", used alone or in combination, refers to an alkyl group containing from two to four carbon atoms wherein two hydrogen atoms on two different carbon atoms have each been replaced by a hydroxy group. For example "dihydroxy($C_2$-$C_4$)alkyl" refers to an alkyl group containing from two to four carbon atoms wherein two hydrogen atoms on two different carbon atoms have each been replaced by a hydroxy group. Preferred dihydroxy($C_2$-$C_4$)alkyl groups are 1,2-dihydroxyethyl and 1,2-dihydroxy-2-methylethyl.

The term "aminoalkyl", used alone or in combination, refers to an alkyl group as defined before wherein one hydrogen atom has been replaced by an amino group. The term "amino($C_x$-$C_y$)alkyl" (x and y each being an integer) refers to an aminoalkyl group as defined before which contains x to y carbon atoms. For example, an amino($C_1$-$C_4$)alkyl group is an aminoalkyl group as defined before which contains from one to four carbon atoms. Representative examples of amino($C_1$-$C_4$)alkyl groups include aminomethyl, 2-aminoethyl, 2-aminopropyl and 3-aminopropyl. Preferred are 2-aminopropyl and 2-amino-2-methylpropyl. Most preferred is 2-aminopropyl.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "hydroxyalkoxy", used alone or in combination, refers to an alkoxy group as defined before wherein one hydrogen atom has been replaced by a hydroxy group. For example "hydroxy($C_1$-$C_4$)alkoxy" refers to an alkoxy group containing from one to four carbon atoms wherein one hydrogen atom has been replaced by a hydroxy group. A preferred hydroxy($C_1$-$C_4$)alkoxy group is 2-hydroxyethoxy.

The term "dihydroxyalkoxy", used alone or in combination, refers to an alkoxy group containing from three to four carbon atoms wherein two hydrogen atoms on two different carbon atoms have each been replaced by a hydroxy group. For example "dihydroxy($C_3$-$C_4$) alkoxy" refers to an alkoxy group containing from three to four carbon atoms wherein two hydrogen atoms on two different carbon atoms have each been replaced by a hydroxy group. A preferred dihydroxy($C_3$-$C_4$)alkoxy group is 2,3-dihydroxypropoxy.

The term "alkoxyalkoxy", used alone or in combination, refers to an alkoxy group containing from two to four carbon atoms wherein one hydrogen atom has been replaced by an alkoxy group containing from one to four carbon atoms. For example "($C_1$-$C_3$)alkoxy($C_2$-$C_3$)alkoxy" refers to a straight or branched chain alkoxy group containing from two to three carbon atoms, one hydrogen atom of which has been replaced by a straight or branched chain alkoxy group containing from one to three carbon atoms. A preferred ($C_1$-$C_3$) alkoxy($C_2$-$C_3$)alkoxy group is 2-methoxyethoxy.

The term "thioalkoxy", used alone or in combination, refers to a straight or branched chain alkoxy group containing from one to four carbon atoms wherein the oxygen atom has been replaced by a sulphur atom. The term "($C_x$-$C_y$)thioalkoxy" (x and y each being an integer) refers to a thioalkoxy group as defined before containing x to y carbon atoms. For example, a ($C_1$-$C_3$)thioalkoxy group contains from one to three carbon atoms. Representative examples of thioalkoxy groups include methylthio, ethylthio, n-propylthio and iso-propylthio. Preferred are methylthio and ethylthio. Most preferred is methylthio.

The term "alkynyloxy", used alone or in combination, refers to a straight or branched chain alkynyloxy group containing from two to five carbon atoms. The term "($C_x$-$C_y$)alkynyloxy" (x and y each being an integer) refers to an alkynyloxy group as defined before containing x to y carbon atoms. For example, a ($C_3$-$C_4$) alkynyloxy group contains from three to four carbon atoms. Representative examples of alkynyloxy groups include prop-2-yn-1-yloxy, but-2-yn-1-yloxy and but-3-yn-1-yloxy. Preferred are but-2-yn-1-yloxy and but-3-yn-1-yloxy.

The term "3-(hydroxy($C_1$-$C_3$)alkyl)oxetan-3-yl" refers to an oxetan-3-yl group wherein the hydrogen on the carbon at position 3 of the oxetane ring has been replaced by a hydroxy($C_1$-$C_3$)alkyl group as defined before. Examples of 3-(hydroxy($C_1$-$C_3$)alkyl)oxetan-3-yl groups are 3-hydroxymethyl-oxetan-3-yl and 3-(2-hydroxyethyl)-oxetan-3-yl. The most preferred 3-(hydroxy($C_1$-$C_3$)alkyl)oxetan-3-yl group is 3-hydroxymethyl-oxetan-3-yl.

The term "3-(di($C_1$-$C_3$)alkylamino)oxetan-3-yl" refers to an oxetan-3-yl group wherein the hydrogen on the carbon at position 3 of the oxetane ring has been replaced by a di($C_1$-$C_3$)alkylamino group as defined before. Examples of 3-(di($C_1$-$C_3$)alkylamino)oxetan-3-yl groups are 3-dimethyl amino-oxetan-3-yl and 3-diethylamino-oxetan-3-yl. The most preferred 3-(di($C_1$-$C_3$)alkylamino)oxetan-3-yl group is 3-dimethylamino-oxetan-3-yl.

The term "morpholin-4-yl-($C_2$-$C_3$)alkoxy" refers to a ($C_2$-$C_3$)alkoxy group as defined before wherein one of the hydrogen atoms has been replaced by a morpholin-4-yl group. Examples of morpholin-4-yl-($C_2$-$C_3$)alkoxy groups are 2-morpholin-4-yl-ethoxy and 3-morpholin-4-yl-propoxy.

The term "morpholin-4-yl-($C_1$-$C_2$)alkyl" refers to a ($C_1$-$C_2$)alkyl group as defined before wherein one of the hydrogen atoms has been replaced by a morpholin-4-yl group. Examples of morpholin-4-yl-($C_1$-$C_2$)alkyl groups are morpholin-4-ylmethyl and 2-morpholin-4-yl-ethyl. The most preferred morpholino($C_1$-$C_2$)alkyl group is morpholin-4-ylmethyl.

The term "halogen" refers to fluorine, chlorine, bromine or iodine, and preferably to fluorine or chlorine, and most preferably to fluorine.

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, aminoglycosides, phosphonic acids, tetracyclins and polymixins. Clinical breakpoints are defined according to the latest available list published by Clinical and Laboratory Standards Institute (Wayne, Pa., USA). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH (2008) and 'Pharmaceutical Salts and Co-crystals', Johan Wouters and Luc Quéré (Eds.), RSC Publishing (2012).

In this text, a bond interrupted by a wavy line shows a point of attachment of the radical drawn to the rest of the molecule. For example, the radical drawn below

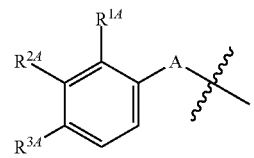

wherein A represents a bond, and each of $R^{1A}$, $R^{2A}$ and $R^{3A}$ represents H is the phenyl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention notably relates to compounds of formula I that are also compounds of formula $I_P$

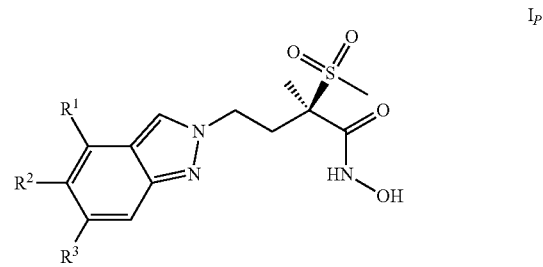

wherein
$R^1$ represents H or halogen;
$R^2$ represents ($C_3$-$C_4$)alkynyloxy or the group M;
$R^3$ represents H or halogen;
M is one of the groups $M^A$ and $M^B$ represented below

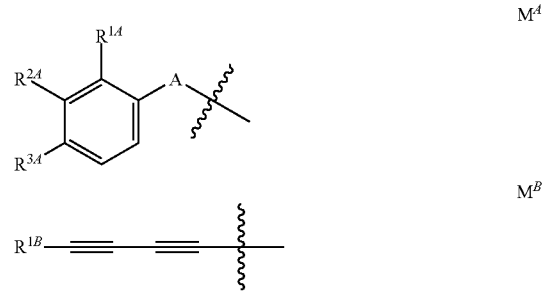

wherein A represents a bond, $CH_2CH_2$, CH=CH or C≡C;
$R^{1A}$ represents H or halogen;
$R^{2A}$ represents H, ($C_1$-$C_3$)alkoxy or halogen;
$R^{3A}$ represents H, ($C_1$-$C_3$)alkoxy, hydroxy($C_1$-$C_4$)alkoxy, ($C_1$-$C_3$)thioalkoxy, trifluoromethoxy, amino, di($C_1$-$C_3$)alkylamino, hydroxy($C_1$-$C_4$)alkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, 3-(di($C_1$-$C_3$)alkylamino)

oxetan-3-yl, 3-hydroxythietan-3-yl, morpholin-4-yl($C_2$-$C_3$)alkoxy, morpholin-4-yl-($C_1$-$C_2$)alkyl, oxazol-2-yl or [1,2,3]triazol-2-yl; and $R^{1B}$ represents 3-hydroxyoxetan-3-yl, 3-hydroxythietan-3-yl, hydroxy($C_1$-$C_3$)alkyl, amino($C_1$-$C_3$)alkyl, trans-2-hydroxymethyl-cycloprop-1-yl or 4-hydroxytetrahydro-2H-pyran-4-yl;

and to salts (in particular pharmaceutically acceptable salts) of compounds of formula Ip.

3) The invention in particular relates to compounds of formula I according to embodiment 1) which are also compounds of formula $I_{CE}$

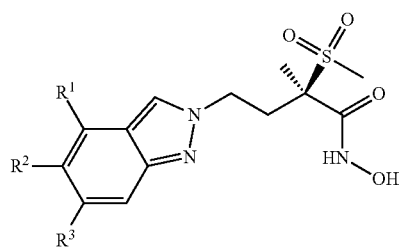

$I_{CE}$ wherein
$R^1$ represents H or halogen;
$R^2$ represents the group M;
$R^3$ represents H or halogen;
M is the one of the groups $M^A$, $M^B$, $M^C$ and $M^D$ represented hereafter

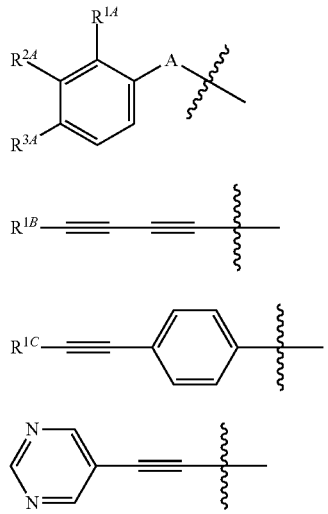

wherein A represents a bond, CH=CH or C≡C;
$R^{1A}$ represents H or halogen;
$R^{2A}$ represents H or halogen;
$R^{3A}$ represents H, ($C_1$-$C_3$)alkoxy, hydroxy($C_1$-$C_4$)alkoxy, ($C_1$-$C_3$)alkoxy($C_2$-$C_3$)alkoxy, ($C_1$-$C_3$)thioalkoxy, trifluoromethoxy, amino, di($C_1$-$C_3$)alkylamino, 2-hydroxyacetamido, hydroxy($C_1$-$C_4$)alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, 3-(di($C_1$-$C_3$)alkylamino)oxetan-3-yl, morpholin-4-yl-($C_1$-$C_2$)alkyl or [1,2,3]triazol-2-yl;

$R^{1B}$ represents 3-hydroxyoxetan-3-yl, 3-aminooxetan-3-yl, 3-hydroxythietan-3-yl, hydroxy($C_1$-$C_3$)alkyl, 1,2-dihydroxyethyl, 1,2-dihydroxy-2-methylethyl, amino($C_1$-$C_4$)alkyl, (dimethylamino)methyl, 1-hydroxymethyl-cycloprop-1-yl, trans-2-(1,2-dihydroxyethyl)cycloprop-1-yl, 1-((phosphonooxy)methyl)cyclopropyl, 1-(((dimethylglycyl)oxy)methyl)cyclopropyl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, trans-2-aminomethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, piperidin-4-yl, 1-(2-hydroxyacetyl)piperidin-4-yl, 1-(2-aminoacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl;
and
$R^{1C}$ represents trans-2-hydroxymethyl-cycloprop-1-yl;
and to salts (in particular pharmaceutically acceptable salts) of compounds of formula $I_{CE}$.

4) The invention notably relates to compounds of formula $I_{CE}$ according to embodiment 3) which are also compounds of formula $I_{CEP}$

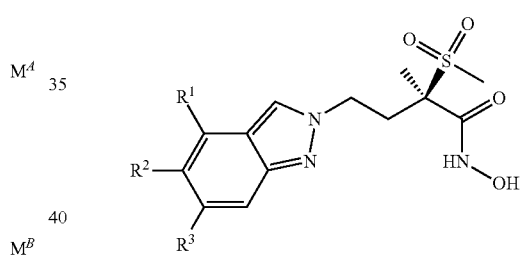

$I_{CEP}$ wherein
$R^1$ represents H or halogen;
$R^2$ represents the group M;
$R^3$ represents H or halogen;
M is the one of the groups $M^A$ and $M^B$ represented below

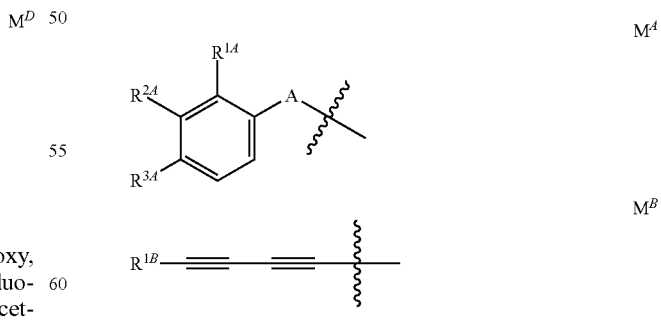

wherein A represents a bond, CH=CH or C≡C;
$R^{1A}$ represents H or halogen;
$R^{2A}$ represents H or halogen;
$R^{3A}$ represents H, ($C_1$-$C_3$)alkoxy, hydroxy($C_1$-$C_4$)alkoxy, ($C_1$-$C_3$)thioalkoxy, trifluoromethoxy, amino, di($C_1$-$C_3$)alkylamino, hydroxy($C_1$-$C_4$)alkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, 3-(di($C_1$-$C_3$)alkylamino)oxetan-3-yl, morpholin-4-yl-($C_1$-$C_2$)alkyl or [1,2,3]triazol-2-yl;

$R^{1B}$ represents 3-hydroxyoxetan-3-yl, -hydroxythietan-3-yl, hydroxy($C_1$-$C_3$)alkyl, amino($C_1$-$C_3$)alkyl, trans-2-hydroxymethyl-cycloprop-1-yl or 4-hydroxytetrahydro-2H-pyran-4-yl;

and to salts (in particular pharmaceutically acceptable salts) of compounds of formula $I_{CEP}$.

5) In particular, the compounds of formula I according to one of embodiments 1) to 4) will be such that $R^1$ represents H or fluorine, $R^3$ represents H or fluorine, $R^{1A}$, when present, represents H or fluorine and $R^{2A}$, when present, represents H or fluorine.

6) According to one main embodiment of this invention, the compounds of formula I as defined in one of embodiments 1) to 5) will be such that $R^2$ represents the group $M^A$.

7) One sub-embodiment of embodiment 6) relates to the compounds of formula I as defined in embodiment 6) wherein A represents a bond.

8) Preferably, the compounds of formula I according to embodiment 7) will be such that $R^{1A}$ represents H or halogen, $R^{2A}$ represents H or ($C_1$-$C_3$)alkoxy and $R^{3A}$ represents ($C_1$-$C_3$)alkoxy, hydroxy($C_2$-$C_4$)alkoxy, ($C_1$-$C_3$)alkoxy($C_1$-$C_3$)alkoxy, dihydroxy($C_3$-$C_4$)alkoxy, ($C_1$-$C_3$)thioalkoxy or [1,2,3]triazol-2-yl.

9) The compounds of formula I according to embodiment 8) will notably be such that $R^{1A}$ represents H or halogen, $R^{2A}$ represents H and $R^{3A}$ represents ($C_1$-$C_3$)alkoxy, ($C_1$-$C_3$)thioalkoxy or [1,2,3]triazol-2-yl).

10) More preferably, the compounds of formula I according to embodiment 7) will be such that $R^{1A}$ represents H or fluorine, $R^{2A}$ represents H or methoxy and $R^{3A}$ represents methoxy, 2-hydroxyethoxy, 2-methoxyethoxy, 2,3-dihydroxypropoxy, methylthio or [1,2,3]triazol-2-yl.

11) The compounds of formula I according to embodiment 10) will notably be such that $R^{1A}$ represents H or fluorine, $R^{2A}$ represents H and $R^{3A}$ represents methoxy, methylthio or [1,2,3]triazol-2-yl).

12) Another sub-embodiment of embodiment 6) relates to the compounds of formula I as defined in embodiment 6) wherein A represents CH=CH.

13) Preferably, the compounds of formula I according to embodiment 12) will be such that $R^{1A}$ represents H, $R^{2A}$ represents H and $R^{3A}$ represents H, hydroxy($C_1$-$C_4$)alkyl, trans-2-hydroxymethyl-cycloprop-1-yl or 3-hydroxyoxetan-3-yl.

14) In particular, the compounds of formula I according to embodiment 12) will be such that $R^{1A}$ represents H, $R^{2A}$ represents H and $R^{3A}$ represents H.

15) Yet another sub-embodiment of embodiment 6) relates to the compounds of formula I as defined in embodiment 4) wherein A represents 16) Preferably, the compounds of formula I according to embodiment 15) will be such that $R^{1A}$ represents H or halogen, $R^{2A}$ represents H or halogen and $R^{3A}$ represents ($C_1$-$C_3$)alkoxy, hydroxy($C_1$-$C_4$)alkoxy, ($C_1$-$C_3$)thioalkoxy, amino, 2-hydroxyacetamido, hydroxy($C_1$-$C_4$)alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, morpholin-4-yl-($C_1$-$C_2$)alkyl or [1,2,3]triazol-2-yl.

17) In particular, the compounds of formula I according to embodiment 16) will be such that $R^{1A}$ represents H or halogen, $R^{2A}$ represents H or halogen and $R^{3A}$ represents ($C_1$-$C_3$)alkoxy, hydroxy($C_1$-$C_4$)alkoxy, ($C_1$-$C_3$)thioalkoxy, amino, hydroxy($C_1$-$C_4$)alkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, morpholin-4-yl-($C_1$-$C_2$)alkyl or [1,2,3]triazol-2-yl.

18) More preferably, the compounds of formula I according to embodiment 15) will be such that $R^{1A}$ represents H or fluorine, $R^{2A}$ represents H and $R^{3A}$ represents hydroxy($C_1$-$C_4$)alkoxy, 2-hydroxyacetamido, hydroxy($C_1$-$C_4$)alkyl, 1-aminocyclopropyl, 1-hydroxymethyl-cycloprop-1-yl, trans-2-hydroxymethyl-cycloprop-1-yl, 1,2-dihydroxyethyl or 3-hydroxyoxetan-3-yl.

19) In particular, the compounds of formula I according to embodiment 18) will be such that $R^{1A}$ represents H or fluorine, $R^{2A}$ represents H and $R^{3A}$ represents hydroxy($C_1$-$C_4$)alkoxy, hydroxy($C_1$-$C_4$)alkyl, 1-hydroxymethyl-cycloprop-1-yl, trans-2-hydroxymethyl-cycloprop-1-yl, 1,2-dihydroxyethyl or 3-hydroxyoxetan-3-yl.

20) Even more preferably, the compounds of formula I according to embodiment 15) will be such that $R^{1A}$ represents H, $R^{2A}$ represents H and $R^{3A}$ represents hydroxy($C_1$-$C_4$)alkyl, trans-2-hydroxymethyl-cycloprop-1-yl, 1,2-dihydroxyethyl or 3-hydroxyoxetan-3-yl (and in particular such that $R^{1A}$ represents H, $R^{2A}$ represents H and $R^{3A}$ represents 1-hydroxyethyl, 2-hydroxyethyl, 2-hydroxypropan-2-yl, 1,2-dihydroxyethyl, trans-2-hydroxymethyl-cycloprop-1-yl or 3-hydroxyoxetan-3-yl).

21) In particular, the compounds of formula I according to embodiment 20) will be such that $R^{1A}$ represents H, $R^{2A}$ represents H and $R^{3A}$ represents hydroxy($C_1$-$C_4$)alkyl, trans-2-hydroxymethyl-cycloprop-1-yl or 3-hydroxyoxetan-3-yl.

22) According to another main embodiment of this invention, the compounds of formula I as defined in one of embodiments 1) to 5) will be such that $R^2$ represents the group $M^B$.

23) Preferably, the compounds of formula I according to embodiment 22) will be such that $R^{1B}$ represents 1,2-dihydroxyethyl, 3-hydroxyoxetan-3-yl, 3-hydroxythietan-3-yl, hydroxy($C_1$-$C_3$)alkyl, amino($C_1$-$C_3$)alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, piperidin-4-yl, 1-(2-hydroxyacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl.

24) In particular, the compounds of formula I according to embodiment 23) will be such that $R^{1B}$ represents 3-hydroxyoxetan-3-yl, 3-hydroxythietan-3-yl, hydroxy($C_1$-$C_3$)alkyl, amino($C_1$-$C_3$)alkyl or trans-2-hydroxymethyl-cycloprop-1-yl.

2S) More preferably, the compounds of formula I according to embodiment 22) will be such that $R^{1B}$ represents 3-hydroxythietan-3-yl, amino($C_1$-$C_3$)alkyl, (dimethylamino)methyl, 1-hydroxymethyl-cycloprop-1-yl, trans-2-(1, 2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxyoxetan-3-yl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, trans-(cis-3,4-dihydroxy)-cyclopent-1-yl, 3-hydroxymethylbicyclo[1,1,1]pentan-1-yl, 1-(2-hydroxyacetyl)piperidin-4-yl, 5-aminotetrahydro-2H-pyran-2-yl or 3-hydroxyoxetan-3-ylmethyl.

26) In particular, the compounds of formula I according to embodiment 2S) will be such that $R^{1B}$ represents 3-hydroxythietan-3-yl, amino($C_1$-$C_3$)alkyl or trans-2-hydroxymethyl-cycloprop-1-yl.

27) Even more preferably, the compounds of formula I according to embodiment 22) will be such that $R^{1B}$ represents 3-hydroxythietan-3-yl, 2-aminopropan-2-yl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(2-aminoacetyl)azetidin-3-yl, 1-glycylazetidin-3-yl, trans-(cis-3,4-dihydroxy)-cyclopent-1-yl or 3-hydroxymethylbicyclo[1,1,1]pentan-1-yl.

28) In particular, the compounds of formula I according to embodiment 27) will be such that $R^{1B}$ represents 3-hydroxythietan-3-yl, 2-aminopropan-2-yl or trans-2-hydroxymethyl-cycloprop-1-yl.

29) According to a further main embodiment of this invention, the compounds of formula I as defined in embodiment 1) or 3) will be such that $R^2$ represents the group $M^C$.

30) Preferably, the compounds of formula I according to embodiment 29) will be such that $R^{1C}$ represents 1-hydroxymethyl-cycloprop-1-yl, trans-2-(1,2-dihydroxy ethyl) cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl or 2-fluoro-2-(hydroxymethyl)cyclopropyl.

31) In particular, the compounds of formula I according to embodiment 29) will be such that $R^{1C}$ represents trans-2-hydroxymethyl-cycloprop-1-yl.

32) According to a yet further main embodiment of this invention, the compounds of formula I as defined in embodiment 1) or 3) will be such that $R^2$ represents the group $M^D$.

33) According to yet a further main embodiment of this invention, the compounds of formula I as defined in embodiment 1) or 2) will be such that $R^2$ represents ($C_3$-$C_4$)alkynyloxy.

34) Preferably, the compounds of formula I according to embodiment 33) will be such that $R^2$ represents but-2-yn-1-yloxy.

35) According to one main variant of this invention, the compounds of formula I according to one of embodiments 1) to 4) will be such that $R^1$ represents H and $R^3$ represents H.

36) According to another main variant of this invention, the compounds of formula I according to one of embodiments 1) to 4) will be such that $R^1$ represents fluorine and $R^3$ represents H.

37) According to yet another main variant of this invention, the compounds of formula I according to one of embodiments 1) to 4) will be such that $R^1$ represents H and $R^3$ represents fluorine.

38) In a preferred embodiment, the compounds of formula I according to embodiment 1) will be such that:
$R^1$ represents H or halogen;
$R^2$ represents the group M;
$R^3$ represents H or halogen; and M is the one of the groups $M^A$, $M^B$ and $M^C$ represented hereafter

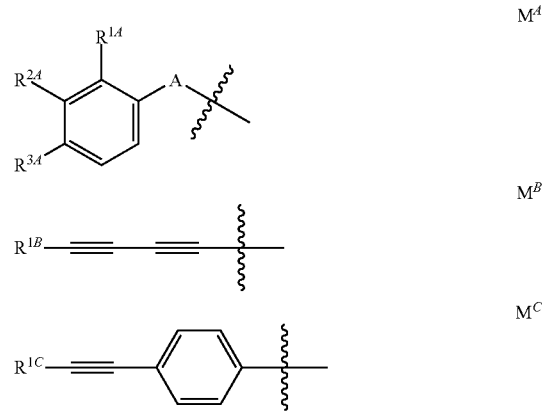

wherein A represents a bond or C≡C;
$R^{1A}$ represents H or halogen;
$R^{2A}$ represents H or halogen;
$R^{3A}$ represents ($C_1$-$C_3$)alkoxy, hydroxy($C_1$-$C_4$)alkoxy, ($C_1$-$C_3$)alkoxy($C_1$-$C_3$)alkoxy, ($C_1$-$C_3$)thioalkoxy, amino, 2-hydroxyacetamido, hydroxy($C_1$-$C_4$)alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-aminooxetan-3-yl, morpholin-4-yl-($C_1$-$C_2$)alkyl or [1,2,3]triazol-2-yl;

$R^{1B}$ represents 1,2-dihydroxyethyl, 3-hydroxyoxetan-3-yl, 3-hydroxythietan-3-yl, hydroxy($C_1$-$C_3$)alkyl, amino($C_1$-$C_3$)alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethyl-bicyclo[1,1,1]pentan-1-yl, piperidin-4-yl, 1-(2-hydroxyacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl; and $R^{1C}$ represents 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl or 2-fluoro-2-(hydroxymethyl)cyclopropyl.

39) In particular, the compounds of formula I according to embodiment 38) will be compounds of formula $I_P$ as defined in embodiment 2) wherein:
$R^1$ represents H or halogen;
$R^2$ represents the group M;
$R^3$ represents H or halogen; and M is the one of the groups $M^A$ and $M^B$ represented below

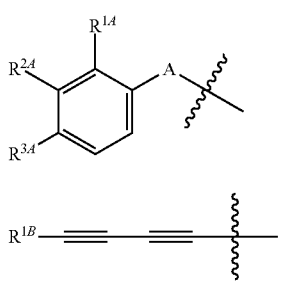

$M^A$ $M^B$ wherein A represents a bond or CC;
$R^{1A}$ represents H or halogen;
$R^{2A}$ represents H or halogen;
$R^{3A}$ represents $(C_1-C_3)$alkoxy, hydroxy$(C_1-C_4)$alkoxy, $(C_1-C_3)$thioalkoxy, amino, hydroxy$(C_1-C_4)$alkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, morpholin-4-yl-$(C_1-C_2)$alkyl or [1,2,3]triazol-2-yl; and
$R^{1B}$ represents 3-hydroxyoxetan-3-yl, 3-hydroxythietan-3-yl, hydroxy$(C_1-C_3)$alkyl, amino$(C_1-C_3)$alkyl, trans-2-hydroxymethyl-cycloprop-1-yl or 4-hydroxytetrahydro-2H-pyran-4-yl.

40) In a more preferred embodiment, the compounds of formula I according to embodiment 1) will be such that:
$R^1$ represents H or fluorine;
$R^2$ represents the group M;
$R^3$ represents H or fluorine; and
M is the one of the groups $M^A$, $M^B$ and $M^C$ represented hereafter

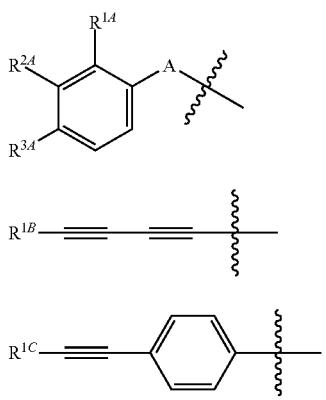

$M^A$ $M^B$ $M^C$ wherein A represents C≡C;
$R^{1A}$ represents H or fluorine;
$R^{2A}$ represents H;
$R^{3A}$ represents hydroxy$(C_1-C_4)$alkoxy, 2-hydroxyacetamido, hydroxy$(C_1-C_4)$alkyl, 1-aminocyclopropyl, 1-hydroxymethyl-cycloprop-1-yl, trans-2-hydroxymethyl-cycloprop-1-yl, 1,2-dihydroxyethyl or 3-hydroxyoxetan-3-yl;
$R^{1B}$ represents 3-hydroxyoxetan-3-yl, 3-hydroxythietan-3-yl, hydroxy$(C_1-C_3)$alkyl, amino$(C_1-C_3)$alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 1-(2-hydroxyacetyl)azetidin-3-yl, 1-(2-aminoacetyl)azetidin-3-yl, 1-glycylazetidin-3-yl, trans-(cis-3,4-dihydroxy)-cyclopent-1-yl, 3-hydroxymethylbicyclo[1,1,1]pentan-1-yl, 1-(2-hydroxyacetyl)piperidin-4-yl, 5-aminotetrahydro-2H-pyran-2-yl or 3-hydroxyoxetan-3-ylmethyl; and
$R^{1C}$ represents 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl or 2-fluoro-2-(hydroxymethyl)cyclopropyl.

41) In particular, the compounds of formula I according to embodiment 40) will be compounds of formula $I_P$ as defined in embodiment 2) wherein:
$R^1$ represents H or fluorine;
$R^2$ represents the group M;
$R^3$ represents H or fluorine; and
M is the one of the groups $M^A$ and $M^B$ represented below

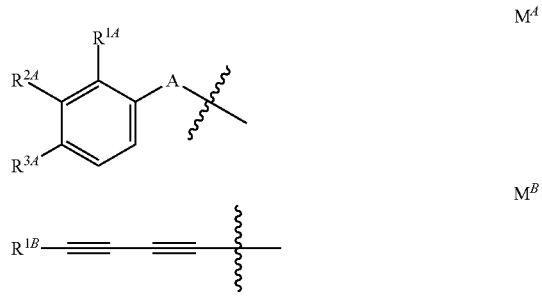

$M^A$ $M^B$ wherein A represents C≡C;
$R^{1A}$ represents H or fluorine;
$R^{2A}$ represents H;
$R^{3A}$ represents hydroxy$(C_1-C_4)$alkoxy, hydroxy$(C_1-C_4)$alkyl, 1-hydroxymethyl-cycloprop-1-yl, trans-2-hydroxymethyl-cycloprop-1-yl, 1,2-dihydroxyethyl or 3-hydroxyoxetan-3-yl; and
$R^{1B}$ represents 3-hydroxyoxetan-3-yl, 3-hydroxythietan-3-yl, hydroxy$(C_1-C_3)$alkyl, amino$(C_1-C_3)$alkyl or trans-2-hydroxymethyl-cycloprop-1-yl.

42) In an even more preferred embodiment, the compounds of formula I according to embodiment 1) will be such that:
$R^1$ represents H or fluorine;
$R^2$ represents the group M;
$R^3$ represents H; and
M is the one of the groups $M^A$, $M^B$ and $M^C$ represented hereafter

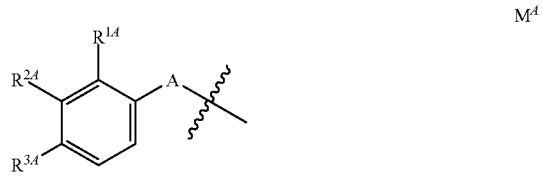

$M^A$

-continued

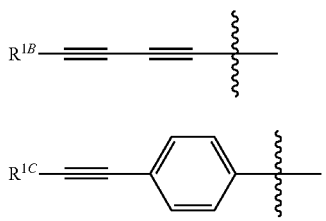

M$^B$

M$^C$ wherein A represents C≡C;
R$^{1A}$ represents H;
R$^{2A}$ represents H;
R$^{3A}$ represents hydroxy(C$_1$-C$_4$)alkyl, trans-2-hydroxymethyl-cycloprop-1-yl, 1,2-dihydroxyethyl or 3-hydroxyoxetan-3-yl (notably 1-hydroxyethyl, 2-hydroxyethyl, 2-hydroxypropan-2-yl, 1,2-dihydroxyethyl, trans-2-hydroxymethyl-cycloprop-1-yl or 3-hydroxyoxetan-3-yl);
R$^{1B}$ represents 3-hydroxythietan-3-yl, amino(C$_1$-C$_3$)alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(2-aminoacetyl)azetidin-3-yl, 1-glycylazetidin-3-yl, trans-(cis-3,4-dihydroxy)-cyclopent-1-yl or 3-hydroxymethylbicyclo[1,1,1]pentan-1-yl; and
R$^{1C}$ represents trans-2-hydroxymethyl-cycloprop-1-yl.

43) In particular, the compounds of formula I according to embodiment 42) will be compounds of formula I$_P$ as defined in embodiment 2) wherein:
R$^1$ represents H or fluorine;
R$^2$ represents the group M;
R$^3$ represents H; and
M is the one of the groups M$^A$ and M$^B$ represented below

M$^A$

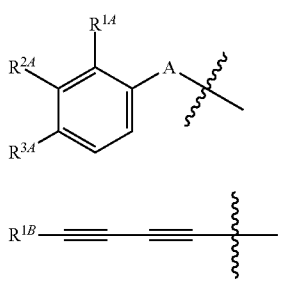

M$^B$ wherein A represents C≡C;
R$^{1A}$ represents H;
R$^{2A}$ represents H;
R$^{3A}$ represents hydroxy(C$_1$-C$_4$)alkyl, trans-2-hydroxymethyl-cycloprop-1-yl or 3-hydroxyoxetan-3-yl; and
R$^{1B}$ represents 3-hydroxythietan-3-yl, amino(C$_1$-C$_3$)alkyl or trans-2-hydroxymethyl-cycloprop-1-yl.

44) Another embodiment of this invention relates to compounds of formula I as defined in one of embodiments 1) to 43) as well as to isotopically labelled, especially $^2$H (deuterium) labelled compounds of formula I as defined in one of embodiments 1) to 43), which compounds are identical to the compounds of formula I as defined in one of embodiments 1) to 43) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

45) Particularly preferred are the following compounds of formula I as defined in embodiment 1) or 2):
(R)-4-[5-(2-fluoro-4-methoxy-phenyl)-indazol-2-yl]-N-hydroxy-2-methylsulfonyl-2-methyl-butanamide;
(R)—N-hydroxy-2-methylsulfonyl-4-[5-(4-methoxy-phenyl)-indazol-2-yl]-2-methyl-butanamide;
(R)-4-[6-fluoro-5-(4-methoxy-phenyl)-indazol-2-yl]-N-hydroxy-2-methylsulfonyl-2-methyl-butanamide;
(R)-4-[4-fluoro-5-(4-methoxy-phenyl)-indazol-2-yl]-N-hydroxy-2-methylsulfonyl-2-methyl-butanamide;
(R)-4-[6-fluoro-5-(2-fluoro-4-methoxy-phenyl)-indazol-2-yl]-N-hydroxy-2-methylsulfonyl-2-methyl-butanamide;
(R)-4-[4-fluoro-5-(2-fluoro-4-methoxy-phenyl)-indazol-2-yl]-N-hydroxy-2-methylsulfonyl-2-methyl-butanamide;
(R)—N-hydroxy-2-methylsulfonyl-2-methyl-4-[5-(4-morpholin-4-ylmethyl-phenylethynyl)-indazol-2-yl]-butanamide;
(R)—N-hydroxy-2-methylsulfonyl-2-methyl-4-[5-(4-trifluoromethoxy-phenyl)-indazol-2-yl]-butanamide;
(R)-4-[5-(2-fluoro-4-methylsulfanyl-phenyl)-indazol-2-yl]-N-hydroxy-2-methylsulfonyl-2-methyl-butanamide;
(R)-4-{5-[4-(3-amino-oxetan-3-yl)-phenylethynyl]-indazol-2-yl}-N-hydroxy-2-methylsulfonyl-2-methyl-butanamide;
(R)-4-[5-(4-dimethylamino-phenyl)-indazol-2-yl]-N-hydroxy-2-methylsulfonyl-2-methyl-butanamide;
(R)—N-hydroxy-2-methylsulfonyl-2-methyl-4-[5-(4-[1,2,3]triazol-2-yl-phenyl)-indazol-2-yl]-butanamide;
(R)—N-hydroxy-4-(5-((3-hydroxythietan-3-yl)buta-1,3-diyn-1-yl)-2H-indazol-2-yl)-2-methyl-2-(methylsulfonyl)butanamide;
(R)-4-(4-fluoro-5-((4-(2-hydroxypropan-2-yl)phenyl)ethynyl)-2H-indazol-2-yl)-N-hydroxy-2-methyl-2-(methylsulfonyl)butanamide;
(R)—N-hydroxy-4-(5-((4-hydroxytetrahydro-2H-pyran-4-yl)buta-1,3-diyn-1-yl)-2H-indazol-2-yl)-2-methyl-2-(methylsulfonyl)butanamide;
(R)—N-hydroxy-4-(5-((4-(1-(hydroxymethyl)cyclopropyl)phenyl)ethynyl)-2H-indazol-2-yl)-2-methyl-2-(methylsulfonyl)butanamide;
(R)—N-hydroxy-2-methylsulfonyl-2-methyl-4-[5-((E)-styryl)-indazol-2-yl]-butanamide;
(R)-4-{4-fluoro-5-[4-((1S*,2S*)-2-hydroxymethyl-cyclopropyl)-buta-1,3-diynyl]-indazol-2-yl}-N-hydroxy-2-methylsulfonyl-2-methyl-butanamide;
(R)-4-[5-(4-amino-phenylethynyl)-indazol-2-yl]-N-hydroxy-2-methylsulfonyl-2-methyl-butanamide;

(R)—N-hydroxy-4-{5-[4-(3-hydroxy-oxetan-3-yl)-phenyl) ethynyl]-indazol-2-yl}-2-methylsulfonyl-2-methyl-butanamide;

(R)—N-hydroxy-4-(5-((4-(hydroxymethyl)phenyl)ethynyl)-2H-indazol-2-yl)-2-methyl-2-(methylsulfonyl)butanamide;

(R)-4-[5-(3-fluoro-4-hydroxymethyl-phenylethynyl)-indazol-2-yl]-N-hydroxy-2-methylsulfonyl-2-methyl-butanamide;

(R)-4-[4-fluoro-5-(4-hydroxymethyl-phenylethynyl)-indazol-2-yl]-N-hydroxy-2-methylsulfonyl-2-methyl-butanamide;

(R)-4-(5-(5-amino-5-methylhexa-1,3-diyn-1-yl)-2H-indazol-2-yl)-N-hydroxy-2-methyl-2-(methylsulfonyl)butanamide;

(R)—N-hydroxy-4-{5-[4-(2-hydroxy-ethyl)-phenyl)ethynyl]-indazol-2-yl}-2-methylsulfonyl-2-methyl-butanamide;

(2R)-4-{5-[4-((R)-1,2-dihydroxy-ethyl)-phenylethynyl]-indazol-2-yl}-N-hydroxy-2-methylsulfonyl-2-methyl-butanamide;

(R)—N-hydroxy-4-(5-((4-(2-hydroxypropan-2-yl)phenyl) ethynyl)-2H-indazol-2-yl)-2-methyl-2-(methylsulfonyl) butanamide;

(R)—N-hydroxy-4-(5-((3-hydroxyoxetan-3-yl)buta-1,3-diyn-1-yl)-2H-indazol-2-yl)-2-methyl-2-(methylsulfonyl) butanamide;

(R)-4-{4-fluoro-5-[4-(3-hydroxy-oxetan-3-yl)-phenylethynyl]-indazol-2-yl}-N-hydroxy-2-methylsulfonyl-2-methyl-butanamide;

(R)-4-{5-[4-(3-dimethylamino-oxetan-3-yl)-phenyl)ethynyl]-indazol-2-yl}-N-hydroxy-2-methylsulfonyl-2-methyl-butanamide;

(R)-4-{6-fluoro-5-[4-(3-hydroxy-oxetan-3-yl)-buta-1,3-diynyl]-indazol-2-yl}-N-hydroxy-2-methylsulfonyl-2-methyl-butanamide;

(R)—N-hydroxy-4-[5-(5-hydroxy-5-methyl-hexa-1,3-diynyl)-indazol-2-yl]-2-methylsulfonyl-2-methyl-butanamide;

(R)—N-hydroxy-4-(5-((4-((R)-1-hydroxyethyl)phenyl) ethynyl)-2H-indazol-2-yl)-2-methyl-2-(methylsulfonyl) butanamide;

(R)—N-hydroxy-4-(5-((4-((S)-1-hydroxyethyl)phenyl) ethynyl)-2H-indazol-2-yl)-2-methyl-2-(methylsulfonyl) butanamide;

(R)-4-[5-(2-fluoro-4-trifluoromethoxy-phenyl)-indazol-2-yl]-N-hydroxy-2-methylsulfonyl-2-methyl-butanamide;

(R)—N-hydroxy-4-(5-4(1S,2S)-2-(hydroxymethyl)cyclopropyl)buta-1,3-diyn-1-yl)-2H-indazol-2-yl)-2-methyl-2-(methylsulfonyl)butanamide;

(R)—N-hydroxy-4-(5-4(1R,2R)-2-(hydroxymethyl)cyclopropyl)buta-1,3-diyn-1-yl)-2H-indazol-2-yl)-2-methyl-2-(methylsulfonyl)butanamide;

(R)-4-{4-fluoro-5-[4-(3-hydroxy-oxetan-3-yl)-buta-1,3-diynyl]-indazol-2-yl}-N-hydroxy-2-methylsulfonyl-2-methyl-butanamide;

(R)-4-[5-(2-fluoro-4-hydroxymethyl-phenylethynyl)-indazol-2-yl]-N-hydroxy-2-methylsulfonyl-2-methyl-butanamide;

4-(6-fluoro-5-((4-(3-hydroxyoxetan-3-yl)phenyl)ethynyl)-2H-indazol-2-yl)-N-hydroxy-2-methyl-2-(methylsulfonyl)butanamide;

(R)—N-hydroxy-4-(5-((4-((1R,2R)-2-(hydroxymethyl)cyclopropyl)phenyl)ethynyl)-2H-indazol-2-yl)-2-methyl-2-(methylsulfonyl)butanamide;

(R)—N-hydroxy-4-(5-((4-((1S,2S)-2-(hydroxymethyl)cyclopropyl)phenyl)ethynyl)-2H-indazol-2-yl)-2-methyl-2-(methylsulfonyl)butanamide;

(R)—N-hydroxy-4-(5-((4-(3-(hydroxymethyl)oxetan-3-yl) phenyl)ethynyl)-2H-indazol-2-yl)-2-methyl-2-(methylsulfonyl)butanamide;

(R)—N-hydroxy-4-(5-((4-(2-hydroxyethoxy)phenyl)ethynyl)-2H-indazol-2-yl)-2-methyl-2-(methylsulfonyl)butanamide;

as well as the salts (in particular the pharmaceutically acceptable salts) thereof.

46) Further preferred are the following compounds of formula I as defined in embodiment 1) or 2):

(R)—N-hydroxy-2-methylsulfonyl-2-methyl-4-{5-[4-(3-morpholin-4-yl-propoxy)-phenyl]-indazol-2-yl}-butanamide;

(R)—N-hydroxy-2-methylsulfonyl-2-methyl-4-{5-[4-(2-morpholin-4-yl-ethoxy)-phenyl]-indazol-2-yl}-butanamide;

(R)-4-{5-[2-fluoro-4-(2-morpholin-4-yl-ethoxy)-phenyl]-indazol-2-yl}-N-hydroxy-2-methylsulfonyl-2-methyl-butanamide;

(R)-4-(5-but-2-ynyloxy-indazol-2-yl)-N-hydroxy-2-methylsulfonyl-2-methyl-butanamide;

(R)—N-hydroxy-2-methylsulfonyl-2-methyl-4-(5-phenethyl-indazol-2-yl)-butanamide;

(R)—N-hydroxy-2-methylsulfonyl-2-methyl-4-[5-(4-oxazol-2-yl-phenyl)-indazol-2-yl]-butanamide;

(R)-4-(5-(2-fluoro-3-methoxyphenyl)-2H-indazol-2-yl)-N-hydroxy-2-methyl-2-(methylsulfonyl)butanamide;

as well as the salts (in particular the pharmaceutically acceptable salts) thereof.

47) Also particularly preferred are the following compounds of formula I as defined in embodiment 1):

(R)-4-(5-((3-fluoro-4-(2-hydroxyacetamido)phenyl)ethynyl)-2H-indazol-2-yl)-N-hydroxy-2-methyl-2-(methylsulfonyl)butanamide;

(R)-4-(5-((R)-5,6-dihydroxy-5-methylhexa-1,3-diyn-1-yl)-2H-indazol-2-yl)-N-hydroxy-2-methyl-2-(methylsulfonyl)butanamide;

(R)—N-hydroxy-4-(5-((4-(2-hydroxyacetamido)phenyl) ethynyl)-2H-indazol-2-yl)-2-methyl-2-(methylsulfonyl) butanamide;

(R)-4-(5-((3-aminooxetan-3-yl)buta-1,3-diyn-1-yl)-2H-indazol-2-yl)-N-hydroxy-2-methyl-2-(methylsulfonyl)butanamide;

(R)—N-hydroxy-4-(5-(4-(2-hydroxyacetamido)phenyl)-2H-indazol-2-yl)-2-methyl-2-(methylsulfonyl)butanamide;

(R)-4-(5-(2-fluoro-4-(2-hydroxyethoxy)phenyl)-2H-indazol-2-yl)-N-hydroxy-2-methyl-2-(methylsulfonyl)butanamide;

(R)-4-(5-((4-((S)-1,2-dihydroxyethyl)phenyl)ethynyl)-2H-indazol-2-yl)-N-hydroxy-2-methyl-2-(methylsulfonyl) butanamide;

(R)—N-hydroxy-4-(5-(4-(2-methoxyethoxy)phenyl)-2H-indazol-2-yl)-2-methyl-2-(methylsulfonyl)butanamide;

(R)-4-(6-fluoro-5-(((1S,2S)-2-(hydroxymethyl)cyclopropyl)buta-1,3-diyn-1-yl)-2H-indazol-2-yl)-N-hydroxy-2-methyl-2-(methyl sulfonyl)butanamide;

(R)-4-(4-fluoro-5-(((1S,2S)-2-(hydroxymethyl)cyclopropyl)buta-1,3-diyn-1-yl)-2H-indazol-2-yl)-N-hydroxy-2-methyl-2-(methyl sulfonyl)butanamide;

(R)-4-(5-((S)-5,6-dihydroxyhexa-1,3-diyn-1-yl)-2H-indazol-2-yl)-N-hydroxy-2-methyl-2-(methylsulfonyl)butanamide;

(R)—N-hydroxy-4-(5-((1-(hydroxymethyl)cyclopropyl)buta-1,3-diyn-1-yl)-2H-indazol-2-yl)-2-methyl-2-(methylsulfonyl)butanamide;

(R)—N-hydroxy-4-(5-((3-(hydroxymethyl)bicyclo[1.1.1]pentan-1-yl)buta-1,3-diyn-1-yl)-2H-indazol-2-yl)-2-methyl-2-(methylsulfonyl)butanamide;

(R)-4-(5-(4-((R)-2,3-dihydroxyprop oxy)-2-fluorophenyl)-2H-indazol-2-yl)-N-hydroxy-2-methyl-2-(methylsulfonyl)butanamide;

(R)—N-hydroxy-2-methyl-2-(methylsulfonyl)-4-(5-(pyrimidin-5-ylethynyl)-2H-indazol-2-yl)butanamide;

(R)—N-hydroxy-4-(5-(4-(((1S*,2S*)-2-(hydroxymethyl)cyclopropyl)ethynyl)phenyl)-2H-indazol-2-yl)-2-methyl-2-(methylsulfonyl)butanamide;

(R)-4-(5-(((2S*,5S*)-5-aminotetrahydro-2H-pyran-2-yl)buta-1,3-diyn-1-yl)-2H-indazol-2-yl)-N-hydroxy-2-methyl-2-(methyl sulfonyl)butanamide;

(R)-(1-(4-((2-(4-(hydroxyamino)-3-methyl-3-(methylsulfonyl)-4-oxobutyl)-2H-indazol-5-yl)ethynyl)phenyl)cyclopropyl)methyl dihydrogen phosphate;

(R)-(1-(4-((2-(4-(hydroxyamino)-3-methyl-3-(methylsulfonyl)-4-oxobutyl)-2H-indazol-5-yl)ethynyl)phenyl)cyclopropyl)methyl dimethylglycinate;

(R)-4-(5-(((1S,3R,4S)-3,4-dihydroxycyclopentyl)buta-1,3-diyn-1-yl)-2H-indazol-2-yl)-N-hydroxy-2-methyl-2-(methylsulfonyl)butanamide;

(R)-4-(5-((1-aminocyclopropyl)buta-1,3-diyn-1-yl)-2H-indazol-2-yl)-N-hydroxy-2-methyl-2-(methylsulfonyl)butanamide;

(R)—N-hydroxy-4-(5-(5-((1S,3R)-1-hydroxy-3-(hydroxymethyl)cyclobutyl)penta-1,3-diyn-1-yl)-2H-indazol-2-yl)-2-methyl-2-(methylsulfonyl)butanamide;

(R)—N-hydroxy-4-(5-(((1R,2R)-2-(hydroxymethyl)-1-methylcyclopropyl)buta-1,3-diyn-1-yl)-2H-indazol-2-yl)-2-methyl-2-(methylsulfonyl)butanamide;

(R)—N-hydroxy-4-(5-((3-(hydroxymethyl)oxetan-3-yl)buta-1,3-diyn-1-yl)-2H-indazol-2-yl)-2-methyl-2-(methylsulfonyl)butanamide;

(R)—N-hydroxy-4-(5-(((1R,2S)-2-(hydroxymethyl)-2-methylcyclopropyl)buta-1,3-diyn-1-yl)-2H-indazol-2-yl)-2-methyl-2-(methylsulfonyl)butanamide;

(R)-4-(5-((3-(2-aminoacetamido)cyclopentyl)buta-1,3-diyn-1-yl)-2H-indazol-2-yl)-N-hydroxy-2-methyl-2-(methylsulfonyl)butanamide;

(R)-4-(5-(((1R,2R)-2-((S)-1,2-dihydroxyethyl)cyclopropyl)buta-1,3-diyn-1-yl)-2H-indazol-2-yl)-N-hydroxy-2-methyl-2-(methyl sulfonyl)butanamide;

(R)-4-(5-(((1R,2R)-2-(aminomethyl)cyclopropyl)buta-1,3-diyn-1-yl)-2H-indazol-2-yl)-N-hydroxy-2-methyl-2-(methylsulfonyl)butanamide;

(R)—N-hydroxy-4-(5-((1-(hydroxymethyl)cyclobutyl)buta-1,3-diyn-1-yl)-2H-indazol-2-yl)-2-methyl-2-(methylsulfonyl)butanamide;

(R)-4-(5-(((1R,2R)-1-fluoro-2-(hydroxymethyl)cyclopropyl)buta-1,3-diyn-1-yl)-2H-indazol-2-yl)-N-hydroxy-2-methyl-2-(methyl sulfonyl)butanamide;

(R)-4-(5-(5-(dimethylamino)penta-1,3-diyn-1-yl)-2H-indazol-2-yl)-N-hydroxy-2-methyl-2-(methylsulfonyl)butanamide;

(R)—N-hydroxy-2-methyl-2-(methylsulfonyl)-4-(5-(piperidin-4-ylbuta-1,3-diyn-1-yl)-2H-indazol-2-yl)butanamide;

(R)-4-(5-(((1R,2R)-2-fluoro-2-(hydroxymethyl)cyclopropyl)buta-1,3-diyn-1-yl)-2H-indazol-2-yl)-N-hydroxy-2-methyl-2-(methyl sulfonyl)butanamide;

(R)—N-hydroxy-4-(5-((1-(2-hydroxyacetyl)piperidin-4-yl)buta-1,3-diyn-1-yl)-2H-indazol-2-yl)-2-methyl-2-(methylsulfonyl)butanamide;

(R)-4-(5-((4-(1-aminocyclopropyl)phenyl)ethynyl)-2H-indazol-2-yl)-N-hydroxy-2-methyl-2-(methylsulfonyl)butanamide;

(R)—N-hydroxy-4-(5-(5-(3-hydroxyoxetan-3-yl)penta-1,3-diyn-1-yl)-2H-indazol-2-yl)-2-methyl-2-(methylsulfonyl)butanamide;

(R)—N-hydroxy-4-(5-((1-(2-hydroxyacetyl)azetidin-3-yl)buta-1,3-diyn-1-yl)-2H-indazol-2-yl)-2-methyl-2-(methylsulfonyl)butanamide;

(R)-4-(5-(6-amino-6-methylhepta-1,3-diyn-1-yl)-2H-indazol-2-yl)-N-hydroxy-2-methyl-2-(methylsulfonyl)butanamide;

(R)-4-(5-((1-glycylpiperidin-4-yl)buta-1,3-diyn-1-yl)-2H-indazol-2-yl)-N-hydroxy-2-methyl-2-(methylsulfonyl)butanamide;

(R)-4-(5-((1-glycylazetidin-3-yl)buta-1,3-diyn-1-yl)-2H-indazol-2-yl)-N-hydroxy-2-methyl-2-(methylsulfonyl)butanamide;

(R)-4-(5-((1-(2-amino-2-methylpropanoyl)azetidin-3-yl)buta-1,3-diyn-1-yl)-2H-indazol-2-yl)-N-hydroxy-2-methyl-2-(methylsulfonyl)butanamide;

as well as the salts (in particular the pharmaceutically acceptable salts) thereof.

48) The invention further relates to the compounds of formula I as defined in embodiment 1) which are selected from the group consisting of the compounds listed in embodiment 45), the compounds listed in embodiment 46) and the compounds listed in embodiment 47). In particular, it also relates to the groups of compounds of formula I selected from the group consisting of the compounds listed in embodiment 45), the compounds listed in embodiment 46) and the compounds listed in embodiment 47), which groups of compounds furthermore correspond to one of embodiments 2) to 43), as well as to the salts (in particular the pharmaceutically acceptable salts) of such compounds. The invention moreover relates to any individual compound of formula I selected from the group consisting of the compounds listed in embodiment 45), the compounds listed in embodiment 46) and the compounds listed in embodiment 47), and to the salts (in particular the pharmaceutically acceptable salts) of such individual compound.

The compounds of formula I according to this invention, i.e. according to one of embodiments 1) to 48) above, exhibit antibacterial activity, especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophila*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. such as *Borrelia Burgdorferi*, *Brucella* spp. such as *Brucella melitensis*, *Burkholderia* spp. such as

*Burkholderia cepacia, Burkholderia pseudomallei* or *Burkholderia mallei, Campylobacter* spp. such as *Campylobacter jejuni, Campylobacter fetus* or *Campylobacter coli, Cedecea, Chlamydia* spp. such as *Chlamydia pneumoniae, Chlamydia trachomatis, Citrobacter* spp. such as *Citrobacter diversus (koseri)* or *Citrobacter freundii, Coxiella burnetii, Edwardsiella* spp. such as *Edwarsiella tarda, Ehrlichia chafeensis, Eikenella corrodens, Enterobacter* spp. such as *Enterobacter cloacae, Enterobacter aerogenes, Enterobacter agglomerans, Escherichia coli, Francisella tularensis, Fusobacterium* spp., *Haemophilus* spp. such as *Haemophilus influenzae* (beta-lactamase positive and negative) or *Haemophilus ducreyi, Helicobacter pylori, Kingella kingae, Klebsiella* spp. such as *Klebsiella oxytoca, Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae, Legionella pneumophila, Mannheimia haemolyticus, Moraxella catarrhalis* (beta-lactamase positive and negative), *Morganella morganii, Neisseria* spp. such as *Neisseria gonorrhoeae* or *Neisseria meningitidis, Pasteurella* spp. such as *Pasteurella multocida, Plesiomonas shigelloides, Porphyromonas* spp. such as *Porphyromonas asaccharolytica, Prevotella* spp. such as *Prevotella corporis, Prevotella intermedia* or *Prevotella endodontalis, Proteus* spp. such as *Proteus mirabilis, Proteus vulgaris, Proteus penneri* or *Proteus myxofaciens, Porphyromonas asaccharolytica, Plesiomonas shigelloides, Providencia* spp. such as *Providencia stuartii, Providencia rettgeri* or *Providencia alcalifaciens, Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens, Ricketsia prowazekii, Salmonella* spp. such as *Salmonella typhi* or *Salmonella paratyphi, Serratia marcescens, Shigella* spp. such as *Shigella flexneri, Shigella boydii, Shigella sonnei* or *Shigella dysenteriae, Streptobacillus moniliformis, Stenotrophomonas maltophilia, Treponema* spp., *Vibrio* spp. such as *Vibrio cholerae, Vibrio parahaemolyticus, Vibrio vulnificus, Vibrio alginolyticus, Yersinia* spp. such as *Yersinia enterocolitica, Yersinia pestis* or *Yersinia pseudotuberculosis.*

The compounds of formula I according to this invention are thus useful for treating a variety of infections caused by fermentative or non-fermentative Gram-negative bacteria, especially infections such as: nosocomial pneumonia (related to infection by *Legionella pneumophila, Haemophilus influenzae,* or *Chlamydia* pneumonia); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis*; pharyngitis, rheumatic fever, and glomerulonephritis related to infection by *Actinobacillus haemolyticum*; sexually transmitted diseases related to infection by *Chlamydia trachormatis, Haemophilus ducreyi, Treponema pallidum, Ureaplasma urealyticum,* or *Neisseria gonorrheae*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae* or *H. influenzae*; gastroenteritis related to infection by *Campylobacter jejuni*; persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and are suitable, for the prevention or treatment of a bacterial infection caused by Gram-negative bacteria selected from the group consisting of *Acinetobacter baumannii, Burkholderia* spp. (e.g. *Burkholderia cepacia*), *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection mediated by quinolone-resistant *Acinetobacter baumannii* bacteria or quinolone-resistant *Klebsiella pneumoniae* bacteria).

The compounds of formula I according to this invention, or the pharmaceutically acceptable salts thereof, may more especially be used for the preparation of a medicament, and are suitable, for the prevention or treatment of a bacterial infection caused by Gram-negative bacteria selected from the group consisting of *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention display intrinsic antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, cefatazidime, cefepime, cefotaxime) a carbapenem antibiotic (such as imipenem, or meropenem), a monobactam antibiotic (such as aztreonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

One aspect of this invention therefore relates to the use of a compound of formula I according to one of embodiments 1) to 48), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 48), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 48), or a pharmaceutically acceptable salt thereof, as a medicament. Yet a further aspect of this invention relates to a pharmaceutical composition containing, as active principle, a compound of formula I according to one of embodiments 1) to 48), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I, $I_P$, $I_{CE}$ or $I_{CEP}$.

Any reference to a compound of formula I, $I_P$, $I_{CE}$ or $I_{CEP}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 48) or a pharmaceutically acceptable salt thereof. Accordingly, the invention provides a method for the prevention or the treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria) in a patient, comprising the administration to said patient of a pharmaceutically active amount of a compound of formula I according to one of embodiments 1) to 48) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 48), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria).

The following embodiments relating to the compounds of formula I according to embodiment 1) are thus possible and intended and herewith specifically disclosed in individualised form:

1, 2+1, 3+1, 4+3+1, 5+1, 5+2+1, 5+3+1, 5+4+3+1, 6+1, 6+2+1, 6+3+1, 6+4+3+1, 6+5+1, 6+5+2+1, 6+5+3+1, 6+5+4+3+1, 7+6+1, 7+6+2+1, 7+6+3+1, 7+6+4+3+1, 7+6+5+1, 7+6+5+2+1, 7+6+5+3+1, 7+6+5+4+3+1, 8+7+6+1, 8+7+6+2+1, 8+7+6+3+1, 8+7+6+4+3+1, 8+7+6+5+1, 8+7+6+5+2+1, 8+7+6+5+3+1, 8+7+6+5+4+3+1, 9+8+7+6+1, 9+8+7+6+2+1, 9+8+7+6+3+1, 9+8+7+6+4+3+1, 9+8+7+6+5+1, 9+8+7+6+5+2+1, 9+8+7+6+5+3+1, 9+8+7+6+5+4+3+1, 10+7+6+1, 10+7+6+2+1, 10+7+6+3+1, 10+7+6+4+3+1, 10+7+6+5+1, 10+7+6+5+2+1, 10+7+6+5+3+1, 10+7+6+5+4+3+1, 11+10+7+6+1, 11+10+7+6+2+1, 11+10+7+6+3+1, 11+10+7+6+4+3+1, 11+10+7+6+5+1, 11+10+7+6+5+2+1, 11+10+7+6+5+3+1, 11+10+7+6+5+4+3+1, 12+6+1, 12+6+2+1, 12+6+3+1, 12+6+4+3+1, 12+6+5+1, 12+6+5+2+1, 12+6+5+3+1, 12+6+5+4+3+1, 13+12+6+1, 13+12+6+2+1, 13+12+6+3+1, 13+12+6+4+3+1, 13+12+6+5+1, 13+12+6+5+2+1, 13+12+6+5+3+1, 13+12+6+5+4+3+1, 14+12+6+1, 14+12+6+2+1, 14+12+6+3+1, 14+12+6+4+3+1, 14+12+6+5+1, 14+12+6+5+2+1, 14+12+6+5+3+1, 14+12+6+5+4+3+1, 15+6+1, 15+6+2+1, 15+6+3+1, 15+6+4+3+1, 15+6+5+1, 15+6+5+2+1, 15+6+5+3+1, 15+6+5+4+3+1, 16+15+6+1, 16+15+6+2+1, 16+15+6+3+1, 16+15+6+4+3+1, 16+15+6+5+1, 16+15+6+5+2+1, 16+15+6+5+3+1, 16+15+6+5+4+3+1, 17+16+15+6+1, 17+16+15+6+2+1, 17+16+15+6+3+1, 17+16+15+6+4+3+1, 17+16+15+6+5+1, 17+16+15+6+5+2+1, 17+16+15+6+5+3+1, 17+16+15+6+5+4+3+1, 18+15+6+1, 18+15+6+2+1, 18+15+6+3+1, 18+15+6+4+3+1, 18+15+6+5+1, 18+15+6+5+2+1, 18+15+6+5+3+1, 18+15+6+5+4+3+1, 19+18+15+6+1, 19+18+15+6+2+1, 19+18+15+6+3+1, 19+18+15+6+4+3+1, 19+18+15+6+5+1, 19+18+15+6+5+2+1, 19+18+15+6+5+3+1, 19+18+15+6+5+4+3+1, 20+15+6+1, 20+15+6+2+1, 20+15+6+3+1, 20+15+6+4+3+1, 20+15+6+5+1, 20+15+6+5+2+1, 20+15+6+5+3+1, 20+15+6+5+4+3+1, 21+20+15+6+1, 21+20+15+6+2+1, 21+20+15+6+3+1, 21+20+15+6+4+3+1, 21+20+15+6+5+1, 21+20+15+6+5+2+1, 21+20+15+6+5+3+1, 21+20+15+6+5+4+3+1, 22+1, 22+2+1, 22+3+1, 22+4+3+1, 22+5+1, 22+5+2+1, 22+5+3+1, 22+5+4+3+1, 23+22+1, 23+22+2+1, 23+22+3+1, 23+22+4+3+1, 23+22+5+1, 23+22+5+2+1, 23+22+5+3+1, 23+22+5+4+3+1, 24+23+22+1, 24+23+22+2+1, 24+23+22+3+1, 24+23+22+4+3+1, 24+23+22+5+1, 24+23+22+5+2+1, 24+23+22+5+3+1, 24+23+22+5+4+3+1, 25+22+1, 25+22+2+1, 25+22+3+1, 25+22+4+3+1, 25+22+5+1, 25+22+5+2+1, 25+22+5+3+1, 25+22+5+4+3+1, 26+25+22+1, 26+25+22+2+1, 26+25+22+3+1, 26+25+22+4+3+1, 26+25+22+5+1, 26+25+22+5+2+1, 26+25+22+5+3+1, 26+25+22+5+4+3+1, 27+22+1, 27+22+2+1, 27+22+3+1, 27+22+4+3+1, 27+22+5+1, 27+22+5+2+1, 27+22+5+3+1, 27+22+5+4+3+1, 28+27+22+1, 28+27+22+2+1, 28+27+22+3+1, 28+27+22+4+3+1, 28+27+22+5+1, 28+27+22+5+2+1, 28+27+22+5+3+1, 28+27+22+5+4+3+1, 29+1, 29+3+1, 30+29+1, 30+29+3+1, 31+29+1, 31+29+3+1, 32+1, 32+3+1, 33+1, 33+2+1, 34+33+1, 34+33+2+1, 35+1, 35+2+1, 35+3+1, 35+4+3+1, 36+1, 36+2+1, 36+3+1, 36+4+3+1, 37+1, 37+2+1, 37+3+1, 37+4+3+1, 38+1, 39+38+1, 40+1, 41+40+1, 42+1, 43+42+1, 44+1, 44+2+1, 45+1, 45+2+1, 46+1, 46+2+1, 47+1, 48+38+1, 48+39+38+1, 48+40+1, 48+41+40+1, 48+42+1 and 48+43+42+1.

In the preceding list, the numbers refer to the embodiments according to their numbering provided hereinabove whereas "+" indicates the dependency from another embodiment. The different individualised embodiments are separated by commas. In other words, "6+2+1" for example refers to embodiment 6) depending on embodiment 2), depending on embodiment 1), i.e. embodiment "6+2+1" corresponds to embodiment 1) further limited by the features of embodiments 2) and 6). Likewise, "13+12+6+1" refers to embodiment 13) depending *mutatis mutandis* on embodiments 12) and 6), depending on embodiment 1), i.e. embodiment "13+12+6+1" corresponds to embodiment 1) further limited by the features of embodiment 6), further limited by the features of embodiments 12) and 13).

The compounds of formula I can be manufactured in accordance with the present invention using the procedures described hereafter.

Preparation of the Compounds of Formula I

Abbreviations:

The following abbreviations are used throughout the specification and the examples:

Ac acetyl
AcOH acetic acid
aq. aqueous
Boc tert-butoxycarbonyl
Bs 4-bromobenzenesulfonyl (brosylate)
BuLi n-butyl lithium
CC column chromatography over silica gel
Cipro ciprofloxacin
conc. concentrated
Cy cyclohexyl
DAD diode array detection
dba dibenzylideneacetone
DCC dicyclohexylcarbodiimide
DCM dichloromethane
DEA diethylamine
DIBAH diisobutylaluminium hydride
DME 1,2-dimethoxyethane
DMF N,N-dimethylformamide
DMSO dimethylsulfoxide
dppf 1,1'-bis(diphenylphosphino)ferrocene
EA ethyl acetate
EDC N-(3-dimethylaminopropyl)-N'-ethylcarbodiimide hydrochloride
e.e. enantiomeric excess
ELSD evaporative light scattering detector
ESI electron spray ionisation
eq. equivalent
Et ethyl
EtOH ethanol
Et$_2$O diethyl ether
HATU 0-(7-azabenzotriazol-1-yl)-N,N,N',N'-tetramethyluronium hexafluorophosphate
Hept heptane
Hex hexane
HOBT hydroxybenzotriazole
HPLC high pressure liquid chromatography
IT internal temperature
LC liquid chromatography
Me methyl
MeCN acetonitrile
MeOH methanol
MS mass spectroscopy
Ms methylsulfonyl (mesyl)
NBS N-bromosuccinimide
Nf nonafluorobutanesulfonyl
NMR Nuclear Magnetic Resonance
Ns 4-nitrobenzenesulfonyl (nosylate)
org. organic
Pd/C palladium on carbon
PE petroleum ether
% w/w percent by weight
PEPPSI™-IPr [1,3-bis(2,6-diisopropylphenyl)imidazol-2-ylidene](3-chloropyridyl)palladium(II) dichloride
Ph phenyl
PPTS para-toluenesulfonic acid pyridinium salt
prep-HPLC preparative high pressure liquid chromatography
Pyr pyridine Q-phos 1,2,3,4,5-pentaphenyl-1'-(di-tert-butylphosphino) ferrocene
quant. quantitative yield
rt room temperature
sat. saturated
SK—CC01-A 2'-(dimethylamino)-2-biphenylyl-palladium (II) chloride dinorbomylphosphine complex
S-Phos 2-dicyclohexylphosphino-2',6'-dimethoxybiphenyl
TBAF tetra-n-butylammonium fluoride
TBDMS tert-butyldimethylsilyl
TBDPS tert-butyldiphenylsilyl
tBu tert-butyl
TEA triethylamine
Tf trifluoromethylsulfonyl (triflyl)
TFA trifluoroacetic acid
THF tetrahydrofuran
THP tetrahydropyranyl
TLC thin layer chromatography
TMS trimethylsilyl
TMSE 2-(trimethylsilyl)ethyl
$t_R$ retention time
$T_S$ para-toluenesulfonyl General Reaction Techniques:

General Reaction Technique 1 (Hydroxamic Acid Protecting Group Removal);

The protecting groups R of the hydroxamic acid ester derivatives (CONHOR) are removed as follows:

When R is THP, (2-methylpropoxy)ethyl, methoxymethyl, tBu, COOtBu or COtBu: by acidic treatment with e.g. TFA or HCl in an org. solvent such as DCM, dioxane, ether or MeOH between 0° C. and rt or by treatment with pyridinium para-toluenesulfonate in EtOH between rt and 80° C.;

When R is trityl: by treatment with diluted acid such as citric acid or HCl in an org. solvent such as MeOH or DCM;

When R is benzyl: by hydrogenation using general reaction technique 5;

When R is TMSE: by using fluoride anion sources such as $BF_3$.etherate complex in MeCN at 0° C., TBAF in THF between 0° C. and +40° C. or HF in MeCN or water between 0° C. and +40° C., or using acidic conditions such as AcOH in THF/MeOH or HCl in MeOH;

When R is allyl: by treatment with $Pd(PPh_3)_4$ in a solvent such as MeOH in presence of $K_2CO_3$ or a scavenger such as dimedone, morpholine or tributyltin hydride;

When R is COMe: by treatment with diluted NaOH or $Na_2CO_3$ in a solvent such as MeOH.

Further general methods to remove hydroxamic acid protecting groups have been described in *Protecting Groups in Organic Synthesis*, 3$^{rd}$ Ed (1999), 23-147; T. W. Greene, P. G. M. Wuts; (Publisher: John Wiley and Sons, Inc., New York, N.Y.).

General Reaction Technique 2 (Amide Coupling);

The carboxylic acid is reacted with the hydroxylamine derivative in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between –20° C. and 60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between –20° and 60° C. Further activating agents can be found in *Comprehensive Organic Transformations. A guide to Functional Group Preparations*; 2$^{nd}$ Edition, R. C. Larock, Wiley-V C; New York, Chichester, Weinheim, Brisbane, Singapore, Toronto, 1999. Section nitriles, carboxylic acids and derivatives p. 1941-1949.

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. S-Phos) or ferrocenylphosphines (e.g. Q-phos). Alternatively, one can use a commercially available precatalyst based on palladacycle (e.g. SK—CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (Sonogashira Coupling):

The alkyne derivative is reacted with the corresponding bromo derivative, using a catalytic amount of a palladium salt, an org. base such as TEA and a catalytic amount of a copper derivative (usually copper iodide) in a solvent such as DMF between 20° C. to 100° C. (see Sonogashira, K. in *Metal-Catalyzed Reactions*, Diederich, F., Stang, P. J., Eds.; Wiley-VCH, New York (1998)).

General Reaction Technique 5 (Hydrogenation of a Double Bond):

The unsaturated derivative dissolved in a solvent such as MeOH, EA or THF is hydrogenated over a noble metal catalyst such as Pd/C or $PtO_2$, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Reaction Technique 6 (Transformation of an Ester into an Acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in *Protecting Groups in Organic Synthesis* 3$^{rd}$ Ed (1999), 369-441; T. W. Greene, P. G. M. Wuts; (Publisher: John Wiley and Sons, Inc., New York, N.Y.).

General Reaction Technique 7 (Alcohol Activation):

The alcohol is reacted with MSCl, TfCl, BsCl, NfCl, NsCl or TsCl in the presence of a base such as TEA in a dry aprotic solvent such as Pyr, THF or DCM between −30° C. and +50° C. In the case of the triflate or mesylate, Tf$_2$O or Ms$_2$O can also be used.

General Reaction Technique 8 (Formation of Iodo, Chloro or Bromo Derivatives):

The sulfonates obtained using general reaction technique 7 can be reacted with a sodium halogenide such as NaI or NaBr in MeCN or DMF between 40° C. and 120° C., delivering the corresponding halogenated derivatives. Alternatively, the corresponding bromides or chlorides can also be obtained by reaction of the corresponding alcohol derivatives with PBr$_3$ or PCl$_3$ respectively.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups $R^1$, $R^2$, $R^3$, M, $M^A$, $M^B$, $M^C$, $M^D$, A, $R^{1A}$, $R^{2A}$, $R^{3A}$, $R^{1B}$ and $R^{1C}$ are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by deprotecting a compound of formula II

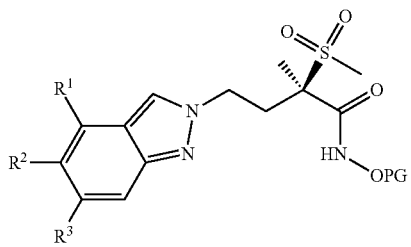

wherein $R^1$, $R^2$ and $R^3$ have the same meanings as in formula I and PG represents THP, TMSE, benzyl, trityl, (2-methylpropoxy)ethyl, methoxymethyl, allyl, tBu, acetyl, COOtBu or COtBu using general reaction technique 1. The reaction can also be performed with racemic material and the (R) enantiomer can be obtained by chiral HPLC separation.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II:

The compounds of formula II can be obtained by:

a) reacting a compound of formula III

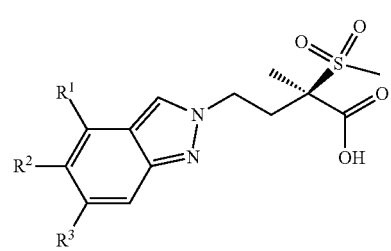

wherein $R^1$, $R^2$ and $R^3$ have the same respective meanings as in formula I with a compound of formula IV $$H_2N-OPG \qquad \qquad IV$$

wherein PG has the same meaning as in formula II using general reaction technique 2 (this reaction can also be performed with racemic compound of formula III and the (R)-enantiomer can then be obtained by chiral HPLC separation of the reaction product); or b) reacting a boron derivative of formula Va or Vb

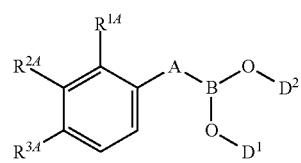

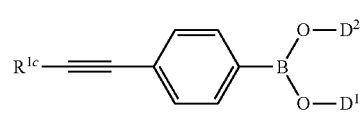

wherein $R^{1A}$, $R^{2A}$, $R^{3A}$ and $R^{1C}$ have the same respective meanings as in formula I, A represents a bond or CH=CH and $D^1$ and $D^2$ represent H, methyl or ethyl or $D^1$ and $D^2$ together represent $CH_2C(Me)_2CH_2$ or $C(Me)_2C(Me)_2$ with a compound of formula VI

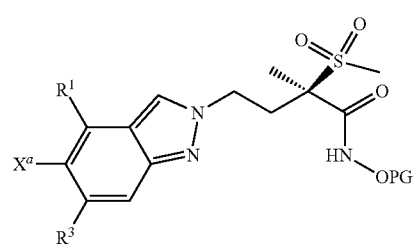

wherein $R^1$ and $R^3$ have the same respective meanings as in formula I, $X^a$ represents a halogen such as bromine or iodine and PG has the same meaning as in formula II, using general reaction technique 3 (this reaction can also be performed with racemic compound of formula VI and the (R)-enantiomer can then be obtained by chiral HPLC separation of the reaction product); or c) reacting a compound of formula VII wherein $R^{1A}$, $R^{2A}$ and $R^{3A}$ have the same respective meanings as in formula I, with a compound of formula VI as defined in section b) above wherein $X^a$ represents iodine, using general reaction technique 4 (this reaction can also be performed with racemic compound of formula VI and the (R)-enantiomer can then be obtained by chiral HPLC separation of the reaction product); or d) reacting a compound of formula VIII wherein $R^{1A}$, $R^{2A}$ and $R^{3A}$ have the same respective meanings as in formula I and $X^b$ represents iodine or bromine (and preferably iodine), with a compound of formula VIa wherein $R^1$ and $R^3$ have the same respective meanings as in formula I, $X^a$ represents ethynyl and PG has the same meaning as in formula II, using general reaction technique 4 (this reaction can also be performed with racemic compound of formula VIa and the (R)-enantiomer can then be obtained by chiral HPLC separation of the reaction product); or e) reacting a compound of formula IX wherein $R^{1B}$ has the same meaning as in formula I and $X^c$ represents iodine or bromine (and preferably iodine), with a compound of formula VIa as defined in section d) above, using general reaction technique 4 (this reaction can also be performed with racemic compound of formula VIa and the (R)-enantiomer can then be obtained by chiral HPLC separation of the reaction product); or f) hydrogenating a compound of formula X wherein $R^1$, $R^3$, $R^{1A}$, $R^{2A}$ and $R^{3A}$ have the same respective meanings as in formula I and PG has the same meaning as in formula II, using general reaction technique 5 (this reaction can also be performed with racemic compound of formula X and the (R)-enantiomer can then be obtained by chiral HPLC separation of the reaction product).

Preparation of the Synthesis Intermediates of Formulae III, IV, Va, Vb, VI, VIa, VII, VIII, IX and X:

Compounds of Formula III:

The compounds of formula III can be prepared as summarised in Scheme 1 hereafter.

Scheme 1

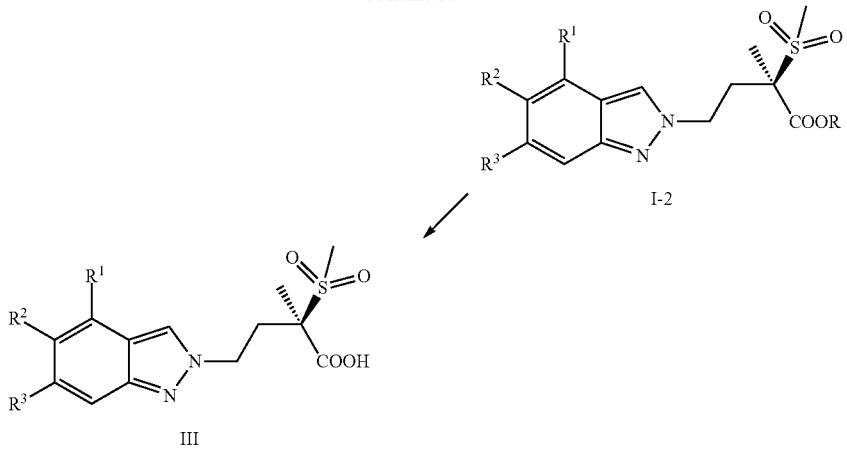

In Scheme 1, $R^1$, $R^2$ and $R^3$ have the same respective meanings as in formula I, $X^a$ represents a halogen such as iodine or bromine and R represents $(C_1\text{-}C_5)$alkyl, allyl or benzyl. The reactions can also be performed with racemic material and the (R)-enantiomer can be obtained by chiral HPLC separation at any step when suitable.

The derivatives of formula I-1 can be reacted (Scheme 1) with the boronic acid or ester derivatives of formula Va or Vb using general reaction technique 3 ($X^a$ represents bromine or iodine) or with the alkyne derivatives of formula VII using general reaction technique 4 ($X^a$ representing iodine), affording the derivatives of formula I-2. Alternatively the latter can also be obtained (after separation of the isomeric 1H-indazol-1-yl derivatives obtained as side products) by reacting the indazole derivatives of formula I-3 with the bromo derivatives of formula I-4. The compounds of formula I-2 can be transformed into the carboxylic acid derivatives of formula III using general reaction technique 6.

Compounds of Formula IV:

The compounds of formula IV are commercially available (PG=THP, tBu, COOtBu or allyl) or can be prepared according to WO 2010/060785 (PG=(2-methylpropoxy)ethyl) or Marmer and Maerker, *J. Org. Chem.* (1972), 37, 3520-3523 (PG=COtBu).

Compounds of Formula Va:

The compounds of formula Va wherein A is a bond and $D^1$ and $D^2$ each represent H or $(C_1\text{-}C_2)$alkyl are commercially available or can be prepared according to Sleveland et al., *Org. Process Res. Dev.* (2012), 16, 1121-1130 starting from tri($(C_1\text{-}C_2)$alkyl)borate and the corresponding commercially available bromo derivatives (optionally followed by acidic hydrolysis). The compounds of formula Va wherein A represents a bond and $D^1$ and $D^2$ together represent $CH_2C(Me)_2CH_2$ or $C(Me)_2C(Me)_2$ are commercially available or can be prepared according to WO 2012/093809, starting from bis(pinacolato)diborane or 5,5-dimethyl-1,3,2-dioxaborinane (both commercially available) with the corresponding commercially available bromo derivatives of formula VIII. The compounds of formula Va wherein A is CH=CH and $D^1$ and $D^2$ each represent H are commercially available or can be prepared according to Perner et al., *Biorg. Med. Chem. Lett.* (2005), 15, 2803-2807 by reaction of catechol borane on the appropriate alkyne derivatives followed by acidic hydrolysis.

Compounds of Formula Vb:

The compounds of formula Vb wherein $D^1$ and $D^2$ each represent H or $(C_1\text{-}C_2)$alkyl can be prepared by reacting a compound of formula VII wherein Xc represents H with a appropriate 4-halo-phenyl boronic acids or boronate esters as described in WO 2010/100475 or WO 03/050132.

Compounds of Formulae VI and VIa:

The compounds of formulae VI and VIa can be prepared as summarised in Scheme 2 hereafter.

Scheme 2

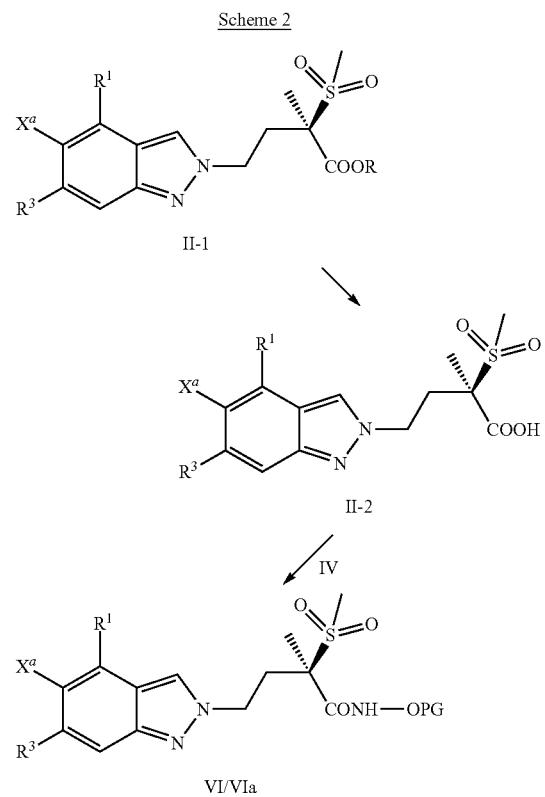

In Scheme 2, $R^1$ and $R^3$ have the same respective meanings as in formula I, R represents $(C_1\text{-}C_5)$alkyl, allyl or benzyl, $X^a$ represents a halogen (such as iodine or bromine) or ethynyl and PG has the same meaning as in formula II.

The reactions can also be performed with racemic material and the (R)-enantiomer can be obtained by chiral HPLC separation at any step when suitable.

The derivatives of formula II-1 can be transformed (Scheme 2) into the carboxylic acid derivatives of formula II-2 using general reaction technique 6 and further reacted with the compounds of formula IV using general reaction technique 2, thus affording the compounds of formula VI ($X^a$=halogen) or VIa ($X^a$=ethynyl).

Compounds of Formula VII:

The compounds of formula VII are commercially available or can be prepared as summarised in Scheme 3 hereafter.

Scheme 3

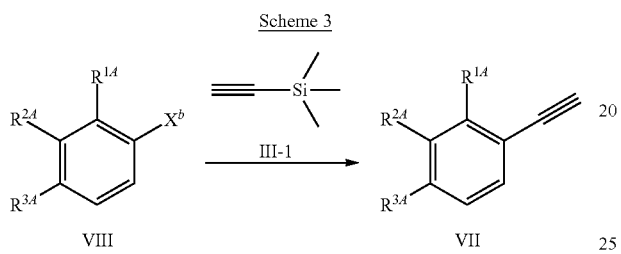

In Scheme 3, $R^{1A}$, $R^{2A}$ and $R^{3A}$ have the same respective meanings as in formula I and $X^b$ represents a halogen such as bromine or iodine.

The derivatives of formula VIII wherein $X^b$ represents bromine can be transformed (Scheme 3) into the corresponding derivatives wherein $X^b$ represents iodine by reaction with NaI in presence CuI and trans-N,N'-dimethylcyclohexanediamine. The resulting compounds of formula VIII wherein $X^b$ represents iodine can be reacted with trimethylsilylacetylene (III-1) in the presence of CuI and $PdCl_2(PPh_3)_2$ followed by treatment with an inorganic base such as $K_2CO_3$ in an appropriate alcoholic solvent such as MeOH, or by treatment with TBAF in THF, affording the derivatives of formula VII.

Compounds of Formula IX:

The compounds of formula IX wherein $X^c$ represents iodine can be prepared by iodination of the corresponding compounds wherein $X^c$ would be H with iodine in the presence of an inorganic base such as KOH.

Compounds of Formula X

The compounds of formula X can be prepared by analogy to the method described in sub-section b) of the section entitled "Preparation of the compounds of formula II".

Other Synthesis Intermediates and Starting Materials:

The compounds of formula I-1 wherein $X^a$ represents bromine can be prepared as summarised in Scheme 4 hereafter.

Scheme 4

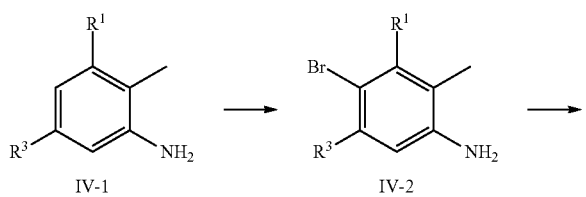

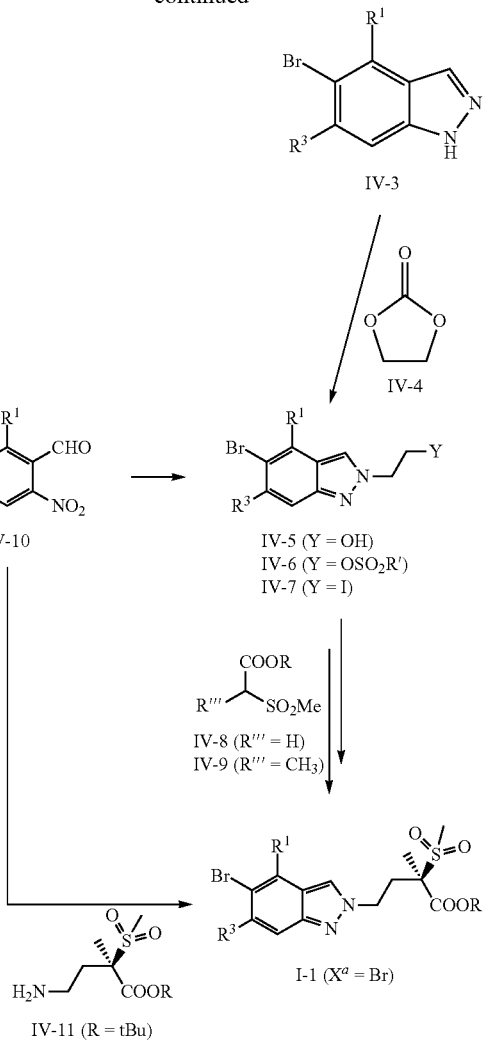

In Scheme 4, $R^1$ and $R^3$ have the same meanings as in formula I, R represents ($C_1$-$C_5$)alkyl, allyl or benzyl and Y represents I, OH or $OSO_2R'$ wherein R' represents Me, $CF_3$ or tolyl. The compounds of formula IV-1 can be reacted (Scheme 4) with NBS, affording the derivatives of formula IV-2. The latter can be reacted as described in WO 2012/037410 with $NaNO_2$ in the presence of AcOH, affording the indazole derivatives of formula IV-3. The compounds of formula IV-3 can be reacted with 1,3-dioxolan-2-one (IV-4) in the presence of NaH, affording, after separation of the isomeric 2-(1H-indazol-1-yl)ethanol derivatives, the compounds of formula IV-5. Alternatively, the latter compounds can be obtained by reacting the compounds of formula IV-10 with ethanolamine in presence of trialkylphosphite. The compounds of formula IV-5 can be sequentially transformed into the derivatives of formulae IV-6 and IV-7 using general reaction techniques 7 and 8 respectively. The compounds of formula IV-7 can be reacted either with the ($C_1$-$C_3$)alkyl 2-(methylsulfonyl)acetate derivatives of formula IV-8 in the presence of NaH, followed by alkylation with MeI in the presence of NaH, or directly with a 2-(methylsulfonyl) propanoate derivative of formula IV-9 in the presence of NaH, affording the compounds of formula I-1 wherein $X^A$ represents bromine. The compounds of formula I-1 wherein R is tert-butyl can also be obtained by reacting the compounds of formula IV-10 with the amine of formula IV-11 in the presence of trialkylphosphite. Eventually the latter can be transformed into the compounds of formula I-1 wherein $X^a$ represents iodine by reaction with NaI in the presence of CuI and trans-N,N-dimethylcyclohexanediamine.

The compounds of formula II-1 wherein $X^a$ represents an ethynyl group can be prepared from the compounds of formula I-1 wherein $X^a$ represents bromine by reaction with NaI in the presence of CuI and trans-N,N'-dimethylcyclohexanediamine. The resulting compounds of formula I-1 wherein $X^a$ represents iodine can be reacted with trimethylsilylacetylene in the presence of CuI and $PdCl_2(PPh_3)_2$, followed by treatment with an inorganic base such as $K_2CO_3$ in an appropriate alcoholic solvent such as MeOH, or by treatment with TBAF in THF.

The compounds of formulae III-1, IV-1, IV-4, IV-8, IV-9 and IV-10 are commercially available or can be prepared by standard methods known to one skilled in the art.

The compound of formula IV-11 can be prepared from the compound of formula I-4 wherein R represents tBu by nucleophilic substitution with sodium azide in DMF at a temperature ranging between rt and 80° C., and subsequent reduction of the azide using hydrogen in presence of a catalyst such as Pd/C in a solvent such as MeOH, EA or a mixture thereof. Alternatively, the azide can be reduced to the corresponding amine of formula IV-11 using $PPh_3$ in an aqueous solvent such as THF at a temperature between rt and 60° C. The chiral amine can be obtained either from the chiral bromide of formula I-4, or by separation of the racemic azide intermediate or of the racemic amine using chiral HPLC techniques. The compound of formula I-4 wherein R represents tBu can be prepared in analogy to the method described in WO 2011/073845 for the compound of formula I-4 wherein R represents Et.

The compounds of formula VIII wherein $X^b$ represents bromine are commercially available or can be prepared by standard methods known to one skilled in the art. The compounds of formula VIII wherein $X^b$ represents iodine can be obtained from the corresponding bromine derivatives by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at 150° C.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

Compounds were characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
MS1 data:
  Column: Zorbax SB-Aq, 3.5 μm, 4.6×50 mm;
  Injection volume: 1 μL;
  Column oven temperature: 40° C.;
  Detection: UV 210 nm, ELSD and MS;
  MS ionization mode: ESI+;
  Eluents: A: $H_2O$+0.04% TFA; and B: MeCN;
  Flow rate: 4.5 mL/min;
  Gradient: 5% B to 95% B (0.0 min 1.0 min), 95% B (1.0 min 1.45 min).
MS2 data:
  Column: Acquity UPLC BEH C18 1.7 μm 2.1×50 mm from Waters, thermostated in the Acquity UPLC Column Manager at 60° C.;
  Pump: Waters Acquity Binary, Solvent Manager;
  MS: Waters SQ Detector;
  DAD: Acquity UPLC PDA Detector;
  ELSD: Acquity UPLC ELSD;
  Eluents: A: $H_2O$+0.05% TFA; and B: MeCN+0.045% TFA;
  Elution method: gradient: 2% B to 98% B over 2.0 min;
  Flow rate: 1.0 mL/min;
  Detection: UV 214 nm and ELSD.

The number of decimals given for the corresponding $[M+H^+]$ peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
Method 1:
  Column: Waters Atlantis T3 OBD, 10 μm, 30×75 mm;
  Flow rate: 75 mL/min;
  Eluents: A: $H_2O$+0.1% HCOOH; B: MeCN+0.1% HCOOH;
  Gradient: 90% A to 5% A (0.0 min 4.0 min), 5% A (4.0 min 6.0 min).
Method 2:
  Column: Waters XBridge C18, 10 μm, 30×75 mm;
  Flow rate: 75 mL/min;
  Eluents: A: $H_2O$+0.1% HCOOH; B: MeCN+0.1% HCOOH;
  Gradient: 70% A to 5% A (0.0 min 3.5 min), 5% A (3.5 min 6.0 min).
Method 3:
  Column: Waters XBridge C18, 10 μm, 30×75 mm;
  Flow rate: 75 mL/min;
  Eluents: A: $H_2O$+0.5% $NH_4OH$ solution (25%); B: MeCN;
  Gradient: 90% A to 5% A (0.0 min 4.0 min), 5% A (4.0 min 6.0 min).

Besides, semi-preparative chiral HPLCs were performed using the conditions hereafter.

Semi-Preparative Chiral HPLC Method A:

The semi-preparative chiral HPLC is performed on a Daicel ChiralPak AS-H column (20×250 mm, 5 μM) using the eluent mixture, flow rate and detection conditions indicated between brackets in the corresponding experimental protocol. The retention times are obtained by elution of analytical samples on a Daicel ChiralPak AS-H column (4.6×250 mm, 5 μM) using the same eluent mixture with the flow rate indicated between brackets in the corresponding experimental protocol.

Semi-Preparative Chiral HPLC Method B: The semi-preparative chiral HPLC is performed on a Daicel ChiralPak AY-H column (20×250 mm, 5 μM) using the eluent mixture, flow rate and detection conditions indicated between brackets in the corresponding experimental protocol. The retention times are obtained by elution of analytical samples on a Daicel ChiralPak AY-H column (4.6×250 mm, 5 μM) using the same eluent mixture with the flow rate indicated between brackets in the corresponding experimental protocol.

Semi-Preparative Chiral HPLC Method C:

The semi-preparative chiral HPLC is performed on a Daicel ChiralCel OD-H column (20×250 mm; 5 μM) using the eluent mixture, flow rate and detection conditions indicated between brackets in the corresponding experimental protocol. The retention times are obtained by elution of analytical samples a Daicel ChiralCel OD-H column (4.6× 250 mm; 5 μM) using the same eluent mixture with the flow rate indicated between brackets in the corresponding experimental protocol.

Semi-Preparative Chiral HPLC Method D:

The semi-preparative chiral HPLC is performed on a Daicel ChiralCel OJ-H column (20×250 mm; 5 μM) using the eluent mixture, flow rate and detection conditions indicated between brackets in the corresponding experimental protocol. The retention times are obtained by elution of analytical samples on a Daicel ChiralCel OJ-H column (4.6×250 mm; 5 μM) using the same eluent mixture with the flow rate indicated between brackets in the corresponding experimental protocol.

Semi-Preparative Chiral HPLC Method E:

The semi-preparative chiral HPLC is performed on a Daicel ChiralCel AD-H column (20×250 mm; 5 μM) using the eluent mixture, flow rate and detection conditions indicated between brackets in the corresponding experimental protocol. The retention times are obtained by elution of analytical samples on a Daicel ChiralCel AD-H column (4.6×250 mm; 5 μM) using the same eluent mixture with the flow rate indicated between brackets in the corresponding experimental protocol.

Semi-Preparative Chiral HPLC Method F:

The semi-preparative chiral HPLC is performed on a Daicel ChiralPak IA column (20×250 mm; 5 μM) using the eluent mixture, flow rate and detection conditions indicated between brackets in the corresponding experimental protocol. The retention times are obtained by elution of analytical samples on a Daicel ChiralPak IA column (4.6×250 mm; 5 μM) using the same eluent mixture with the flow rate indicated between brackets in the corresponding experimental protocol.

Semi-Preparative Chiral HPLC Method G:

The semi-preparative chiral HPLC is performed on a Daicel ChiralPak ASV column (20×250 mm; 5 μM) using the eluent mixture, flow rate and detection conditions indicated between brackets in the corresponding experimental protocol.

PREPARATIONS

Preparation A: (RS)-4-(5-bromo-2H-indazol-2-yl)-2-methyl-2-(methylsulfonyl)-N—(((RS)-tetrahydro-2H-pyran-2-yl)oxy)butanamide A.i. 2-(5-bromo-2H-indazol-2-yl)ethanol Variant I:

A solution of 5-bromo-1H-indazole (10 g; commercial) in DMF (330 mL) was cooled to 0° C. and treated portionwise with NaH (in 60% mineral oil; 2.41 g). The reaction mixture was allowed to reach rt, further stirred at rt for 1 h, treated with ethylene carbonate (17.9 g) and heated for 3 h at 80° C. The reaction mixture was concentrated under reduced pressure, diluted with 10% aq. $NaHSO_4$ solution (150 mL) and extracted with EA (2×50 mL). The combined org. layers were washed with brine, dried over $Na_2SO_4$, concentrated under reduced pressure and purified by CC (Hept-EA) to afford the title compound as a yellow oil (5.4 g; 44% yield).

$^1$H NMR (d6-DMSO) δ: 8.33 (d, J=0.9 Hz, 1H); 7.95 (dd, J=0.9, 1.9 Hz, 1H); 7.57 (td, J=0.9, 9.1 Hz, 1H); 7.29 (dd, J=1.9, 9.1 Hz, 1H); 4.94 (t, J=5.4 Hz, 1H); 4.44 (t, J=5.4 Hz, 2H); 3.85 (q, J=5.4 Hz, 2H).

MS1 (ESI, m/z): 243.0 [M+H$^+$] for $C_9H_9N_2OBr$; $t_R$=0.65 min.

Variant II:

To a solution of 5-bromo-2-nitrobenzaldehyde (4.89 g; 21.3 mmol) in MeOH (53.9 mL) was added ethanolamine (1.3 mL, 21.5 mmol) The mixture was stirred at reflux for 1 h. After cooling, the solvent was evaporated to dryness. The residue was taken up in $P(OEt)_3$ (36.5 mL) and the mixture was immersed in an oil bath heated to 150° C. for 20 min. After cooling and concentration to dryness, the residue was purified by CC (Hept-EA) afford the title indazole as a yellow solid (2.12 g; 41% yield).

NMR data are identical to those reported for the product of Variant I.

A.ii. 3-(5-bromo-2H-indazol-2-yl)ethyl methanesulfonate

A solution of intermediate A.i (5.37 g) in DCM (80 mL) and TEA (4.5 mL) was cooled to 0° C. and treated with MsCl (1.94 mL). The reaction mixture was stirred at 0° C. for 30 min, allowed to reach rt and treated with sat. aq. $Na_2CO_3$ solution (50 mL). The org. layer was washed with a sat. aq. $NaHCO_3$ solution, dried over $Na_2SO_4$, concentrated under reduced pressure and purified by purified by CC (Hept-EA) to afford the title compound as a yellow oil (3.3 g, 47% yield).

MS1 (ESI, m/z): 320.9 [M+H$^+$] for $C_{10}H_{11}N_2O_3BrS$; $t_R$=0.76 min.

A.iii. 5-bromo-2-(3-iodoethyl)-2H-indazole

A solution of intermediate Aii (3.3 g) in 2-butanone (42 mL) and NaI (2.89 mg, 19.3 mmol) was added. The reaction mixture was stirred at 80° C. for 2 h. The reaction mixture was diluted with water (15 mL) and EA (25 mL). The aq. layer was extracted with EA (4×10 mL). The combined org. layers were washed with a sat. solution of $Na_2SO_3$ (25 mL) and brine (15 mL), dried over $Na_2SO_4$, filtered and concentrated to afford the desired compound as a yellow solid (3.22 g).

¹H NMR (d6-DMSO) δ: 8.41 (d, J=0.9 Hz, 1H); 7.99 (dd, J=0.9, 1.9 Hz, 1H); 7.59 (td, J=0.9, 9.1 Hz, 1H); 7.31 (dd, J=1.9, 9.1 Hz, 1); 4.76 (t, J=5.4 Hz, 2H); 3.73 (t, J=6.4 Hz, 2H).

MS1 (ESI, m/z): 350.84 [M+H⁺] for $C_9H_9N_2BrI$; $t_R$=0.86 min.

A.iv. (RS)-ethyl 4-(5-bromo-2H-indazol-2-yl)-2-(methylsulfonyl)butanoate

To a suspension of NaH (0.556 g; 13.9 mmol) in DMF (15 mL) at 0° C. was added slowly ethyl methylsulfonyl acetate (3 mL; 25 mmol). The reaction was allowed to warm to rt and stirred for 30 min. A solution of intermediate A.iii (3.21 g; 9.17 mmol) in DMF (53 mL) was added dropwise and the reaction mixture was stirred at rt overnight. An aq. 20% $NaHSO_4$ solution (25 mL) was added and the mixture was extracted with EA (3×40 mL). The combined org. layers were washed with brine (25 mL), dried over $MgSO_4$ and concentrated to dryness. The crude product (6.33 g) was purified by CC (Hept-EA) to afford the title compound as a yellow oil (4.68 g), contaminated with the excess of ethyl-methylsulfonyl acetate.

¹H NMR (d6-DMSO) δ: 8.37 (d, J=0.9 Hz, 1H); 7.96 (dd, J=0.9, 1.9 Hz, 1H); 7.57 (td, J=0.9, 9.1 Hz, 1H); 7.30 (dd, J=1.9, 9.1 Hz, 1H); 4.56 (t, J=5.9 Hz, 2H); 4.27 (m, 1H); 3.96-4.08 (m, 2H); 3.11 (s, 3H); 2.55-2.63 (m, 2H); 1.14 (t, J=6.9 Hz, 3H).

A.v. (RS)-ethyl 4-(5-bromo-2H-indazol-2-yl)-2-methyl-2-(methylsulfonyl)butanoate Variant I:

$Cs_2CO_3$ (4.96 g; 15.2 mmol) was added at rt, to a solution of intermediate A.iv (4.68 g; 12 mmol) in DMF (67.1 mL) and the mixture was stirred for 15 min. $CH_3I$ (3 mL; 48.1 mmol) was added and the mixture was stirred overnight. More $Cs_2CO_3$ (1.96 g, 6.02 mmol) and $CH_3I$ (0.751 mL; 12 mmol) were then added and the reaction mixture was stirred overnight. Water (20 mL) and EA (40 mL) were added. The two layers were separated. The aq. layer was extracted with EA (4×35 mL). The combined org. layers were washed with brine (20 mL), dried over $MgSO_4$, filtered and evaporated under reduced pressure. The crude product was purified by CC (Hept-EA) to afford the title compound as a yellow oil (2.91 g, 60% yield).

¹H NMR (d6-DMSO) δ: 8.41 (s, 1H); 7.96 (m, 1H); 7.57 (d, J=9.1 Hz, 1H); 7.30 (dd, J=1.9, 9.1 Hz, 1H); 4.58-4.69 (m, 1H); 4.42-4.54 (m, 1H); 3.88-4.05 (m, 2H); 3.10 (s, 3H); 2.78-2.89 (m, 1H); 2.44 (overlapped m, 1H); 1.58 (s, 3H); 1.12 (t, J=7.1 Hz, 3H).

Variant II:

To a solution of intermediate A.iii (0.537 g; 1.53 mmol) and ethyl 2-(methylsulfonyl)propanoate (0.303 g; 1.68 mmol) in DMF (3 mL) was added $Cs_2CO_3$ (0.997 g; 3.06 mmol). The reaction was stirred at 80° C. for 2 h. Water (30 mL) was added and the two layers were diluted with EA (40 mL). The aq. layer was extracted with EA (30 mL). The combined org. layers were washed with brine (20 mL), dried over $Na_2SO_4$, filtered and concentrated to dryness. The crude product was purified by CC (Hept-EA) to afford the title compound as a colourless oil (0.171 g, 28% yield).

NMR data are identical to those reported for the product of Variant I.

A.vi. (RS)-4-(5-bromo-2H-indazol-2-yl)-2-methyl-2-(methylsulfonyl)-N-((tetrahydro-2H-pyran-2-yl)oxy)butanamide To an ice-chilled solution of intermediate A.v (2.91 g; 7.23 mmol) in a THF-MeOH—$H_2O$ (2-2-1, 81 mL) was added $LiOH.H_2O$ (1.19 g; 16 mmol). The reaction mixture was stirred at rt overnight. Solvents were evaporated in vacuo and the residue was dried to a constant weight. The resulting solid was taken up in DMF (70 mL) and $HOBT.H_2O$ (1.96 g, 14.5 mmol), TEA (3.2 mL; 23 mmol), $NH_2$—OTHP (1.72 g, 14.7 mmol) and EDC (2.72 g, 14.2 mmol) were successively added. The suspension was then stirred at 60° C. for 2 h. More EDC (0.699 g, 3.65 mmol), $NH_2$—OTHP (0.86 g, 7.36 mmol) were added and the reaction mixture was heated at 60° C. overnight. The reaction mixture was concentrated to dryness. Water (50 mL) and EA (70 mL) were added. The org. layer was washed with water (15 mL), sat. $NaHCO_3$ (15 mL) and brine (20 mL). The org. layer was dried over $Na_2SO_4$, filtered and concentrated to dryness. The residue was purified by CC (DCM-MeOH) to afford the title compound as a yellowish oil (2.17 g, 63% yield).

¹H NMR (d6-DMSO) δ (mixture of stereoisomers): 11.3 (br. s, 1H); 8.39 (m, 1H); 7.92-7.96 (m, 1H); 7.55-7.60 (m, 1H); 7.30 (dd, J=1.9, 9.1 Hz, 1H); 4.89-4.95 (m, 1H); 4.49-4.59 (m, 1H); 4.32-4.43 (m, 1H); 3.95-4.16 (m, 1H); 3.47-3.53 (m, 1H); 3.05 (s, 1.5H); 3.03 (s, 1.5H); 2.76-2.86 (m, 1H); 2.34-2.46 (m, 1H); 1.61-1.71 (m, 3H); 1.46-1.58 (m, 3H); 1.51 (s, 1.5H); 1.48 (s, 1.5H).

MS1 (ESI, m/z): 474.05 [M+H⁺] for $C_{18}H_{24}N_3O_5BrS$; $t_R$=0.80 min.

Preparation B: (RS)-4-(5-bromo-6-fluoro-2H-indazol-2-yl)-2-methyl-2-(methylsulfonyl)-N-((tetrahydro-2H-pyran-2-yl)oxy)butanamide

B.i. 2-(5-bromo-6-fluoro-2H-indazol-2-yl)ethanol

To a solution of 5-bromo-4-fluoro-2-nitrobenzaldehyde (2.0 g; 8.06 mmol; commercial) in MeOH (5 mL) was added ethanolamine (0.61 mL) The mixture was stirred at reflux for 1 h. After cooling, the solvent was evaporated to dryness. The residue was taken up in $P(OEt)_3$ (14 mL) and the mixture was immersed in an oil bath heated to 150° C. for 20 min. After cooling and concentration to dryness, the residue was purified by CC (Hept-EA) to afford the title indazole as a yellow solid (1.17 g, 56% yield).

¹H NMR (CDCl₃) δ: 7.95 (s, 1H); 7.90 (d, J=6.7 Hz, 1H); 7.38 (d, J=6.7 Hz, 1H); 4.49-4.53 (m, 2H); 4.09-4.15 (m, 2H).

MS1 (ESI, m/z): 258.97 [M+H⁺] for $C_9H_8N_2OBrF$; $t_R$=0.64 min.

B.ii. (RS)-4-(5-bromo-6-fluoro-2H-indazol-2-yl)-2-methyl-2-(methylsulfonyl)-N-((tetrahydro-2H-pyran-2-yl)oxy)butanamide Starting from intermediate B.i (1.3 g, 5.02 mmol) and proceeding in analogy to Preparation A, steps A.ii to A.v, the title compound was obtained as a colourless foam (1.2 g; yields: 95% for mesylate formation, 96% for iodide formation, 93% (Variant I) and 86% (Variant II) for alkylation, 60% for saponification, and 95% for amide coupling with THPO—$NH_2$).

¹H NMR (d6-DMSO) δ (mixture of stereoisomers): 11.4 (br. s, 0.5H); 11.3 (br. s, 0.5H); 8.44 (br. s, 1H); 8.16 (d, J=7.1 Hz, 1H); 7.54-7.60 (m, 1H); 4.92-4.96 (m, 0.5H); 4.87-4.91 (m, 0.5H); 4.47-4.59 (m, 1H); 4.30-4.43 (m, 1H); 3.97-4.16 (m, 1H); 3.72 (m, 0.5H); 3.45-3.55 (m, 1H); 3.05 (s, 1.5H); 3.03 (s, 1.5H); 2.76-2.86 (m, 1H); 2.34-2.46 (m, 1H); 1.61-1.71 (m, 2H); 1.46-1.58 (m, 2H); 1.51 (s, 1.5H); 1.49 (s, 1.5H). MS1 (ESI, m/z): 492.04 [M+H$^+$] for $C_{18}H_{23}N_3O_5BrFS$; $t_R$=0.81 min.

Preparation C: (R)-ethyl 4-(5-bromo-4-fluoro-2H-indazol-2-yl)-2-methyl-2-(methylsulfonyl)butanoate To an ice-chilled suspension of NaH (60% in mineral oil, 0.21 g, 5.12 mmol) in DMF (3.2 mL) was slowly added a solution of 5-bromo-4-fluoro-1H-indazole (1 g; 4.65 mmol) in DMF (3.7 mL), keeping IT below 6° C. The reaction mixture was stirred for 1 h at 0° C.; then (R)-ethyl 4-bromo-2-methyl-2-(methylsulfonyl)butanoate (1.67 g; 5.81 mmol; prepared as described in WO 2012/137099) in solution in DMF (1.8 mL) was added, keeping IT below 3° C. The mixture was warmed to rt and stirred for 3 h. The reaction mixture was diluted with aq. NaHSO$_4$ (15%, 5 mL), water (50 mL) and EA (25 mL). The two phases were separated and the aq. layer was extracted with EA (2×25 mL). The combined org. layers were dried over MgSO$_4$ and filtered and concentrated to dryness. The residue was purified by CC (Hept-EA gradient) to afford first the 1-indazole regioisomer (0.9 g, 46% yield) and then the title regioisomer (0.8 g, 39% yield), still contaminated with 20% of the 1-indazole regioisomer.

$^1$H NMR (d6-DMSO) δ: 8.68 (s, 1H); 7.35-7.45 (m, 2H); 4.65 (m, 1H); 4.49 (m, 1H); 3.85-4.06 (m, 2H); 3.10 (s, 3H); 2.86 (m, 1H); 2.47 (overlaid with DMSO; m, 1H); 1.60 (s, 3H); 1.11 (t, J=7.1 Hz, 3H).

MS1 (ESI, m/z): 423.01 [M+H$^+$] for $C_{15}H_{18}N_2O_4BrFS$; $t_R$=0.86 min.

Preparation D: 2-(2-fluoro-4-(methylthio)phenyl)-4,4,5,5-tetramethyl-1,3,2-dioxaborolane A mixture of bis(pinacolato)diboron (1.15 g; 4.5 mmol), Pd(dppf)Cl$_2$ (0.248 g; 0.3 mmol) and KOAc (1.27 g; 13 mmol) was flushed with nitrogen for 15 min and treated with a solution of 4-bromo-3-fluorothioanisole (1 g; 4.3 mmol; commercial) in dioxane (17 mL). The reaction mixture was heated to reflux for 3 h. After cooling, the reaction mixture was filtered and the filtrate was concentrated to dryness. The residue was purified by CC (Hept-EA) to afford the title compound as a yellow oil (0.84 g, 73% yield).

$^1$H NMR (CDCl$_3$) δ: 7.61 (dd, J=6.5, 7.9 Hz, 1H); 6.98 (dd, J=1.7, 7.9 Hz, 1H); 6.87 (dd, J=1.7, 10.2 Hz, 1H); 2.47 (s, 3H); 1.34 (s, 12H).

MS1 (ESI, m/z): 269.2 [M+H$^+$] for $C_{13}H_{18}O_2BFS$; $t_R$=0.96 min.

Preparation E: (2RS)-4-(5-ethynyl-2H-indazol-2-yl)-2-methyl-2-(methylsulfonyl)-N—(((RS)-tetrahydro-2H-pyran-2-yl)oxy)butanamide

E.i. (RS)-4-(5-Iodo-indazol-2-yl)-2-methylsulfonyl-2-methyl-butyric acid ethyl ester Into a microwave vial were added a solution of intermediate A.v (0.592 g; 1.47 mmol) in 1,4-dioxane (2.4 mL), trans-N,N'-dimethylcyclohexane-1,2-diamine (0.026 mL; 0.165 mmol; 0.11 eq.), NaI (0.445 g, 2.94 mmol) and then CuI (0.029 g, 0.149 mmol). The reaction mixture was microwaved at 180° C. for 20 min. Water (10 mL) and EA (30 mL) were added. The aq. layer was extracted once with EA (30 mL). The combined org. layers were washed with brine, dried over MgSO$_4$, filtered and concentrated to dryness. The residue was purified by CC (Hept-EA) to afford the title compound as a colourless oil (0.55 g; 74% yield).

$^1$H NMR (d6-DMSO) δ: 8.37 (br. s, 1H); 8.14 (br. s, 1H); 7.43 (br. s, 2H); 4.56-4.68 (m, 1H); 4.40-4.52 (m, 1H); 3.89-4.04 (m, 2H); 3.10 (s, 3H); 2.76-2.89 (m, 1H); 2.39-2.45 (overlapped m, 1H); 1.57 (s, 3H); 1.12 (t, J=7.1 Hz, 3H).

MS1 (ESI, m/z): 451.0 [M+H$^+$] for $C_{15}H_{19}N_2O_4IS$; $t_R$=0.85 min.

E.ii. (RS)-ethyl 2-methyl-2-(methylsulfonyl)-4-(5-((trimethylsilyl)ethynyl)-2H-indazol-2-yl)butanoate CuI (0.04 g, 0.22 mmol) and PdCl$_2$(PPh$_3$)$_2$ (0.08 g, 0.11 mmol) were introduced in a two-necked round-bottom flask. After flushing with nitrogen for 30 min, a solution of intermediate E.i (0.5 g; 1.11 mmol) in degassed THF (8 mL) was added followed with trimethylsilylacetylene (0.17 mL; 1.22 mmol). Degassed TEA (0.39 mL, 2.78 mmol) was added dropwise and the reaction proceeded at 50° C. for 2 h. The mixture was concentrated to dryness and the residue was purified by CC (Hept-EA) to afford the title compound as a brown gum (0.43 g, 93% yield).

$^1$H NMR (d6-DMSO) δ: 8.46 (s, 1H); 7.91 (s, 1H); 7.58 (d, J=8.9 Hz, 1H); 7.21 (dd, J=1.2, 8.9 Hz, 1H); 4.58-4.71 (m, 1H); 4.42-4.55 (m, 1H); 3.84-4.07 (m, 2H); 3.12 (s, 3H); 2.79-2.92 (m, 1H); 2.39-2.53 (overlapped m, 1H); 1.61 (s, 3H); 1.11 (t, J=7.2 Hz, 3H); 0.24 (s, 9H).

MS (ESI, m/z): 421.2 [M+H$^+$] for $C_{20}H_{28}N_2O_4SSi$; $t_R$=0.96 min.

E.iii. (RS)-ethyl 4-(5-ethynyl-2H-indazol-2-yl)-2-methyl-2-(methylsulfonyl)butanoate To a solution of intermediate E.ii (0.2 g; 0.48 mmol) in THF (1 mL) was added TBAF (1M in THF; 0.37 mL). The mixture was stirred at rt during 2 h. The solvent was removed in vacuo and the residue was purified by CC (Hept-EA gradient) to afford the title compound as a pinkish gum (0.1 g, 61% yield).

$^1$H NMR (d6-DMSO) δ: 8.46 (s, 1H); 7.92 (s, 1H); 7.59 (d, J=8.9 Hz, 1H); 7.24 (dd, J=1.2, 8.9 Hz, 1H); 4.59-4.71 (m, 1H); 4.42-4.55 (m, 1H); 4.04 (s, 1H); 3.86-4.07 (overlapped m, 2H); 3.11 (s, 3H); 2.78-2.92 (m, 1H); 2.39-2.54 (overlapped m, 1H); 1.60 (s, 3H); 1.12 (t, J=7.1 Hz, 3H).

MS (ESI, m/z): 349.1 [M+H$^+$] for $C_{17}H_{20}N_2O_4S$; $t_R$=0.80 min.

E.iv. (2RS)-4-(5-ethynyl-2H-indazol-2-yl)-2-methyl-2-(methylsulfonyl)-N—(((RS)-tetrahydro-2H-pyran-2-yl)oxy)butanamide Starting from intermediate E.iii (0.1 g; 0.28 mmol) and proceeding in analogy to Preparation A, step A.vi (saponification and amide coupling with THPO—NH$_2$), the title amide was obtained as an off-white foam (0.087 g; 75% yield after the 2 steps).

$^1$H NMR (d6-DMSO) δ (mixture of stereoisomers): 11.4 (s, 1H); 8.44 (br. s, 1H); 7.91 (s, 1H); 7.56-7.62 (m, 1H); 7.23 (dd, J=1.2, 8.9 Hz, 1H); 4.90-4.97 (m, 1H); 4.48-4.61 (m, 1H); 4.31-4.45 (m, 1H); 4.03-4.14 (overlapped m, 1H); 4.03 (s, 1H); 3.46-3.56 (m, 1H); 3.06 (s, 3×0.5H); 3.04 (s, 3×0.5H); 2.76-2.90 (m, 1H); 2.34-2.48 (overlapped m, 1H); 1.62-1.72 (m, 3H); 1.47-1.58 (m, 6H).

MS (ESI, m/z): 420.2 [M+H$^+$] for C$_{20}$H$_{25}$N$_3$O$_5$S; t$_R$=0.77 min.

Preparation F: (R)-ethyl 4-(5-(2-fluoro-4-methoxyphenyl)-2H-indazol-2-yl)-2-methyl-2-(methylsulfonyl)butanoate F.i. 5-(2-fluoro-4-methoxyphenyl)-2H-indazole A mixture of 5-bromo-1H-indazole (9.1 g, 46.2 mmol), 2-fluoro-4-methoxyphenylboronic acid (8.24 g, 48.5 mmol), K$_2$CO$_3$ (21 g, 152 mmol) and Pd(PPh$_3$)$_4$ (3.2 g, 2.77 mmol) was flushed with nitrogen for 15 min. Dioxane (255 mL) and water (70 mL) were added. The mixture was heated at 90° C. for 23 h. After cooling, water (100 mL) and EA (80 mL) were added and the two layers were separated. The aq. layer was extracted with EA (2×100 mL) and the combined org. layers were washed with brine, dried over MgSO$_4$ and concentrated to dryness. The residue was triturated in DCM (30 mL) to afford the title compound as a white solid (4.08 g, 36% yield). The filtrate was concentrated and the residue was purified by CC (Hept-EA with gradient) to afford more title compound as a light yellow solid (3.65 g, 33% yield).
$^1$H NMR (d6-DMSO) δ: 13.0 (br. s, 1H); 8.09 (br. s, 1H); 7.83 (br. s, 1H); 7.55-7.60 (m, 1H); 7.41-7.49 (m, 2H); 6.83-6.95 (m, 2H); 3.79 (s, 3H).
MS1 (ESI, m/z): 434.2 [M+H$^+$] for C$_{14}$H$_{11}$N$_2$OF; t$_R$=0.84 min.

F.ii. (R)-ethyl 4-(5-(2-fluoro-4-methoxyphenyl)-2H-indazol-2-yl)-2-methyl-2-(methylsulfonyl)butanoate Starting from intermediate F.i (4.07 g; 15.1 mmol) and (R)-ethyl 4-bromo-2-methyl-2-(methylsulfonyl)butanoate (5.22 g; 18.2 mmol, prepared as described in WO 2012/137099), and proceeding in analogy to Preparation C, the title compound was obtained as a colourless gum (2.03 g, 30% yield). The residue was purified by CC (Hept-EA with gradient).
$^1$H NMR (d6-DMSO) δ: 8.46 (s, 1H); 7.79 (s, 1H); 7.66 (d, J=8.8 Hz, 1H); 7.47 (t, J=8.8 Hz, 1H); 7.34-7.40 (m, 1H); 6.97-6.85 (m, 2H); 4.60-4.71 (m, 1H); 4.44-4.57 (m, 1H); 3.92-4.08 (m, 2H); 3.82 (s, 3H); 3.13 (s, 3H); 2.81-2.93 (m, 1H); 2.37-2.53 (overlapped m, 1H); 1.62 (s, 3H); 1.15 (t, J=7.1 Hz, 3H).
MS1 (ESI, m/z): 449.1 [M+H$^+$] for C$_{22}$H$_{25}$N$_2$O$_5$FS; t$_R$=0.90 min.
The e.e. was determined by chiral HPLC using a ChiralPak IA (4.6×250 mm, 5 μM) column at a flow rate of 1.4 mL/min (UV detection at 210 nm), eluting with Hept-EtOH 1-9. The retention times obtained for the racemate produced accordingly from rac-ethyl 4-bromo-2-methyl-2-(methylsulfonyl)butanoate were respectively 5.6 and 10.8 min. The title (R)-enantiomer was the second eluting compound. The e.e. was >99%.

Preparation G: 3-(iodoethynyl)oxetan-3-ol

To a solution of 3-ethynyloxetan-3-ol (1.097 g; 11.2 mmol; commercial) in MeOH (50 mL) and 1M aq. KOH (28 mL) was added iodine (3.549 g; 14 mmol). The reaction mixture was stirred for 2 h at rt. Water (150 mL) and DCM (500 mL) were added. The aq. layer was extracted with EA (500 mL). The org. layer were washed with brine, dried over MgSO$_4$, filtered and concentrated down to afford the desired compound as a light yellow solid (2.21 g, 88% yield).

$^1$H NMR (d6-DMSO) δ: 4.60 (d, J=6.5 Hz, 2H); 4.45 (d, J=6.5 Hz, 2H).

Preparation H: (R)-4-(5-iodo-indazol-2-yl)-2-methylsulfonyl-2-methyl-N—[(RS)-(tetrahydro-pyran-2-yl)oxy]-butanamide H.i. (R)-4-(5-bromo-indazol-2-yl)-2-methylsulfonyl-2-methyl-butyric acid ethyl ester Starting from 5-bromo-1H-indazole (2 g; 10.2 mmol) and proceeding in analogy to Preparation C, the title (R)-enantiomer was obtained, after purification by CC (DCM-EA), as an orange gum (1.71 g, 42% yield).
$^1$H NMR (d6-DMSO) δ: 8.42 (s, 1H); 7.97 (d, J=1.2 Hz, 1H); 7.59 (d, J=9.1 Hz, 1H); 7.32 (dd, J=9.1, 1.8 Hz, 1H); 4.57-4.70 (m, 1H); 4.42-4.55 (m, 1H); 3.86-4.08 (m, 2H); 3.12 (s, 3H); 2.71-2.91 (m, 1H); 2.40-2.55 (overlapped m, 1H); 1.60 (s, 3H); 1.13 (t, J=7.1 Hz, 3H).
MS (ESI, m/z): 403.0 [M+H+] for C$_{15}$H$_{19}$N$_2$O$_4$BrS; t$_R$=0.83 min.

H.ii. (R)-4-(5-iodo-indazol-2-yl)-2-methylsulfonyl-2-methyl-butyric acid ethyl ester Starting from intermediate H.i (1.57 g; 3.91 mmol) and proceeding in analogy to Preparation E, step E.i, the title iodide was obtained as a yellow gum (1.32 g, 75% yield).
MS1 (ESI, m/z): 451.0 [M+H$^+$] for C$_{15}$H$_{19}$N$_2$O$_4$IS; t$_R$=0.85 min.

H.iii. (R)-4-(5-iodo-indazol-2-yl)-2-methylsulfonyl-2-methyl-N—[(RS)-(tetrahydro-pyran-2-yl)oxy]-butanamide Starting from intermediate H.ii (1 g; 2.22 mmol) and proceeding in analogy to Preparation A, step A.vi (saponification and amide coupling with THPO—NH$_2$), the title compound was obtained as an orange thick oil (0.833 g; 75% yield after the 2 steps).
$^1$H NMR (d6-DMSO) δ (mixture of stereoisomers): 11.3 (br. s, 1H); 8.35 (s, 1H); 8.14 (d, J=0.6 Hz, 1H); 7.39-7.46 (m, 2H); 4.91 (m, 1H); 4.52 (m, 1H); 4.37 (m, 1H); 4.05 (br. s, 1H); 3.49 (m, 1H); 3.04 (s, 3×0.5H); 3.02 (s, 3×0.5H); 2.82 (m, 1H); 2.41 (overlaid m, 1H); 1.60-1.71 (m, 3H); 1.45-1.57 (m, 3H); 1.49 (s, 3×0.5H); 1.47 (s, 3×0.5H).
MS1 (ESI, m/z): 522.1 [M+H$^+$] for C$_{18}$H$_{24}$N$_3$O$_5$IS; t$_R$=0.81 min.

Preparation I: (R)-4-(5-iodo-2H-indazol-2-yl)-2-methyl-2-(methylsulfonyl)-N-(2-(trimethylsilyl)ethoxy)butanamide Starting from intermediate H.ii (0.326 g; 0.72 mmol) and proceeding in analogy to Preparation A, step A.vi (saponification and amide coupling with O-(2-trimethylsilylethyl) hydroxylamine hydrochloride (commercial)), the title compound was obtained as an orange thick oil (0.36 g; 90% yield after the 2 steps).
$^1$H NMR (d6-DMSO) δ: 11.38 (s, 1H); 8.40 (s, 1H); 8.15 (s, 1H); 7.43-7.48 (m, 2H); 4.52-4.61 (m, 1H); 4.34-4.43 (m, 1H); 3.77-3.84 (m, 2H); 3.06 (s, 3H); 2.82-2.90 (m, 1H); 2.35-2.42 (m, 1H); 1.53 (s, 3H); 0.91-0.97 (m, 2H); 0.02 (s, 9H).
MS1 (ESI, m/z): 538.1 [M+H$^+$] for C$_{18}$H$_{28}$N$_3$O$_4$ISSi; t$_R$=0.81 min.

Preparation J: (2R)-4-(5-ethynyl-2H-indazol-2-yl)-2-methyl-2-(methylsulfonyl)-N-((tetrahydro-2H-pyran-2-yl)oxy)butanamide Starting from the compound of Preparation H (0.502 g; 0.96 mmol) and trimethysilyl acetylene (0.151 mL, 1.1 eq.), and proceeding in analogy to Preparation E, steps E.ii and E.iii, the title compound was obtained, after purification by CC (DCM-MeOH), as an off-white foam (0.3 g; yields: 97% for Sonogashira coupling; 76% for silyl cleavage).

$^1$H NMR (d6-DMSO) δ (mixture of stereoisomers): 11.42 (br. s, 1H); 8.45 (s, 1H); 7.92 (s, 1H); 7.61 (d, J=8.9 Hz, 1H); 7.24 (dd, J=1.1, 8.9 Hz, 1H); 4.90-4.97 (m, 1H); 4.50-4.62 (m, 1H); 4.34-4.46 (m, 1H); 4.04 (s, 1H); 3.98-4.15 (overlapped m, 1H); 3.46-3.57 (m, 1H); 3.08 (s, 1.5H); 3.05 (s, 1.5H); 2.72-2.91 (m, 1H); 2.34-2.53 (overlapped m, 1H); 1.63-1.74 (m, 3H); 1.46-1.59 (overlapped m, 3H); 1.53 (s, 1.5H); 1.50 (s, 1.5H).

MS (ESI, m/z): 420.0 [M+H$^+$] for $C_{20}H_{25}N_3O_5S$; $t_R$=0.77 min.

Preparation K: (2R)-4-(4-fluoro-5-iodo-2H-indazol-2-yl)-2-methyl-2-(methylsulfonyl)-N—((RS)-(tetrahydro-2H-pyran-2-yl)oxy)butanamide

K.i. (R)-ethyl 4-(4-fluoro-5-iodo-2H-indazol-2-yl)-2-methyl-2-(methylsulfonyl)butanoate To a solution of the compound of Preparation C (0.49 g; 1.16 mmol) in 1,4-dioxane (1.9 mL) were added trans-N—N'-dimethylcyclohexane-1,2-diamine (0.07 mL, 0.47 mmol), NaI (0.35 g, 2.4 mmol) and CuI (0.045 g, 0.23 mmol). The reaction mixture was irradiated in a microwave at 180° C. for 20 min. Water (20 mL) and EA (30 mL) were added. The aq. layer was extracted with EA (2×20 mL). The combined org. layers were washed with brine (10 mL), dried over MgSO$_4$, filtered and concentrated to dryness. The crude product was purified by CC (Hept-EA) to afford the title product as a yellowish solid (0.21 g).

1H NMR (d6-DMSO) δ: 8.62 (s, 1H); 7.43-7.51 (m, 1H); 7.30 (d, J=9.1 Hz, 1H); 4.57-4.70 (m, 1H); 4.50 (m, 1H); 3.82-4.04 (m, 2H); 3.10 (s, 3H); 2.79-2.92 (m, 1H); 2.42-2.55 (overlapped m, 1H); 1.59 (s, 3H); 1.11 (t, J=7.3 Hz, 3H).

MS1 (ESI, m/z): 469.01 [M+H$^+$] for $C_{15}H_{18}N_2O_4$FIS; $t_R$=0.87 min.

K.ii. (2S)-4-(4-fluoro-5-iodo-2H-indazol-2-yl)-2-methyl-2-(methylsulfonyl)-N—((RS)-(tetrahydro-2H-pyran-2-yl)oxy)butanamide Starting from intermediate K.i (0.197 g, 0.42 mmol) and proceeding in analogy to Preparation A, step A.vi (saponification and amide coupling with THPO—NH$_2$), the title amide was obtained as a beige foam (0.197 g; 86% yield after the 2 steps).

$^1$H NMR (d6-DMSO) δ (mixture of stereoisomers): 11.3 (br. s, 1H); 8.58 (s, 1H); 7.44-7.50 (m, 1H); 7.27-7.33 (m, 1H); 4.90-4.94 (m, 0.5H); 4.85-4.88 (m, 0.5H); 4.49-4.60 (m, 1H); 4.33-4.46 (m, 1H); 3.96-4.13 (m, 1H); 3.41-3.54 (m, 1H); 3.05 (s, 1.5H); 3.03 (s, 1.5H); 2.76-2.91 (m, 1H); 2.34-2.44 (m, 1H); 1.61-1.71 (m, 2H); 1.42-1.58 (m, 5H).

MS1 (ESI, m/z): 540.1 [M+H$^+$] for $C_{18}H_{23}N_3O_5$FIS; $t_R$=0.84 min.

Preparation L: 3-(4-iodophenyl)oxetan-3-amine hydrochloride

L.i. N-(3-(4-iodophenyl)oxetan-3-yl)-2-methylpropane-2-sulfinamide

BuLi (1.1M in hexanes, 11.4 mL) was added dropwise to a solution of 1,4-iodobenzene (4.36 g) in THF (50 mL) at −78° C. After stirring for 1 h, a solution of 2-methyl-N-oxetan-3-ylidenepropane-2-sulfinamide (1.64 g; commercial) in THF (10 mL) was added dropwise over the course of 30 min at −78° C. The reaction mixture was gradually warmed to rt. After 1 h, sat. NH$_4$Cl was added and the aq. layer was extracted with EA. The combined org. layer was washed with sat. NaHCO$_3$ and brine, dried over Na$_2$SO$_4$, filtered and concentrated to dryness. The residue was purified by CC (EA-Hept) to give the title compound as a colourless oil (0.751 g, 21% yield).

$^1$H NMR (d6-DMSO) δ: 7.77 (d, J=8.4 Hz, 2H); 7.30 (d, J=8.4 Hz, 2H); 6.35 (s, 1H); 4.98 (d, J=6.3 Hz, 1H); 4.90-4.94 (m, 1H); 4.85-4.88 (m, 1H); 4.67 (d, J=6.3 Hz, 1H); 1.11 (s, 9H).

MS1 (ESI, m/z): 379.97 [M+H$^+$] for $C_{13}H_{18}NO_2$IS; $t_R$=0.78 min.

L.ii. 3-(4-iodophenyl)oxetan-3-amine hydrochloride

To a solution of intermediate L.i (0.751 g, 1.98 mmol) in DCM (20 mL) was added a 4M solution of HCl in dioxane (1.06 mL). After stirring for 30 min at rt, the solids were filtered off and washed with Hex (3 mL) to afford the title compound as a white solid (0.624 g, 100% yield).

$^1$H NMR (d6-DMSO) δ: 9.14-9.30 (m, 3H); 7.82-7.90 (m, 2H); 7.34-7.40 (d, J=8.5 Hz, 2H); 4.80-5.00 (m, 4H).

MS1 (ESI, m/z): 299.89 [M+Na$^+$] for $C_9H_{10}$NOI; $t_R$=0.50 min.

Preparation M: 3-(4-iodophenyl)-N,N-dimethyloxetan-3-amine

To a solution of the compound of Preparation L (0.2 g; 0.642 mmol) in DCM (8 mL) were added an aq. solution of formaldehyde (37%; 0.15 mL; 1.93 mmol), NaBH(OAc)$_3$ (0.816 g; 3.85 mmol) and sodium sulfate (0.03 g). The reaction mixture was stirred at rt for 2 h. Water (15 mL) and DCM (25 mL) were added. The aq. layer was extracted with DCM (15 mL). The combined org. layers were washed with brine, dried over MgSO$_4$, filtered and concentrated to dryness to afford the title compound as a light yellow solid (0.188 g).

$^1$H NMR (d6-DMSO) δ: 7.73 (d, J=8.4 Hz, 2H); 6.96 (d, J=8.4 Hz, 2H); 4.63-4.67 (m, 4H); 1.87 (s, 6H).

MS1 (ESI, m/z): 304.1 [M+H$^+$] for $C_{11}H_{14}$NOI; $t_R$=0.54 min.

Preparation N: ((1S*,2S*)-2-(bromoethynyl)cyclopropyl)methyl acetate

N.i.a ((1S*,2S*)-2-(2,2-dibromovinyl)cyclopropyl)methyl acetate and

N.i.b. rac-[(1S*,2S*)-2-(2,2-dibromo-vinyl)-cyclopropyl]-methanol

To a solution of CBr$_4$ (30.0 g, 88.9 mmol) in DCM (60 mL) cooled at −20° C., was added dropwise over 45 min a solution of PPh$_3$ (45.8 g, 175 mmol) in DCM (100 mL). The mixture was kept stirred at this temperature for 30 min and then cooled to −78° C. A solution of ((1S*,2S*)-2-formyl-cyclopropyl)methyl acetate (6.18 g, 43.5 mmol, prepared as described in WO 2012/154204) in DCM (80 mL) was added dropwise over 45 min, keeping IT below −70° C. The mixture was stirred at this temperature for 30 min and allowed to warm to rt over 1 h. The solvent was removed in vacuo and the residue was purified by CC (EA-Hept) to afford the title acetate as a clear oil (4.84 g, 37% yield), and then the title alcohol as a clear oil (2.2 g, 20% yield).

For intermediate N.i.a:
$^1$H NMR (CDCl$_3$) δ: 5.84 (d, J=9.0 Hz, 1H); 3.97 (m, 2H); 2.07 (s, 3H); 1.61 (m, 1H); 1.33 (m, 1H); 0.78-0.92 (m, 2H).
MS1 (ESI, m/z): 295.0 [M+H$^+$] for C$_8$H$_{10}$O$_2$Br$_2$; $t_R$=0.87 min.

For intermediate N.i.b:
$^1$H NMR (CDCl$_3$) δ: 5.86 (d, J=9.0 Hz, 1H); 3.47-3.61 (m, 2H); 1.61-1.53 (m, 1H); 1.43 (m, 1H); 1.22-1.34 (m, 1H); 0.74-0.89 (m, 2H).

N.ii.
((1S*,2S*)-2-(bromoethynyl)cyclopropyl)methyl acetate

To a solution of intermediate N.i.a (0.5 g; 1.68 mmol) in THF (9.5 mL) was added tetrabutylammonium fluoride trihydrate (2.98 g; 9.35 mmol). The reaction mixture was heated at 60° C. for 4 h. The reaction mixture was cooled to rt and diluted with diethyl ether (50 mL). The org. phase was washed with water (20 mL) and brine (20 mL), dried over MgSO$_4$ and concentrated to dryness. The residue was purified by CC (EA-Hept) to afford the title compound as a yellow oil (0.24 g, 68% yield).
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

Preparation O: (R)-4-(5-bromo-6-fluoro-indazol-2-yl)-2-methylsulfonyl-2-methyl-butyric acid tert-butyl ester O.i.
(RS)-4-bromo-2-methylsulfonyl-2-methyl-butyric acid tert-butyl ester To a two-necked round-bottom flask containing an ice-chilled suspension of ethyl 2-(methylsulfonyl)propanoate (87.8 g, 0.422 mol) in DMF (0.6 L) was added portionwise NaH (60% in oil dispersion, 21.6 g, 0.54 mol) The mixture was stirred at this temperature for 5 min and at rt for 25 min. 1,2-dibromoethane (0.111 L, 1.28 mol) was added slowly and the reaction mixture was stirred at 70° C. for 19 h. The reaction mixture was partitioned between water (600 mL) and EA (600 mL) and the aq. layer was extracted 3 times with EA (3×200 mL). The combined org. layers were washed with brine (250 mL), dried over MgSO$_4$, filtered and concentrated to dryness. The residue was purified by CC (Hept-EA with gradient) to afford the title compound as a colourless oil (80.8 g, 60% yield). $^1$H NMR (CDCl$_3$) δ: 3.49 (m, 1H); 3.37 (m, 1H); 3.03 (s, 3H); 2.73 (m, 1H); 2.50 (m, 1H); 1.59 (s, 3H); 1.51 (s, 9H).

O.ii.
(R)-4-bromo-2-methylsulfonyl-2-methyl-butyric acid tert-butyl ester

Intermediate O.i (4 g) was separated by semi-preparative chiral HPLC Method A (Hept-EtOH 9-1; flow rate: 16 mL/min; UV detection at 220 nM); the respective retention times (flow rate: 0.8 mL/min) were 9.3 and 10.7 min. The title (R)-enantiomer, identified as the second eluting compound, was obtained as a colourless oil (1.68 g).

O.iii.
(R)-4-azido-2-methylsulfonyl-2-methyl-butyric acid tert-butyl ester

A mixture of intermediate O.ii (1.59 g; 5.04 mmol) and NaN$_3$ (0.83 g; 12.6 mmol) in DMF (45 mL) was heated at 80° C. for 2.5 h. Water (150 mL) and EA (50 mL) were added and the phases were separated. The aq. layer was extracted with EA (2×30 mL). The combined org. layers were washed with brine (15 mL), dried over Na$_2$SO$_4$, filtered and concentrated to dryness to afford the title azide as a colourless oil (1.4 g, 100% yield).
$^1$H NMR (d6-DMSO) δ: 3.58 (m, 1H); 3.29 (overlaid m, 1H); 3.08 (s, 3H); 2.42 (m, overlaid with DMSO, 1H); 1.98 (m, 1H); 1.44 (s, 9H); 1.43 (s, 3H).

An analytical sample was eluted on a Daicel ChiralPak AS-H column (4.6×250 mm, 5 μM) at a flow rate of 0.8 mL/min, using Hept/EtOH/DEA 9:1:0.005 as mobile phase and UV detection at 210 nM. The respective retention times for a racemic sample were 10.6 and 12.1 min. The title (R)-enantiomer was the second eluting compound (e.e.: 98.4%).

O.iv.
(R)-4-amino-2-methylsulfonyl-2-methyl-butyric acid tert-butyl ester

To a solution of intermediate O.iii (1.39 g; 5.01 mmol) in THF (50.1 mL) was added PPh$_3$ (1.99 g; 7.52 mmol). The reaction mixture was heated for 30 min. at 60° C. before water (10.4 mL) was added. The mixture was stirred at 60° C. for 1.5 h. The volatiles were removed under reduced pressure and the aq. residue was diluted with DCM-MeOH (9:1; 25 mL) and water (10 mL). The phases were separated and the aq. layer was extracted with DCM-MeOH (9:1; 2×15 mL). The combined org. layers were dried over MgSO$_4$, filtered and evaporated under reduced pressure. The residue was purified by CC (DCM-MeOH containing a gradient of aq. NH$_4$OH) to afford the title compound as a white solid (1.25 g, 99% yield).
$^1$H NMR (d6-DMSO) δ: 3.06 (s, 3H); 2.63-2.75 (m, 1H); 2.40-2.53 (m, overlaid with DMSO, 1H); 2.16-2.28 (m, 1H); 1.74-1.85 (m, 1H); 1.44 (s, 9H); 1.40 (s, 3H).
MS1 (ESI, m/z): 252.1 [M+H$^+$] for C$_{10}$H$_{21}$NO$_4$S; $t_R$=0.47 min.

O.v. (R)-4-(5-bromo-6-fluoro-indazol-2-yl)-2-methylsulfonyl-2-methyl-butyric acid tert-butyl ester Starting from 5-bromo-4-fluoro-2-nitrobenzaldehyde (0.6 g; 2.42 mmol; commercial) and intermediate O.iv (0.64 g; 2.54 mmol) and proceeding in analogy to Preparation A, step A.i, Variant II, the title compound was obtained, after purification by CC (Hept-EA gradient), as a yellowish oil (1.1 g, 100% yield).
$^1$H NMR (d6-DMSO) δ: 8.51 (s, 1H); 8.17 (d, J=7.1 Hz, 1H); 7.59 (d, J=10.1 Hz, 1H); 4.56-4.68 (m, 1H); 4.37-4.50 (m, 1H); 3.13 (s, 3H); 2.70-2.84 (m, 1H); 2.38-2.58 (m, overlaid with DMSO, 1H); 1.55 (s, 3H); 1.39 (s, 9H).
MS (ESI, m/z): 450.9 [M+H$^+$] for C$_{17}$H$_{22}$N$_2$O$_4$BrFS; $t_R$=0.91 min.

Preparation P: rac-tert-butyl-((1R*,2R*)-2-iodoethynyl-cyclopropylmethoxy)-dimethyl-silane

P.i. rac-tert-butyl-[(1S*,2S*)-2-(2, 2-dibromo-vinyl)-cyclopropylmethoxy]-dimethyl-silane To a mixture of intermediate N.i.b (1.52 g, 5.96 mmol) in THF (14 mL) were added imidazole (0.823 g, 12.1 mmol) and TBDMS-Cl (1.4 g, 9.3 mmol). The mixture was stirred at rt for 1 h. Water (50 mL) and EA (40 mL) were added and the two layers were decanted. The org. layer was extracted with EA (2×30 mL), washed with aq. sat. $NaHCO_3$ (50 mL), brine (50 mL), dried over $MgSO_4$, filtered and concentrated to dryness to afford the crude product. The crude was purified by CC (Hept-EA gradient) to afford the title compound as a colourless oil (1.56 g, 71% yield).

$^1$H NMR ($CDCl_3$) δ: 5.83 (d, J=9.2 Hz, 1H); 3.58 (d, J=5.5 Hz, 3H); 1.55 (m, 1H); 1.19 (m, 1H); 0.87 (s, 9H); 0.87 (overlapped m, 1H); 0.69 (m, 1H); 0.04 (s, 6H).

P.ii. Rac-tert-butyl-((1R*,2R*)-2-iodoethynyl-cyclopropylmethoxy)-dimethyl-silane To a solution of intermediate P.i (1.56 g, 4.22 mmol) in THF (20 mL) cooled at −74° C. was added, dropwise over 25 min, BuLi (1.97M in hexanes; 4.29 mL; 8.45 mmol), keeping the IT below −70° C. After stirring for 1 h, the solution was warmed to 0° C. and iodine (1.76 g, 6.97 mmol) in solution in THF (14.2 mL) was added dropwise over 47 min. The reaction mixture was stirred at rt for 18 h. The reaction mixture was quenched with a sat. $Na_2S_2O_3$ solution (50 mL). The two phases were separated. The aq. layer was extracted with DCM (2×150 mL). The combined org. layers were dried over $Mg_2SO_4$ and concentrated to dryness to give the desired compound as a yellow oil (1.61 g, quant.).

$^1$H NMR ($CDCl_3$) δ: 3.58 (d, J=4.7 Hz, 2H); 1.24-1.44 (m, 2H); 0.86 (s, 9H); 0.86 (overlapped m, 1H); 0.78 (overlapped m, 1H); 0.04 (s, 6H).

Preparation Q: (4-ethynyl-3-fluorophenyl)methanol

Starting from (3-fluoro-4-iodophenyl)methanol (0.510 g; 2.0 mmol; commercial) and trimethysilyl acetylene (0.31 mL, 1.1 eq.), and proceeding in analogy to Preparation E, steps E.ii and E.iii, the title compound was obtained, after purification by CC (DCM-MeOH), as a colourless oil (0.23 g; yields: 96% for Sonogashira coupling and 79% for silyl cleavage).

$^1$H NMR δ (d6-DMSO): 7.51 (t, J=7.7 Hz, 1H); 7.18-7.24 (m, 1H); 7.12-7.17 (m, 1H); 5.42 (t, J=5.8 Hz, 1H); 4.53 (d, J=5.8 Hz, 2H); 4.45 (s, 1H).

Preparation R: (R)-4-(5-ethynyl-6-fluoro-indazol-2-yl)-2-methylsulfonyl-2-methyl-N—[(R)-(tetrahydropyran-2-yl)oxy]-butanamide

R.i. (R)-4-(5-bromo-6-fluoro-indazol-2-yl)-2-methylsulfonyl-2-methyl-butyric acid To a mixture of the compound of Preparation O (0.586 g, 1.3 mmol) with 4N HCl in dioxane (7 mL) was added water (0.26 mL). The resulting mixture was stirred at rt for 16 h. The mixture was concentrated to dryness and co-evaporated with diethyl ether (3×15 mL) to give the title acid as a beige solid (0.52 g; quant.).

$^1$H NMR (d6-DMSO) δ: 8.50 (s, 1H); 8.17 (d, J=7.1 Hz, 1H); 7.59 (d, J=10.0 Hz, 1H); 4.57-4.70 (m, 1H); 4.41-4.53 (m, 1H); 3.13 (s, 3H); 2.71-2.83 (m, 1H); 2.38-2.56 (overlapped m, 1H); 1.56 (s, 3H).

MS1 (ESI, m/z): 395.01 [M+H$^+$] for $C_{13}H_{14}N_2O_4BrFS$; $t_R$=0.73 min.

R.ii. (R)-4-(5-bromo-6-fluoro-indazol-2-yl)-2-methylsulfonyl-2-methyl-N—[(RS)-(tetrahydro-pyran-2-yl)oxy]-butanamide To a solution of intermediate R.i (0.52 g, 0.56 mmol) in DMF (12 mL) were added successively HOBT (0.411 g, 3.04 mmol), TEA (0.64 mL, 4.63 mmol), THP—$ONH_2$ (0.387 g, 3.3 mmol) and EDC (0.583 g, 3.04 mmol). The suspension was then stirred at rt overnight. Water (50 mL) and EA (50 mL) were added. The org. layer was washed with water (50 mL), aq. $NaHSO_4$ (5% w/w, 30 mL), sat. $NaHCO_3$ (50 mL) and brine (20 mL). The org. layer was dried over $Na_2SO_4$, filtered and concentrated to dryness to afford the title compound as a yellow gum (0.43 g, 66% yield).

$^1$H NMR (d6-DMSO) δ (mixture of isomers): 11.41 (br. s, 1H); 8.46 (s, 1H); 8.18 (d, J=7.1 Hz, 1H); 7.59 (d, J=10.2 Hz, 1H); 4.96 (br. s, 0.5H); 4.91 (br. s, 0.5H); 4.48-4.63 (m, 1H); 4.31-4.45 (m, 1H); 3.97-4.16 (m, 1H); 3.40-3.57 (m, 1H); 3.07 (s, 1.5H); 3.05 (s, 1.5H); 2.75-2.91 (m, 1H); 2.34-2.58 (overlapped m, 1H); 1.63-1.77 (m, 3H); 1.53 (s, 1.5H); 1.38-1.62 (overlapped m, 3H); 1.51 (s, 1.5H).

MS1 (ESI, m/z): 491.9 [M+H$^+$] for $C_{18}H_{23}N_3O_5BrFS$; $t_R$=0.81 min.

R.iii. (R)-4-(5-ethynyl-6-fluoro-indazol-2-yl)-2-methylsulfonyl-2-methyl-N—[(RS)-(tetrahydro-pyran-2-yl)oxy]-butanamide In a 7 mL flask, intermediate R.ii (0.42 g; 0.85 mmol), bis(tri-tert-butylphosphine)palladium (0.037 g; 0.07 mmol), cesium fluoride (0.258 g; 1.71 mmol), degassed dioxane (0.77 mL) and ethynyltri-n-butyltin (0.52 mL; 1.71 mmol) were introduced successively. The solution was stirred at 80° C. for 2.5 h. The mixture was concentrated to dryness and purified by CC (Hept-EA with gradient) to afford the title compound as a yellowish foam (0.106 g, 28% yield), $^1$H NMR (d6-DMSO) δ (mixture of isomers): 11.37-11.45 (m, 1H); 8.50 (br. s, 1H); 8.05 (d, J=7.1 Hz, 1H); 7.40-7.49 (m, 1H); 4.90-4.97 (m, 1H); 4.48-4.62 (m, 1H); 4.31-4.45 (overlapped m, 1H); 4.33 (s, 1H); 3.98-4.15 (m, 1H); 3.47-3.57 (m, 1H); 3.07 (s, 1.5H); 3.05 (s, 1.5H); 2.73-2.92 (m, 1H); 2.34-2.54 (overlapped m, 1H); 1.62-1.74 (m, 3H); 1.46-1.60 (overlapped m, 3H); 1.54 (s, 1.5H); 1.52 (s, 1.5H).

MS1 (ESI, m/z): 438.0 [M+H$^+$] for $C_{20}H_{24}N_3O_5FS$; $t_R$=0.79 min.

Preparation S: 3-(iodoethynyl)thietan-3-ol

S.i. 3-((trimethylsilyl)ethynyl)thietan-3-ol

To a solution of TMS-acetylene (2.1 mL; 14.8 mmol) in THF (33 mL), cooled at −78° C., was added dropwise BuLi (1.97M; 8.5 mL; 16.7 mmol) over 20 min, keeping IT below −68° C. The reaction mixture was stirred at the same temperature for 5 min, then allowed to warm to −20° C. and cooled again at −76° C. A solution of 3-thietanone (1.02 g; 11.3 mmol, commercial) in THF (4.2 mL) was then added dropwise over 10 min (IT below −69° C.) and the reaction mixture was stirred for 80 min before warming to rt. The reaction mixture was quenched by addition of brine (30 mL)

and extracted twice with EA (2×40 mL). The combined org. layers were dried over MgSO$_4$, filtered and evaporated under reduced pressure to give a brown solid (1.91 g, 91% yield).

$^1$H NMR (CDCl$_3$) δ: 3.50 (s, 4H); 2.67 (br. s, 1H); 0.19 (s, 9H).

S.ii. 3-ethynylthietan-3-ol

Starting from intermediate S.i (1.91 g, 10.3 mmol) and proceeding in analogy to Preparation E, step E.iii, the title alkyne was obtained as a yellowish oil (1.07 g; 91% yield).

$^1$H NMR (CDCl$_3$) δ: 3.44-3.58 (m, 4H); 2.71 (br. s, 1H); 2.64 (s, 1H).

S.iii. 3-(iodoethynyl)thietan-3-ol

Starting from intermediate S.ii (1.07 g; 9.38 mmol) and proceeding in analogy to Preparation G, the title compound was obtained as a brown solid (1.83 g; 81% yield).

$^1$H NMR (CDCl$_3$) δ: 3.43-3.57 (m, 4H); 2.71 (br. s, 1H).

Preparation T: (1-(4-ethynylphenyl)cyclopropyl)methanol

Starting from (1-(4-iodophenyl)cyclopropyl)methanol (0.660 g; 2.4 mmol; commercial) and TMS-acetylene (0.51 mL; 1.5 eq.), and proceeding in analogy to Preparation E, steps E.ii and E.iii (Sonogashira coupling: 96% yield; silyl cleavage: 39% yield), the title compound was obtained, after purification by CC (Hept-EA), as yellowish needles (0.167 g).

$^1$H NMR (d6-DMSO) δ: 7.37 (d, J=8.2 Hz, 2H), 7.29 (d, J=8.2 Hz, 2H), 4.68 (t, J=5.7 Hz, 1H), 4.08 (s, 1H), 3.53 (d, J=5.6 Hz, 2H), 0.81-0.92 (m, 2H), 0.67-0.79 (m, 2H).

Preparation U: ((1S,2S)-2-(bromoethynyl)cyclopropyl)methyl acetate and ((1R,2R)-2-(bromoethynyl)cyclopropyl)methyl acetate The racemic product of Preparation N (1.75 g) was separated by semi-preparative chiral HPLC Method B (Hept-EtOH 9-1; flow rate: 20 mL/min, UV detection at 223 nM); the respective retention times (flow rate: 0.8 mL/min) were 5.9 and 8.7 min. The title enantiomers were obtained as clear oils (0.64 g each).

First-Eluting Enantiomer, (1S,2S)-Configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H). [α]$_D$=+96° (c=1.03; MeOH).

Second-Eluting Enantiomer, (1R,2R)-Configurated:
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=−94° (c=1.01; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation V: tert-butyl (4-iodo-2-methylbut-3-yn-2-yl)carbamate

Starting from tert-butyl (2-methylbut-3-yn-2-yl)carbamate (1.02 g; 5.6 mmol; commercial) and proceeding in analogy to Preparation G, the title compound was obtained as a yellow solid (1.49 g; 86% yield).

$^1$H NMR (CDCl$_3$) δ: 4.64 (s, 1H); 1.55 (s, 6H); 1.46 (s, 9H).

Preparation W: ((1R,2R)-2-(4-iodophenyl)cyclopropyl)methanol and ((1S,2S)-2-(4-iodophenyl)cyclopropyl)methanol Rac-(trans-2-(4-iodophenyl)cyclopropyl)methanol (0.956 g; prepared as described in WO 2005/103032) was separated by semi-preparative chiral HPLC Method F (Hept-EtOH 3-1; flow rate: 16 mL/min, UV detection at 210 nM); the respective retention times (flow rate: 0.8 mL/min) were 5.7 and 7.1 min. The title enantiomers were obtained as white powders (0.45 g each).

First-Eluting Enantiomer, (1R,2R)-Configurated:
$^1$H NMR (CDCl$_3$) δ: 7.54 (d, J=8.0 Hz, 2H); 6.86 (d, J=8.0 Hz, 2H); 4.56 (br. s, 1H); 3.43 (m, 1H); 3.32 (m, 1H); 1.73 (m, 1H); 1.23 (m, 1H); 0.75-0.90 (m, 2H). [α]$_D$=−61° (c=1.04, MeOH).

Second-Eluting Enantiomer, (1S,2S)-Configurated:
$^1$H NMR (CDCl$_3$) δ: 7.54 (d, J=8.0 Hz, 2H); 6.86 (d, J=8.0 Hz, 2H); 4.56 (br. s, 1H); 3.43 (m, 1H); 3.32 (m, 1H); 1.73 (m, 1H); 1.23 (m, 1H); 0.75-0.90 (m, 2H).

[α]$_D$=+62° (c=1.04, MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation X: (3-(4-iodophenyl)oxetan-3-yl)methanol

Starting from (3-(4-bromophenyl)oxetan-3-yl)methanol (0.24 g; 0.98 mmol; commercial) and proceeding in analogy to Preparation E, step E.i, the title iodide was obtained, after purification by CC (Hept-EA), as an off-white solid (0.27 g, 94% yield).

$^1$H NMR (d6-DMSO) δ: 7.69 (d, J=7.1 Hz, 2H); 6.96 (d, J=7.1 Hz, 2H); 5.10 (t, J=5.6 Hz, 1H); 4.60.4.73 (m, 4H); 3.69 (d, J=5.3 Hz, 2H).

Preparation Y: N-(2-fluoro-4-iodophenyl)-2-hydroxyacetamide

Starting from 2-((4-bromo-2-fluorophenyl)amino)-2-oxoethyl acetate (1.0 g; 3.45 mmol; commercial) and proceeding in analogy to Preparation E, step E.i, the title iodide was obtained in mixture with the corresponding acetate. The mixture was dissolved in MeOH (20 mL) and K$_2$CO$_3$ (2.5 g; 17.2 mmol) was added. The reaction mixture was stirred at rt for 10 min. EA (100 mL) and water (60 mL) were added. The aq. phase was extracted with EA (100 mL). The combined org. phases were washed with brine, dried over MgSO$_4$ and filtered. The filtrate concentrated to dryness to afford the title compound as a brown solid (0.8 g; 79% yield).

$^1$H NMR (300 MHz, d$_6$-DMSO) δ: 7.66-7.78 (m, 2H); 7.51-7.57 (m, 1H); 5.85 (t, J=5.9 Hz, 1H); 4.02 (d, J=5.9 Hz, 2H).

Preparation Z: (RS)-1-((tert-butyldiphenylsilyl)oxy)-4-iodo-2-methylbut-3-yn-2-ol Starting from (RS)-2-methylbut-3-yne-1,2-diol (1.031 g; 10.3 mmol; prepared as reported by Knight and Qing in

*Tetrahedron Lett.* (2009), 50(26), 3534-3537) and TBDPS-Cl (3.95 mL; 15.4 mmol) and proceeding successively in analogy to Preparation P, step P.i. (adding a catalytic amount of DMAP; 90% yield) and Preparation G (100% yield), the title compound was obtained, after purification by CC (DCM), as a colourless oil (0.77 g).

$^1$H NMR (300 MHz, d$_6$-DMSO) δ: 7.62-7.71 (m, 4H); 7.36-7.50 (m, 6H); 5.52 (s, 1H); 3.56 (d, J=8.6 Hz, 1H); 3.43 (d, J=8.6 Hz, 1H); 1.39 (s, 3H); 1.02 (s, 9H).

Preparation AA: tert-butyl (3-(iodoethynyl)oxetan-3-yl)carbamate

AA.i. Tert-butyl (3-((trimethylsilyl)ethynyl)oxetan-3-yl)carbamate

To a solution of 3-((trimethylsilyl)ethynyl)oxetan-3-amine hydrochloride (0.123 g; 0.6 mmol; commercial) in DCM (3 mL) were added TEA (0.18 mL; 1.29 mmol) and Boc$_2$O (0.272 g; 1.25 mmol). The reaction mixture was stirred at rt for 6 h. Boc$_2$O (0.272 g; 1.25 mmol) was added again and the reaction was stirred overnight. The reaction mixture was diluted with DCM (5 mL) and sat. aq. NaHCO$_3$ (5 mL) was added. The phases were separated and the aq. layer was extracted twice with DCM (2×5 mL). The combined org. layers were washed with brine (5 mL), dried over MgSO$_4$, filtered and the filtrate concentrated to dryness to afford the title compound, slightly contaminated by Boc$_2$O, as a white gum (0.312 g).

$^1$H NMR (CDCl$_3$) δ: 4.72-4.81 (m, 4H); 3.05 (br. s, 1H); 1.47 (s, 9H); 0.18 (s, 9H).

AA.ii. Tert-butyl (3-ethynyloxetan-3-yl)carbamate

To a solution of intermediate AA.i (0.211 g; 0.783 mmol) in MeOH (1.6 mL) was added K$_2$CO$_3$ (0.162 g; 1.17 mmol). The mixture was stirred at rt for 30 min. Water (5 mL) was added. The mixture was extracted twice with DCM (2×10 mL) and the org. layer was dried over MgSO$_4$, filtered and the filtrate concentrated to dryness. The crude was purified by CC (PE-EA) to afford the title compound as white solid (0.173 g).

$^1$H NMR (500 MHz, CDCl$_3$) δ: 5.02 (br. s, 1H); 4.84 (d, J=6.2 Hz, 2H); 4.73 (d, J=6.2 Hz, 2H); 2.57 (s, 1H); 1.47 (s, 9H).

AA.iii. Tert-butyl (3-(iodoethynyl)oxetan-3-yl)carbamate

Starting from intermediate AA.ii (crude; 0.154 g; 0.783 mmol) and proceeding in analogy to Preparation P, step P.ii, the title compound was obtained as a yellow oil (0.234 g; 92% yield).

$^1$H NMR (500 MHz, CDCl$_3$) δ: 5.02 (br. s, 1H); 4.81-4.85 (m, 2H); 4.70-4.75 (m, 2H); 1.47 (s, 9H).

Preparation AB: 2-oxo-2-((4-(4,4,5,5-tetramethyl-1,3,2-dioxaborolan-2-yl)phenyl)amino)ethyl acetate AB.i. 2((4-iodophenyl)amino)-2-oxoethyl acetate To a solution of 4-iodoaniline (2.15 g; 9.82 mmol; commercial) in DCM (25 mL) was added dropwise acetoxyacetylchloride (1.16 mL; 10.8 mmol) over 15 min. The mixture was stirred for 1.5 h at rt. Water (30 mL) was added. The org. layer was dried over Na$_2$SO$_4$, filtered and concentrated to dryness to afford the title compound as a light purple solid (3.12 g, 100% yield).

$^1$H NMR (500 MHz, d$_6$-DMSO) δ: 10.18 (s, 1H); 7.66 (d, J=8.8 Hz, 2H); 7.42 (d, J=8.8 Hz, 2H); 4.64 (s, 2H); 2.12 (s, 3H).

MS1 (ESI, m/z): 318.8 [M+H$^+$] for C$_{10}$H$_{10}$NO$_3$I; t$_R$=0.76 min.

AB.ii. 2-oxo-2-((4-(4,4,5,5-tetramethyl-1,3,2-dioxaborolan-2-yl)phenyl)amino)ethyl acetate Starting from intermediate AB.i (1.0 g; 3.15 mmol) and proceeding in analogy to Preparation D, the title compound was obtained, after purification by CC (Hept-EA), as a brown oil (0.43 g; 43% yield).

$^1$H NMR (500 MHz, d$_6$-DMSO) δ: 10.20 (s, 1H); 7.57-7.64 (m, 4H); 4.63-4.68 (m, 2H);

2.13 (s, 3H); 1.29 (s, 12H).

MS1 (ESI, m/z): 320.0 [M+H$^+$] for C$_{16}$H$_{22}$NO$_5$B; t$_R$=0.82 min.

Preparation AC: 2-(3-fluoro-4-(4,4,5,5-tetramethyl-1,3,2-dioxaborolan-2-yl)phenoxy)ethan-1-ol AC.i. Ethyl 2-(3-fluoro-4-(4,4,5,5-tetramethyl-1,3,2-dioxaborolan-2-yl)phenoxy)acetate Starting from ethyl 2-(4-bromo-3-fluorophenoxy)acetate (1.0 g; 3.61 mmol; commercial) and proceeding in analogy to Preparation D, the title compound was obtained, after purification by CC (Hept-EA), as a yellow oil (0.816 g, 70% yield).

$^1$H NMR (500 MHz, d$_6$-DMSO) δ: 7.53-7.57 (m, 1H); 6.75-6.81 (m, 2H); 4.86 (s, 2H); 4.17 (q, J=7.1 Hz, 2H); 1.28 (s, 12H); 1.21 (t, J=7.1 Hz, 3H).

MS1 (ESI, m/z): 324.9 [M+H$^+$] for C$_{16}$H$_{22}$NO$_5$BF; t$_R$=0.93 min.

AC.ii. 2-(3-fluoro-4-(4,4,5,5-tetramethyl-1,3,2-dioxaborolan-2-yl)phenoxy)ethan-1-ol NaBH$_4$ (0.14 g; 3.76 mmol) was added portionwise to an ice chilled ethanol (4.5 mL) solution of intermediate AC.i (0.81 g; 2.5 mmol). The mixture was stirred for 2 h. Acetone (0.37 mL), EA (5 mL) and water (10 mL) were added sequentially at rt. Solvents were distilled off under reduced pressure. EA (20 mL) was added to the resulting residue. This org. phase was washed with water (10 mL) and brine (10 mL), dried over Na$_2$SO$_4$, filtered then concentrated to dryness. The residue was purified by CC (DCM-MeOH gradient) to afford the title compound as a colourless oil (0.48 g; 68% yield).

$^1$H NMR (500 MHz, d$_6$-DMSO) δ: 7.52-7.57 (m, 1H); 6.79 (dd, J=2.3, 8.4 Hz, 1H); 6.74 (dd, J=2.2, 11.5 Hz, 1H); 4.90 (t, J=5.5 Hz, 1H); 4.00-4.05 (m, 2H); 3.68-3.73 (m, 2H); 1.28 (s, 12H).

Preparation AD: ((1-(bromoethynyl)cyclopropyl)methoxy)(tert-butyl)diphenylsilane To a mixture of (dibromomethyl)triphenylphosphonium bromide (8.527 g; 16.6 mmol, prepared as described in Fuerst et al., *J. Org. Chem.* (2013), 78(17), 8748-8758) and THF (40 mL) was added a solution of tBuOK (1M in THF; 16.6 mL; 16.6 mmol). The solution was stirred for 3 min at rt, then cooled to 0° C. A solution of 1-(((tert-butyldiphenylsilyl)oxy)methyl)cyclopropanecarbaldehyde (2.2 g; 6.62 mmol; prepared as described in WO 2010/135536) in THF (23 mL) was added dropwise. The reaction was stirred at 0° C. for 40 min. The reaction mixture was cooled to −78° C. and tBuOK (1M in THF; 29.1 mL; 29.1 mmol) was added rapidly and stirred at −78° C. for 30 min. The reaction mixture was quenched with brine (150 mL). The aq. layer was extracted with Et$_2$O (3×150 mL). The combined org. phases were washed with brine, dried over MgSO$_4$, filtered, and concentrated to dryness. The residue was purified by CC (Hept/EA) to afford the title compound as a colourless oil (2.052 g, 75% yield). $^1$H NMR (500 MHz, d$_6$-DMSO) δ: 7.59-7.70 (m, 4H); 7.37-7.53 (m, 6H); 3.56 (s, 2H); 1.01 (s, 9H); 0.82-0.89 (m, 2H); 0.71-0.76 (m, 2H).

Preparation AE: ((3-(bromoethynyl)bicyclo[1.1.1]pentan-1-yl)methoxy)(tert-butyl)diphenylsilane AE.i. Bicyclo[1.1.1]pentane-1,3-diyldimethanol To a solution of dimethyl bicyclo[1.1.1]pentane-1,3-dicarboxylate (1.74 g; 9.45 mmol; commercial) in THF (12 mL), cooled at 0° C. was added dropwise LiAlH$_4$ (2.4M in THF; 5.29 mL; 12.7 mmol) over 45 min keeping IT below 15° C. The suspension was stirred at rt for 3 h. The crude mixture was cooled to 0° C. and carefully quenched successively with water (0.48 mL), a 15% NaOH solution (0.48 mL) and water (1.44 mL). The mixture was stirred at rt for 35 min. THF (17 mL) and MgSO$_4$ were then added and the mixture was stirred at rt for 10 min before being filtered and concentrated to dryness. The residue was purified by CC (Hept-EA) to afford the title compound as a colourless oil (1.2 g; 99% yield).
$^1$H NMR (500 MHz, d$_6$-DMSO) δ: 4.40 (t, J=5.5 Hz, 2H); 3.35 (d, J=5.6 Hz, 4H); 1.46 (s, 6H).

AE.ii. (3-(((tert-butyldiphenylsilyl)oxy)methyl)bicyclo[1.1.1]pentan-1-yl)methanol To a suspension of NaH (60% in mineral oil; 0.23 g; 5.67 mmol) in THF (4.5 mL) was added slowly at rt a solution of intermediate AE.i (0.66 g; 5.16 mmol) in THF (3.3 mL) keeping IT below 27° C. After 1 h stirring, a solution of TBDPS-Cl (1.36 mL; 5.16 mmol) in THF (2.8 mL) was added dropwise over 15 min. The solution was stirred for 4 h then diluted in Et$_2$O (20 mL). The org. phase was washed with brine (2×20 mL), dried over Na$_2$SO$_4$, filtered and concentrated to dryness. The residue was purified by CC (Hept-EA) to afford the title compound as a colourless oil (0.49 g; 26% yield).
$^1$H NMR (500 MHz, d$_6$-DMSO) δ: 7.56-7.64 (m, 4H); 7.39-7.50 (m, 6H); 4.43 (t, J=5.6 Hz, 1H); 3.64 (s, 2H); 3.36 (d, J=5.5 Hz, 2H); 1.49 (s, 6H); 1.01 (s, 9H).

AE.iii. 3-(((tert-butyldiphenylsilyl)oxy)methyl)bicyclo[1.1.1]pentane-1-carbaldehyde To a solution of intermediate AE.ii (1.09 g; 2.98 mmol) in DCM (6.9 mL) cooled to −10° C., was added DIPEA (1.59 mL; 9.31 mmol) over 15 min. A solution of Pyr.SO$_3$ complex (45%; 1.44 g; 4.07 mmol) in DMSO (4.03 mL) was then dropwise added over 10 min. The reaction mixture was stirred for 1.5 h at 0° C. and 1 h at rt. The reaction mixture was partitioned between water (35 mL) and DCM (20 mL). The two layers were separated and the aq. layer was extracted with DCM (15 mL). The combined org. layers were dried over Na$_2$SO$_4$, filtered and concentrated to dryness. The residue was co-evaporated with toluene (2×10 mL) and then purified by CC (Hept-EA) to afford the title compound as a colourless oil (0.94 g, 87% yield).
$^1$H NMR (500 MHz, d$_6$-DMSO) δ: 9.53 (s, 1H); 7.57-7.62 (m, 4H); 7.41-7.49 (m, 6H); 3.68 (s, 2H); 1.86 (s, 6H); 1.01 (s, 9H).

AE.iv. Tert-butyl((3-(2,2-dibromovinyl)bicyclo[1.1.1]pentan-1-yl)methoxy)diphenylsilane Starting from intermediate AE.iii (0.94 g; 2.58 mmol) and proceeding in analogy to Preparation N, step N.i, the title compound was obtained, after purification by CC (Hept-EA), as a yellow oil (1.2 g; 89% yield).
$^1$H NMR (500 MHz, d$_6$-DMSO) δ: 7.57-7.61 (m, 4H); 7.41-7.49 (m, 6H); 6.74 (s, 1H); 3.64 (s, 2H); 1.90 (s, 6H); 1.01 (s, 9H).

AE.v. ((3-(bromoethynyl)bicyclo[1.1.1]pentan-1-yl)methoxy)(tert-butyl)diphenylsilane A solution of intermediate AE.iv (0.45 g; 0.86 mmol) in THF (2 mL) cooled at −78° C. was treated with a solution of tBuOK (1M; 3.8 mL; 3.8 mmol). The reaction mixture was stirred for 30 min at −78° C. then was diluted with brine (8 mL) and was allowed to reach rt. Et$_2$O (15 mL) was added. The aq. phase was extracted with Et$_2$O (15 mL). The combined org. layers were washed with brine (10 mL), dried over Na$_2$SO$_4$, filtered and concentrated to dryness to afford the title compound as a yellow oil (0.37 g, 97% yield).
$^1$H NMR (500 MHz, d$_6$-DMSO) δ: 7.55-7.60 (m, 4H); 7.41-7.49 (m, 6H); 3.60 (s, 2H); 1.91 (s, 6H); 1.00 (s, 9H).

Preparation AF: (S)-2-(4-((2,2-dimethyl-1,3-dioxolan-4-yl)methoxy)-2-fluorophenyl)-4,4,5,5-tetramethyl-1,3,2-dioxaborolane A suspension of 3-fluoro-4-(4,4,5,5-tetramethyl-1,3,2-dioxaborolan-2-yl)phenol (0.5 g; 2.1 mmol; commercial), (R)-(2,2-dimethyl-1,3-dioxolan-4-yl)methyl 4-methylbenzenesulfonate (0.6 g; 2.1 mmol; commercial) and K$_2$CO$_3$ (0.58 g; 4.2 mmol) in DMF (4 mL) was stirred at 100° C. overnight. The mixture was cooled to rt and diluted with water (40 mL). The mixture was extracted with EA (3×20 mL). The combined org. layers were washed with brine (15 mL), dried over Na$_2$SO$_4$, filtered and concentrated to dryness. The residue was purified by CC (Hept-EA) to afford the title compound as a yellow oil which crystallized on standing (0.38 g; 51% yield).
$^1$H NMR (500 MHz, d$_6$-DMSO) δ: 7.52-7.58 (m, 1H); 6.75-6.83 (m, 2H); 4.37-4.44 (m, 1H); 4.06-4.11 (m, 2H); 3.99-4.04 (m, 1H); 3.74 (dd, J=6.4, 8.4 Hz, 1H); 1.35 (s, 3H); 1.31 (s, 3H); 1.28 (s, 12H).
MS1 (ESI, m/z): 353.1 [M+H$^+$] for C$_{18}$H$_{26}$O$_5$BF; t$_R$=0.95 min.

Preparation AG: (4-(((1S*,2S*)-2-(((tert-butyldiphenylsilyl)oxy)methyl)cyclopropyl)ethynyl)phenyl)boronic acid AG.i. (1S*,2S*)-2-(((tert-butyldiphenylsilyl)oxy)methyl)cyclopropane-1-carbaldehyde Starting from diethyl trans-1,2-cyclopropane-1,2-dicarboxylate (24.96 g; 130 mmol; commercial) and proceeding successively in analogy to Preparation AE, steps AE.i to AE.iii (reduction: 100% yield; silyl protection: 67% yield;

and Swern oxidation: 76% yield), the title compound was obtained, after purification by CC (Hept-EA), as a colourless oil.
$^1$H NMR (500 MHz, CDCl$_3$) δ: 9.07 (s, 0.5H), 9.06 (s, 0.5H); 7.65-7.69 (m, 4H); 7.40-7.49 (m, 6H); 3.76-3.81 (m, 1H); 3.64-3.69 (m, 1H); 1.83-1.89 (m, 1H); 1.73-1.80 (m, 1H); 1.25-1.30 (m, 1H); 1.10-1.15 (m, 1H); 1.06-1.08 (m, 9H).

AG.ii. Ter t-butyl(((1S*,2S*)-2-ethenylcyclopropyl)methoxy)diphenylsilane

A suspension of intermediate AG.i (1.890 g; 5.58 mmol) and K$_2$CO$_3$ (1.543 g; 11.2 mmol) in MeOH (50 mL) was treated dropwise with dimethyl 1-diazo-2-oxopropylphosphonate (1.180 g; 6.14 mmol; commercial). The reaction mixture was stirred at rt for 24 h before being concentrated to dryness. The residue was dissolved in DCM (50 mL) and washed with water (40 mL) and brine. The org. layer was dried over MgSO$_4$, filtered and the filtrate concentrated to dryness. The residue was purified by CC (Hept-EA) to afford the title compound as a colourless oil (1.65 g; 88% yield).
$^1$H NMR (500 MHz, CDCl$_3$) δ: 7.65-7.70 (m, 4H); 7.39-7.47 (m, 6H); 3.65-3.73 (m, 1H); 3.58-3.64 (m, 1H); 1.79-1.85 (m, 1H); 1.39-1.47 (m, 1H); 1.20-1.27 (m, 1H); 1.04-1.10 (m, 9H); 0.84-0.89 (m, 1H); 0.78-0.84 (m, 1H).

AG.iii. (4-(((1S*,2S*)-2-(((tert-butyldiphenylsilyl)oxy)methyl)cyclopropyl)ethynyl)phenyl)boronic acid A mixture of 4-iodophenylboronic acid (1.214 g; 4.9 mmol; commercial) and Pd(PPh$_3$)$_4$ (0.085 g; 0.0735 mmol) in pyrrolidine (10.1 mL; 123 mmol) was degassed. The mixture was cooled to 0° C. and treated with intermediate AG.ii (1.64 g; 4.9 mmol). The reaction was stirred at rt overnight and concentrated to dryness. The residue was diluted with water (80 mL) and EA (100 mL). The aq. phase was acidified with 1N HCl to pH=3 and extracted with EA (100 mL). The org. layer was washed with water (80 mL) and brine, dried over MgSO$_4$, filtered and the filtrate concentrated to dryness. The residue was purified by CC (Hept-EA) to afford the title compound as a yellow foam (1.1 g; 49% yield).
$^1$H NMR (500 MHz, CDCl$_3$) δ: 8.11-8.18 (m, 2H); 7.68-7.74 (m, 4H); 7.49-7.55 (m, 2H); 7.39-7.49 (m, 6H); 3.63-3.82 (m, 2H); 1.53-1.60 (m, 1H); 1.44-1.52 (m, 1H); 1.09 (s, 9H); 0.91-1.04 (m, 2H).

Preparation AH: tert-butyl ((3R,6S)-6-(bromoethynyl)tetrahydro-2H-pyran-3-yl)carbamate Starting from tert-butyl ((3R,6S)-6-formyltetrahydro-2H-pyran-3-yl)carbamate (3.1 g; 13.6 mmol, prepared as described in Surivet et al., *J. Med. Chem.* (2013), 56, 7396-7415) and proceeding successively in analogy to Preparation N, step N.i (68% yield) and Preparation AE, step AE.v (97% yield), the title compound was obtained, after purification by CC (Hept-EA), as a white solid (2.7 g).
$^1$H NMR (500 MHz, d$_6$-DMSO) δ: 6.84 (d, J=7.6 Hz, 1H); 4.13 (dd, J=2.7, 10.1 Hz, 1H); 3.76 (dd, J=3.0, 10.5 Hz, 1H); 3.59-3.63 (m, 1H); 3.00-3.05 (m, 1H); 1.87-1.93 (m, 1H); 1.80-1.86 (m, 1H); 1.75-1.79 (m, 1H); 1.52-1.61 (m, 1H); 1.38 (s, 9H).

Preparation AI: di-tert-butyl ((1-(4-ethynylphenyl)cyclopropyl)methyl)phosphate

To a solution of the compound of Preparation T (0.051 g; 0.3 mmol) in THF (1.8 mL) at 0° C. were added tetrazole (0.45M in MeCN; 0.12 mL; 1.38 mmol) and di-tert-butyl diisopropylphosphoramidite (0.36 mL; 1.14 mmol; commercial). The reaction mixture was stirred at 0° C. overnight. Tetrazole (0.45M in MeCN; 0.04 mL; 0.46 mmol) and di-tert-butyl diisopropylphosphoramidite (0.12 mL; 0.38 mmol) were added and stirring was pursued at rt overnight. Tetrazole (0.45M in MeCN; 0.08 mL; 0.92 mmol) and di-tert-butyl diisopropylphosphoramidite (0.24 mL; 0.76 mmol) was added at 0° C. and the mixture was stirred at 40° C. for 2 days. Then tetrazole (0.45M in MeCN; 0.04 mL; 0.46 mmol) and di-tert-butyl diisopropylphosphoramidite (0.12 mL; 0.38 mmol) was added at 0° C. and the reaction mixture was stirred at 40° C. over a weekend. The mixture was cooled to 0° C. and H$_2$O$_2$ (35%; 3.2 mL) was added slowly over 30 min. The reaction was stirred for 30 min at 0° C. Water (5 mL) was added. The aq. layer was extracted with EA (2×15 mL). The combined org. layers were washed with brine (10 mL), dried over MgSO$_4$ and filtered. The filtrate concentrated to dryness. After purification of the residue by CC (Hept-EA), the title compound was obtained as a white solid (0.067 g; 62% yield).
$^1$H NMR (500 MHz, CDCl$_3$) δ: 7.39-7.43 (m, 2H); 7.29-7.32 (m, 2H); 4.02 (d, J=5.5 Hz, 2H); 3.04 (s, 1H); 1.40 (s, 18H); 0.98-1.01 (m, 2H); 0.91-0.94 (m, 2H).

Preparation AJ: (1-(4-ethynylphenyl)cyclopropyl)methyl dimethylglycinate

To a solution of the compound of Preparation T (0.20 g; 1.18 mmol) in DCM (13 mL) were added N,N-dimethylglycine (0.13 g; 1.18 mmol), EDC (0.31 g; 1.6 mmol) and DMAP (0.19 g; 1.53 mmol). The reaction was stirred at rt for 27 h. A solution of aq. NaHCO$_3$ (5%; 5 mL) was added to the reaction mixture. The aq. layer was extracted with DCM (2×20 mL). The combined org. layers were dried over MgSO$_4$, filtered and concentrated to dryness. The residue was purified by CC (DCM-MeOH) to afford the title compound as a yellow oil (0.23 g; 76% yield).
$^1$H NMR (500 MHz, d$_6$-DMSO) δ: 7.37-7.41 (m, 2H); 7.26-7.30 (m, 2H); 4.21 (s, 2H); 4.13 (s, 1H); 3.10 (s, 2H); 2.17 (s, 6H); 0.97-1.01 (m, 2H); 0.90-0.94 (m, 2H).
MS (ESI, m/z): 258.07 [M+H$^+$] for C$_{16}$H$_{19}$NO$_2$; t$_R$=0.63 min.

Preparation AK: (3aR,5S,6aS)-5-(bromoethynyl)-2,2-dimethyltetrahydro-4H-cyclopenta[d][1,3]dioxole Starting from (3aR,5S,6aS)-5-(2,2-dibromoyinyl)-2,2-dimethyltetrahydro-4H-cyclopenta[d][1,3]dioxole (2.06 g; 6.32 mmol; prepared as described in WO 2013/170030) and proceeding in analogy to Preparation AE, step AE.v, the title compound was obtained as a yellow oil (1.37 g, 88% yield).
$^1$H NMR (500 MHz, CDCl$_3$) δ: 4.60-4.63 (m, 2H); 2.85-2.93 (m, 1H); 2.12-2.17 (m, 2H); 1.51-1.60 (overlapped m, 2H); 1.41 (s, 3H); 1.26 (s, 3H).

Preparation AL: tert-butyl (1-(iodoethynyl)cyclopropyl)carbamate

Starting from tert-butyl 1-ethynylcyclopropylcarbamate (0.855 g; 4.88 mmol; commercial) and proceeding in analogy to Preparation G (91% yield), the title compound was obtained as a yellow solid (1.36 g).
$^1$H NMR (500 MHz, CDCl$_3$) δ: 4.85-5.16 (br. s, 1H); 1.49 (s, 9H); 1.18-1.24 (m, 2H); 1.05-1.11 (m, 2H).

Preparation AM: (1S,3R)-3-(hydroxymethyl)-1-(3-iodoprop-2-yn-1-yl)cyclobutan-1-ol AM.i. (1S,3R)-3-(((tert-butyldiphenylsilyl)oxy)methyl)-1-(3-(trimethylsilyl)prop-2-yn-1-yl)cyclobutan-1-ol To a solution of 3-(((tert-butyldiphenylsilyl)oxy)methyl)cyclobutan-1-one (2 g; 3.54 mmol; prepared as described in WO 2006/063281) in dry THF (5.9 mL) at rt under nitrogen atmosphere, was added a solution of trimethyl(3-(4,4,5,5-tetramethyl-1,3,2-dioxaborolan-2-yl)prop-1-yn-1-yl)silane (1.27 g; 5.32 mmol; commercial) in dry THF (5.9 mL) followed by $ZnEt_2$ (15% in toluene; 0.73 mL; 1.06 mmol). The reaction was stirred at rt for 4 h. Water (10 mL) was added, carefully followed by aq. HCl (6M; 0.3 mL) and the reaction mixture was stirred for 15 min. The mixture was extracted with EA (3×15 mL). The combined org. layers were washed with brine (15 mL), dried over $Na_2SO_4$, filtered and the filtrate concentrated under reduced pressure. The residue was purified by CC (Hept.-EA) to afford the dirty desired product as a colourless oil (2 g; quant.).

$^1$H NMR (500 MHz, $d_6$-DMSO) δ: 7.59-7.63 (m, 4H); 7.41-7.49 (m, 6H); 5.09 (s, 1H); 3.62 (d, J=6.8 Hz, 2H); 2.31 (s, 2H); 1.88-1.99 (m, 3H); 1.22-1.31 (m, 2H); 1.00 (s, 9H); 0.07 (s, 9H).

MS1 (ESI, m/z): 451.0 [M+H$^+$] for $C_{27}H_{38}O_2Si_2$, $t_R$=1.14 min.

AM.ii. (1S,3R)-3-(hydroxymethyl)-1-(3-iodoprop-2-yn-1-yl)cyclobutan-1-ol

Starting from intermediate AM.i (crude; 2 g; 1.77 mmol) and proceeding successively in analogy to Preparation E, step E.iii (72% yield) and Preparation G (48% yield), the title compound was obtained, after purification by CC (Hept-EA), as a yellow oil (0.4 g) which crystallized.

$^1$H NMR (500 MHz, CDCl$_3$) δ: 3.69 (d, J=5.5 Hz, 2H); 2.71 (s, 2H); 2.29-2.35 (m, 2H); 2.15 (m, 1H); 1.89-1.95 (m, 2H).

MS1 (ESI, m/z): 266.95 [M+H$^+$] for $C_8H_{11}O_2I$; $t_R$=0.52 min.

Preparation AN: (41S,2S)-2-(bromoethynyl)-2-methylcyclopropyl)methoxy)(tert-butyl)diphenylsilane AN.i. ((1R,2R)-2-(hydroxymethyl)-1-methylcyclopropyl)methyl acetate To a solution of ((1R,2R)-2-formyl-1-methylcyclopropyl)methyl acetate (0.925 g; 5.92 mmol, prepared as described in WO 2012/154204) in MeOH (10 mL) was added NaBH$_4$ (0.297 g; 7.7 mmol) portion wise at 0° C. The reaction was stirred for 80 min at 0° C. then for 30 min at rt. Water (10 mL) and DCM (40 mL) were added and the phases were separated. The aq. layer was extracted with DCM-MeOH 9-1 (2×15 mL) and the combined org. layers were dried over Na$_2$SO$_4$ and filtered. The filtrate was concentrated to dryness to yield the title compound as a colourless oil (0.968 g; quant.).

$^1$H NMR (500 MHz, CDCl$_3$) δ: 3.89 (d, J=11.3 Hz, 1H); 3.82 (d, J=11.3 Hz, 1H); 3.74-3.80 (m, 1H); 3.49-3.56 (m, 1H); 2.08 (s, 3H); 1.19 (s, 3H); 1.09-1.15 (m, 1H); 0.70-0.76 (m, 1H); 0.27-0.31 (m, 1H).

AN.ii. ((1R,2R)-2-(((tert-butyldiphenylsilyl)oxy)methyl)-1-methylcyclopropyl)methyl acetate Starting from intermediate AN.i (0.94 g; 5.92 mmol) and TBDPSCl (1.6 mL; 6.03 mmol) and proceeding in analogy to Preparation P, step P.i, the title compound was obtained, after purification by CC (Hept-EA), as a colourless oil (2.29 g; 97% yield).

$^1$H NMR (500 MHz, CDCl$_3$) δ: 7.66-7.70 (m, 4H); 7.35-7.45 (m, 6H); 3.84 (s, 2H); 3.82-3.88 (overlapped m, 1H); 3.46-3.55 (m, 1H); 2.07 (s, 3H); 1.14 (s, 3H); 1.05 (s, 9H), 1.03-1.11 (overlapped m, 1H); 0.59-0.65 (m, 1H); 0.14-0.19 (m, 1H).

MS1 (ESI, m/z): 397.01 [M+H$^+$] for $C_{24}H_{32}O_3Si$; $t_R$=1.13 min.

AN.iii. ((1R,2R)-2-(((tert-butyldiphenylsilyl)oxy)methyl)-1-methylcyclopropyl)methanol To a solution of intermediate AN.ii (2.29 g; 5.77 mmol) in MeOH (50 mL) was added K$_2$CO$_3$ (1.59 g; 11.5 mmol). The suspension was stirred at rt for 4 h. The reaction mixture was filtered and the solid was washed with DCM. The filtrate was evaporated under reduced pressure. The residue was partitioned between water (30 mL) and DCM (40 mL). The aq. layer was extracted with DCM-MeOH 9-1 (40 mL) and EA-MeOH 9-1 (40 mL). The combined org. layers were dried over MgSO$_4$, filtered and evaporated under reduced pressure. The residue was purified by CC (Hept-EA) to afford the title compound as a colourless oil (1.59 g; 78% yield).

$^1$H NMR (500 MHz, CDCl$_3$) δ: 7.66-7.72 (m, 4H); 7.36-7.45 (m, 6H); 3.86 (dd, J=5.8, 11.1 Hz, 1H); 3.49 (dd, J=8.7, 11.1 Hz, 1H); 3.38 (d, J=11.0 Hz, 1H); 3.30 (d, J=11.0 Hz, 1H); 1.16 (s, 3H); 1.05 (s, 9H); 0.95-1.02 (m, 1H); 0.55 (dd, J=4.8, 9.0 Hz, 1H); 0.12-0.16 (m, 1H).

AN.iv. (((1R,2R)-2-(bromoethynyl)-2-methylcyclopropyl)methoxy)(tert-butyl)diphenylsilane Starting from intermediate AN.iii (1.59 g; 4.5 mmol) and proceeding successively in analogy to Preparation AE, step AE.iii (92% yield), Preparation N, step N.i (85% yield) and Preparation AE, step AE.v (98% yield), the title compound was obtained as a yellow oil (1.48 g).

$^1$H NMR (500 MHz, CDCl$_3$) δ: 7.65-7.72 (m, 4H); 7.36-7.46 (m, 6H); 3.79 (dd, J=5.6, 11.5 Hz, 1H); 3.49 (dd, J=8.4, 11.5 Hz, 1H); 1.43-1.51 (m, 1H); 1.25 (s, 3H); 1.05 (s, 9H); 1.02 (dd, J=4.7, 9.1 Hz, 1H); 0.37 (dd, J=4.7, 6.4 Hz, 1H).

Preparation AO: tert-butyl((3-(iodoethynyl)oxetan-3-yl)methoxy)diphenylsilane

AO.i. 3-(((tert-butyldiphenylsilyl)oxy)methyl)oxetane-3-carbaldehyde

Starting from oxetane-3,3-diyldimethanol (5 g; 42.3 mmol; commercial) and proceeding successively in analogy to Preparation AE, steps AE.i (95% yield) and AE.ii (90% yield), the title compound was obtained, after purification by CC (Hept-EA), as a colourless oil (12.87 g).

$^1$H NMR (500 MHz, $d_6$-DMSO) δ: 9.82 (s, 1H); 7.59-7.62 (m, 4H); 7.44-7.50 (m, 6H); 4.66 (d, J=6.3 Hz, 2H); 4.43 (d, J=6.3 Hz, 2H); 4.15 (s, 2H); 0.98 (s, 9H).

AO.ii. Tert-butyl((3-(iodoethynyl)oxetan-3-yl)methoxy)diphenylsilane

Starting from intermediate AO.i (2 g; 5.64 mmol) and proceeding successively in analogy to Preparation AG, step AG.ii (87% yield) and Preparation G (41% yield), the title compound was obtained, after purification by prep-HPLC (Method 3), as a colourless oil (0.94 g).

$^1$H NMR (500 MHz, d$_6$-DMSO) δ: 7.64-7.72 (m, 4H); 7.42-7.54 (m, 6H); 4.58 (d, J=5.8 Hz, 2H); 4.48 (d, J=5.8 Hz, 2H); 3.90 (s, 2H); 1.03 (s, 9H).

Preparation AP: 01S,2S)-2-(bromoethynyl)-1-methylcyclopropyl)methyl acetate

AP.i. (R,E)-3-(2,2-dimethyl-1,3-dioxolan-4-yl)-2-methylallyl acetate

To a solution of (R,E)-3-(2,2-dimethyl-1,3-dioxolan-4-yl)-2-methylprop-2-en-1-ol (1.4 g; 8.1 mmol; prepared as reported in Smith III et al., *Tetrahedron* (2009), 65(33), 6470-6488) in THF (48 mL) was added TEA (2.8 mL; 20.1 mmol). Then AcCl (1.2 mL; 16.5 mmol) was added dropwise over 10 min at 0° C. The reaction mixture was stirred at 0° C. for 2 h. The reaction mixture was poured into water (80 mL) and extracted with EA (3×50 mL). The combined org. layers were dried over MgSO$_4$, filtered and the filtrate removed under reduce pressure. The crude product was purified by CC (PE-EA) to afford the title compound as a colourless oil (1.64 g; 94% yield).

$^1$H NMR (500 MHz, CDCl$_3$) δ: 5.48-5.51 (m, 1H); 4.79-4.84 (m, 1H); 4.44-4.52 (m, 2H); 4.07-4.11 (m, 1H); 3.55 (t, J=8.0 Hz, 1H); 2.09 (s, 3H); 1.75 (d, J=1.3 Hz, 3H); 1.43 (s, 3H); 1.40 (s, 3H).

AP.ii. ((1S,2S)-24(R)-2,2-dimethyl-1,3-dioxolan-4-yl)-1-methylcyclopropyl)methyl acetate To a mechanically stirred solution of intermediate AP.i (1.64 g; 7.65 mmol) in toluene (102 mL), cooled to −25° C., was added dropwise ZnEt$_2$ (15% in toluene; 34.5 mL; 38.3 mmol) over 20 min, keeping IT below −20° C. Then diiodomethane (6.5 mL; 79.9 mmol) was added dropwise over 10 min, keeping IT below −20° C. The reaction mixture was stirred at −20° C. for 2 h, then allowed to slowly warm up to rt and stirred overnight. The reaction mixture was quenched with sat. aq. NH$_4$Cl (33 mL) and extracted with Et$_2$O (4×30 mL). The combined org. layers were washed with sat. aq. Na$_2$S$_2$O$_3$ (30 mL), water (30 mL) and brine (30 mL), then dried over MgSO$_4$ and filtered. After evaporation of the filtrate under reduced pressure, a yellow oil (22.4 g) was obtained. The crude product was purified by CC (PE-EA) to afford the title compound as a colourless oil (1.4 g; 80% yield).

$^1$H NMR (500 MHz, CDCl$_3$) δ: 4.09 (dd, J=5.9, 7.9 Hz, 1H); 3.89 (d, J=11.3 Hz, 1H); 3.77 (d, J=11.3 Hz, 1H); 3.70-3.76 (overlapped m, 1H); 3.61-3.66 (m, 1H); 2.07 (s, 3H); 1.45 (s, 3H); 1.36 (s, 3H); 1.13 (s, 3H); 0.85-0.95 (m, 2H); 0.56 (t, J=5.0 Hz, 1H).

AP.iii. ((1S,2S)-24(R)-1, 2-dihydroxyethyl)-1-methylcyclopropyl)methyl acetate A mixture of intermediate AP.ii (1.4 g; 6.1 mmol) in AcOH (80%; 14 mL) was stirred at rt for 23 h. The mixture was added to sat. aq. NaHCO$_3$ (100 mL; pH 6-7) and the aq. layer was extracted with DCM (3×60 mL). The combined org. layers were washed with water (10 mL) and brine (20 mL), dried over MgSO$_4$, filtered and concentrated to dryness. The residue was co-evaporated with cyclohexane. The crude was purified by CC (DCM-MeOH) to afford the title compound as a colourless oil (1 g; 87% yield).

$^1$H NMR (500 MHz, CDCl$_3$) δ: 3.89 (d, J=11.3 Hz, 1H); 3.74 (d, J=11.3 Hz, 1H); 3.68 (dd, J=3.4, 11.2 Hz, 1H); 3.57 (dd, J=7.4, 11.2 Hz, 1H); 3.33-3.39 (m, 1H); 2.07 (s, 3H); 1.16 (s, 3H); 0.89 (td, J=5.7, 9.0 Hz, 1H); 0.80 (dd, J=4.9, 8.8 Hz, 1H); 0.48 (t, J=5.3 Hz, 1H).

AP.iv. ((1S,2S)-2-formyl-1-methylcyclopropyl)methyl acetate

To a solution of intermediate AP.iii (1 g; 5.3 mmol) in THF (16.5 mL), water (3.4 mL) and sat. aq. NaHCO$_3$ (1.6 mL), cooled to 0° C., was added NaIO$_4$ (1.48 g; 6.9 mmol). The reaction mixture was stirred at 0° C. for 30 min, then filtered and washed with Et$_2$O. The aq. layer was extracted with Et$_2$O (3×40 mL). The combined org. layers were dried over MgSO$_4$, filtered and concentrated to dryness. The title compound was obtained as a colourless oil (0.81 g; 98% yield).

$^1$H NMR (500 MHz, CDCl$_3$) δ: 9.47 (d, J=4.7 Hz, 1H); 4.00 (d, J=11.4 Hz, 1H); 3.85 (d, J=11.4 Hz, 1H); 2.09 (s, 3H); 1.92-1.97 (m, 1H); 1.39 (t, J=5.3 Hz, 1H); 1.32 (s, 3H); 1.21 (dd, J=5.0, 8.3 Hz, 1H).

AP.v. ((1S,2S)-2-(bromoethynyl)-1-methylcyclopropyl)methyl acetate

Starting from intermediate AP.iv (0.81 g; 5.19 mmol) and proceeding successively in analogy to Preparation N, steps N.i (81% yield) and N.ii (62% yield), the title compound was obtained, after purification by CC (PE/TBME), as a colourless oil (0.6 g).

$^1$H NMR (500 MHz, CDCl$_3$) δ: 3.89 (d, J=11.4 Hz, 1H); 3.80 (d, J=11.4 Hz, 1H); 2.07 (s, 3H); 1.39 (dd, J=5.5, 8.9 Hz, 1H); 1.27 (s, 3H); 0.94 (dd, J=4.8, 8.9 Hz, 1H); 0.65 (t, J=5.1 Hz, 1H).

Preparation AQ: tert-butyl (2-((3-(iodoethynyl)cyclopentyl)amino)-2-oxoethyl)carbamate

AQ.i. Methyl 3-(2-((tert-butoxycarbonyl)amino)acetamido)cyclopentane-1-carboxylate To a solution of methyl 3-aminocyclopentane carboxylate hydrochloride (0.87 g; 4.58 mmol; commercial) in DMF (17 mL) were added successively HOBT (1.29 g; 9.26 mmol), TEA (2.2 mL; 15.8 mmol); Boc-Gly-OH (0.845 g; 4.82 mmol; commercial) and EDC (1.58 g; 8.14 mmol). The reaction mixture was diluted with DMF (6 mL) and the suspension was stirred at rt for 3 days. The reaction mixture was concentrated in vacuo and partitioned between water (20 mL) and EA (40 mL). The org. layer was washed with water (20 mL), aq. NaHSO$_4$ (15%; 20 mL), sat. aq. NaHCO$_3$ (20 mL) and brine (20 mL), dried over MgSO$_4$ and filtered. The filtrate was concentrated to dryness to give the title compound as a colourless oil (1.41 g; quant.).

$^1$H NMR (500 MHz, d$_6$-DMSO) δ: 7.78 (d, J=7.3 Hz, 1H); 6.86 (t, J=6.0 Hz, 1H); 3.60 (s, 3H); 3.47 (d, J=6.1 Hz, 2H); 2.76-2.85 (m, 1H); 2.08-2.16 (m, 1H); 1.77-1.87 (m, 3H); 1.54-1.62 (m, 1H); 1.41-1.48 (m, 1H); 1.33-1.39 (overlapped m, 1H); 1.37 (s, 9H).

MS1 (ESI, m/z): 301.05 [M+H⁺] for C₁₄H₂₄N₂O₅; t_R=0.67 min.

AQ.ii. Tert-butyl (2((3-(hydrozymethyl)cyclopentyl)amino)-2-oxoethyl)carbamate To a solution of intermediate AQ.i (1.38 g; 4.58 mmol) in THF (9 mL) was added DIBAH (1M in toluene; 19 mL) at 0° C. over 1.5 h, keeping IT below 5° C. The reaction mixture was stirred at rt overnight. The reaction mixture was quenched with the slow addition of water (11 mL) over 10 min. After 2 h stirring, the mixture was filtered through a Celite bed and the filtrate was evaporated under reduced pressure. The crude was purified by CC (DCM-MeOH) to afford the title compound as a white foam (0.604 g; 48% yield).

¹H NMR (500 MHz, d₆-DMSO) δ: 7.68 (d, J=7.4 Hz, 1H); 6.82 (t, J=5.9 Hz, 1H); 4.50 (t, J=5.2 Hz, 1H); 3.91-4.06 (m, 1H); 3.46 (d, J=6.1 Hz, 2H); 3.28-3.32 (m, 2H); 1.90-2.02 (m, 2H); 1.72-1.81 (m, 1H); 1.56-1.64 (m, 1H); 1.31-1.44 (overlapped m, 2H); 1.37 (s, 9H); 1.01-1.11 (m, 1H).

MS1 (ESI, m/z): 273.07 [M+H⁺] for C₁₃H₂₄N₂O₄; t_R=0.56 min.

AQ.iii. Tert-butyl (24(3-formylcyclopentyl)amino)-2-oxoethyl)carbamate

Starting from intermediate AQ.ii (0.604 g; 2.22 mmol) and proceeding in analogy to Preparation AE, step AE.iii, the title compound was obtained, after purification by CC (DCM-MeOH), as a yellow oil (0.483 g; 81% yield).

MS1 (ESI, m/z): 271.09 [M+H⁺] for C₁₃H₂₂N₂O₄; t_R=0.59 min.

AQ.iv. Tert-butyl (2-((3-(iodoethynyl)cyclopentyl)amino)-2-oxoethyl)carbamate Starting from intermediate AQ.iii (0.483 g; 1.79 mmol) and proceeding successively in analogy to Preparation AG, step AG.ii (87% yield) and Preparation G (90% yield), the title compound was obtained, after purification by CC (DCM-MeOH), as a yellow foam (0.55 g; 1-1 cis-trans mixture).

¹H NMR (500 MHz, CDCl₃) δ: 6.13-6.20 (m, 0.5H); 6.01-6.08 (m, 0.5H); 5.08 (br. s, 1H); 4.26-4.41 (m, 1H); 3.75 (d, J=5.3 Hz, 1H); 3.72 (d, J=5.9 Hz, 1H); 2.88-3.00 (m, 1H); 2.26-2.33 (m, 0.5H); 2.16-2.24 (m, 0.5H); 1.99-2.12 (m, 0.5H); 1.90-1.98 (m, 0.5H); 1.67-1.88 (m, 2H); 1.54-1.66 (overlapped m, 1H); 1.36-1.49 (overlapped m, 1H); 1.47 (s, 4.5H); 1.45 (s, 4.5H).

MS1 (ESI, m/z): 392.88 [M+H⁺] for C₁₄H₂₁N₂O₃I; t_R=0.80 min.

Preparation AR: (S)-4-((1R,2R)-2-(bromoethynyl)cyclopropyl)-2,2-dimethyl-1,3-dioxolane Starting from (1R,2R)-2-((S)-2,2-dimethyl-1,3-dioxolan-4-yl)cyclopropane-1-carbaldehyde (1 g; 5.88 mmol; prepared as described in Mohapatra et al., *Tetrahedron Lett.* (2012), 53(49), 6718-6720) and proceeding successively in analogy to Preparation N, step N.i (79% yield) and Preparation AE, step AE.v (92% yield), the title compound was obtained, after purification by CC (PE-TBME), as a yellow oil (1.05 g).

¹H NMR (500 MHz, CDCl₃) δ: 4.08-4.13 (m, 1H); 3.72-3.77 (m, 1H); 3.63-3.68 (m, 1H); 1.41 (s, 3H); 1.20-1.35 (overlapped m, 2H); 1.32 (s, 3H); 0.83-1.00 (m, 2H).

Preparation AS: tert-butyl a/R,2R)-2-(iodoethynyl)cyclopropyl)methyl)carbamate Starting from tert-butyl (((1R,2R)-2-formylcyclopropyl)methyl)carbamate (0.56 g; 2.81 mmol; commercial) and proceeding successively in analogy to Preparation AG, step AG.ii (quant.) and Preparation G (87% yield), the title compound was obtained as a yellow oil (0.746 g).

¹H NMR (500 MHz, CDCl₃) δ: 4.64 (br. s, 1H); 3.08-3.17 (m, 1H); 2.90-2.97 (m, 1H); 1.44 (s, 9H); 1.30-1.38 (m, 1H); 1.24-1.30 (m, 1H); 0.90-0.95 (m, 1H); 0.68-0.74 (m, 1H).

Preparation AT: ((1-(bromoethynyl)cyclobutyl)methoxy)(tert-butyl)diphenylsilane Starting from cyclobutane-1,1-diyldimethanol (3.03 g; 24.8 mmol; commercial) and proceeding successively in analogy to Preparation AE, steps AE.ii (98% yield) and AE.iii (86% yield), Preparation N, step N.i (93% yield) and Preparation AE, step AE.v (quant.), the title compound was obtained as a colourless oil (4.79 g).

¹H NMR (500 MHz, CDCl₃) δ: 7.70-7.74 (m 4H); 7.40-7.48 (m, 6H); 3.67 (s, 2H); 2.18-2.29 (m, 4H); 2.00-2.08 (m, 1H); 1.86-1.95 (m, 1H); 1.11 (s, 9H).

Preparation AU: (4/R,2R)-2-(bromoethynyl)-2-fluorocyclopropyl)methoxy)(tert-butyl)diphenylsilane

AU.i. ((1R,2R)-2-(((tert-butyldiphenylsilyl)oxy)methyl)-1-fluorocyclopropyl)methanol To a solution of ethyl (1R,2R)-2-0(tert-butyldiphenylsilyl)oxy)methyl)-1-fluorocyclopropane-1-carboxylate (0.5 g; 1.25 mmol; prepared as described in Sakagami et al., *Bioorg. Med. Chem.* (2008), 16(8), 4359-4366) in THF (9 mL), cooled to −78° C., was added dropwise LiBH₄ (2M in THF; 2.2 mL; 4.4 mmol). The reaction mixture was allowed to reach rt and stirred at rt for 24 h. MeOH (2 mL) was carefully added, the reaction mixture was stirred for 20 min, concentrated to dryness and partitioned between water (10 mL) and DCM (15 mL). The aq. layer was extracted with DCM (2×10 mL). The combined org. layers were dried over Na₂SO₄ and filtered. After concentration of the filtrate to dryness, the title compound was obtained as a colourless oil (0.429 g; 96% yield).

¹H NMR (500 MHz, CDCl₃) δ: 7.66-7.72 (m, 4H); 7.36-7.45 (m, 6H); 3.89 (ddd, J=1.6, 6.0, 11.0 Hz, 1H); 3.80-3.83 (m, 1H); 3.70-3.78 (m, 2H); 1.74 (t, J=6.4 Hz, 1H); 1.24-1.33 (m, 1H); 1.05 (s, 9H); 0.79-0.88 (m, 2H).

MS1 (ESI, m/z): 358.95 [M+H⁺] for C₂₁H₂₇O₂FSi; t_R=1.01 min.

AU.ii. (((1R,2R)-2-(bromoethynyl)-2-fluorocyclopropyl)methoxy)(tert-butyl)diphenylsilane Starting from intermediate AU.i (2.04 g; 5.7 mmol) and proceeding successively in analogy to Preparation AE, step AE.iii (83% yield), Preparation N, step N.i (17% yield) and Preparation AE, step AE.v (99% yield), the title compound was obtained as a brown oil (0.351 g).

¹H NMR (500 MHz, CDCl₃) δ: 7.66-7.70 (m 4H); 7.36-7.45 (m, 6H); 3.84 (ddd, J=1.6, 5.8, 11.3 Hz, 1H); 3.71 (ddd, J=1.1, 8.0, 11.3 Hz, 1H); 1.56-1.64 (m, 1H); 1.14-1.20 (m, 1H); 1.06 (s, 9H); 0.98-1.04 (m, 1H).

Preparation AV: 3-iodo-N,N-dimethylprop-2-yn-1-amine

Starting from N,N-dimethylprop-2-yn-1-amine (1 g; 12 mmol; commercial) and proceeding in analogy to Preparation G, the title compound was obtained as a yellow solid (0.746 g; 56% yield).

$^1$H NMR (500 MHz, CDCl$_3$) δ: 3.45 (s, 2H); 2.33 (s, 6H).

Preparation AW: tert-butyl 4-(iodoethynyl)piperidine-1-carboxylate

Starting from tert-butyl 4-ethynylpiperidine-1-carboxylate (0.952 g; 4.55 mmol; commercial) and proceeding in analogy to Preparation G, the title compound was obtained as a yellow solid (1.51 g; 99% yield).

$^1$H NMR (500 MHz, CDCl$_3$) δ: 3.62-3.74 (m, 2H); 3.14-3.23 (m, 2H); 2.70-2.78 (m, 1H); 1.72-1.80 (m, 2H); 1.55-1.63 (m, 2H); 1.45 (s, 9H).

MS1 (ESI, m/z): 335.85 [M+H$^+$] for C$_{12}$H$_{18}$NO$_2$I; t$_R$=0.93 min.

Preparation AX: ((1R,2R)-2-(bromoethynyl)-1-fluorocyclopropyl)methyl acetate

AX.i. ((1R,2R)-2-(((tert-butyldiphenylsilyl)oxy)methyl)-1-fluorocyclopropyl)methyl acetate Starting from intermediate AU.i (2.12 g; 5.91 mmol) and proceeding in analogy to Preparation AP, step AP.i, the crude product was obtained as a yellow oil (2.3 g).

$^1$H NMR (500 MHz, CDCl$_3$) δ: 7.66-7.71 (m, 4H); 7.36-7.45 (m, 6H); 4.27-4.35 (m, 2H); 3.90 (ddd, J=1.6, 5.8, 11.0 Hz, 1H); 3.69 (ddd, J=1.2, 8.3, 11.0 Hz, 1H); 2.11 (s, 3H); 1.31-1.40 (m, 1H); 1.06 (s, 9H); 0.80-0.94 (m, 2H).

MS1 (ESI, m/z): 400.98 [M+H$^+$] for C$_{12}$H$_{18}$NO$_2$; t$_R$=1.09 min.

AX.ii. ((JR, 2R)-1-fluoro-2-(hydroxymethyl)cyclopropyl)methyl acetate

To a solution of intermediate AX.i (2.16 g; 5.39 mmol) in THF (10 mL) was added TBAF (1M in THF; 7 mL). The reaction mixture was stirred at rt for 1 h. The reaction mixture was concentrated in vacuo and purified by CC (DCM-MeOH) to afford the title alcohol as a yellow oil (0.726 g; 83% yield).

$^1$H NMR (500 MHz, CDCl$_3$) δ: 4.27-4.41 (m, 2H); 3.94 (m, 1H); 3.64 (m, 1H); 2.13 (s, 3H); 1.51 (m, 1H); 1.41 (m, 1H); 0.98-1.06 (m, 2H).

AX.iii. ((1R,2R)-2-(bromoethynyl)-1-fluorocyclopropyl)methyl acetate

Starting from intermediate AX.ii (0.725 g; 4.46 mmol) and proceeding successively in analogy to Preparation AE, step AE.iii (100% yield), Preparation N, step N.i (52% yield) and Preparation AE, step AE.v (57% yield), the title compound was obtained as a colourless oil (0.351 g).

$^1$H NMR (500 MHz, CDCl$_3$) δ: 6.21 (dd, J=1.3, 8.8 Hz, 1H); 4.32-4.38 (m, 2H); 2.14 (s, 3H); 1.90-1.98 (m, 1H); 1.22-1.35 (m, 2H).

Preparation AY: 2-hydroxy-1-(4-(iodoethynyl)piperidin-1-yl)ethan-1-one

AY.i. 1-(4-ethynylpiperidin-1-yl)-2-hydroxyethan-1-one

To a solution of 4-ethynylpiperidine hydrochloride (0.720 g; 4.94 mmol; commercial) in MeCN (9.5 mL) and DMF (4.5 mL) was added TEA (3 mL; 21.5 mmol), EDC (1.17 g; 5.97 mmol), HOBT (0.935 g, 6.71 mmol) and glycolic acid (0.425 g; 5.54 mmol). The reaction mixture was stirred at rt for 20 h. The solvent was removed under reduced pressure. The residue was diluted with water (15 mL) and EA (15 mL). The two phases were separated and the aq. layer was extracted with EA (3×15 mL). The combined org. layers were washed with NaHCO$_3$ (30 mL) and brine (30 mL), dried over MgSO$_4$ and concentrated to dryness. The residue was purified by CC (DCM-MeOH) to afford the title compound as a white solid (0.569 g).

$^1$H NMR (300 MHz, DMSO-d6) δ: 4.44 (t, J=5.4 Hz, 1H); 4.05 (d, J=5.3 Hz, 2H); 3.80 (m, 1H); 3.47 (m, 1H); 3.05-3.18 (m, 2H); 2.95 (d, J=2.4 Hz, 1H); 2.65 (m, 1H); 1.66-1.81 (m, 2H); 1.31-1.53 (m, 2H).

AY.ii. 2-hydroxy-1-(4-(iodoethynyl)piperidin-1-yl)ethan-1-one

Starting from intermediate AY.i (0.255 g; 1.52 mmol; commercial) and proceeding in analogy to Preparation G, the title compound was obtained as a yellow solid (0.400 g; 90% yield).

MS1 (ESI, m/z): 293.84 [M+H$^+$] for C$_9$H$_{12}$NO$_2$I; t$_R$=0.63 min.

Preparation AZ: 3-(3-iodoprop-2-yn-1-yl)oxetan-3-ol

A flask charged with ZnBr$_2$ (1.08 g, 4.80 mmol) and Mg turnings (5.85 g) was heated with stirring under vacuum at 150° C. for 2 h and then cooled to rt. Et$_2$O (90 mL) and a few drops of 1,2-dibromoethane were added. Propargyl bromide (9 mL; 118.78 mmol) in Et$_2$O (70 mL) was then added dropwise. The mixture was stirred at the same temperature for 1 h. In a separate flask were introduced 3-oxetanone (3.15 g; 43.71 mmol) and THF (420 mL). The Grignard reagent solution (127 mL; 65.56 mmol), cannulated in a graduated addition funnel, was added dropwise. The solution was stirred at the same temperature for 1 h and diluted with sat. aq. NH$_4$Cl and Hex (100 mL). The two layers were separated and the aq. layer was extracted with Hex (100 mL). The combined org. layers were dried over MgSO$_4$, filtered and concentrated under reduced pressure. Starting from the crude intermediate thus obtained (4.33 g; 38.63 mmol) and proceeding in analogy to Preparation G, the title compound was obtained as a yellow solid (3.01 g; 33% yield).

$^1$H NMR (500 MHz, CDCl$_3$) δ: 4.51 (d, J=7.4 Hz, 2H); 4.66 (d, J=7.1 Hz, 2H); 2.98 (s, 2H); 2.55 (s, 1H).

Preparation BA: 2-hydroxy-1-(3-(iodoethynyl)azetidin-1-yl)ethan-1-one

BA.i. 3-ethynylazetidine hydrochloride

A solution of tert-butyl 3-ethynylazetidine-1-carboxylate (1.34 g; 7.37 mmol) in 4N HCl in dioxane (19 mL) was stirred at rt for 1.5 h. The reaction mixture was concentrated to dryness to give the title compound as a white solid (0.865 g; quant.).
$^{1}$H NMR (500 MHz, CDCl$_3$) δ: 10.09 (br. s, 1H); 9.80 (br. s, 1H); 4.13-4.28 (m, 4H); 3.77 (m, 1H); 2.42 (d, J=2.4 Hz, 1H).

BA.ii. 2-hydroxy-1-(3-(iodoethynyl)azetidin-1-yl)ethan-1-one

Starting from intermediate BA.i (0.865 g; 7.37 mmol) and proceeding in analogy to Preparation AY, the title compound was obtained as a brown solid (0.142 g; 31% yield).
$^{1}$H NMR (500 MHz, CDCl$_3$) δ: 4.26-4.38 (m, 2H); 4.07-4.18 (m, 2H); 3.97-4.06 (m, 2H); 3.67 (m, 1H); 3.02 (br. s, 1H).
MS1 (ESI, m/z): 265.86 [M+H$^+$] for C$_7$H$_8$NO$_2$I; t$_R$=0.71 min.

Preparation BB: tert-butyl (5-iodo-2-methylpent-4-yn-2-yl)carbamate

Starting from tert-butyl (2-methyl-4-oxobutan-2-yl)carbamate (0.51 g; 2.57 mmol) and proceeding successively in analogy to Preparation AG, step AG.ii (93% yield) and Preparation G (96% yield), the title compound was obtained as a crude yellowish oil (0.74 g).
$^{1}$H NMR (500 MHz, CDCl$_3$) δ: 4.59 (s, 1H); 2.80 (s, 2H); 1.48 (s, 9H); 1.35 (s, 6H).

Preparation BC: tert-butyl (2-(4-(iodoethynyl)piperidin-1-yl)-2-oxoethyl)carbamate Starting from tert-butyl (2-(4-ethynylpiperidin-1-yl)-2-oxoethyl)carbamate (1.14 g; 4.29 mmol, prepared as described in WO 03/051797) and proceeding in analogy to Preparation G, the title compound was obtained as a crude yellowish oil (1.56 g; 93% yield).
$^{1}$H NMR (500 MHz, CDCl$_3$) δ: 6.70 (M, 1H); 3.80 (m, 1H); 3.74-3.76 (m, 2H); 3.55 (m, 1H); 3.15 (m, 1H); 3.03 (m, 1H); 2.80 (m, 1H); 1.68-1.80 (m, 2H); 1.38-1.50 (m, 2H); 1.37 (s, 9H).
MS1 (ESI, m/z): 392.87 [M+H$^+$] for C$_{14}$H$_{21}$N$_2$O$_3$I; t$_R$=0.82 min.

Preparation BD: tert-butyl (2-(3-(bromoethynyl)azetidin-1-yl)-2-oxoethyl)carbamate BD.i. Tert-butyl (2-(3-ethynylazetidin-1-yl)-2-oxoethyl)carbamate Starting from intermediate BA.i (0.406 g; 3.45 mmol) and Boc-Gly-OH (0.641 g; 3.66 mmol) and proceeding in analogy to Preparation AY, step AY.i, the title compound was obtained as a yellowish oil which crystallized on standing (0.535 g; 65% yield).
$^{1}$H NMR (500 MHz, CDCl$_3$) δ: 5.24 (s, 1H); 4.36 (t, J=8.5 Hz, 1H); 4.29 (t, J=9.1 Hz, 1H); 4.13 (m, 1H); 4.05 (dd, J=6.4, 9.3 Hz, 1H); 3.71-3.75 (m, 2H); 3.45 (m, 2H); 2.33 (d, J=2.5 Hz, 1H); 1.44 (s, 9H).
MS1 (ESI, m/z): 239.13 [M+H$^+$] for C$_{12}$H$_{18}$N$_2$O$_3$; t$_R$=0.63 min.

BD.ii. Tert-butyl (2-(3-(bromoethynyl)azetidin-1-yl)-2-oxoethyl)carbamate

To a stirring solution of intermediate BD.i (0.206 g; 0.87 mmol) and NBS (0.185 g; 1.04 mmol) in acetone (3.4 mL) was added AgNO$_3$ (0.15 g; 0.09 mmol). The mixture was stirred at rt for 2 h. After filtration and evaporation of solvent under reduced pressure, the crude (0.44 g) was purified by CC (Hept-EA) to give the title compound as a white solid (0.214 g; 78% yield).
$^{1}$H NMR (500 MHz, CDCl$_3$) δ: 5.24 (br. s, 1H); 4.34 (t, J=8.5 Hz, 1H); 4.27 (t, J=9.2 Hz, 1H); 4.14 (m, 1H); 4.04 (dd, J=6.3, 9.3 Hz, 1H); 3.72 (t, J=5.2 Hz, 2H); 3.47 (m, 1H); 1.44 (s, 9H).
MS1 (ESI, m/z): 318.89 [M+H$^+$] for C$_{12}$H$_{17}$N$_2$O$_3$Br; t$_R$=0.73 min.

Preparation BE: tert-butyl (1-(3-(iodoethynyl)azetidin-1-yl)-2-methyl-1-oxopropan-2-yl)carbamate BE.i. Tert-butyl (1-(3-ethynylazetidin-1-yl)-2-methyl-1-oxopropan-2-yl)carbamate Starting from intermediate BA.i (0.235 g; 2 mmol) and 2-((tert-butoxycarbonyl)amino)-2-methylpropanoic acid (0.429 g; 2.11 mmol), and proceeding in analogy to Preparation AY, step AY.i, the title compound was obtained as a white solid (0.29 g; 54% yield).
$^{1}$H NMR (500 MHz, CDCl$_3$) δ: 4.93 (br. s, 1H); 3.94-4.60 (m, 4H); 3.32-3.40 (m, 1H); 2.29 (d, J=2.4 Hz, 1H); 1.58 (s, 3H); 1.40-1.52 (m, 12H). MS1 (ESI, m/z): 267.1 [M+H$^+$] for C$_{14}$H$_{22}$N$_2$O$_3$; t$_R$=0.67 min.

BE.ii. Tert-butyl (1-(3-(iodoethynyl)azetidin-1-yl)-2-methyl-1-oxopropan-2-yl)carbamate Starting from intermediate BE.i (0.288 g; 1.05 mmol) and proceeding in analogy to Preparation G, the title compound was obtained as a white solid (0.367 g; 88% yield).
$^{1}$H NMR (500 MHz, CDCl$_3$) δ: 4.84-5.01 (br. s, 1H); 3.94-4.55 (m, 4H); 3.46-3.53 (m, 1H); 1.40-1.51 (m, 15H).
MS1 (ESI, m/z): 392.7 [M+H$^+$] for C$_{14}$H$_{21}$N$_2$O$_3$I; t$_R$=0.76 min.

REFERENCE EXAMPLES

Reference Example 1: (RS)—N-hydroxy-2-methylsulfonyl-2-methyl-4-{5-[4-(3-morpholin-4-yl-propoxy)-phenyl]-indazol-2-yl}-butanamide formic acid salt Starting from the compound of Preparation A (0.088 g; 0.19 mmol) and 4-[3-[4-(4,4,5,5-tetramethyl-1,3,2-dioxaborolan-2-yl)phenoxy]propyl]morpholine (0.068 g; 0.19 mmol; commercial), and proceeding in analogy to Example 1, steps 1.i and 1.ii (Suzuki coupling: 33% yield; deprotection using aq. TFA (50%, 0.5 mL) instead of PPTS/MeOH: 39% yield), the title compound was obtained, after purification by prep-HPLC (Method 1), as an off-white foam (0.013 g).
$^{1}$H NMR (d6-DMSO) δ: 11.0 (s, 1H); 9.61 (br. s, 1H); 9.24 (br. s, 1H); 8.41 (s, 1H); 7.86 (s, 1H); 7.58-7.67 (m, 3H); 7.52 (dd, J=1.7, 9.1 Hz, 1H); 7.02 (d, J=8.8 Hz, 2H); 4.48-4.60 (m, 1H); 4.29-4.40 (m, 1H); 4.06-4.13 (m, 2H); 3.94-4.03 (m, 2H); 3.57-3.69 (m, 2H); 3.35-3.52 (m, 4H); 3.05-3.17 (overlapped m, 2H); 3.05 (s, 3H); 2.78-2.90 (m, 1H); 2.35-2.44 (overlapped m, 1H); 2.08-2.19 (m, 2H); 1.50 (s, 3H).
MS1 (ESI, m/z): 531.2 [M+H$^+$] for C$_{27}$H$_{36}$N$_4$O$_8$S; t$_R$=0.55 min.

Reference Example 2: (RS)—N-hydroxy-2-methyl-sulfonyl-2-methyl-4-{5-[4-(2-morpholin-4-yl-ethoxy)-phenyl]-indazol-2-yl}-butanamide formic acid salt Starting from the compound of Preparation A (0.087 g, 0.18 mmol) and 4-[2-[4-(4,4,5,5-tetramethyl-1,3,2-dioxaborolan-2-yl)phenoxy]ethyl]morpholine (0.064 g, 0.19 mmol; commercial), and proceeding in analogy to Example 1, steps 1.i and 1.ii, the title compound was obtained, after purification by prep-HPLC (Method 1), as an off-white foam (0.025 g; Suzuki coupling: 35% yield; deprotection using aq. TFA (50%, 0.5 mL) instead of PPTS/MeOH: 77% yield).

$^1$H NMR (d6-DMSO) δ: 11.0 (s, 1H); 9.96 (br. s, 1H); 9.25 (br. s, 1H); 8.42 (s, 1H); 7.87 (s, 1H); 7.62-7.68 (m, 3H); 7.52 (dd, J=1.7, 9.1 Hz, 1H); 7.09 (d, J=8.8 Hz, 2H); 4.48-4.60 (m, 1H); 4.29-4.40 (m, 3H); 3.33-3.77 (m, 8H); 3.05-3.17 (overlapped m, 2H); 3.05 (s, 3H); 2.78-2.90 (m, 1H); 2.35-2.44 (overlapped m, 1H); 1.50 (s, 3H).

MS1 (ESI, m/z): 517.2 [M+H$^+$] for C$_{26}$H$_{34}$N$_4$O$_8$S; t$_R$=0.53 min.

Reference Example 3: (RS)-4-{5-[2-fluoro-4-(2-morpholin-4-yl-ethoxy)-phenyl]-indazol-2-yl}-N-hydroxy-2-methylsulfonyl-2-methyl-butanamide formic acid salt Starting from the compound of Preparation A (0.097 g, 0.2 mmol) and 4-[2-[3-fluoro-4-(4,4,5,5-tetramethyl-1,3,2-dioxaborolan-2-yl)phenoxy] ethyl]-morpholine (0.075 g, 0.21 mmol; commercial), and proceeding in analogy to Example 1, steps 1.i and 1.ii, the title compound was obtained, after purification by prep-HPLC (Method 1), as an off-white foam (0.025 g; Suzuki coupling: 63% yield; deprotection using aq. TFA (50%, 0.5 mL) instead of PPTS/MeOH: 42% yield).

$^1$H NMR (d6-DMSO) δ: 11.0 (s, 1H); 9.96 (br. s, 1H); 9.28 (br. s, 1H); 8.42 (s, 1H); 7.78 (s, 1H); 7.66 (d, J=8.9 Hz, 1H); 7.51 (t, J=8.9 Hz, 1H); 7.33-7.38 (m, 1H); 6.91-7.06 (m, 2H); 4.48-4.61 (m, 1H); 4.31-4.45 (m, 3H); 3.35-3.82 (m, 8H); 3.06-3.18 (overlapped m, 2H); 3.05 (s, 3H); 2.78-2.89 (m, 1H); 2.35-2.45 (overlapped m, 1H); 1.50 (s, 3H).

MS1 (ESI, m/z): 535.1 [M+H$^+$] for C$_{26}$H$_{33}$N$_4$O$_8$FS; t$_R$=0.55 min.

Reference Example 4: (RS)-4-(5-but-2-ynyloxy-indazol-2-yl)-N-hydroxy-2-methylsulfonyl-2-methyl-butanamide

RE4.i. Rac-1-(tetrahydro-pyran-2-yl)-1H-indazol-5-ol

To a solution of 1H-indazol-5-ol (2.0 g; commercial) in THF (20 mL) and DCM (20 mL) were added 3,4-dihydro-2H-pyran (1.4 mL) in DCM (4 mL) and MsOH (0.1 mL). The reaction mixture was stirred at rt overnight. The reaction mixture was diluted with DCM and washed with aq. 10% NaHSO$_4$. The aq. layer was extracted with DCM. The combined org. layers were dried over MgSO$_4$, filtered, concentrated under reduced pressure. After purification by CC (DCM-MeOH), the title compound was obtained as a non pure reddish oil (2.74 g, 84% yield), still contained with an unknown compound.

$^1$H NMR (d6-DMSO) δ: 9.11 (s, 1H); 8.15 (s, 1H); 7.42-7.46 (m, 1H); 6.78-6.87 (m, 2H); 5.61 (dd, J=2.5, 9.5 Hz, 1H); 3.89-3.97 (m, 1H); 3.61-3.74 (m, 1H); 1.86-2.04 (m, 2H); 1.63-1.80 (m, 2H); 1.50-1.60 (m, 2H).

RE4.ii. (RS)-5-but-2-ynyloxy-2-(tetrahydro-pyran-2-yl)-2H-indazole and (RS)-5-but-2-ynyloxy-1-(tetrahydro-pyran-2-yl)-1H-indazole A suspension of intermediate RE4.i (2.7 g, 12.6 mmol), K$_2$CO$_3$ (2.1 g, 15.3 mmol) and 1-bromo-2-butyne (1.1 mL, 12.6 mmol) in acetone (10 mL) was refluxed overnight. The reaction mixture was filtered off, the filtrate was evaporated under reduced pressure and purified by CC (Hept-EA) to afford the title compound as a yellow oil (1.95 g, 57% yield).

MS1 (ESI, m/z): 271.1 [M+H$^+$] for C$_{16}$H$_{18}$N$_2$O$_2$; t$_R$=0.87 min.

RE4.iii. 5-but-2-ynyloxy-1H-indazole

A solution of intermediate RE4.ii (1.95 g) in DCM (56 mL) and TFA (14 mL) was stirred at rt for 2 h. The reaction mixture was evaporated to dryness and the residue was taken up in DCM and washed with sat. aq. NaHCO$_3$ (to adjust pH at 7). The aq. layer was extracted with DCM. The combined org. layers were washed with brine, dried over MgSO$_4$, filtered and concentrated under reduced pressure. The residue was purified by CC (Hept-EA) to afford the title compound as a brown oil (2.20 g).

MS1 (ESI, m/z): 187.3 [M+H$^+$] for C$_{11}$H$_{10}$N$_2$O; t$_R$=0.73 min.

RE4.iv. 2-(5-but-2-ynyloxy-indazol-1-yl)-ethanol

Starting from intermediate RE4.iii (2.25 g) and ethylene carbonate (2.13 g), and proceeding in analogy to Preparation A, step A.i, Variant I, the title compound was obtained, after purification by CC (Hept-EA), in 1-1 mixture with the 1-indazole regioisomer (brown oil; 1.11 g; 40% yield).

MS1 (ESI, m/z): 231.2 [M+H$^+$] for C$_{13}$H$_{14}$N$_2$O$_2$; t$_R$=0.66 min and 0.69 min (2 regioisomers).

RE4.v. Methanesulfonic acid 2-(5-but-2-ynyloxy-indazol-2-yl)-ethyl ester

Starting from intermediate RE4.iv (1.11 g) and MsCl (0.49 mL), and proceeding in analogy to Preparation A, step A.ii, the title compound was obtained, after purification by CC (Hept-EA), in mixture with some 1-indazole derivative (yellow oil; 0.37 g; 25% yield).

MS1 (ESI, m/z): 308.9 [M+H$^+$] for C$_{14}$H$_{16}$N$_2$O$_4$S; t$_R$=0.76 min.

RE4.vi. 5-but-2-ynyloxy-2-(2-iodo-ethyl)-2H-indazole

Starting from intermediate RE4.v (0.37 g) and NaI (0.32 g), and proceeding in analogy to Preparation A, step A.iii, the title compound was obtained, after purification by CC (Hept-EA), in mixture with some 1-indazole regioisomer (yellow oil; 0.24 g; 58% yield).

MS1 (ESI, m/z): 340.8 [M+H$^+$] for C$_{13}$H$_{13}$N$_2$OI; t$_R$=0.85 min.

RE4.vii. (RS)-4-(5-but-2-ynyloxy-indazol-2-yl)-2-methylsulfonyl-2-methyl-butanoic acid ethyl ester Starting from intermediate RE4.vi (0.24 g) and 2-(methylsulfonyl)-propanoic acid ethyl ester (0.14 g; commercial), and proceeding in analogy to Preparation A, step A.v, the title compound was obtained, after purification by CC (Hept-EA), in mixture with some 1-indazole derivative (yellow oil; 0.137 g; 50% yield).

MS1 (ESI, m/z): 393.2 [M+H$^+$] for $C_{19}H_{24}N_2O_5S$; $t_R$=0.82 min.

RE4.viii. (RS)-4-(5-but-2-ynyloxy-indazol-2-yl)-N-hydroxy-2-methylsulfonyl-2-methyl-butanamide Starting from intermediate RE4.vii (0.137 g), and proceeding successively in analogy to Preparation A, step A.vi (35% yield) and Example 1, step 1.ii (62% yield), the title compound was obtained, after purification by prep-HPLC (Method 2), as a colourless solid (0.03 g).

$^1$H NMR (d6-DMSO) δ: 11.0 (br. s, 1H); 9.24 (s, 1H); 8.23 (s, 1H); 7.50 (d, J=9.3 Hz, 1H); 7.04 (d, J=2.3 Hz, 1H); 6.90 (dd, J=2.4 Hz, 1H); 4.67-4.71 (m, 2H); 4.40-4.52 (m, 1H); 4.22-4.33 (m, 1H); 3.04 (s, 3H); 2.74-2.85 (m, 1H); 2.30-2.40 (m, 1H); 1.82 (t, J=2.3 Hz, 3H); 1.48 (s, 3H).

MS1 (ESI, m/z): 380.0 [M+H$^+$] for $C_{17}H_{21}N_3O_5S$; $t_R$=0.66 min.

Reference Example 5: (RS)—N-hydroxy-2-methylsulfonyl-2-methyl-4-(5-phenethyl-indazol-2-yl)-butanamide

RE5.i. (RS)-(E)-3-methyl-3-(methylsulfonyl)-5-(5-styryl-2H-indazol-2-yl)-N-((tetrahydro-2H-pyran-2-yl)oxy)butanamide Starting from the compound of Preparation A (0.107 g, 0.205 mmol) and trans-2-phenylvinylboronic acid (0.035 g; commercial), and proceeding in analogy to Example 1, step 1.i, the title compound was obtained, after purification by CC (Hept-EA), as a white foam (0.086 g, 85% yield).

MS1 (ESI, m/z): 498.2 [M+H$^+$] for $C_{26}H_{31}N_3O_5S$; $t_R$=0.90 min.

RE5.ii. (RS)-3-methyl-3-(methylsulfonyl)-5-(5-phenethyl-2H-indazol-2-yl)-N-((tetrahydro-2H-pyran-2-yl)oxy)butanamide A suspension of intermediate RE5.i (0.102 g) and 10% Pd/C (0.030 g) in EtOH (2 mL) and THF (3 mL) was stirred under hydrogen atmosphere for 14 h at rt. The catalyst was filtered off, thoroughly washed with EA (2×) and the filtrate was evaporated under reduced pressure to give the title compound as a grey gum (0.095 g; 93% yield).

MS1 (ESI, m/z): 500.2 [M+H$^+$] for $C_{26}H_{33}N_3O_5S$; $t_R$=0.90 min.

RE5.iii. (R)—N-hydroxy-2-methylsulfonyl-2-methyl-4-(5-phenethyl-indazol-2-yl)-butanamide Starting form intermediate RE5.ii (0.095 g) and proceeding in analogy to Example 1, step 1.ii, the title compound was obtained, after purification by prep-HPLC (Method 1), as a colourless solid (0.031 g, 41% yield).

MS1 (ESI, m/z): 416.1 [M+H$^+$] for $C_{21}H_{25}N_3O_4S$; $t_R$=0.78 min.

Reference Example 6: (RS)—N-hydroxy-2-methylsulfonyl-2-methyl-4-[5-(4-oxazol-2-yl-phenyl)-indazol-2-yl]-butanamide formic acid salt Starting from the compound of Preparation A (0.090 g, 0.19 mmol) and 2-(4-(4,4,5,5-tetramethyl-1,3,2-dioxaborolan-2-yl)phenyl)oxazole (0.055 g; 0.21 mmol; commercial), and proceeding in analogy to Example 1, steps 1.i and 1.ii (Suzuki coupling: 32% yield; deprotection 27% yield), the title compound was obtained as an off-white solid (0.009 g).

$^1$H NMR (d6-DMSO) δ: 11.0 (s, 1H); 9.24 (s, 1H); 8.49 (s, 1H); 8.00-8.11 (m, 3H); 7.81-7.88 (m, 2H); 7.60-7.73 (m, 2H); 7.38 (s, 1H); 4.48-4.60 (m, 1H); 4.30-4.44 (m, 1H); 3.05 (s, 3H); 2.78-2.90 (m, 1H); 2.35-2.44 (overlapped m, 1H); 1.50 (s, 3H).

MS1 (ESI, m/z): 455.2 [M+H$^+$] for $C_{22}H_{22}N_4O_5S$; $t_R$=0.73 min.

Reference Example 7: (RS)-4-(5-(2-fluoro-3-methoxyphenyl)-2H-indazol-2-yl)-N-hydroxy-2-methyl-2-(methylsulfonyl)butanamide Starting from the compound of Preparation A (0.090 g, 0.2 mmol) and (2-fluoro-3-methoxyphenyl)boronic acid (0.045 g; 0.26 mmol; commercial), and proceeding in analogy to Example 1, steps 1.i and 1.ii (Suzuki coupling: 45% yield; deprotection: 51% yield), the title compound was obtained, after purification by prep-HPLC (Method 1), as an off-white solid (0.017 g).

$^1$H NMR (d6-DMSO) δ: 11.02 (s, 1H); 9.24 (s, 1H); 8.46 (s, 1H); 7.82 (s, 1H); 7.66 (d, J=8.9 Hz, 1H); 7.38 (m, 1H); 6.99-7.21 (m, 3H); 4.48-4.60 (m, 1H); 4.30-4.44 (m, 1H); 3.86 (s, 3H); 3.05 (s, 3H); 2.78-2.90 (m, 1H); 2.35-2.44 (overlapped m, 1H); 1.50 (s, 3H).

MS1 (ESI, m/z): 436.1 [M+H$^+$] for $C_{20}H_{22}N_3O_5FS$; $t_R$=0.73 min.

EXAMPLES OF COMPOUNDS ACCORDING TO THE INVENTION

Example 1: (R)-4-[5-(2-fluoro-4-methoxy-phenyl)-indazol-2-yl]-N-hydroxy-2-methylsulfonyl-2-methyl-butanamide

1.i. (RS)-4-(5-(2-fluoro-4-methoxyphenyl)-2H-indazol-2-yl)-2-methyl-2-(methylsulfonyl)-N—(((RS)-tetrahydro-2H-pyran-2-yl)oxy)butanamide A mixture of 2-fluoro-4-methoxyphenylboronic acid (0.8 g, 4.61 mmol), Pd(PPh$_3$)$_4$ (0.203 g, 0.176 mmol), Na$_2$CO$_3$ (1.63 g, 15.1 mmol) was flushed under N$_2$ for 15 min. A solution of the compound of Preparation A (1.47 g, 3.1 mmol) in DME (21.1 mL) and water (8.6 mL) was added. The mixture was stirred at rt for 5 min and then heated at 90° C. overnight. Water (40 mL) and EA (40 mL) were added. The two layers were separated and the aq. layer was extracted with EA (5×10 mL). The combined org. layers were washed with brine, dried over MgSO$_4$ and concentrated to dryness. The residue was purified by CC (Hept-EA) afford the title product as a white foam (1.15 g, 72% yield).

$^1$H NMR (d6-DMSO) δ (mixture of stereoisomers): 11.4 (br. s, 1H); 8.45 (s, 1H); 7.80 (br. s, 1H); 7.64 (d, J=8.9 Hz, 1H); 7.45 (t, J=8.9 Hz, 1H); 7.35 (d, J=8.9 Hz, 1H); 6.83-6.94 (m, 2H); 4.89-4.97 (m, 1H); 4.48-4.60 (m, 1H); 4.30-4.45 (m, 1H); 3.79 (s, 3H); 3.51 (m, 1H); 3.09-3.17 (m, 1H); 3.06 (s, 1.5H); 3.04 (s, 1.5H); 2.77-2.93 (m, 1H); 2.46 (overlapped m, 1H); 1.64-1.76 (m, 2H); 1.47-1.57 (m, 2H); 1.52 (s, 1.5H); 1.49 (s, 1.5H).

MS1 (ESI, m/z): 520.2 [M+H$^+$] for $C_{25}H_{30}N_3O_6FS$; $t_R$=0.87 min.

1.ii. Rac-4-[5-(2-fluoro-4-methoxy-phenyl)-indazol-2-yl]-N-hydroxy-2-methylsulfonyl-2-methyl-butanamide To a solution of intermediate 1.i (1.15 g, 2.22 mmol) in EtOH (22.1 mL) was added PPTS (0.35 g, 1.38 mmol). The reaction mixture was stirred at 75° C. overnight. Water (50 mL) was added and the mixture was stirred at rt for 1.5 h. The solid that precipitated was filtered and washed with water. The latter was purified with prep-HPLC (Method 2) to afford the title product as a white solid (0.42 g, 44% yield).

$^1$H NMR (d6-DMSO) δ: 9.25 (br. s, 1H); 8.43 (s, 1H); 7.77 (br. s, 1H); 7.64 (d, J=8.9 Hz, 1H); 7.45 (t, J=8.9 Hz, 1H); 7.35 (d, J=8.9 Hz, 1H); 6.83-6.94 (m, 2H); 4.48-4.60 (m, 1H); 4.29-4.41 (m, 1H); 3.79 (s, 3H); 3.05 (s, 3H); 2.78-2.89 (m, 1H); 2.38-2.48 (m, 1H); 1.50 (s, 3H).

MS1 (ESI, m/z): 436.1 [M+H$^+$] for $C_{20}H_{22}N_3O_5FS$; $t_R$=0.88 min.

1.iii. (R)-4-[5-(2-fluoro-4-methoxy-phenyl)-indazol-2-yl]-N-hydroxy-2-methylsulfonyl-2-methyl-butanamide Variant I:

Intermediate 1.ii (0.265 g) was separated by semi-preparative chiral HPLC Method C (Hept-EtOH-TFA 1-1-0.002; flow rate: 20 mL/min; UV detection at 210 nM); the respective retention times of analytical samples (flow rate: 0.8 mL/min) were 6.7 and 8.7 min. The title (R)-enantiomer, identified as the second eluting compound, was obtained as a beige solid (0.089 g).

MS1 (ESI, m/z): 436.1 [M+H$^+$] for $C_{20}H_{22}N_3O_5FS$; $t_R$=0.88 min.

Variant II:

Starting from the compound of Preparation F (2 g, 4.46 mmol) and proceeding successively in analogy to Preparation A, step A.vi (82% yield) and Example 1, step 1.ii (92% yield), the title compound was obtained, after filtration of the solid that formed during the course of the deprotection step, as a white solid (1.36 g).

MS data equivalent to those obtained regarding Variant I. The e.e., determined using the analytical chiral HPLC conditions mentioned for Variant I, was >99%.

Example 2: (R)—N-hydroxy-2-methylsulfonyl-4-[5-(4-methoxy-phenyl)-indazol-2-yl]-2-methyl-butanamide

2.i. (RS)-2-methylsulfonyl-4-[5-(4-methoxy-phenyl)-indazol-2-yl]-2-methyl-butanoic acid ethyl ester Starting from intermediate A.v (0.171 g, 0.425 mmol) and 4-methoxybenzene boronic acid (0.101 g; 0.65 mmol; commercial), and proceeding in analogy to Example 1, step 1.i, the title compound was obtained, after purification by CC (eluent: Hept-EA mixture with gradient), as a colourless oil (0.156 g, 86% yield).

$^1$H NMR (d6-DMSO) δ: 8.39 (d, J=0.9 Hz, 1H); 7.96 (dd, J=0.9, 1.9 Hz, 1H); 7.57 (td, J=0.9, 9.1 Hz, 1H); 7.30 (dd, J=1.9, 9.1 Hz, 1); 4.63 (m, 1H); 4.47 (m, 1H); 3.88-4.02 (m, 2H); 3.1 (s, 3H); 2.84 (m, 1H); 2.44 (m, 1H); 1.58 (s, 3H); 1.12 (t, J=7.1 Hz, 3H).

MS1 (ESI, m/z): 431.1 [M+H$^+$] for $C_{22}H_{26}N_2O_5S$; $t_R$=0.88 min.

2.ii. (RS)-4-(5-(4-methoxyphenyl)-2H-indazol-2-yl)-2-methyl-2-(methylsulfonyl)-N-((tetrahydro-2H-pyran-2-yl)oxy)butanamide To a solution of intermediate 2.i (0.157 g; 0.364 mmol) in a THF-MeOH—H$_2$O mixture (2-2-1; 5 mL) was added in one portion LiOH (0.059 g; 0.79 mmol). The reaction mixture was stirred at rt for 1 h. Solvents were evaporated under vacuum. The residue was taken up in water and directly purified by prep-HPLC (Method 2) to afford the desired product as a beige solid (0.056 g, 0.14 mmol). The latter was taken up in a DCM (2 mL). TEA (0.06 mL, 0.427 mmol), THPO—NH$_2$ (0.034 g, 0.291 mmol), EDC (0.053 g, 0.277 mmol) and HOBT.H$_2$O (0.038 g, 0.279 mmol) were added. The mixture was stirred at rt overnight. The mixture was concentrated to dryness. The residue was taken up in DCM (20 mL). The org. layer was washed with sat. NaHCO$_3$ (10 mL) and brine (20 mL), dried over MgSO$_4$, filtered and concentrated under reduced pressure. The residue was purified by CC (eluent: DCM-MeOH mixture with gradient) to afford the desired product as a colourless oil (0.08 g).

MS1 (ESI, m/z): 502.12 [M+H$^+$] for $C_{25}H_{31}N_3O_6S$; $t_R$=0.85 min.

2.iii (RS)—N-hydroxy-2-methylsulfonyl-4-[5-(4-methoxy-phenyl)-indazol-2-yl]-2-methyl-butanamide Starting from intermediate 2.ii (0.08 g; 0.159 mmol) and proceeding in analogy to Example 1, step 1.ii, the title compound was obtained, after purification by prep-HPLC (Method 2), as a white solid (0.041 g; 62% yield).

$^1$H NMR (d6-DMSO) δ: 11.0 (br. s, 1H); 9.27 (br. s, 1H); 8.41 (s, 1H); 7.86 (s, 1H); 7.56-7.67 (m, 3H); 7.52 (dd, J=1.5, 9.1 Hz, 1H); 7.00 (d, J=8.8 Hz, 2H); 4.47-4.59 (m, 1H); 4.29-4.44 (m, 1H); 3.77 (s, 3H); 3.06 (s, 3H); 2.79-2.90 (m, 1H); 2.35-2.40 (m, 1H); 1.50 (s, 3H).

MS1 (ESI, m/z): 418.07 [M+H$^+$] for $C_{20}H_{23}N_3O_5S$; $t_R$=0.65 min.

2.iv. (R)—N-hydroxy-2-methylsulfonyl-4-[5-(4-methoxy-phenyl)-indazol-2-yl]-2-methyl-butanamide Intermediate 2.iii (0.08 g) was separated by semi-preparative chiral HPLC Method D (MeCN-EtOH-TFA 3-17-0.02; flow rate: 16 mL/min; UV detection at 257 nM); the respective retention times (flow rate: 0.8 mL/min) were 11.2 and 13.3 min. The title (R)-enantiomer, identified as the second eluting compound, was obtained as a beige solid (0.017 g).

MS2 (ESI, m/z): 418.1 [M+H$^+$] for $C_{20}H_{23}N_3O_5S$; $t_R$=0.85 min.

Example 3: (R)-4-[6-fluoro-5-(4-methoxy-phenyl)-indazol-2-yl]-N-hydroxy-2-methylsulfonyl-2-methyl-butanamide

3.i. (R)-4-[6-fluoro-5-(4-methoxy-phenyl)-indazol-2-yl]-2-methylsulfonyl-2-methyl-butanoic acid tert-butyl ester Starting from the compound of Preparation O (0.1 g, 0.22 mmol) and 4-methoxyphenylboronic acid (0.025 g, 0.17 mmol), and proceeding in analogy to Example 1, step 1.i, the title compound was obtained, after purification by CC (eluent: Hept-EA mixture with gradient), as a beige gum (0.089 g; 84% yield).

$^1$H NMR (d6-DMSO) δ: 8.48 (s, 1H); 7.75 (d, J=8.0 Hz, 1H); 7.37-7.48 (m, 3H); 7.01 (d, J=8.7 Hz, 2H); 4.59 (m, 1H); 4.42 (m, 1H); 3.78 (s, 3H); 2.74 (m, 1H); 2.43 (m, overlaid with DMSO, 1H); 1.53 (s, 3H); 1.39 (m, 9H).

MS1 (ESI, m/z): 477.1 [M+H$^+$] for $C_{24}H_{29}N_2O_5FS$; $t_R$=0.96 min.

3.ii. (R)-4-[6-fluoro-5-(4-methoxy-phenyl)-indazol-2-yl]-2-methylsulfonyl-2-methyl-butanoic acid To intermediate 3.i (0.08 g, 0.18 mmol) in 4N HCl in dioxane (1.1 mL) was added water (0.04 mL). The resulting mixture was stirred at rt overnight. The reaction mixture was concentrated to dryness. The crude residue was co-evaporated twice with Et$_2$O (4 mL) to give the title acid as an off-white solid (0.08 g; quant.).

$^1$H NMR (d6-DMSO) δ: 8.50 (s, 1H); 7.77 (d, J=7.9 Hz, 1H); 7.40-7.50 (m, 3H); 7.03 (d, J=8.7 Hz, 2H); 4.38-4.70 (m, 2H); 3.80 (s, 3H); 3.14 (s, 3H); 2.68-2.86 (m, 1H); 2.39-2.58 (overlapped m, 1H); 1.57 (s, 3H) MS1 (ESI, m/z): 421.0 [M+H$^+$] for $C_{20}H_{21}N_2O_5FS$; $t_R$=0.79 min.

3.iii. (R)-4-[6-fluoro-5-(4-methoxy-phenyl)-indazol-2-yl]-N-hydroxy-2-methylsulfonyl-2-methyl-butanamide Starting from intermediate 3.ii (0.072 g, 0.17 mmol), and proceeding successively in analogy to Example 2, step ii (only the coupling reaction using THPO—NH$_2$ and EDC; 100% yield) and Example 1, step 1.ii (56% yield), the title compound was obtained as a white solid (0.04 g).

$^1$H NMR (d6-DMSO) δ: 11.0 (d, J=1.7 Hz, 1H); 9.24 (d, J=1.7 Hz, 1H); 8.46 (s, 1H); 7.75 (d, J=8.0 Hz, 1H); 7.39-7.48 (m, 3H); 7.01 (d, J=8.8 Hz, 2H); 4.46-4.57 (m, 1H); 4.26-4.38 (m, 1H); 3.78 (s, 3H); 3.05 (s, 3H); 2.78-2.89 (m, 1H); 2.33-2.46 (m, 1H); 1.50 (s, 3H).

MS1 (ESI, m/z): 436.1 [M+H$^+$] for $C_{25}H_{30}N_3O_6PS$; $t_R$=0.74 min.

Example 4: (R)-4-[4-fluoro-5-(4-methoxy-phenyl)-indazol-2-yl]-N-hydroxy-2-methylsulfonyl-2-methyl-butanamide Starting from the compound of Preparation C (0.11 g, 0.26 mmol) and 4-methoxyphenylboronic acid (0.049 g, 0.32 mmol), and proceeding successively in analogy to Example 1, step 1.i (61% yield), Example 2, step 2.ii (90% yield) and Example 1, step 1.ii (80% yield), the title compound was obtained, after purification by prep-HPLC (Method 1), as a white solid (0.043 g).

$^1$H NMR (d6-DMSO) δ: 11.0 (s, 1H); 9.24 (s, 1H); 8.62 (s, 1H); 7.50 (d, J=8.8 Hz, 2H); 7.38 (t, J=8.7 Hz, 1H); 7.03 (d, J=8.8 Hz, 2H); 4.50-4.61 (m, 1H); 4.30-4.43 (m, 1H); 3.78 (s, 3H); 3.06 (s, 3H); 2.80-2.90 (m, 1H); 2.35-2.45 (overlapped m, 1H); 1.53 (s, 3H).

MS1 (ESI, m/z): 436.2 [M+H$^+$] for $C_{25}H_{30}N_3O_6FS$; $t_R$=0.75 min.

Example 5: (R)-4-[6-fluoro-5-(2-fluoro-4-methoxy-phenyl)-indazol-2-yl]-N-hydroxy-2-methylsulfonyl-2-methyl-butanamide

5.i. (RS)-5-(6-fluoro-5-(2-fluoro-4-methoxyphenyl)-2H-indazol-2-yl)-N-hydroxy-3-methyl-3-(methylsulfonyl)butanamide Starting from the compound of Preparation B (0.3 g, 0.61 mmol) and 2-fluoro-4-methoxyphenylboronic acid (0.137 g, 0.79 mmol), and proceeding in analogy to Example 1, steps 1.i and 1.ii (Suzuki coupling 70% yield, deprotection 49% yield), the title compound was obtained as a white foam (0.095 g).

$^1$H NMR (d6-DMSO) δ: 11.0 (s, 1H); 9.24 (s, 1H); 8.48 (s, 1H); 7.73 (d, J=7.5 Hz, 1H); 7.43 (d, J=11.4 Hz, 1H); 7.35 (t, J=8.8 Hz, 1H); 6.84-6.95 (m, 2H); 4.48-4.59 (m, 1H); 4.28-4.39 (m, 1H); 3.81 (s, 3H); 3.05 (s, 3H); 2.77-2.89 (m, 1H); 2.35-2.44 (overlapped m, 1H); 1.50 (s, 3H).

MS1 (ESI, m/z): 454.1 [M+H$^+$] for $C_{20}H_{21}N_3O_5F_2S$; $t_R$=0.75 min.

5.ii. (R)-4-[6-fluoro-5-(2-fluoro-4-methoxy-phenyl)-indazol-2-yl]-N-hydroxy-2-methylsulfonyl-2-methyl-butanamide Intermediate 5.i (0.095 g) was separated by semi-preparative chiral HPLC Method C (Hept-EtOH-TFA 1-1-0.002; flow rate: 23 mL/min; UV detection at 210 nM); the respective retention times (flow rate: 1.2 mL/min) were 4.4 and 6.9 min. The title (R)-enantiomer, identified as the second eluting compound, was obtained as a white solid (0.031 g).

MS2 (ESI, m/z): 454.3 [M+H$^+$] for $C_{20}H_{21}N_3O_5F_2S$; $t_R$=0.9 min.

Example 6: (R)-4-[4-fluoro-5-(2-fluoro-4-methoxy-phenyl)-indazol-2-yl]-N-hydroxy-2-methylsulfonyl-2-methyl-butanamide Starting from the compound of Preparation C (0.16 g; 0.38 mmol) and (2-fluoro-4-methoxy)phenylboronic acid (0.085 g, 0.49 mmol), and proceeding successively in analogy to Example 1, step 1.i (66% yield), Example 2, step 2.ii (96% yield) and Example 1, step 1.ii (74% yield), the title compound was obtained, after purification by prep-HPLC (Method 1), as a white solid (0.069 g).

$^1$H NMR (d6-DMSO) δ: 11.0 (s, 1H); 9.23 (s, 1H); 8.65 (s, 1H); 7.51 (d, J=8.8 Hz, 1H); 7.38 (t, J=8.7 Hz, 1H); 7.18-7.24 (m, 1H); 6.85-6.95 (m, 2H); 4.50-4.62 (m, 1H); 4.31-4.43 (m, 1H); 3.81 (s, 3H); 3.07 (s, 3H); 2.79-2.92 (m, 1H); 2.35-2.45 (overlapped m, 1H); 1.53 (s, 3H).

MS1 (ESI, m/z): 454.1 [M+H$^+$] for $C_{20}H_{21}N_3O_5F_2S$; $t_R$=0.77 min.

Example 7: (R)—N-hydroxy-2-methylsulfonyl-2-methyl-4-[5-(4-morpholin-4-ylmethyl-phenylethynyl)-indazol-2-yl]-butanamide formate

7.i. (R)-2-methylsulfonyl-2-methyl-4-[5-(4-morpholin-4-ylmethyl-phenylethynyl)-indazol-2-yl]-N—[(RS)-(tetrahydro-pyran-2-yl)oxy]-butanamide CuI (0.01 g; 0.04 mmol), PdCl$_2$(PPh$_3$)$_2$ (0.01 g, 0.02 mmol), the compound of Preparation H (0.1 g; 0.19 mmol) and 4-(4-ethynylbenzyl)morpholine (0.05 g; 0.23 mmol; prepared as described in WO 2008/154642) were introduced in a two-necked round flask. The atmosphere was flushed with nitrogen during 30 min then degassed THF (1.3 mL) and degassed TEA (0.07 mL, 0.48 mmol) were added. The suspension was stirred under nitrogen atmosphere at 50° C. for 45 min. After concentration to dryness, the residue was purified by CC (DCM-MeOH+NH$_4$OH gradient) to afford the title compound, slightly contaminated with a bis-alkyne residue, as a yellow foam (0.1 g; 91% yield).

$^1$H NMR (d6-DMSO) δ (mixture of isomers): 11.39-11.48 (m, 1H); 8.45-8.49 (m, 1H); 7.98 (s, 1H); 7.65 (d, J=9.0 Hz, 1H); 7.47-7.54 (m, 2H); 7.32-7.39 (m, 3H); 4.92-5.00 (m, 1H); 4.51-4.64 (m, 1H); 4.32-4.47 (m, 1H); 3.98-4.18 (m, 1H); 3.44-3.65 (overlapped m, 5H); 3.49 (s, 2H); 3.08 (s, 1.5H); 3.06 (s, 1.5H); 2.77-2.95 (m, 1H); 2.30-2.59 (overlapped m, 5H); 1.65-1.74 (m, 3H); 1.55 (s, 1.5H); 1.49-1.59 (overlapped m, 3H); 1.53 (s, 1.5H).

MS1 (ESI, m/z): 595.2 [M+H$^+$] for $C_{31}H_{38}N_4O_6S$; $t_R$=0.66 min.

7.ii. (R)—N-hydroxy-2-methylsulfonyl-2-methyl-4-[5-(4-morpholin-4-ylmethyl-phenylethynyl)-indazol-2-yl]-butanamide formate Starting from intermediate 7.i (0.1 g, 0.16 mmol) and proceeding in analogy to Example 1, step 1.ii, the title compound was obtained, after purification by prep-HPLC (Method 1), as a yellowish foam (0.085 g; 92% yield).

$^1$H NMR (d6-DMSO) δ: 11.0 (s, 1H); 9.94 (br. s, 1H); 9.24 (br. s, 1H); 8.50 (s, 1H); 8.11 (br. s, 1H); 7.99 (s, 1H); 7.59-7.65 (m, 3H); 7.47-7.55 (m, 2H); 7.32 (m, 1H); 4.55 (m, 1H); 4.26-4.42 (m, 2H); 3.84-4.08 (m, 2H); 3.05-3.68 (multiple m, 5H); 3.15 (s, 2H); 3.05 (s, 3H); 2.85 (m, 1H); 2.46 (m, 1H); 1.60 (s, 3H).

MS1 (ESI, m/z): 511.2 [M+H$^+$] for $C_{26}H_{30}N_4O_5S$; $t_R$=0.57 min.

Example 8: (R)—N-hydroxy-2-methylsulfonyl-2-methyl-4-[5-(4-trifluoromethoxy-phenyl)-indazol-2-yl]-butanamide Starting from the compound of Preparation H (0.103 g, 0.19 mmol) and (4-(trifluoromethoxy)phenyl)boronic acid (0.043 g, 0.21 mmol), and proceeding in analogy to Example 1, steps 1.i and 1.ii (Suzuki coupling: 41% yield; deprotection: 11% yield), the title compound was obtained, after purification by prep-HPLC (Method 1), as a white foam (0.011 g).

$^1$H NMR (d6-DMSO) δ: 11.0 (s, 1H); 9.24 (s, 1H); 8.47 (s, 1H); 7.98 (s, 1H); 7.79 (d, J=8.2 Hz, 2H); 7.69 (d, J=9.0 Hz, 1H); 7.55 (dd, J=1.5, 9.0 Hz, 1H); 7.42 (d, J=8.2 Hz, 2H); 4.49-4.60 (m, 1H); 4.29-4.41 (m, 1H); 3.05 (s, 3H); 2.78-2.90 (m, 1H); 2.35-2.44 (overlapped m, 1H); 1.50 (s, 3H).

MS1 (ESI, m/z): 472.1 [M+H$^+$] for $C_{20}H_{20}N_3O_5F_3S$; $t_R$=0.81 min.

Example 9: (R)-4-[5-(2-fluoro-4-methylsulfanyl-phenyl)-indazol-2-yl]-N-hydroxy-2-methylsulfonyl-2-methyl-butanamide Starting from the compound of Preparation H (0.1 g, 0.192 mmol) and the compound of Preparation D (0.062 g, 0.23 mmol), and proceeding in analogy to Example 1, steps 1.i and 1.ii (Suzuki coupling: 59% yield; deprotection: 51% yield), the title compound was obtained, after purification by triturations in diethyl ether, as a white solid (0.024 g).

$^1$H NMR (d6-DMSO) δ: 11.0 (s, 1H); 9.24 (s, 1H); 8.47 (s, 1H); 7.83 (s, 1H); 7.66 (d, J=8.4 Hz, 1H); 7.38 (dd, J=1.4, 7.5 Hz, 1H); 7.13-7.23 (m, 2H); 4.48-4.60 (m, 1H); 4.30-4.41 (m, 1H); 3.05 (s, 3H); 2.78-2.90 (m, 1H); 2.35-2.44 (overlapped m, 1H); 1.50 (s, 3H).

MS1 (ESI, m/z): 452.2 [M+H$^+$] for $C_2OH_{22}N_3O_4FS_2$; $t_R$=0.81 min.

Example 10: (R)-4-{5-[4-(3-amino-oxetan-3-yl)-phenylethynyl]-indazol-2-yl}-N-hydroxy-2-methyl-sulfonyl-2-methyl-butanamide toluene-4-sulfonate Starting from the compound of Preparation L (0.072 g; 0.23 mmol) and the compound of Preparation J (0.081 g; 0.2 mmol), and proceeding successively in analogy to Example 7, step 7.i (69% yield) and Example 1, step 1.ii (44% yield), the title compound was obtained, after purification by prep-HPLC (Method 2), as a yellowish solid (0.04 g).

$^1$H NMR (d6-DMSO δ: 9.24 (br. s, 1H); 8.49 (s, 1H); 8.11 (s, 1H); 7.99 (s, 1H); 7.61 (m, 5H); 7.45 (d, J=8.0 Hz, 2H); 7.33 (dd, J=1.2, 8.9 Hz, 1H); 7.08 (d, J=8.0 Hz, 2H); 4.76-4.85 (m, 4H); 4.55 (m, 1H); 4.34 (m, 1H); 3.25 (br. s, 3H); 2.84 (m, 1H); 2.48 (m, overlaid with DMSO, 1H); 2.26 (s, 3H); 1.53 (s, 3H).

MS1 (ESI, m/z): 483.1 [M+H$^+$] for $C_{24}H_{26}N_4O_5S$; $t_R$=0.54 min.

Example 11: (R)-4-[5-(4-dimethylamino-phenyl)-indazol-2-yl]-N-hydroxy-2-methylsulfonyl-2-methyl-butanamide

11.i. (R)-4-[5-(4-dimethylamino-phenyl)-indazol-2-yl]-2-methylsulfonyl-2-methyl-N-(2-trimethylsilanyl-ethoxy)-butanamide Starting from the compound of Preparation I (0.103 g, 0.192 mmol) and [4-(dimethylamino)phenyl]boronic acid (0.038 g; commercial), and proceeding in analogy to Example 1, step 1.i, the title compound was obtained as a yellowish oil (0.095 g; 94% yield).

MS1 (ESI, m/z): 531.1 [M+H$^+$] for $C_{26}H_{38}N_4O_4SSi$; $t_R$=0.76 min.

11.ii. (R)-4-[5-(4-dimethylamino-phenyl)-indazol-2-yl]-N-hydroxy-2-methylsulfonyl-2-methyl-butanamide An ice-chilled solution of intermediate 11.i (0.095 g, 0.18 mmol) in MeCN (3 mL) was treated with BF$_3$.OEt$_2$ (0.205 mL) and the mixture stirred at 0° C. for 30 min. The solvent was evaporated under reduced pressure and the residue was purified by prep-HPLC (Method 2) to afford the title compound as an off-white solid (0.033 g; 45% yield).

$^1$H NMR (d6-DMSO) δ: 11.0 (s, 1H); 9.24 (s, 1H); 8.36 (s, 1H); 7.79 (s, 1H); 7.61 (d, J=8.1 Hz, 1H); 7.47-7.53 (m, 3H); 6.79 (d, J=8.9 Hz, 2H); 4.45-4.57 (m, 1H); 4.38-4.27 (m, 1H); 3.05 (s, 3H); 2.91 (s, 6H); 2.78-2.90 (m, 1H); 2.35-2.44 (overlapped m, 1H); 1.50 (s, 3H).

MS1 (ESI, m/z): 431.2 [M+H$^+$] for $C_{21}H_{26}N_4O_4S$; $t_R$=0.56 min.

Example 12: (R)—N-hydroxy-2-methylsulfonyl-2-methyl-4-[5-(4-[1,2,3]triazol-2-yl-phenyl)-indazol-2-yl]-butanamide Starting from intermediate H.i (0.11 g, 0.27 mmol) and 2-[4-(4,4,5,5-tetramethyl-1,3,2-dioxaborolan-2-yl)phenyl]-2H-1,2,3-triazole (0.077 g; 0.28 mmol; commercial), and proceeding successively in analogy to Example 1, step 1.i (76% yield), Preparation A, step A.vi (78% yield) and Example 1, step 1.ii (82% yield), the title compound was obtained as an off-white solid (0.052 g).

$^1$H NMR (d6-DMSO) δ: 11.0 (s, 1H); 9.24 (s, 1H); 8.47 (s, 1H); 8.11 (s, 2H); 8.01-8.09 (m, 3H); 7.85-7.89 (m, 2H); 7.67-7.71 (m, 1H); 7.58-7.63 (m, 1H); 4.48-4.60 (m, 1H); 4.29-4.40 (m, 1H); 3.05 (s, 3H); 2.78-2.90 (m, 1H); 2.35-2.44 (overlapped m, 1H); 1.50 (s, 3H).

MS1 (ESI, m/z): 455.1 [M+H$^+$] for $C_{21}H_{22}N_6O_4S$; $t_R$=0.75 min.

Example 13: (R)—N-hydroxy-4-(5-((3-hydroxythietan-3-yl)buta-1,3-diyn-1-yl)-2H-indazol-2-yl)-2-methyl-2-(methylsulfonyl)butanamide

13.i. (R)-4-(5-((3-hydroxythietan-3-yl)buta-1,3-diyn-1-yl)-2H-indazol-2-yl)-2-methyl-2-(methylsulfonyl)-N—(((RS)-tetrahydro-2H-pyran-2-yl)oxy)butanamide Starting from the compound of Preparation J (0.103 g, 0.246 mmol) and the compound of Preparation S (0.063 g, 0.26 mmol), and proceeding in analogy to Example 7, step 7.i, the title compound was obtained, after purification by CC (DCM-MeOH), as a yellow gum (0.123 g; 94% yield).

$^1$H NMR (300 MHz, $d_6$-DMSO) δ (mixture of stereoisomers): 11.38-11.44 (m, 1H); 8.52 (s, 1H); 8.10 (s, 1H); 7.61-7.68 (m, 1H); 7.29-7.37 (m, 1H); 6.80 (s, 1H); 4.91-4.98 (m, 1H); 4.5-4.64 (m, 1H); 4.33-4.48 (m, 1H); 3.99-4.16 (m, 1H); 3.44-3.57 (m, 3H); 3.38 (d, J=10.3 Hz, 2H); 3.08 (s, 1.5H); 3.05 (s, 1.5H); 2.78-2.92 (m, 1H); 2.36-2.55 (overlapped m, 1H); 1.63-1.74 (m, 3H); 1.48-1.60 (overlapped m, 3H); 1.54 (s, 1.5H); 1.52 (s, 1.5H).

MS1 (ESI, m/z): 532.00 [M+H$^+$] for $C_{25}H_{29}N_3O_6S_2$; $t_R$=0.82 min.

13.ii. (R)—N-hydroxy-4-(5((3-hydroxythietan-3-yl)buta-1,3-diyn-1-yl)-2H-indazol-2-yl)-2-methyl-2-(methylsulfonyl)butanamide A solution of intermediate 13.i (0.123 g; 0.23 mmol) in water (0.42 mL) and TFA (0.68 mL) was stirred at rt for 15 min. The reaction mixture was purified by prep-HPLC (Method 1) to afford the title compound as an off-white solid (0.012 g; 11% yield).

$^1$H NMR (d6-DMSO) δ: 11.02 (s, 1H); 9.25 (s, 1H); 8.54 (s, 1H); 8.10 (s, 1H); 7.65 (d, J=8.9 Hz, 1H); 7.33 (d, J=9.2 Hz, 1H); 6.80 (s, 1H); 4.50-4.63 (m, 1H); 4.30-4.43 (m, 1H); 3.50 (d, J=9.4 Hz, 2H); 3.38 (d, J=9.4 Hz, 2H); 3.07 (s, 3H); 2.79-2.91 (m, 1H); 2.35-2.55 (overlapped m, 1H); 1.52 (s, 3H).

MS1 (ESI, m/z): 448.0 [M+H$^+$] for $C_{20}H_{21}N_3O_5S_2$; $t_R$=0.70 min.

Example 14: (R)-4-(4-fluoro-5-((4-(2-hydroxypropan-2-yl)phenyl)ethynyl)-2H-indazol-2-yl)-N-hydroxy-2-methyl-2-(methylsulfonyl)butanamide Starting from 2-(4-ethynylphenyl)propan-2-ol (0.028 g; 0.17 mmol; prepared as described in WO 2006/099972) and the compound of Preparation K (0.086 g; 0.16 mmol), and proceeding successively in analogy to Example 7, step 7.i (64% yield) and Example 1, step 1.ii (35% yield), the title compound was obtained, after purification by prep-HPLC (Method 1), as an orange solid (0.016 g).

$^1$H NMR (d6-DMSO) δ: 11.02 (br. s, 1H); 9.25 (br. s, 1H); 8.74 (s, 1H); 7.45-7.56 (m, 5H); 7.29-7.38 (m, 1H); 5.10 (s, 1H); 4.52-4.65 (m, 1H); 4.33-4.44 (m, 1H); 3.08 (s, 3H); 2.82-2.94 (m, 1H); 2.40-2.60 (overlapped m, 1H); 1.54 (s, 3H); 1.44 (s, 6H).

MS1 (ESI, m/z): 488.0 [M+H$^+$] for $C_{24}H_{26}N_3O_5FS$; $t_R$=0.75 min.

Example 15: (R)—N-hydroxy-4-(5-((4-hydroxytetrahydro-2H-pyran-4-yl)buta-1,3-diyn-1-yl)-2H-indazol-2-yl)-2-methyl-2-(methylsulfonyl)butanamide

15.i. 4-(iodoethynyl)tetrahydro-2H-pyran-4-ol

Starting from 4-ethynyltetrahydro-2H-pyran-4-ol (1.17 g; 9.33 mmol; commercial) and proceeding in analogy to Preparation G, the title iodide was obtained, after purification by CC (Hept-EA), as a yellowish solid (1.57 g, 67% yield).

$^1$H NMR (d6-DMSO) δ: 5.64 (s, 1H); 3.64-3.74 (m, 2H); 3.40-3.51 (m, 2H); 1.68-1.79 (m, 2H); 1.51-1.62 (m, 2H).

15.ii. (R)—N-hydroxy-4-(5((4-hydroxytetrahydro-2H-pyran-4-yl)buta-1, 3-diyn-1-yl)-2H-indazol-2-yl)-2-methyl-2-(methylsulfonyl)butanamide Starting from the compound of Preparation J (0.100 g; 0.24 mmol) and intermediate 15.i (0.078 g; 0.31 mmol), and proceeding successively in analogy to Example 7, step 7.i (74% yield) and Example 1, step 1.ii (62% yield), the title compound was obtained, after purification by prep-HPLC (Method 1), as an orange solid (0.048 g).

$^1$H NMR (d6-DMSO) δ: 11.02 (s, 1H); 9.25 (s, 1H); 8.52 (s, 1H), 8.07 (s, 1H); 7.64 (d, J=9.1 Hz, 1H); 7.30 (d, J=9.1 Hz, 1H); 5.86-5.91 (m, 1H); 4.50-4.63 (m, 1H); 4.29-4.42 (m, 1H); 3.69-3.82 (m, 2H); 3.46-3.57 (m, 2H); 3.07 (s, 3H); 2.78-2.92 (m, 1H); 2.34-2.55 (overlapped m, 1H); 1.79-1.90 (m, 2H); 1.61-1.74 (m, 2H); 1.52 (s, 3H).

MS1 (ESI, m/z): 459.9 [M+H$^+$] for $C_{22}H_{25}N_3O_6S$; $t_R$=0.64 min.

Example 16: (R)—N-hydroxy-4-(5-((4-(1-(hydroxymethyl)cyclopropyl)phenyl)ethynyl)-2H-indazol-2-yl)-2-methyl-2-(methylsulfonyl)butanamide Starting from the compound of Preparation T (0.032 g, 0.19 mmol) and the compound of Preparation H (0.097 g; 0.19 mmol), and proceeding successively in analogy to Example 7, step 7.i (69% yield) and Example 1, step 1.ii (44% yield), the title compound was obtained as a beige solid (0.048 g).

$^1$H NMR (d6-DMSO δ: 11.03 (br. s, 1H); 9.26 (s, 1H); 8.49 (s, 1H); 7.97 (s, 1H); 7.64 (d, J=8.9 Hz, 1H); 7.45 (d, J=8.2 Hz, 2H); 7.29-7.36 (m, 3H); 4.66-4.75 (m, 1H); 4.49-4.62 (m, 1H); 4.29-4.42 (m, 1H); 3.56 (d, J=4.0 Hz, 2H); 3.08 (s, 3H); 2.80-2.92 (m, 1H); 2.34-2.57 (overlapped m, 1H); 1.54 (s, 3H); 0.84-0.93 (m, 2H); 0.73-0.82 (m, 2H)

MS1 (ESI, m/z): 482.0 [M+H$^+$] for $C_{25}H_{27}N_3O_5S$; $t_R$=0.74 min.

Example 17: (R)—N-hydroxy-2-methylsulfonyl-2-methyl-4-[5-((E)-styryl)-indazol-2-yl]-butanamide

17.i. (RS)-(E)-3-methyl-3-(methylsulfonyl)-5-(5-styryl-2H-indazol-2-yl)-N-((tetrahydro-2H-pyran-2-yl)oxy)butanamide Starting from the compound of Preparation H (0.107 g, 0.205 mmol) and trans-2-phenylvinylboronic acid (0.035 g; commercial), and proceeding in analogy to Example 1, step 1.i, the title compound was obtained, after purification by CC (Hept-EA), as a white foam (0.086 g, 85% yield).

MS1 (ESI, m/z): 498.2 [M+H$^+$] for $C_{26}H_{31}N_3O_5S$; $t_R$=0.90 min.

17.ii. (R)—N-hydroxy-2-methylsulfonyl-2-methyl-4-[5-((E)-styryl)-indazol-2-yl]-butanamide Starting from intermediate 17.i (0.086 g, 0.17 mmol), and proceeding in analogy to Example 1, step 1.ii, the title compound was obtained, after purification by trituration with MeCN and then with diethyl ether, as a white solid (0.018 g; 25% yield).

¹H NMR (d6-DMSO) δ: 11.0 (s, 1H); 9.96 (br. s, 1H); 9.28 (br. s, 1H); 8.42 (s, 1H);

7.78 (s, 1H); 7.66 (d, J=8.9 Hz, 1H); 7.51 (t, J=8.9 Hz, 1H); 7.33-7.38 (m, 1H); 6.91-7.06 (m, 2H); 4.48-4.61 (m, 1H); 4.31-4.45 (m, 3H); 3.35-3.82 (m, 8H); 3.06-3.18 (overlapped m, 2H); 3.05 (s, 3H); 2.78-2.89 (m, 1H); 2.35-2.45 (overlapped m, 1H); 1.50 (s, 3H).

MS1 (ESI, m/z): 414.1 [M+H$^+$] for $C_{21}H_{23}N_3O_4S$; $t_R$=0.78 min.

Example 18: (R)-4-{4-fluoro-5-[4-((1S*,2S*)-2-hydroxymethyl-cyclopropyl)-buta-1,3-diynyl]-indazol-2-yl}-N-hydroxy-2-methylsulfonyl-2-methyl-butanamide 18.i. 4-(4-fluoro-5-((trimethylsilyl)ethynyl)-2H-indazol-2-yl)-2-methyl-2-methylsulfonyl-N—(((RS)-tetrahydro-2H-pyran-2-yl)oxy)butanamide Starting from the compound of Preparation K (0.52 g, 0.96 mmol) and trimethysilyl acetylene (0.16 mL, 1.12 mmol), and proceeding in analogy to Preparation E, step E.ii, the title compound was obtained as an orange solid (0.5 g; 100% yield).

MS1 (ESI, m/z): 510.0 [M+H$^+$] for $C_{23}H_{32}N_3O_5FSSi$; $t_R$=0.95 min.

18.ii. (R)-4-(5-ethynyl-4-fluoro-indazol-2-yl)-2-methylsulfonyl-2-methyl-N—[(RS)-(tetrahydro-pyran-2-yl)oxy]-butanamide A solution of intermediate 18.i (0.5 g; 0.96 mmol) in MeOH (3.4 mL) was treated with $K_2CO_3$ (0.240 g, 1.73 mmol). The mixture was stirred at rt for 45 min. The reaction mixture was diluted with DCM (30 mL) and water (20 mL) was added. The two layers were separated. The aq. layer was extracted twice with DCM (2×15 mL) then twice with DCM-MeOH 9-1 (2×15 mL). The combined org. layers were washed with brine (30 mL), dried over $MgSO_4$, filtered and concentrated to dryness to afford the desired product as a yellowish solid (0.260 g; 62% yield).

¹H NMR (d6-DMSO) δ (mixture of diastereomers): 11.40 (br. s, 1H); 8.70 (s, 1H); 7.47 (d, J=8.8 Hz, 1H); 7.25 (dd, J=6.8, 8.8 Hz, 1H); 4.88-4.97 (m, 1H); 4.52-4.64 (m, 1H); 4.35-4.49 (overlapped m, 1H); 4.38 (s, 1H); 3.96-4.14 (m, 1H); 3.45-3.56 (m, 1H); 3.08 (s, 1.5H); 3.05 (s, 1.5H); 2.79-2.93 (m, 1H); 2.36-2.55 (overlapped m, 1H); 1.62-1.72 (m, 3H); 1.48-1.60 (overlapped m, 3H); 1.53 (s, 1.5H); 1.52 (s, 1.5H).

MS1 (ESI, m/z): 438.0 [M+H$^+$] for $C_{20}H_{24}N_3O_5FS$; $t_R$=0.80 min.

18.iii. (R)-4-(5-{4-[(1S*,2S*)-2-(tert-butyl-dimethyl-silanyloxymethyl)-cyclopropyl]-buta-1, 3-diynyl}-4-fluoro-indazol-2-yl)-2-methylsulfonyl-2-methyl-N—[(RS)-(tetrahydro-pyran-2-yl)oxy]-butanamide Starting from intermediate 18.ii (0.130 g, 0.30 mmol) and the compound of Preparation P (0.135 g, 0.4 mmol), and proceeding in analogy to Preparation E, step E.ii, the title compound was obtained, after purification by CC (DCM-MeOH gradient) as a brownish gum (0.167 g, 87% yield).

¹H NMR (d6-DMSO) δ (mixture of diastereomers): 11.37-11.44 (m, 1H); 8.69-8.81 (m, 1H); 7.44-7.68 (m, 1H); 7.22-7.42 (m, 1H); 4.86-4.97 (m, 1H); 4.51-4.67 (m, 1H); 4.33-4.50 (m, 1H); 3.97-4.16 (m, 1H); 3.43-3.57 (m, 1H); 3.24-3.31 (overlapped m, 2H); 3.01-3.09 (m, 3H); 2.81-2.93 (m, 1H); 2.35-2.53 (overlapped m, 1H); 1.41-1.73 (m, 12H); 0.94-1.03 (m, 1H); 0.76-0.93 (m, 9H); 0.00-0.10 (m, 6H).

MS1 (ESI, m/z): 646.0 [M+H$^+$] for $C_{32}H_{44}N_3O_6FSSi$; $t_R$=1.10 min.

18.iv. (R)-4-{4-fluoro-5-[4-((1S*,2S*)-2-hydroxymethyl-cyclopropyl)-buta-1, 3-diynyl]-indazol-2-yl}-N-hydroxy-2-methylsulfonyl-2-methyl-butanamide A solution of the intermediate 18.iii (0.168 g, 0.26 mmol) in water (0.91 mL) and TFA (0.91 mL) was stirred at rt for 30 min. The reaction mixture was purified by prep-HPLC (Method 1) to afford the title compound as a brown solid (0.022 g, 19% yield).

¹H NMR (d6-DMSO) δ (mixture of diastereomers): 11.01 (s, 1H); 9.24 (br. s, 1H); 8.74 (s, 1H); 7.47 (d, J=8.8 Hz, 1H); 7.22-7.31 (m, 1H); 4.49-4.63 (m, 1H); 4.31-4.44 (m, 1H); 3.20-3.47 (m, 3H); 3.07 (s, 3H); 2.80-2.93 (m, 1H); 2.32-2.58 (overlapped m, 1H); 1.39-1.56 (overlapped m, 2H); 1.52 (s, 3H); 0.84-0.99 (m, 2H).

MS1 (ESI, m/z): 448.0 [M+H$^+$] for $C_{21}H_{22}N_3O_5FS$; $t_R$=0.70 min.

Example 19: (R)-4-[5-(4-amino-phenylethynyl)-indazol-2-yl]-N-hydroxy-2-methylsulfonyl-2-methyl-butanamide 19.i. (R)-4-(5-iodo-2H-indazol-2-yl)-2-methyl-2-(methylsulfonyl)-N-(2-(trimethylsilyl)ethoxy)butanamide Starting from 4-ethynylaniline (0.039 g, 0.33 mmol; commercial) and the compound of Preparation I (0.153 g, 0.28 mmol), and proceeding in analogy to Example 7, step 7.i, the title alkyne was obtained, after purification by CC (DCM-MeOH), as a brown oil (0.144 g; 97% yield).

¹H NMR (d6-DMSO) δ: 11.3 (s, 1H); 8.46 (s, 1H); 7.86 (s, 1H); 7.60 (d, J=8.9 Hz, 1H); 7.27 (d, J=8.9 Hz, 1H); 7.20 (d, J=8.5 Hz, 2H); 6.57 (d, J=8.5 Hz, 2H); 5.54 (br. s, 2H); 4.49-4.64 (m, 1H); 4.31-4.45 (m, 1H); 3.80-3.86 (m, 2H); 3.07 (s, 3H); 2.81-2.90 (m, 1H); 2.33-2.47 (m, 1H); 1.55 (s, 3H); 0.91-0.99 (m, 2H); 0.03 (s, 9H).

MS1 (ESI, m/z): 527.2 [M+H+] for $C_{26}H_{34}N_4O_4SSi$; $t_R$=0.95 min.

19.ii. (R)-4-[5-(4-amino-phenylethynyl)-indazol-2-yl]-N-hydroxy-2 methylsulfonyl-2-methyl-butanamide An ice-chilled solution of intermediate 19.i (0.144 g, 0.28 mmol) in MeCN (5 mL) was treated with $BF_3.OEt_2$ (0.31 mL) and the mixture stirred at 0° C. for 30 min. The solvent was evaporated under reduced pressure and the residue was purified by prep-HPLC (Method 2) to afford the title compound as a beige solid (0.063 g, 54% yield).

¹H NMR (d6-DMSO) δ: 9.32 (br. s, 1H); 8.41 (s, 1H); 7.82 (s, 1H); 7.24 (dd, J=1.5, 8.9 Hz, 1H); 7.17 (d, J=8.6 Hz, 2H); 6.54 (d, J=8.6 Hz, 2H); 5.48 (br. s, 2H); 4.47-4.59 (m, 1H); 4.26-4.38 (m, 3H); 3.05 (s, 3H); 2.77-2.89 (m, 1H); 2.32-2.44 (m, 1H); 1.50 (s, 3H).

MS1 (ESI, m/z): 427.1 [M+H$^+$] for $C_{21}H_{22}N_4O_4S$; $t_R$=0.61 min.

Example 20: (R)—N-hydroxy-4-{5-[4-(3-hydroxy-oxetan-3-yl)-phenylethynyl]-indazol-2-yl}-2-methyl-sulfonyl-2-methyl-butanamide

20.i. 3-(4-iodophenyl)oxetan-3-ol

A solution of 1,4-diiodobenzene (0.800 g, 2.43 mmol) in THF (8 mL) was treated at −78° C. with BuLi (1.68M in Hex; 2.23 mL). After stirring at this temperature for 30 min, the solution was treated with a suspension of 3-oxetanone (0.24 g, 3.34 mmol) in THF (3 mL). The reaction mixture was allowed to reach rt and was further stirred overnight. The reaction mixture was treated with 10% aq. NaHSO$_4$ solution (4 mL) and diluted water and EA. The aq. layer was extracted with EA. The combined org. layers were washed with brine, dried over MgSO$_4$, filtered and concentrated under reduced pressure. The residue was purified by CC (Hept-EA) to afford the title alcohol as a colourless solid (0.2 g; 55% yield).

$^1$H NMR (d6-DMSO) δ: 7.73 (d, J=8.5 Hz, 2H); 7.39 (d, J=8.5 Hz, 2H); 6.39 (s, 1H); 4.73 (d, J=6.8 Hz, 2H); 4.60 (d, J=6.8 Hz, 2H).

20.ii. 3-(4-ethynylphenyl)oxetan-3-ol

Starting from intermediate 20.i (0.2 g; 0.73 mmol) and proceeding in analogy to Preparation E, step E.ii, the intermediate 3-(4-((trimethylsilyl)ethynyl)phenyl)oxetan-3-ol was obtained, after purification by CC (Hept-EA), as a light brown solid (0.17 g; 94% yield). The latter was dissolved in MeOH (3 mL), treated with K$_2$CO$_3$ (0.182 g) and further stirred at rt for 90 min. The reaction mixture was diluted with DCM and washed with water. The aq. layer was extracted with DCM. The combined org. layers were washed with brine, dried over MgSO$_4$, filtered and concentrated under reduced pressure to afford the terminal alkyne as a brown oil (0.13 g; 100% yield).

$^1$H NMR (d6-DMSO) δ: 7.56-7.61 (m, 2H); 7.45-7.51 (m, 2H); 6.40 (s, 1H); 4.75 (d, J=6.8 Hz, 2H); 4.63 (d, J=6.8 Hz, 2H); 4.13 (s, 1H).

20.iii. (RS)-4-((2R)-5((4-(3-hydroxyoxetan-3-yl)phenyl)ethynyl)-2H-indazol-2-yl)-2-methyl-2-(methylsulfonyl)-N-((tetrahydro-2H-pyran-2-yl)oxy)butanamide Starting from intermediate 20.ii (0.239 g, 1.37 mmol) and the compound of Preparation H (0.550 g; 1.05 mmol), and proceeding in analogy to Example 7, step 7.i, the title compound was obtained as a yellowish foam (0.481 g; 80% yield).

MS1 (ESI, m/z): 568.3 [M+H$^+$] for C$_{29}$H$_{33}$N$_3$O$_7$S; t$_R$=0.79 min.

20.iv. (R)—N-hydroxy-4-{5-[4-(3-hydroxy-oxetan-3-yl)-phenylethynyl]-indazol-2-yl}-2-methylsulfonyl-2-methyl-butanamide Starting from the intermediate 20.iii (0.477 g; 0.84 mmol) and proceeding in analogy to Example 1, step 1.ii, the title compound was obtained, after purification by prep-HPLC (Method 2), as a brownish foam (0.17 g, 42% yield).

$^1$H NMR (d6-DMSO) δ: 8.48 (br. s, 1H); 7.97 (br. s, 1H); 7.51-7.66 (m, 6H); 7.32 (dd, J=1.3, 8.8 Hz, 1H); 6.41 (br. s, 1H); 4.77 (d, J=6.6 Hz, 2H); 4.66 (d, J=6.6 Hz, 2H); 4.44-4.62 (m, 1H); 4.29-4.41 (m, 1H); 3.05 (s, 3H); 2.79-2.88 (m, 1H); 2.35-2.45 (m, 1H); 1.50 (s, 3H).

MS1 (ESI, m/z): 484.0 [M+H$^+$] for C$_{25}$H$_{27}$N$_3$O$_8$S; t$_R$=0.67 min.

Example 21: (R)—N-hydroxy-4-(5-((4-(hydroxymethyl)phenyl)ethynyl)-2H-indazol-2-yl)-2-methyl-2-(methylsulfonyl)butanamide

21.i. (RS)-ethyl 4-(54(4-(hydroxymethyl)phenyl)ethynyl)-2H-indazol-2-yl)-2-methyl-2-(methylsulfonyl)butanoate Starting from (4-ethynylphenyl)methanol (0.031 g; commercial) and intermediate E.i (0.097 g; 0.2 mmol) and proceeding in analogy to Example 7, step 7.i, the title compound was obtained, after purification by CC (Hept-EA), as a yellowish solid (0.093 g, 95% yield).

MS1 (ESI, m/z): 455.2 [M+H$^+$] for C$_{24}$H$_{26}$N$_2$O$_5$S; t$_R$=0.83 min.

21.ii. (RS)—N-hydroxy-4-(54(4-(hydroxymethyl)phenyl)ethynyl)-2H-indazol-2-yl)-2-methyl-2-(methylsulfonyl)butanamide Starting from intermediate 21.i (0.090 g) and proceeding successively in analogy to Preparation A, step A.vi (100% yield) and Example 1, step 1.ii (52% yield), the title compound was obtained, after purification by prep-HPLC (Method 1), as a yellow solid (0.044 g).

MS1 (ESI, m/z): 442.1 [M+H$^+$] for C$_{22}$H$_{23}$N$_3$O$_5$S; t$_R$=0.67 min.

21.iii. (R)—N-hydroxy-4-(54(4-(hydroxymethyl)phenyl)ethynyl)-2H-indazol-2-yl)-2-methyl-2-(methylsulfonyl)butanamide Intermediate 21.ii (0.04 g) was separated by semi-preparative chiral HPLC Method C (Hept-EtOH-TFA 1-3-0.0025; flow rate: 20 mL/min; UV detection at 278 nM); the respective retention times (flow rate: 1 mL/min) were 4.2 and 5.4 min. The title (R)-enantiomer, identified as the second eluting compound, was obtained as a beige solid (0.089 g).

$^1$H NMR (d6-DMSO) δ: 11.0 (br. s, 1H); 9.23 (br. s, 1H); 8.47 (s, 1H); 7.96 (s, 1H); 7.62 (d, J=8.9 Hz, 1H); 7.49 (d, J=8.4 Hz, 2H); 7.34 (d, J=8.4 Hz, 2H); 7.31 (overlapped m, 1H); 5.24 (t, J=5.8 Hz, 1H); 4.51 (d, J=5.8 Hz, 2H); 4.50-4.60 (overlapped m, 1H); 4.29-4.41 (m, 1H); 3.05 (s, 3H); 2.78-2.89 (m, 1H); 2.33-2.45 (m, 1H); 1.50 (s, 3H).

MS2 (ESI, m/z): 436.1 [M+H$^+$] for C$_{20}$H$_{22}$N$_3$O$_5$FS; t$_R$=0.88 min.

Example 22: (R)-4-[5-(3-fluoro-4-hydroxymethyl-phenylethynyl)-indazol-2-yl]-N-hydroxy-2-methyl-sulfonyl-2-methyl-butanamide

22.i. (RS)-4-[5-(3-fluoro-4-hydroxymethyl-phenylethynyl)-indazol-2-yl]-2-methanesulfonyl-2-methyl-butyric acid ethyl ester Starting from (4-ethynylphenyl)-2-fluoro-methanol (0.034 g; prepared according to WO 2011/021209) and intermediate E.i (0.097 g) and proceeding in analogy to Example 7, step 7.i, the title compound was obtained, after purification by CC (Hept-EA), as a brown gum (0.089 g, 87% yield).

MS1 (ESI, m/z): 473.2 [M+H$^+$] for C$_{24}$H$_{25}$N$_2$O$_5$FS; t$_R$=0.85 min.

22.ii. (R)-4-[5-(3-fluoro-4-hydroxymethyl-phenyl-ethynyl)-indazol-2-yl]-N-hydroxy-2-methylsulfonyl-2-methyl-butanamide Starting from intermediate 22.i (0.085 mg) and proceeding successively in analogy to Example 21, steps 21.ii and 21.iii (saponification and amide coupling: 89% yield; deprotection: 66% yield), the title compound was obtained as a mixture of enantiomers. The racemate was separated by semi-preparative chiral HPLC Method C (Hept-EtOH-TFA 1-9-0.01; flow rate: 20 mL/min; UV detection at 277 nM); the respective retention times (flow rate: 1 mL/min) were 4.0 and 5.6 min. The title (R)-enantiomer, identified as the second eluting compound, was collected as a white solid (0.01 g; chiral separation: 44% yield).

$^1$H NMR (d6-DMSO) δ: 11.0 (br. s, 1H); 9.23 (br. s, 1H); 8.49 (s, 1H); 7.98 (s, 1H); 7.63 (d, J=8.9 Hz, 1H); 7.49 (t, J=7.8 Hz, 1H); 7.29-7.39 (m, 3H); 5.32 (t, J=5.8 Hz, 1H); 4.55 (d, J=5.8 Hz, 2H); 4.50-4.60 (overlapped m, 1H); 4.29-4.41 (m, 1H); 3.05 (s, 3H); 2.78-2.90 (m, 1H); 2.33-2.45 (m, 1H); 1.50 (s, 3H).

MS1 (ESI, m/z): 460.2 [M+H$^+$] for C$_{22}$H$_{22}$N$_3$O$_5$FS; t$_R$=0.70 min.

Example 23: (R)-4-[4-fluoro-5-(4-hydroxymethyl-phenylethynyl)-indazol-2-yl]-N-hydroxy-2-methylsulfonyl-2-methyl-butanamide trifluoro-acetic acid salt

23.i. (RS)-4-(4-fluoro-5-((4-(hydroxymethyl)phenyl)ethynyl)-2H-indazol-2-yl)-2-methyl-2-(methylsulfonyl)-N—(((RS)-tetrahydro-2H-pyran-2-yl)oxy)butanamide Starting from (4-ethynylphenyl)methanol (0.021 g; commercial) and the compound of Preparation C (0.080 g) and proceeding in analogy to Example 7, step 7.i, the title compound was obtained, after purification by CC (Hept-EA), as a brownish solid (0.098 g, 100% yield).

MS1 (ESI, m/z): 544.3 [M+H$^+$] for C$_{27}$H$_{30}$N$_3$O$_6$FS; t$_R$=0.81 min.

23.ii. (R)-4-[4-fluoro-5-(4-hydroxymethyl-phenyl-ethynyl)-indazol-2-yl]-N-hydroxy-2-methylsulfonyl-2-methyl-butanamide trifluoro-acetic acid salt Starting from the intermediate 23.i (0.091 g) and proceeding in analogy to Example 1, step 1.ii, the crude product obtained was triturated with ether to provide a racemate. The racemate was separated by semi-preparative chiral HPLC Method E (Hept-EtOH-TFA 1-1-0.01; flow rate: 23 mL/min; UV detection at 220 nM); the respective retention times (flow rate: 1.4 mL/min) were 8.7 and 11.6 min. The title (R)-enantiomer, identified as the second eluting compound, was collected as a beige solid (0.012 g; 38% yield).

$^1$H NMR (d6-DMSO) δ: 10.9 (br. s, 1H); 9.23 (br. s, 1H); 8.72 (s, 1H); 7.45-7.53 (m, 3H); 7.28-7.39 (m, 3H); 4.47-4.53 (m, 3H); 4.44-4.22 (m, 1H); 3.92 (br. s, 2H); 3.05 (s, 3H); 2.78-2.92 (m, 1H); 2.35-2.45 (m, 1H); 1.50 (s, 3H).

MS1 (ESI, m/z): 460.1 [M+H$^+$] for C$_{22}$H$_{22}$N$_3$O$_5$FS; t$_R$=0.53 min.

Example 24: (R)-4-(5-(5-amino-5-methylhexa-1,3-diyn-1-yl)-2H-indazol-2-yl)-N-hydroxy-2-methyl-2-(methylsulfonyl)butanamide Starting from intermediate A.vi (0.090 g; 0.19 mmol) and 2-(4-(4,4,5,5-tetramethyl-1,3,2-dioxaborolan-2-yl)phenyl)oxazole (0.055 g; 0.21 mmol; commercial), and proceeding successively in analogy to Example 1, steps 1.i and 1.ii (Suzuki coupling: 32% yield; deprotection: 27% yield), the title compound was obtained as an off-white solid (0.009 g).

$^1$H NMR (d6-DMSO) δ: 11.0 (s, 1H); 9.24 (s, 1H); 8.49 (s, 1H); 8.00-8.11 (m, 3H); 7.81-7.88 (m, 2H); 7.60-7.73 (m, 2H); 7.38 (s, 1H); 4.48-4.60 (m, 1H); 4.30-4.44 (m, 1H); 3.05 (s, 3H); 2.78-2.90 (m, 1H); 2.35-2.44 (overlapped m, 1H); 1.50 (s, 3H).

MS1 (ESI, m/z): 455.2 [M+H$^+$] for C$_{22}$H$_{22}$N$_4$O$_5$S; t$_R$=0.73 min.

Example 25: (R)—N-hydroxy-4-{5-[4-(2-hydroxy-ethyl)-phenylethynyl]-indazol-2-yl}-2-methylsulfonyl-2-methyl-butanamide Starting from the compound of Preparation J (0.081 g; 0.155 mmol) and 2-(4-iodophenyl)ethanol (0.025 g; 0.174 mmol; commercial), and proceeding successively in analogy to Example 7, step 7.i (68% yield) and Example 1, step 1.ii (84% yield), the title compound was obtained, after purification by prep-HPLC (Method 2), as a beige solid (0.037 g).

$^1$H NMR (d6-DMSO) δ: 8.47 (s, 1H); 7.95 (s, 1H); 7.62 (d, J=8.8 Hz, 1H); 7.44 (d, J=8.2 Hz, 2H); 7.31 (d, J=8.8 Hz, 1H); 7.26 (d, J=8.2 Hz, 2H); 4.63 (t, J=5.2 Hz, 1H); 4.48-4.58 (m, 1H); 4.27-4.41 (m, 1H); 3.60 (q, J=6.7 Hz, 2H); 3.06 (s, 3H); 2.75-2.90 (m, 1H); 2.74 (t, J=7.0 Hz, 2H); 2.33-2.43 (m, 1H); 1.52 (s, 3H).

MS1 (ESI, m/z): 456.1 [M+H$^+$] for C$_{23}$H$_{25}$N$_3$O$_5$S; t$_R$=0.59 min.

Example 26: (2R)-4-{5-[4-((R)-1,2-dihydroxy-ethyl)-phenylethynyl]-indazol-2-yl}-N-hydroxy-2-methylsulfonyl-2-methyl-butanamide Starting from the compound of Preparation J (0.082 g; 0.195 mmol) and (R)-1-(4-iodophenyl)-1,2-ethanediol (0.058 g, 0.22 mmol), and proceeding successively in analogy to Example 7, step 7.i (50% yield) and Example 1, step 1.ii (37% yield), the title compound was obtained, after purification by prep-HPLC (Method 2), as a beige solid (0.017 g).

$^1$H NMR (d6-DMSO) δ: 8.47 (s, 1H); 7.96 (s, 1H); 7.63 (d, J=8.8 Hz, 1H); 7.48 (d, J=8.2 Hz, 2H); 7.37 (d, J=8.2 Hz, 2H); 7.32 (d, J=8.8 Hz, 1H); 5.29 (br. s, 1H); 4.71 (br. s, 1H); 4.48-4.61 (m, 2H); 4.28-4.42 (m, 1H); 3.39-3.47 (m, 2H); 3.06 (s, 3H); 2.78-2.90 (m, 1H); 2.32-2.51 (overlapped m, 1H); 1.52 (s, 3H).

MS1 (ESI, m/z): 472.15 [M+H$^+$] for C$_{23}$H$_{25}$N$_3$O$_6$S; t$_R$=0.61 min.

Example 27: (R)—N-hydroxy-4-(5-((4-(2-hydroxy-propan-2-yl)phenyl)ethynyl)-2H-indazol-2-yl)-2-methyl-2-(methylsulfonyl)butanamide Starting from the compound of Preparation H (0.1 g, 0.19 mmol) and 2-(4-ethynylphenyl)propan-2-ol (0.034 g, 0.21 mmol; prepared as described in WO 2006/099972), and proceeding successively in analogy to Example 7, step 7.i (79% yield) and Example 1, step 1.ii (32% yield), the title compound was obtained, after purification by prep-HPLC (Method 1), as a beige solid (0.022 g).

$^1$H NMR (d6-DMSO) δ: 11.03 (s, 1H); 9.26 (s, 1H); 8.49 (s, 1H); 7.98 (s, 1H); 7.65 (d, J=9.1 Hz, 1H); 7.44-7.55 (m, 4H); 7.33 (dd, J=9.1, 1.0 Hz, 1H); 5.08 (br. s, 1H); 4.49-4.63 (m, 1H); 4.28-4.42 (m, 1H); 3.08 (s, 3H); 2.79-2.93 (m, 1H); 2.33-2.54 (overlapped m, 1H); 1.54 (s, 3H); 1.44 (s, 6H).

MS1 (ESI, m/z): 470.2 [M+H$^+$] for $C_{24}H_{27}N_3O_5S$; $t_R$=0.72 min.

Example 28: (R)—N-hydroxy-4-(5-((3-hydroxyoxetan-3-yl)buta-1,3-diyn-1-yl)-2H-indazol-2-yl)-2-methyl-2-(methylsulfonyl)butanamide Starting from the compound of Preparation J (0.148 g, 0.35 mmol) and the compound of Preparation G (0.090 g, 0.40 mmol), and proceeding successively in analogy to Example 7, step 7.i (54% yield) and Example 1, step 1.ii (60% yield), the title compound was obtained, after purification by prep-HPLC (Method 2), as a beige solid (0.049 g).

$^1$H NMR (d6-DMSO) δ: 9.27 (br. s, 1H); 8.51 (s, 1H); 8.07 (s, 1H); 7.62 (d, J=8.9 Hz, 1H); 7.29 (dd, J=1.4, 8.9 Hz, 1H); 6.71 (br. s, 1H); 4.70 (d, J=6.7 Hz, 2H); 4.54 (d, J=6.7 Hz, 2H); 4.54 (overlaid m, 1H); 4.34 (m, 1H); 3.04 (s, 3H); 2.82 (m, 1H); 2.39 (overlaid m, 1H); 1.54 (s, 3H).

MS1 (ESI, m/z): 431.7 [M+H+] for $C_{20}H_{21}N_3O_6S$; $t_R$=0.63 min.

Example 29: (R)-4-{4-fluoro-5-[4-(3-hydroxy-oxetan-3-yl)-phenylethynyl]-indazol-2-yl}-N-hydroxy-2-methylsulfonyl-2-methyl-butanamide Starting from intermediate 20.ii (0.04 g, 0.2 mmol) and the compound of Preparation K (0.1 g; 0.185 mmol), and proceeding successively in analogy to Example 7, step 7.i (57% yield) and Example 1, step 1.ii (64% yield), the title compound was obtained, after purification by prep-HPLC (Method 1), as a yellowish foam (0.032 g).

$^1$H NMR (d6-DMSO) δ: 11.0 (br. s, 1H); 9.22 (br. s, 1H); 8.73 (s, 1H); 7.46-7.70 (m, 5H); 7.33 (m, 1H); 6.43 (br. s, 1H); 4.73-4.79 (m, 2H); 4.61-4.68 (m, 2H); 4.55 (m, 1H); 4.37 (m, 1H); 3.05 (s, 3H); 2.79-2.88 (m, 1H); 2.35-2.45 (m, 1H); 1.50 (s, 3H).

MS1 (ESI, m/z): 502.1 [M+H$^+$] for $C_{24}H_{24}N_3O_6FS$; $t_R$=0.69 min.

Example 30: (R)-4-{5-[4-(3-dimethylamino-oxetan-3-yl)-phenylethynyl]-indazol-2-yl}-N-hydroxy-2-methylsulfonyl-2-methyl-butanamide toluene-4-sulfonic acid salt Starting from the compound of Preparation J (0.1 g, 0.248 mmol) and the compound of Preparation M (0.085 g, 0.28 mmol), and proceeding successively in analogy to Example 7, step 7.i (44% yield) and Example 1, step 1.ii (39% yield), the title compound was obtained, after purification by prep-HPLC (Method 2), as a beige solid (0.030 g).

MS1 (ESI, m/z): 511.1 [M+H$^+$] for $C_{33}H_{38}N_4O_8S_2$; $t_R$=0.45 min.

Example 31: (R)-4-{6-fluoro-5-[4-(3-hydroxy-oxetan-3-yl)-buta-1,3-diynyl]-indazol-2-yl}-N-hydroxy-2-methylsulfonyl-2-methyl-butanamide Starting from the compound of Preparation R (0.1 g, 0.23 mmol) and the compound of Preparation G (0.056 g, 0.25 mmol), and proceeding successively in analogy to Preparation E, step E.ii (47% yield) and Example 1, step 1.iii (27% yield), the title compound was obtained, after purification by prep-HPLC (Method 1), as an orange foam (0.012 g).

$^1$H NMR (d6-DMSO) δ: 9.15-9.33 (m, 1H); 8.59 (s, 1H); 8.21 (d, J=7.0 Hz, 1H); 7.51 (d, J=10.9 Hz, 1H); 6.77 (s, 1H); 4.73 (d, J=6.6 Hz, 2H); 4.56 (d, J=6.6 Hz, 2H); 4.49-4.62 (overlapped m, 1H); 4.28-4.41 (m, 1H); 3.06 (s, 3H); 2.77-2.92 (m, 1H); 2.32-2.57 (overlapped m, 1H); 1.52 (s, 3H).

MS1 (ESI, m/z): 449.9 [M+H$^+$] for $C_{20}H_{20}N_3O_6FS$; $t_R$=0.64 min.

Example 32: (R)—N-hydroxy-4-[5-(5-hydroxy-5-methyl-hexa-1,3-diynyl)-indazol-2-yl]-2-methylsulfonyl-2-methyl-butanamide Starting from the compound of Preparation J (0.1 g; 0.248 mmol) and 4-iodo-2-methylbut-3-yn-2-ol (0.060 g; 0.28 mmol; prepared as reported in Rajender Reddy et al., *Tetrahedron Lett.* (2010), 51, 2170-2173), and proceeding successively in analogy to Example 7, step 7.i (93% yield) and Example 1, step 1.ii (66% yield), the title compound was obtained, after purification by prep-HPLC (Method 2), as a beige solid (0.063 g).

$^1$H NMR (d6-DMSO): 8.49 (s, 1H); 8.01 (s, 1H); 7.61 (d, J=8.9 Hz, 1H); 7.27 (d, J=8.9 Hz, 1H); 4.46-4.61 (m, 1H); 4.28-4.40 (m, 1H); 2.76-2.90 (m, 3H); 2.31-2.50 (m, overlaid with DMSO, 1H); 1.49 (s, 3H); 1.40 (s, 6H).

MS1 (ESI, m/z): 418.1 [M+H$^+$] for $C_{20}H_{23}N_3O_5S$; $t_R$=0.68 min.

Example 33: (R)—N-hydroxy-4-(5-((4-((R)-1-hydroxyethyl)phenyl)ethynyl)-2H-indazol-2-yl)-2-methyl-2-(methylsulfonyl)butanamide Starting from the compound of Preparation J (0.1 g, 0.24 mmol) and (R)-1-(4-iodophenyl)ethan-1-ol (0.082 g; 0.33 mmol; commercial), and proceeding successively in analogy to Example 7, step 7.i (73% yield) and Example 1, step 1.ii (71% yield), the title compound was obtained as a beige solid (0.055 g) recovered by filtration from water.

$^1$H NMR (d6-DMSO) δ: 11.01 (s, 1H); 9.24 (s, 1H); 8.47 (s, 1H); 7.96 (s, 1H); 7.62 (d J=8.9 Hz, 1H); 7.44-7.51 (m, 2H); 7.34-7.40 (m, 2H); 7.31 (dd, J=1.3, 8.9 Hz, 1H); 5.14-5.25 (m, 1H); 4.72 (q, J=6.4 Hz, 1H); 4.48-4.60 (m, 1H); 4.27-4.40 (m, 1H); 3.05 (s, 3H); 2.78-2.90 (m, 1H); 2.32-2.52 (overlapped m, 1H); 1.52 (s, 3H); 1.31 (d, J=6.4 Hz, 3H).

MS1 (ESI, m/z): 456.1 [M+H$^+$] for $C_{23}H_{25}N_3O_5S$; $t_R$=0.70 min.

Example 34: (R)—N-hydroxy-4-(5-4-((4(S)-1-hydroxyethyl)phenyl)ethynyl)-2H-indazol-2-yl)-2-methyl-2-(methylsulfonyl)butanamide Starting from the compound of Preparation J (0.1 g, 0.24 mmol) and (S)-1-(4-iodophenyl)ethan-1-ol (0.082 g; 0.33 mmol; commercial), and proceeding successively in analogy to Example 7, step 7.i (54% yield) and Example 1, step 1.ii (79% yield), the title compound was obtained as a beige solid (0.043 g) recovered by filtration from water.

$^1$H NMR (d6-DMSO) δ: 11.01 (s, 1H); 9.24 (s, 1H); 8.47 (s, 1H); 7.96 (s, 1H); 7.62 (d, J=8.9 Hz, 1H); 7.44-7.51 (m, 2H); 7.34-7.40 (m, 2H); 7.31 (dd, J=1.3, 8.9 Hz, 1H); 5.14-5.25 (m, 1H); 4.72 (q, J=6.4 Hz, 1H); 4.48-4.60 (m,

1H); 4.27-4.40 (m, 1H); 3.05 (s, 3H); 2.78-2.90 (m, 1H); 2.32-2.52 (overlapped m, 1H); 1.52 (s, 3H); 1.31 (d, J=6.4 Hz, 3H).

MS1 (ESI, m/z): 456.1 [M+H$^+$] for $C_{23}H_{25}N_3O_5S$; $t_R$=0.70 min.

Example 35: (R)-4-[5-(2-fluoro-4-trifluoromethoxyphenyl)-indazol-2-yl]-N-hydroxy-2-methylsulfonyl-2-methyl-butanamide Starting from the compound of Preparation H (0.10 g; 0.19 mmol) and 2-fluoro-4-trifluoromethoxyphenylboronic acid (0.052 g; 0.23 mmol; commercial), and proceeding successively in analogy to Example 1, step 1.i (83% yield) and step 1.ii (75% yield), the title compound was obtained as an off-white solid (0.056 g) recovered by filtration from water.

$^1$H NMR (d6-DMSO) δ: 11.04 (br. s, 1H); 9.27 (br. s, 1H); 8.52 (s, 1H); 7.90 (s, 1H); 7.66-7.74 (m, 2H); 7.46-7.53 (m, 1H); 7.38-7.45 (m, 1H); 7.30-7.37 (m, 1H); 4.51-4.64 (m, 1H); 4.32-4.45 (m, 1H); 3.08 (s, 3H); 2.80-2.94 (m, 1H); 2.36-2.56 (overlapped m, 1H); 1.53 (s, 3H).

MS1 (ESI, m/z): 490.1 [M+H$^+$] for $C_{20}H_{19}N_3O_5F_4S$; $t_R$=0.82 min.

Example 36: (R)—N-hydroxy-4-(5-(((1S,2S)-2-(hydroxymethyl)cyclopropyl)buta-1,3-diyn-1-yl)-2H-indazol-2-yl)-2-methyl-2-(methylsulfonyl)butanamide formate

36.i. ((1S,2S)-24(2-((R)-3-methyl-3-(methylsulfonyl)-4-oxo-4-((((RS)-tetrahydro-2H-pyran-2-yl)oxy)amino)butyl)-2H-indazol-5-yl)buta-1,3-diyn-1-yl)cyclopropyl)methyl acetate Starting from the compound of Preparation J (0.254 g; 0.605 mmol) and the dextrorotatory compound of Preparation U (0.177 g; 0.81 mmol), and proceeding in analogy to Example 7, step 7.i, the title compound was obtained, after purification by CC (Hept-EA), as a yellowish oil (0.077 g, 23% yield).

MS1 (ESI, m/z): 555.97 [M+H$^+$] for $C_{28}H_{33}N_3O_7S$; $t_R$=0.90 min.

36.ii. (R)-4-(5-(((1S,2S)-2-(hydroxymethyl)cyclopropyl)buta-1,3-diyn-1-yl)-2H-indazol-2-yl)-2-methyl-2-(methylsulfonyl)-N—(((RS)-tetrahydro-2H-pyran-2-yl)oxy)butanamide To a solution of intermediate 36.i (0.124 g; 0.223 mmol) in MeOH (1 mL) was added K$_2$CO$_3$ (0.062 g; 0.447 mmol). The suspension was stirred at rt for 30 min. The reaction mixture was diluted with DCM (10 mL) and washed with an aq. 15% NaHSO$_4$ solution (8 mL). The aq. layer was extracted with DCM/MeOH (9/1, 4×10 mL). The combined org. layers were dried over MgSO$_4$, filtered and evaporated under reduced pressure to afford the desired product as a yellow oil (0.108 g).

MS1 (ESI, m/z): 513.91 [M+H$^+$] for $C_{26}H_{31}N_3O_6S$; $t_R$=0.80 min.

36.iii. (R)—N-hydroxy-4-(5-(((1S,2S)-2-(hydroxymethyl)cyclopropyl)buta-1,3-diyn-1-yl)-2H-indazol-2-yl)-2-methyl-2-(methylsulfonyl)butanamide formate Starting from intermediate 36.ii (0.108 g; 0.24 mmol) and proceeding in analogy to Example 1, step 1.ii, the title compound was obtained, after purification by prep-HPLC (Method 2), as a beige solid (0.052 g, 57% yield).

$^1$H NMR (d6-DMSO) δ: 11.98 (s, 1H); 9.22 (br. s, 1H); 8.46 (br. s, 1H); 8.11 (br. s, 1H); 7.97 (br. s, 1H); 7.23 (d, J=8.8 Hz, 1H); 7.58 (d, J=8.8 Hz, 1H); 4.65 (m, 1H); 4.52 (m, 1H); 4.32 (m, 1H); 3.40 (m, 1H); 3.25 (overlapped m, 1H); 3.04 (s, 3H); 2.81 (m, 1H); 2.38 (overlapped m, 1H); 1.49 (s, 3H); 1.34-1.45 (m, 2H); 0.79-0.97 (m, 2H).

MS1 (ESI, m/z): 429.94 [M+H$^+$] for $C_{21}H_{23}N_3O_5S$; $t_R$=0.68 min.

Example 37: (R)—N-hydroxy-4-(5-((((R,2R)-2-(hydroxymethyl)cyclopropyl)buta-1,3-diyn-1-yl)-2H-indazol-2-yl)-2-methyl-2-(methylsulfonyl)butanamide formate Starting from the compound of Preparation J (0.252 g; 0.602 mmol) and the levorotatory compound of Preparation U (0.177 g; 0.81 mmol); and proceeding in analogy to Example 36, steps 36.i to 36.iii (Sonogashira coupling: 10% yield; acetate cleavage and deprotection: 63% yield), the title compound was obtained, after purification by prep-HPLC (Method 2), as a beige solid (0.056 g).

$^1$H NMR (d6-DMSO) δ: 11.98 (s, 1H); 9.22 (br. s, 1H); 8.46 (br. s, 1H); 8.11 (br. s, 1H); 7.97 (br. s, 1H); 7.23 (d, J=8.8 Hz, 1H); 7.58 (d, J=8.8 Hz, 1H); 4.65 (m, 1H); 4.52 (m, 1H); 4.32 (m, 1H); 3.23-3.40 (m, 2H); 3.04 (s, 3H); 2.81 (m, 1H); 2.38 (overlapped m, 1H); 1.49 (s, 3H); 1.34-1.45 (m, 2H); 0.79-0.97 (m, 2H).

MS1 (ESI, m/z): 429.95 [M+H$^+$] for $C_{21}H_{23}N_3O_5S$; $t_R$=0.68 min.

Example 38: (R)-4-{4-fluoro-5-[4-(3-hydroxy-oxetan-3-yl)-buta-1,3-diynyl]-indazol-2-yl}-N-hydroxy-2-methylsulfonyl-2-methyl-butanamide Starting from intermediate 36.i (0.130 g; 0.30 mmol) and the compound of Preparation G (0.073 g; 0.32 mmol), and proceeding successively in analogy to Preparation E, step E.ii (50% yield) and Example 1, step 1.ii (45% yield), the title compound was obtained, after purification by prep-HPLC (Method 1), as a beige solid (0.030 g).

$^1$H NMR (d6-DMSO) δ: 11.01 (s, 1H); 9.24 (br. s, 1H); 8.79 (s, 1H); 7.47-7.54 (m, 1H); 7.28-7.37 (m, 1H); 6.77 (br. s, 1H); 4.73 (d, J=6.3 Hz, 2H); 4.56 (d, J=6.3 Hz, 2H); 4.52-4.61 (overlapped m, 1H); 4.32-4.46 (m, 1H); 3.07 (s, 3H); 2.80-2.94 (m, 1H); 2.33-2.57 (overlapped m, 1H); 1.53 (s, 3H).

MS (ESI, m/z): 449.86 [M+H$^+$] for $C_{20}H_{20}N_3O_6FS$; $t_R$=0.65 min.

Example 39: (R)-4-[5-(2-fluoro-4-hydroxymethyl-phenylethynyl)-indazol-2-yl]-N-hydroxy-2-methylsulfonyl-2-methyl-butanamide Starting from the compound of Preparation H (0.1 g; 0.19 mmol) and the compound of Preparation Q (0.037 g; 0.21 mmol; prepared as described in WO 2006/099972), and proceeding successively in analogy to Example 7, step 7.i (79% yield) and Example 1, step 1.ii (32% yield), the title compound was obtained, after purification by prep-HPLC (Method 1), as a beige solid (0.022 g).

1H NMR (d6-DMSO) δ: 11.03 (br. s, 1H); 9.26 (s, 1H); 8.51 (s, 1H); 8.01 (s, 1H); 7.66 (d, J=8.8 Hz, 1H); 7.58 (t, J=7.8 Hz, 1H); 7.31-7.36 (m, 1H); 7.17-7.27 (m, 2H);

5.36-5.43 (m, 1H); 4.49-4.63 (m, 3H); 4.30-4.42 (m, 1H); 3.08 (s, 3H), 2.79-2.92 (m, 1H); 2.34-2.56 (overlapped m, 1H); 1.54 (s, 3H).

MS1 (ESI, m/z): 460.0 [M+H$^+$] for $C_{22}H_{22}N_3O_5FS$; $t_R$=0.69 min.

Example 40: 4-(6-fluoro-5-((4-(3-hydroxyoxetan-3-yl)phenyl)ethynyl)-2H-indazol-2-yl)-N-hydroxy-2-methyl-2-(methylsulfonyl)butanamide Starting from the compound of Preparation R (0.1 g, 0.18 mmol) and intermediate 20.ii (0.042 g, 0.24 mmol), and proceeding successively in analogy to Preparation E, step E.ii (67% yield) and Example 1, step 1.iii (76% yield), the title compound was obtained, after purification by prep-HPLC (Method 1), as a yellowish foam (0.046 g).

$^1$H NMR (d6-DMSO) δ: 11.03 (s, 1H); 9.25 (s, 1H); 8.56 (s, 1H); 8.12 (d, J=7.2 Hz, 1H); 7.67 (d, J=7.6 Hz, 2H); 7.60 (d, J=7.6 Hz, 2H); 7.50 (d, J=10.9 Hz, 1H); 6.46 (s, 1H); 4.79 (d, J=6.0 Hz, 2H); 4.68 (d, J=6.0 Hz, 2H); 4.49-4.62 (m, 1H); 4.28-4.41 (m, 1H); 3.07 (s, 3H); 2.79-2.92 (m, 1H); 2.34-2.55 (overlapped m, 1H); 1.54 (s, 3H).

MS1 (ESI, m/z): 501.9 [M+H$^+$] for $C_{24}H_{24}N_3O_6FS$; $t_R$=0.68 min.

Example 41: (R)—N-hydroxy-4-(5-((4-((1R,2R)-2-(hydroxymethyl)cyclopropyl)phenyl)ethynyl)-2H-indazol-2-yl)-2-methyl-2-(methylsulfonyl)butanamide Starting from the compound of Preparation J (0.106 g; 0.253 mmol) and the first-eluting enantiomer of Preparation W (0.079 g; 0.288 mmol), and proceeding successively in analogy to Example 7, step 7.i (90% yield) and Example 1, step 1.ii (38% yield), the title compound was obtained, after purification by prep-HPLC (Method 2), as a beige solid (0.041 g).

$^1$H NMR (d6-DMSO) δ: 11.0 (s, 1H); 9.23 (s, 1H); 8.46 (s, 1H); 7.93 (s, 1H); 7.61 (d, J=8.8 Hz, 1H); 7.39 (d, J=7.0 Hz, 2H); 7.30 (d, J=9.1 Hz, 1H); 7.09 (d, J=7.9 Hz, 2H); 4.46-4.63 (overlapped m, 2H); 4.26-4.40 (m, 1H); 3.40-3.53 (m, 1H); 3.26-3.38 (overlapped m, 1H); 3.05 (s, 3H); 2.75-2.88 (m, 1H); 2.30-2.51 (overlapped m, 1H); 1.75-1.86 (m, 1H); 1.51 (s, 3H); 1.22-1.35 (m, 1H); 0.80-0.95 (m, 2H).

MS1 (ESI, m/z): 481.95 [M+H$^+$] for $C_{25}H_{27}N_3O_5S$; $t_R$=0.62 min.

Example 42: (R)—N-hydroxy-4-(5-((4-((1S,2S)-2-(hydroxymethyl)cyclopropyl)phenyl)ethynyl)-2H-indazol-2-yl)-2-methyl-2-(methylsulfonyl)butanamide Starting from the compound of Preparation J (0.106 g; 0.253 mmol) and the second-eluting enantiomer of Preparation W (0.079 g; 0.288 mmol), and proceeding successively in analogy to Example 7, step 7.i (71% yield) and Example 1, step 1.ii (46% yield), the title compound was obtained, after purification by prep-HPLC (Method 2), as a beige solid (0.041 g).

$^1$H NMR (d6-DMSO) δ: 11.0 (s, 1H), 9.23 (s, 1H); 8.46 (s, 1H), 7.93 (s, 1H), 7.61 (d, J=8.8 Hz, 1H), 7.39 (d, J=7.0 Hz, 2H), 7.30 (d, J=9.1 Hz, 1H), 7.09 (d, J=7.9 Hz, 2H), 4.46-4.63 (overlapped m, 2H), 4.26-4.40 (m, 1H), 3.40-3.53 (m, 1H), 3.26-3.38 (overlapped m, 1H), 3.05 (s, 3H), 2.75-2.88 (m, 1H), 2.30-2.51 (overlapped m, 1H), 1.75-1.86 (m, 1H), 1.51 (s, 3H), 1.22-1.35 (m, 1H); 0.80-0.95 (m, 2H).

MS1 (ESI, m/z): 481.95 [M+H$^+$] for $C_{25}H_{27}N_3O_5S$; $t_R$=0.62 min.

Example 43: (R)—N-hydroxy-4-(5-((4-(3-(hydroxymethyl)oxetan-3-yl)phenyl)ethynyl)-2H-indazol-2-yl)-2-methyl-2-(methylsulfonyl)butanamide Starting from the compound of Preparation J (0.100 g; 0.24 mmol) and the compound of Preparation X (0.079 g; 0.27 mmol), and proceeding successively in analogy to Example 7, step 7.i (72% yield) and Example 1, step 1.ii (53% yield), the title compound was obtained, after purification by prep-HPLC (Method 1), as a yellowish solid (0.041 g).

$^1$H NMR (d6-DMSO) δ: 11.03 (s, 1H); 9.26 (s, 1H); 8.50 (s, 1H); 7.99 (s, 1H); 7.63 (s, 1H); 7.53 (d, J=8.1 Hz, 2H); 7.35 (s, 1H); 7.20 (d, J=8.1 Hz, 2H); 5.08-5.20 (m, 1H); 4.72 (br. s, 4H); 4.47-4.65 (s, 1H); 4.29-4.42 (m, 1H); 3.68-3.76 (m, 2H); 3.07 (s, 3H); 2.79-2.93 (m, 1H); 2.36-2.55 (overlapped m, 1H); 1.54 (s, 3H).

MS1 (ESI, m/z): 497.8 [M+H$^+$] for $C_{25}H_{27}N_3O_6S$; $t_R$=0.66 min.

Example 44: (R)—N-hydroxy-4-(5-((4-(2-hydroxyethoxy)phenyl)ethynyl)-2H-indazol-2-yl)-2-methyl-2-(methylsulfonyl)butanamide Starting from the compound of Preparation J (0.100 g; 0.24 mmol) and 2-(4-iodophenoxy)ethanol (0.06 g; 0.28 mmol; commercial) and proceeding successively in analogy to Example 7, step 7.i (39% yield) and Example 1, step 1.ii (67% yield), the title compound was obtained, after precipitation from the reaction mixture and washing with water, as a beige solid (0.041 g).

$^1$H NMR (d6-DMSO) δ: 11.03 (s, 1H); 9.24 (s, 1H); 8.45 (s, 1H); 7.92 (s, 1H); 7.62 (d, J=8.0 Hz, 1H); 7.45 (d, J=8.2 Hz, 2H); 7.30 (dd, J=0.9, 8.0 Hz, 1H); 6.96 (d, J=8.1 Hz, 2H); 4.84 (m, 1H); 4.54 (m, 1H); 4.34 (m, 1H); 3.96-4.04 (m, 2H); 3.66-3.74 (m, 2H); 3.05 (s, 3H); 2.83 (m, 1H); 2.39 (overlapped m, 1H); 1.51 (s, 3H).

MS1 (ESI, m/z): 471.9 [M+H$^+$] for $C_{23}H_{25}N_3O_6S$; $t_R$=0.66 min.

Example 45: (R)-4-(5-((3-fluoro-4-(2-hydroxyacetamido)phenyl)ethynyl)-2H-indazol-2-yl)-N-hydroxy-2-methyl-2-(methylsulfonyl)butanamide Starting from the compound of Preparation J (0.100 g; 0.24 mmol) and the compound of Preparation Y (0.084 g; 0.29 mmol), and proceeding successively in analogy to Example 7, step 7.i (42% yield) and Example 1, step 1.ii (64% yield), the title compound was obtained, after filtration from water and trituration in Et$_2$O, as an orange solid (0.029 g).

$^1$H NMR (500 MHz, d$_6$-DMSO) δ: 11.06 (s, 1H); 9.44 (s, 1H); 9.29 (s, 1H); 8.52 (s, 1H); 8.08 (t, J=8.3 Hz, 1H); 8.01 (s, 1H); 7.66 (d, J=8.9 Hz, 1H); 7.52 (d, J=11.5 Hz, 1H); 7.40 (d, J=8.5 Hz, 1H); 7.35 (d, J=8.9 Hz, 1H); 5.91 (t, J=5.9 Hz, 1H); 4.54-4.61 (m, 1H); 4.32-4.40 (m, 1H); 4.07 (d, J=5.6 Hz, 2H); 3.08 (s, 3H); 2.83-2.90 (m, 1H); 2.35-2.46 (m, 1H); 1.54 (s, 3H).

MS1 (ESI, m/z): 502.9 [M+H$^+$] for $C_{23}H_{23}N_4O_6PS$; $t_R$=0.67 min.

Example 46: (R)-4-(5-((R)-5,6-dihydroxy-5-methyl-hexa-1,3-diyn-1-yl)-2H-indazol-2-yl)-N-hydroxy-2-methyl-2-(methylsulfonyl)butanamide

46.i. (2R)-4-(5-((R)-6-((tert-butyldiphenylsilyl)oxy)-5-hydroxy-5-methylhexa-1,3-diyn-1-yl)-2H-indazol-2-yl)-2-methyl-2-(methylsulfonyl)-N—(((RS)-tetrahydro-2H-pyran-2-yl)oxy)butanamide Starting from the compound of Preparation J (0.100 g; 0.24 mmol) and the compound of Preparation Z (0.133 g; 0.29 mmol), and proceeding in analogy to Example 7, step 7.i, the title compound was obtained, after purification by CC (DCM-MeOH), as an orange foam (0.103 g, 57% yield).

$^1$H NMR (300 MHz, d$_6$-DMSO) δ (mixture of stereoisomers): 11.43 (s, 0.5H); 11.40 (s, 0.5H); 8.50 (br. s, 1H); 8.06 (br. s, 1H); 7.40-7.72 (m, 11H); 7.26-7.32 (m, 1H); 5.77 (s, 1H); 5.75 (s, 1H); 4.89-4.98 (m, 1H); 4.50-4.64 (m, 1H); 4.33-4.47 (m, 1H); 3.62-3.68 (m, 1H); 3.47-3.57 (m, 2H); 3.08 (s, 1.5H); 3.05 (s, 1.5H); 2.78-2.93 (m, 1H); 2.32-2.53 (overlapped m, 1H); 1.63-1.75 (m, 3H); 1.51 (s, 3H); 1.41-1.60 (overlapped m, 6H); 1.04 (s, 9H).

MS1 (ESI, m/z): 755.9 [M+H$^+$] for C$_{41}$H$_{49}$N$_3$O$_7$SSi; t$_R$=1.06 min.

46.ii. (2R)-4-(5-((R)-5,6-dihydroxy-5-methylhexa-1,3-diyn-1-yl)-2H-indazol-2-yl)-2-methyl-2-(methylsulfonyl)-N—(((RS)-tetrahydro-2H-pyran-2-yl)oxy)butanamide To a stirred solution of intermediate 46.i (0.1 g; 0.13 mmol) in MeOH (2 mL) was added ammonium fluoride (0.04 g; 1.06 mmol) at reflux for 6.5 h. The resulting mixture was concentrated to the dryness. The residue was purified by CC (DCM-MeOH) to afford the title compound as a yellowish foam (0.064 g; 93% yield).

$^1$H NMR (300 MHz, d$_6$-dmso) δ: 11.34-11.42 (m, 1H); 8.46 (s, 1H); 8.01 (s, 1H); 7.60 (d, J=8.9 Hz, 1H); 7.22-7.29 (m, 1H); 5.72 (s, 1H); 5.52 (s, 1H); 5.00-5.07 (m, 1H); 4.87-4.95 (m, 1H); 4.47-4.60 (m, 1H); 4.30-4.44 (m, 1H); 3.95-4.13 (m, 1H); 3.22-3.54 (overlapped m, 2H); 3.04 (s, 1.5H); 3.02 (s, 1.5H); 2.74-2.88 (m, 1H); 2.32-2.52 (overlapped m, 1H); 1.61-1.71 (m, 3H); 1.44-1.57 (m, 6H); 1.32 (s, 3H).

MS (ESI, m/z): 518.2 [M+H$^+$] for C$_{25}$H$_{31}$N$_3$O$_7$S; t$_R$=0.71 min.

46.iii. (R)-4-(5-((R)-5,6-dihydroxy-5-methylhexa-1,3-diyn-1-yl)-2H-indazol-2-yl)-N-hydroxy-2-methyl-2-(methylsulfonyl)butanamide Starting from intermediate 46.ii (0.06 g; 0.116 mmol) and proceeding in analogy to Example 1, step 1.ii, the title compound was obtained, after purification by prep-HPLC (Method 1), as an orange solid (0.025 g; 49% yield).

$^1$H NMR (400 MHz, d$_6$-DMSO) δ: 8.53 (s, 1H); 8.05 (s, 1H); 7.64 (d, J=8.9 Hz, 1H); 7.29 (d, J=9.3 Hz, 1H); 5.50-5.76 (m, 1H); 4.99-5.27 (m, 1H); 4.50-4.62 (m, 1H); 4.29-4.41 (m, 1H); 3.28-3.44 (overlapped m, 2H); 3.07 (s, 3H); 2.78-2.89 (m, 1H); 2.32-2.43 (m, 1H); 1.51 (s, 3H); 1.36 (s, 3H).

MS1 (ESI, m/z): 434.2 [M+H$^+$] for C$_{20}$H$_{23}$N$_3$O$_6$S; t$_R$=0.59 min.

Example 47: (R)—N-hydroxy-4-(5-((4-(2-hydroxyacetamido)phenyl)ethynyl)-2H-indazol-2-yl)-2-methyl-2-(methylsulfonyl)butanamide Starting from the compound of Preparation J (0.100 g; 0.24 mmol) and 2-hydroxy-N-(4-iodophenyl)acetamide (0.069 g; 0.25 mmol; commercial) and proceeding successively in analogy to Example 7, step 7.i (51% yield) and Example 1, step 1.ii (73% yield), the title compound was obtained, after filtration from water, as a beige solid (0.0411 g).

$^1$H NMR (500 MHz, d6-DMSO) δ: 11.06 (s, 1H); 9.88 (s, 1H); 9.29 (s, 1H); 8.50 (s, 1H); 7.97 (s, 1H); 7.79 (d, J=8.3 Hz, 2H); 7.65 (d, J=8.9 Hz, 1H); 7.50 (d, J=8.3 Hz, 2H); 7.33 (d, J=8.9 Hz, 1H); 5.62-5.76 (m, 1H); 4.52-4.61 (m, 1H); 4.31-4.40 (m, 1H); 4.02 (d, J=4.1 Hz, 2H); 3.08 (s, 3H); 2.82-2.90 (m, 1H); 2.35-2.45 (m, 1H); 1.54 (s, 3H).

MS1 (ESI, m/z): 484.9 [M+H$^+$] for C$_{23}$H$_{24}$N$_4$O$_6$S; t$_R$=0.64 min.

Example 48: (R)-4-(5-((3-aminooxetan-3-yl)buta-1,3-diyn-1-yl)-2H-indazol-2-yl)-N-hydroxy-2-methyl-2-(methylsulfonyl)butanamide formate Starting from the compound of Preparation J (0.124 g; 0.296 mmol) and the compound of Preparation AA (0.177 g; 0.57 mmol) and proceeding successively in analogy to Example 7, step 7.i (quant.) and Example 13, step 13.ii (4% yield), the title compound was obtained, after purification by prep-HPLC (Method 1), as a yellow solid (0.005 g).

$^1$H NMR (500 MHz, d$_6$-DMSO) δ: 11.00 (br. s, 1H); 9.32 (br. s, 1H); 8.54 (s, 1H); 8.18 (s, 1H); 8.07 (s, 1H); 7.65 (d, J=8.9 Hz, 1H); 7.31 (d, J=8.9 Hz, 1H); 4.67 (d, J=5.8 Hz, 2H); 4.54-4.63 (m, 1H); 4.46 (d, J=5.8 Hz, 2H); 4.33-4.41 (m, 1H); 3.08 (s, 3H); 2.82-2.92 (m, 1H); 2.33-2.60 (overlapped m, 1H); 1.52 (s, 3H).

MS1 (ESI, m/z): 471.91 [M+H$^+$] for C$_{21}$H$_{24}$N$_4$O$_7$S; t$_R$=0.49 min.

Example 49: (R)—N-hydroxy-4-(5-(4-(2-hydroxyacetamido)phenyl)-2H-indazol-2-yl)-2-methyl-2-(methylsulfonyl)butanamide Starting from the compound of Preparation H (0.124 g; 0.296 mmol) and the compound of Preparation AB (0.0735 g; 0.23 mmol) and proceeding in analogy to Example 1, steps 1.i (39% yield) and 1.ii (38% yield), the title compound was obtained, after purification by prep-HPLC (Method 2), as a white solid (0.012 g).

$^1$H NMR (500 MHz, d$_6$-DMSO) δ: 10.95-11.15 (m, 1H); 9.75 (s, 1H); 9.30 (br. s, 1H); 8.46 (br. s, 1H); 7.94 (dd, J=0.8, 1.4 Hz, 1H); 7.80 (d, J=8.7 Hz, 2H); 7.68 (m, 1H); 7.65 (d, J=8.7 Hz, 2H); 7.58 (dd, J=1.7, 9.0 Hz, 1H); 5.69 (t, J=6.1 Hz, 1H); 4.52-4.60 (m, 1H); 4.33-4.40 (m, 1H); 4.02 (d, J=5.9 Hz, 2H); 3.09 (s, 3H); 2.83-2.91 (m, 1H); 2.39-2.46 (m, 1H); 1.53 (s, 3H).

MS1 (ESI, m/z): 460.9 [M+H$^+$] for C$_{21}$H$_{24}$N$_4$O$_6$S; t$_R$=0.57 min.

Example 50: (R)-4-(5-(2-fluoro-4-(2-hydroxyethoxy)phenyl)-2H-indazol-2-yl)-N-hydroxy-2-methyl-2-(methylsulfonyl)butanamide Starting from the compound of Preparation H (0.1 g; 0.192 mmol) and the compound of Preparation AC (0.065 g; 0.23 mmol) and proceeding in analogy to Example 1, steps 1.i (77% yield) and 1.ii (51% yield), the title compound was obtained, after purification by prep-HPLC (Method 2), as a beige solid (0.034 g).

$^1$H NMR (500 MHz, d$_6$-DMSO) δ: 10.95-11.18 (m, 1H); 9.16-9.41 (m, 1H); 8.47 (s, 1H); 7.80 (s, 1H); 7.67 (d, J=9.0 Hz, 1H); 7.47 (t, J=8.9 Hz, 1H); 7.38 (d, J=9.0 Hz, 1H); 6.85-6.99 (m, 2H); 4.92 (t, J=5.4 Hz, 1H); 4.52-4.61 (m,

1H); 4.33-4.42 (m, 1H); 4.06 (t, J=4.7 Hz, 2H); 3.74 (q, J=4.9 Hz, 2H); 3.09 (s, 3H); 2.82-2.91 (m, 1H); 2.38-2.46 (m, 1H); 1.53 (s, 3H).

MS1 (ESI, m/z): 465.9 [M+H$^+$] for $C_{21}H_{24}N_3O_6FS$; $t_R$=0.64 min.

Example 51: (R)-4-(5-((4-((S)-1,2-dihydroxyethyl)phenyl)ethynyl)-2H-indazol-2-yl)-N-hydroxy-2-methyl-2-(methylsulfonyl)butanamide Starting from the compound of Preparation J (0.105 g; 0.25 mmol) and (S)-1-(4-iodophenyl)-1,2-ethanediol (0.0743 g; 0.281 mmol; commercial), and proceeding successively in analogy to Example 7, step 7.i (70% yield) and Example 1, step 1.ii (31% yield), the title compound was obtained, after purification by prep-HPLC (Method 2), as a yellow solid (0.026 g).

$^1$H NMR (500 MHz, d$_6$-DMSO) δ: 11.0 (s, 1H); 9.28 (s, 1H); 8.50 (s, 1H); 7.99 (s, 1H); 7.65 (d, J=8.8 Hz, 1H); 7.50 (d, J=8.2 Hz, 2H); 7.39 (d, J=8.2 Hz, 2H); 7.34 (d, J=8.8 Hz, 1H); 5.34 (d, J=4.3 Hz, 1H); 4.76 (t, J=6.1 Hz, 1H); 4.53-4.61 (m, 2H); 4.32-4.40 (m, 2H); 3.39-3.48 (m, 1H); 3.08 (s, 3H); 2.85 (m, 1H); 2.35-2.45 (m, 1H); 1.54 (s, 3H).

MS1 (ESI, m/z): 471.93 [M+H$^+$] for $C_{23}H_{25}N_3O_6S$; $t_R$=0.60 min.

Example 52: (R)—N-hydroxy-4-(5-(4-(2-methoxyethoxy)phenyl)-2H-indazol-2-yl)-2-methyl-2-(methylsulfonyl)butanamide Starting from the compound of Preparation H (0.1 g; 0.192 mmol) and 2-(4-(2-methoxyethoxy)phenyl)-4,4,5,5-tetramethyl-1,3,2-dioxaborolane (0.064 g; 0.23 mmol; commercial), and proceeding in analogy to Example 1, steps 1.i (57% yield) and 1.ii (29% yield), the title compound was obtained, after purification by prep-HPLC (Method 2), as a beige solid (0.013 g).

$^1$H NMR (500 MHz, d$_6$-DMSO) δ: 11.06 (s, 1H); 9.29 (s, 1H); 8.44 (s, 1H); 7.89 (s, 1H); 7.65-7.68 (m, 1H); 7.62 (d, J=8.7 Hz, 2H); 7.55 (dd, J=1.6, 9.0 Hz, 1H); 7.03 (d, J=8.7 Hz, 2H); 4.51-4.60 (m, 1H); 4.32-4.40 (m, 1H); 4.11-4.17 (m, 2H); 3.66-3.71 (m, 2H); 3.33 (overlapped s, 3H); 3.09 (s, 3H); 2.82-2.91 (m, 1H); 2.38-2.46 (m, 1H); 1.53 (s, 3H).

MS1 (ESI, m/z): 462.0 [M+H$^+$] for $C_{22}H_{27}N_3O_6S$; $t_R$=0.71 min.

Example 53: (R)-4-(6-fluoro-5-(((1S,2S)-2-(hydroxymethyl)cyclopropyl)buta-1,3-diyn-1-yl)-2H-indazol-2-yl)-N-hydroxy-2-methyl-2-(methylsulfonyl)butanamide Starting from the compound of Preparation R (0.1 g; 0.229 mmol) and the (1S,2S)-configurated compound of Preparation U (0.0546 g; 0.251 mmol), and proceeding successively in analogy to Example 37, step 37.i (quant.), Example 36, step 36.ii (99% yield) and Example 1, step 1.ii (66% yield), the title compound was obtained, after filtration from water and trituration in Et$_2$O, as a brown solid (0.065 g).

$^1$H NMR (500 MHz, d$_6$-DMSO) δ: 11.03 (s, 1H); 9.19-9.37 (m, 1H); 8.55 (s, 1H); 8.13 (d, J=7.1 Hz, 1H); 7.48 (d, J=10.7 Hz, 1H); 4.50-4.58 (m, 1H); 4.29-4.38 (m, 1H); 3.41-3.46 (m, 1H); 3.23-3.29 (m, 1H); 3.07 (s, 3H); 2.80-2.88 (m, 1H); 2.34-2.42 (m, 1H); 1.52 (s, 3H); 1.42-1.49 (m, 2H); 0.93-0.98 (m, 1H); 0.85-0.91 (m, 1H).

MS1 (ESI, m/z): 447.9 [M+H$^+$] for $C_{21}H_{22}N_3O_5FS$; $t_R$=0.69 min.

Example 54: (R)-4-(4-fluoro-5-(((1S,2S)-2-(hydroxymethyl)cyclopropyl)buta-1,3-diyn-1-yl)-2H-indazol-2-yl)-N-hydroxy-2-methyl-2-(methylsulfonyl)butanamide Starting from intermediate 18.ii (0.2 g; 0.459 mmol) and the (1S,2S)-configurated compound of Preparation U, and proceeding successively in analogy to Example 37, step 37.i and Example 36, step 36.ii (91% yield over the two steps) and Example 1, step 1.ii (29% yield), the title compound was obtained, after purification by prep-HPLC (Method 1), as a beige foam (0.054 g).

$^1$H NMR (500 MHz, d$_6$-DMSO) δ: 11.05 (br. s, 1H); 9.28 (br. s, 1H); 8.75 (s, 1H); 7.47 (d, J=8.9 Hz, 1H); 7.24-7.29 (m, 1H); 4.71 (s, 1H); 4.53-4.60 (m, 1H); 4.33-4.41 (m, 1H); 3.39-3.45 (m, 1H); 3.22-3.34 (m, 1H); 3.07 (s, 3H); 2.82-2.89 (m, 1H); 2.35-2.44 (m, 1H); 1.52 (s, 3H); 1.41-1.48 (m, 2H); 0.92-0.97 (m, 1H); 0.85-0.90 (m, 1H).

MS1 (ESI, m/z): 447.97 [M+H$^+$] for $C_{21}H_{22}N_3O_5FS$; $t_R$=0.70 min.

Example 55: (R)-4-(5-((S)-5,6-dihydroxyhexa-1,3-diyn-1-yl)-2H-indazol-2-yl)-N-hydroxy-2-methyl-2-(methylsulfonyl)butanamide Starting from the compound of Preparation J (0.1 g; 0.238 mmol) and (S)-4-iodobut-3-yne-1,2-diol (0.061 g; 0.286 mmol; prepared as reported in Wang et al., J. Org. Chem. (2001), 66, 2146-2148), and proceeding successively in analogy to Example 37, step 37.i and Example 13, step 13.ii, the title compound was obtained, after purification by prep-HPLC (Method 2), as a brown foam (0.0213 g; 20% yield over the two steps).

$^1$H NMR (500 MHz, d$_6$-DMSO) δ: 11.04 (s, 1H); 9.22-9.34 (m, 1H); 8.53 (d, J=0.7 Hz, 1H); 8.04-8.08 (m, 1H); 7.64 (d, J=8.9 Hz, 1H); 7.30 (dd, J=1.5, 8.9 Hz, 1H); 4.52-4.62 (m, 1H); 4.32-4.40 (m, 1H); 4.35 (t, J=6.1 Hz, 1H); 3.47 (d, J=6.1 Hz, 2H); 3.08 (s, 3H); 2.81-2.89 (m, 1H); 2.35-2.44 (m, 1H); 1.52 (s, 3H).

MS1 (ESI, m/z): 419.8 [M+H$^+$] for $C_{19}H_{21}N_3O_6S$; $t_R$=0.55 min.

Example 56: (R)—N-hydroxy-4-(5-((1-(hydroxymethyl)cyclopropyl)buta-1,3-diyn-1-yl)-2H-indazol-2-yl)-2-methyl-2-(methylsulfonyl)butanamide Starting from the compound of Preparation J (0.1 g; 0.238 mmol) and the compound of Preparation AD (0.112 g; 0.262 mmol), and proceeding successively in analogy to Example 37, step 37.i (70% yield), Example 46, step 46.ii (87% yield), and Example 1, step 1.ii (59% yield) the title compound was obtained, after purification by prep-HPLC (Method 2), as a white foam (0.035 g).

$^1$H NMR (500 MHz, d$_6$-DMSO) δ: 11.04 (s, 1H); 9.28 (s, 1H); 8.51 (s, 1H); 7.99-8.02 (m, 1H); 7.62 (d, J=8.9 Hz, 1H); 7.27 (dd, J=1.5, 8.9 Hz, 1H); 5.03 (t, J=6.1 Hz, 1H); 4.52-4.60 (m, 1H); 4.32-4.39 (m, 1H); 3.40 (d, J=6.1 Hz, 2H); 3.07 (s, 3H); 2.81-2.88 (m, 1H); 2.36-2.43 (m, 1H); 1.52 (s, 3H); 0.91-0.95 (m, 2H); 0.86-0.90 (m, 2H).

MS1 (ESI, m/z): 430.0 [M+H$^+$] for $C_{21}H_{23}N_3O_5S$; $t_R$=0.68 min.

Example 57: (R)—N-hydroxy-4-(5-((3-(hydroxymethyl)bicyclo[1.1.1]pentan-1-yl)buta-1,3-diyn-1-yl)-2H-indazol-2-yl)-2-methyl-2-(methylsulfonyl)butanamide Starting from the compound of Preparation J (0.07 g; 0.167 mmol) and the compound of Preparation AE (0.077 g; 0.167 mmol), and proceeding successively in analogy to Example 37, step 37.i (86% yield) and Example 13, step 13.ii (47% yield), the title compound was obtained, after purification by prep-HPLC (Method 2), as an off-white solid (0.03 g).

$^1$H NMR (500 MHz, d$_6$-DMSO) δ: 11.04 (s, 1H); 9.28 (s, 1H); 8.52 (s, 1H); 8.04 (s, 1H); 7.63 (d, J=8.9 Hz, 1H); 7.28 (dd, J=1.5, 8.9 Hz, 1H); 4.59 (t, J=5.6 Hz, 1H); 4.52-4.61 (overlapped m, 1H); 4.32-4.40 (m, 1H); 3.35 (d, J=5.6 Hz, 2H); 3.07 (s, 3H); 2.80-2.89 (m, 1H); 2.36-2.43 (m, 1H); 1.98 (s, 6H); 1.52 (s, 3H).

MS1 (ESI, m/z): 456.0 [M+H$^+$] for $C_{23}H_{25}N_3O_5S$; $t_R$=0.72 min.

Example 58: (R)-4-(5-(4-((R)-2,3-dihydroxypropoxy)-2-fluorophenyl)-2H-indazol-2-yl)-N-hydroxy-2-methyl-2-(methylsulfonyl)butanamide Starting from the compound of Preparation H (0.12 g; 0.23 mmol) and the compound of Preparation AF (0.097 g; 0.276 mmol), and proceeding successively in analogy to Example 1, step 1.i (80% yield) and Example 13, step 13.ii (50% yield), the title compound was obtained, after purification by prep-HPLC (Method 2), as a white foam (0.044 g).

$^1$H NMR (500 MHz, d$_6$-DMSO) δ: 11.06 (s, 1H); 9.30 (s, 1H); 8.47 (s, 1H); 7.80 (s, 1H); 7.67 (d, J=9.0 Hz, 1H); 7.47 (t, J=8.9 Hz, 1H); 7.39 (dt, J=1.6, 8.9 Hz, 1H); 6.87-6.95 (m, 2H); 4.86-5.14 (m, 1H); 4.50-4.82 (overlapped m, 1H); 4.50-4.63 (m, 1H); 4.31-4.43 (m, 1H); 4.07 (dd, J=4.1, 10.0 Hz, 1H); 3.94 (dd, J=6.2, 10.0 Hz, 1H); 3.78-3.85 (m, 1H); 3.46 (d, J=5.7 Hz, 2H); 3.09 (s, 3H); 2.82-2.91 (m, 1H); 2.38-2.46 (m, 1H); 1.53 (s, 3H).

MS1 (ESI, m/z): 496.0 [M+H$^+$] for $C_{22}H_{26}N_3O_7FS$; $t_R$=0.59 min.

Example 59: (R)—N-hydroxy-2-methyl-2-(methylsulfonyl)-4-(5-(pyrimidin-5-ylethynyl)-2H-indazol-2-yl)butanamide Starting from the compound of Preparation H (0.11 g; 0.211 mmol) and 5-ethynylpyrimidine (0.025 g; 0.232 mmol; commercial), and proceeding successively in analogy to Example 7, step 7.i (71% yield) and Example 1, step 1.ii (77% yield), the title compound was obtained, after filtration from water, as a yellow solid (0.045 g).

$^1$H NMR (500 MHz, d$_6$-DMSO) δ: 11.06 (d, J=1.3 Hz, 1H); 9.29 (d, J=1.7 Hz, 1H); 9.20 (s, 1H); 9.03 (s, 2H); 8.57 (s, 1H); 8.10 (s, 1H); 7.70 (d, J=8.9 Hz, 1H); 7.40 (dd, J=1.5, 8.9 Hz, 1H); 4.55-4.63 (m, 1H); 4.33-4.43 (m, 1H); 3.09 (s, 3H); 2.87 (m, 1H); 2.38-2.45 (m, 1H); 1.55 (s, 3H).

MS1 (ESI, m/z): 413.9 [M+H$^+$] for $C_{19}H_{19}N_5O_4S$; $t_R$=0.67 min.

Example 60: (R)—N-hydroxy-4-(5-(4-(((1S*,2S*)-2-(hydroxymethyl)cyclopropyl)ethynyl)phenyl)-2H-indazol-2-yl)-2-methyl-2-(methylsulfonyl)butanamide Starting from the compound of Preparation C (0.1 g; 0.248 mmol) and the compound of Preparation AG (0.118 g; 0.26 mmol), and proceeding successively in analogy to Example 1, step 1.i (48% yield), Example 2, step 2.ii (saponification: 94% yield; amide coupling with THPO—NH$_2$: 77% yield) and Example 13, step 13.ii (36% yield), the title compound was obtained, after purification by prep-HPLC (Method 2), as an off-white solid (0.013 g).

$^1$H NMR (500 MHz, d$_6$-DMSO) δ: 11.06 (s, 1H); 9.30 (s, 1H); 8.49 (s, 1H); 8.00 (s, 1H); 7.65-7.74 (m, 3H); 7.59 (dd, J=1.7, 9.1 Hz, 1H); 7.44 (d, J=8.4 Hz, 2H); 4.64-4.79 (m, 1H); 4.53-4.61 (m, 1H); 4.33-4.42 (m, 1H); 3.46 (dd, J=5.4, 11.5 Hz, 1H); 3.29 (dd, J=6.4, 11.5 Hz, 1H); 3.09 (s, 3H); 2.83-2.91 (m, 1H); 2.39-2.46 (m, 1H); 1.53 (s, 3H); 1.36-1.48 (m, 2H); 0.81-0.94 (m, 2H).

MS1 (ESI, m/z): 482.0 [M+H$^+$] for $C_{25}H_{27}N_3O_5S$; $t_R$=0.72 min.

Example 61: (R)-4-(5-(((2S*,5S*)-5-aminotetrahydro-2H-pyran-2-yl)buta-1,3-diyn-1-yl)-2H-indazol-2-yl)-N-hydroxy-2-methyl-2-(methylsulfonyl)butanamide Starting from the compound of Preparation J (0.1 g; 0.238 mmol) and the compound of Preparation AH (0.087 g; 0.29 mmol), and proceeding successively in analogy to Example 37, step 37.i (84% yield) and Example 13, step 13.ii (67% yield), the title compound was obtained, after purification by prep-HPLC (Method 3), as an off-white solid (0.058 g).

$^1$H NMR (500 MHz, d$_6$-DMSO) δ: 8.54 (d, J=0.6 Hz, 1H); 8.09 (s, 1H); 7.64 (d, J=8.9 Hz, 1H); 7.31 (dd, J=1.5, 8.9 Hz, 1H); 4.53-4.61 (m, 1H); 4.30-4.41 (overlapped m, 1H); 4.33 (dd, J=2.7, 9.9 Hz, 1H); 3.77-3.84 (m, 1H); 3.07 (s, 3H); 3.03 (dd, J=9.1, 10.8 Hz, 1H); 2.81-2.89 (m, 1H); 2.68-2.75 (m, 1H); 2.36-2.44 (m, 1H); 1.88-1.99 (m, 2H); 1.57-1.67 (m, 1H); 1.52 (s, 3H); 1.24-1.35 (m, 1H).

MS1 (ESI, m/z): 459.0 [M+H$^+$] for $C_{22}H_{26}N_4O_5S$; $t_R$=0.54 min.

Example 62: (R)-(1-(4-((2-(4-(hydroxyamino)-3-methyl-3-(methylsulfonyl)-4-oxobutyl)-2H-indazol-5-yl)ethynyl)phenyl)cyclopropyl)methyl dihydrogen phosphate 62.i. (R)-di-tert-butyl ((1-(4-((2-(3-methyl-3-(methylsulfonyl)-4-oxo-4-((((RS)-tetrahydro-2H-pyran-2-yl)oxy)amino)butyl)-2H-indazol-5-yl)ethynyl)phenyl)cyclopropyl)methyl) phosphate Starting from the compound of Preparation H (0.16 g; 0.3 mmol) and the compound of Preparation AI (0.067 g; 0.184 mmol), and proceeding in analogy to Example 7, step 7.i, the title compound was obtained, after purification by CC (Hept-EA), as a yellow oil (0.06 g; 43% yield).

$^1$H NMR (500 MHz, d$_6$-DMSO) δ: 11.47 (s, 0.5H); 11.44 (s, 0.5H); 8.48 (s, 0.5H); 8.47 (s, 0.5H); 7.98 (s, 1H); 7.59-7.68 (m, 1H); 7.48 (d, J=8.2 Hz, 2H); 7.31-7.38 (overlapped m, 1H); 7.36 (d, J=8.2 Hz, 2H); 4.94-4.98 (m, 1H); 4.53-4.62 (m, 1H); 4.34-4.46 (m, 1H); 3.96-4.16 (m, 3H); 3.49-3.57 (m, 1H); 3.08 (s, 1.5H); 3.06 (s, 1.5H); 2.79-2.91 (m, 1H); 2.39-2.59 (overlapped m, 1H); 1.65-1.74 (m, 3H); 1.47-1.60 (m, 6H); 1.35 (s, 18H); 0.99-1.04 (m, 2H); 0.92-0.97 (m, 2H).

MS1 (ESI, m/z): 757.9 [M+H$^+$] for $C_{38}H_{52}N_3O_9PS$; $t_R$=0.99 min.

62.ii. (R)-(1-(4-((2-(4-(hydroxyamino)-3-methyl-3-(methylsulfonyl)-4-oxobutyl)-2H-indazol-5-yl)ethynyl)phenyl)cyclopropyl)methyl dihydrogen phosphate To a solution of intermediate 62.i (0.058 g; 0.077 mmol) in DCM (1.9 mL) was added TFA (0.87 mL; 11 mmol). The reaction was stirred at rt for 20 min and concentrated to dryness. The residue was purified by prep-HPLC (Method 1) to afford the title compound as a white solid (0.005 g; 11% yield).

$^1$H NMR (500 MHz, d$_6$-DMSO) δ: 11.05 (s, 1H); 9.29 (br. s, 1H); 8.49 (s, 1H); 7.98 (s, 1H); 7.64 (d, J=8.9 Hz, 1H); 7.46 (d, J=8.2 Hz, 2H); 7.31-7.35 (m, 3H); 4.51-4.64 (m, 1H); 4.31-4.45 (m, 1H); 3.95 (d, J=5.3 Hz, 2H); 3.07 (s, 3H); 2.82-2.91 (m, 1H); 2.35-2.60 (overlapped m, 1H); 1.53 (s, 3H); 0.98-1.03 (m, 2H); 0.89-0.95 (m, 2H).

MS1 (ESI, m/z): 561.91 [M+H$^+$] for C$_{25}$H$_{28}$N$_3$O$_8$PS; t$_R$=0.64 min.

Example 63: (R)-(1-(4-((2-(4-(hydroxyamino)-3-methyl-3-(methylsulfonyl)-4-oxobutyl)-2H-indazol-5-yl)ethynyl)phenyl)cyclopropyl)methyl dimethylglycinate hydrochloride Starting from the compound of Preparation H (0.25 g; 0.48 mmol) and the compound of Preparation AJ (0.122 g; 0.48 mmol), and proceeding successively in analogy to Example 7, step 7.i (43% yield) and Example 13, step 13.ii (14% yield), the title compound was obtained, after purification by prep-HPLC (Method 1) and lyophilisation from a diluted HCl solution, as a white solid (0.017 g).

$^1$H NMR (500 MHz, d$_6$-DMSO) δ: 11.00-11.13 (br. s, 1H); 10.01-10.17 (br. s, 1H); 8.50 (s, 1H); 7.97 (s, 1H); 7.65 (d, J=8.9 Hz, 1H); 7.49 (d, J=8.2 Hz, 2H); 7.36 (d, J=8.2 Hz, 2H); 7.32 (dd, J=1.2, 8.9 Hz, 1H); 4.53-4.61 (m, 1H); 4.38 (s, 2H); 4.32-4.38 (overlapped m, 1H); 4.19 (d, J=2.1 Hz, 2H); 3.07 (s, 3H); 2.82-2.90 (m, 1H); 2.80 (s, 6H); 2.38-2.50 (overlapped, 1H); 1.53 (s, 3H); 1.05-1.09 (m, 2H); 0.98-1.02 (m, 2H).

MS1 (ESI, m/z): 567.02 [M+H$^+$] for C$_{29}$H$_{34}$N$_4$O$_6$S; t$_R$=0.66 min.

Example 64: (R)-4-(5-(((1S,3R,4S)-3,4-dihydroxycyclopentyl)buta-1,3-diyn-1-yl)-2H-indazol-2-yl)-N-hydroxy-2-methyl-2-(methylsulfonyl)butanamide Starting from the compound of Preparation J (0.1 g; 0.24 mmol) and the compound of Preparation AK (0.066 g; 0.27 mmol), and proceeding successively in analogy to Example 37, step 37.i (91% yield) and Example 13, step 13.ii (30% yield), the title compound was obtained, after purification by prep-HPLC (Method 2), as a beige solid (0.029 g).

$^1$H NMR (500 MHz, d$_6$-DMSO) δ: 11.04 (s, 1H); 9.28 (br. s, 1H); 8.51 (d, J=0.6 Hz, 1H); 8.00-8.02 (m, 1H); 7.61-7.64 (m, 1H); 7.27 (dd, J=1.4, 8.7 Hz, 1H); 4.53-4.60 (m, 1H); 4.32-4.39 (m, 1H); 3.94-3.98 (m, 2H); 3.13-3.21 (m, 1H); 3.07 (s, 3H); 2.82-2.89 (m, 1H); 2.37-2.44 (m, 1H); 1.90-1.97 (m, 2H); 1.75-1.82 (m, 2H); 1.52 (s, 3H).

MS1 (ESI, m/z): 459.99 [M+H$^+$] for C$_{22}$H$_{25}$N$_3$O$_6$S; t$_R$=0.62 min.

Example 65: (R)-4-(5-((1-aminocyclopropyl)buta-1,3-diyn-1-yl)-2H-indazol-2-yl)-N-hydroxy-2-methyl-2-(methylsulfonyl)butanamide Starting from the compound of Preparation J (0.11 g; 0.262 mmol) and the compound of Preparation AL (0.0926 g; 0.302 mmol), and proceeding successively in analogy to Example 7, step 7.i (46% yield) and Example 13, step 13.ii (47% yield), the title compound was obtained, after purification by prep-HPLC (Method 3), as a beige solid (0.023 g).

$^1$H NMR (500 MHz, d$_6$-DMSO) δ: 10.72-11.35 (m, 1H); 9.11-9.53 (m, 1H); 8.51 (d, J=0.7 Hz, 1H); 8.01 (s, 1H); 7.62 (d, J=8.9 Hz, 1H); 7.27 (dd, J=1.5, 8.9 Hz, 1H); 4.52-4.61 (m, 1H); 4.32-4.40 (m, 1H); 3.07 (s, 3H); 2.81-2.89 (m, 1H); 2.36-2.45 (m, 1H); 1.52 (s, 3H); 0.98-1.02 (m, 2H); 0.88-0.92 (m, 2H).

MS1 (ESI, m/z): 415.0 [M+H$^+$] for C$_{20}$H$_{22}$N$_4$O$_4$S; t$_R$=0.52 min.

Example 66: (R)—N-hydroxy-4-(5-(5-01S,3R)-1-hydroxy-3-(hydroxymethyl)cyclobutyl)penta-1,3-diyn-1-yl)-2H-indazol-2-yl)-2-methyl-2-(methylsulfonyl)butanamide Starting from the compound of Preparation J (0.1 g; 0.238 mmol) and the compound of Preparation AM (0.0856 g; 0.322 mmol), and proceeding successively in analogy to Example 7, step 7.i (64% yield) and Example 1, step 1.ii (34% yield), the title compound was obtained, after purification by prep-HPLC (Method 2), as a yellow foam (0.023 g).

$^1$H NMR (500 MHz, d$_6$-DMSO) δ: 10.95-11.12 (m, 1H); 9.22-9.34 (m, 1H); 8.51 (s, 1H); 8.03-8.04 (m, 1H); 7.62 (d, J=8.9 Hz, 1H); 7.29 (dd, J=1.5, 8.9 Hz, 1H); 5.24 (s, 1H); 4.53-4.60 (m, 1H); 4.49 (t, J=5.3 Hz, 1H); 4.32-4.40 (m, 1H); 3.37 (t, J=5.7 Hz, 2H); 3.07 (s, 3H); 2.81-2.89 (m, 1H); 2.63 (s, 2H); 2.36-2.44 (m, 1H); 2.04-2.11 (m, 2H); 1.92-2.00 (m, 1H); 1.70-1.77 (m, 2H); 1.52 (s, 3H).

MS1 (ESI, m/z): 474.0 [M+H$^+$] for C$_{23}$H$_{27}$N$_3$O$_6$S; t$_R$=0.62 min.

Example 67: (R)—N-hydroxy-4-(5-(((1R,2R)-2-(hydroxymethyl)-1-methylcyclopropyl)buta-1,3-diyn-1-yl)-2H-indazol-2-yl)-2-methyl-2-(methylsulfonyl)butanamide Starting from the compound of Preparation J (0.1 g; 0.238 mmol) and the compound of Preparation AN (0.122 g; 0.286 mmol), and proceeding successively in analogy to Example 37, step 37.i (91% yield) and Example 13, step 13.ii (40% yield), the title compound was obtained, after purification by prep-HPLC (Method 2), as an off-white solid (0.037 g).

$^1$H NMR (500 MHz, d$_6$-DMSO) δ: 11.04 (s, 1H); 9.28 (s, 1H); 8.50 (d, J=0.6 Hz, 1H); 8.00-8.01 (m, 1H); 7.60-7.63 (m, 1H); 7.27 (dd, J=1.5, 8.9 Hz, 1H); 4.69 (t, J=5.4 Hz, 1H); 4.52-4.61 (m, 1H); 4.32-4.41 (m, 1H); 3.59-3.65 (m, 1H); 3.23-3.31 (m, 1H); 3.07 (s, 3H); 2.81-2.89 (m, 1H); 2.36-2.44 (m, 1H); 1.52 (s, 3H); 1.40-1.48 (m, 1H); 1.32 (s, 3H); 1.11 (dd, J=4.4, 9.3 Hz, 1H); 0.63 (dd, J=4.6, 6.6 Hz, 1H).

MS1 (ESI, m/z): 444.0 [M+H$^+$] for C$_{22}$H$_{25}$N$_3$O$_5$S; t$_R$=0.70 min.

Example 68: (R)—N-hydroxy-4-(5-((3-(hydroxymethyl)oxetan-3-yl)buta-1,3-diyn-1-yl)-2H-indazol-2-yl)-2-methyl-2-(methylsulfonyl)butanamide

68.i. (R)-4-(5-((3-(((tert-butyldiphenylsilyl)oxy)methyl)oxetan-3-yl)buta-1, 3-diyn-1-yl)-2H-indazol-2-yl)-2-methyl-2-(methylsulfonyl)-N—(((RS)-tetrahydro-2H-pyran-2-yl)oxy)butanamide Starting from the compound of Preparation J (0.1 g; 0.238 mmol) and the compound of Preparation AO (0.129 g; 0.271 mmol), and proceeding in analogy to Example 7, step 7.i, the title compound was obtained, after purification by CC (DCM-MeOH), as a yellow oil (0.064 g; 35% yield).
MS1 (ESI, m/z): 768.01 [M+H$^+$] for $C_{42}H_{49}N_3O_7SSi$; $t_R$=1.10 min.

68.ii. (R)-4-(5-((3-(hydroxymethyl)oxetan-3-yl)buta-1, 3-diyn-1-yl)-2H-indazol-2-yl)-2-methyl-2-(methylsulfonyl)-N-(OS)-tetrahydro-2H-pyran-2-yl)oxy)butanamide To a stirred solution of intermediate 68.i (0.64 g; 0.836 mmol) in THF (1 mL) was added TBAF.3H$_2$O (0.109 g; 0.334 mmol). The mixture was stirred at rt for 3 h and then concentrated to dryness. The residue was purified by CC (DCM-MeOH) to afford the title compound as a yellow oil (0.026 g).
$^1$H NMR (500 MHz, d$_6$-DMSO) δ: 11.45 (s, 1H); 8.51 (s, 1H); 8.07 (s, 1H); 7.64 (d, J=8.9 Hz, 1H); 7.31 (d, J=9.0 Hz, 1H); 5.48 (t, J=5.9 Hz, 1H); 4.91-4.98 (m, 1H); 4.61 (d, J=5.7 Hz, 2H); 4.51-4.62 (overlapped m, 1H); 4.53 (d, J=5.7 Hz, 2H); 4.35-4.46 (m, 1H); 4.04-4.15 (m, 1H); 3.73 (d, J=5.8 Hz, 2H); 3.49-3.55 (m, 1H); 3.08 (s, 1.5H); 3.06 (s, 1.5H); 2.79-2.90 (m, 1H); 2.34-2.45 (m, 1H); 1.65-1.77 (m, 3H); 1.47-1.63 (overlapped m, 3H); 1.53 (s, 1.5H); 1.50 (s, 1.5H).
MS1 (ESI, m/z): 530.0 [M+H$^+$] for $C_{26}H_{31}N_3O_7S$; $t_R$=0.75 min.

68.iii. (R)—N-hydroxy-4-(5-((3-(hydroxymethyl)oxetan-3-yl)buta-1, 3-diyn-1-yl)-2H-indazol-2-yl)-2-methyl-2-(methylsulfonyl)butanamide Starting from intermediate 68.ii (0.026 g; 0.0498 mmol) and proceeding in analogy to Example 1, step 1.ii, the title compound was obtained, after purification by prep-HPLC (Method 2), as a beige solid (0.019 g; 86% yield).
$^1$H NMR (500 MHz, d$_6$-DMSO) δ: 11.00 (s, 1H); 9.28 (s, 1H); 8.53 (s, 1H); 8.06 (s, 1H); 7.64 (d, J=8.9 Hz, 1H); 7.31 (d, J=8.9 Hz, 1H); 5.48 (t, J=5.9 Hz, 1H); 4.61 (d, J=5.7 Hz, 1H); 4.55-4.60 (overlapped m, 1H); 4.53 (d, J=5.7 Hz, 2H); 4.33-4.42 (m, 1H); 3.73 (d, J=5.9 Hz, 2H); 3.08 (s, 3H); 2.81-2.89 (m, 1H); 2.35-2.45 (m, 1H); 2.08 (s, 1H); 1.53 (s, 3H).
MS1 (ESI, m/z): 445.96 [M+H$^+$] for $C_{21}H_{23}N_3O_6S$; $t_R$=0.63 min.

Example 69: (R)—N-hydroxy-4-(5-((1R,2S)-2-(hydroxymethyl)-2-methylcyclopropyl)buta-1,3-diyn-1-yl)-2H-indazol-2-yl)-2-methyl-2-(methylsulfonyl)butanamide Starting from the compound of Preparation J (0.1 g; 0.238 mmol) and the compound of Preparation AP (0.066 g; 0.286 mmol), and proceeding successively in analogy to Example 37, step 37.i and Example 36, step 36.ii (79% yield over the two steps) and Example 1, step 1.ii (82% yield), the title compound was obtained, after purification by prep-HPLC (Method 2), as a yellow foam (0.07 g).
$^1$H NMR (500 MHz, d$_6$-DMSO) δ: 10.95-11.12 (m, 1H); 9.22-9.36 (m, 1H); 8.50 (s, 1H); 8.02 (s, 1H); 7.61 (d, J=8.9 Hz, 1H); 7.28 (dd, J=1.5, 8.9 Hz, 1H); 4.75 (t, J=5.8 Hz, 1H); 4.52-4.60 (m, 1H); 4.31-4.40 (m, 1H); 3.31 (dd, J=6.0, 11.3 Hz, 1H); 3.23 (dd, J=5.6, 11.2 Hz, 1H); 3.07 (s, 3H); 2.81-2.90 (m, 1H); 2.36-2.44 (m, 1H); 1.57 (dd, J=5.3, 8.7 Hz, 1H); 1.52 (s, 3H); 1.20 (s, 3H); 1.05 (dd, J=4.1, 8.7 Hz, 1H); 0.63-0.66 (m, 1H).
MS1 (ESI, m/z): 444.0 [M+H$^+$] for $C_{22}H_{25}N_3O_5S$; $t_R$=0.70 min.

Example 70: (R)-4-(5-((3-(2-aminoacetamido)cyclopentyl)buta-1,3-diyn-1-yl)-2H-indazol-2-yl)-N-hydroxy-2-methyl-2-(methylsulfonyl)butanamide Starting from the compound of Preparation J (0.08 g; 0.191 mmol) and the compound of Preparation AQ (0.097 g; 0.248 mmol), and proceeding successively in analogy to Example 7, step 7.i (57% yield) and Example 13, step 13.ii (28% yield), the title compound was obtained, after purification by prep-HPLC (Method 3), as a beige foam (0.014 g).
MS1 (ESI, m/z): 499.9 [M+H$^+$] for $C_{24}H_{29}N_5O_5S$; $t_R$=0.58 min.

Example 71: (R)-4-(5-(((1R,2R)-2-((S)-1,2-dihydroxyethyl)cyclopropyl)buta-1,3-diyn-1-yl)-2H-indazol-2-yl)-N-hydroxy-2-methyl-2-(methylsulfonyl)butanamide Starting from the compound of Preparation J (0.08 g; 0.191 mmol) and the compound of Preparation AR (0.14 g; 0.286 mmol), and proceeding successively in analogy to Example 37, step 37.i (84% yield) and Example 13, step 13.ii (41% yield), the title compound was obtained, after purification by prep-HPLC (Method 2), as a white solid (0.029 g).
$^1$H NMR (500 MHz, d$_6$-DMSO) δ: 11.03 (s, 1H); 9.27 (s, 1H); 8.49 (d, J=0.6 Hz, 1H); 7.99-8.00 (m, 1H); 7.61 (dt, J=0.9, 9.0 Hz, 1H); 7.25 (dd, J=1.5, 9.0 Hz, 1H); 4.70 (d, J=5.1 Hz, 1H); 4.61 (t, J=5.8 Hz, 1H); 4.52-4.59 (m, 1H); 4.31-4.38 (m, 1H); 3.33-3.37 (overlapped m, 2H); 3.26-3.31 (m, 1H); 3.06 (s, 3H); 2.80-2.88 (m, 1H); 2.35-2.43 (m, 1H); 1.51 (s, 3H); 1.48 (dt, J=4.9, 8.5 Hz, 1H); 1.33-1.39 (m, 1H); 0.92-0.96 (m, 1H); 0.81-0.85 (m, 1H).
MS1 (ESI, m/z): 460.0 [M+H$^+$] for $C_{22}H_{25}N_3O_6S$; $t_R$=0.61 min.

Example 72: (R)-4-(5-(((1R,2R)-2-(aminomethyl)cyclopropyl)buta-1,3-diyn-1-yl)-2H-indazol-2-yl)-N-hydroxy-2-methyl-2-(methylsulfonyl)butanamide Starting from the compound of Preparation J (0.1 g; 0.238 mmol) and the compound of Preparation AS (0.14 g; 0.286 mmol), and proceeding successively in analogy to Example 7, step 7.i (23% yield) and Example 13, step 13.ii (59% yield), the title compound was obtained, after purification by prep-HPLC (Method 3), as a white solid (0.013 g).
$^1$H NMR (500 MHz, d$_6$-DMSO) δ: 8.49 (s, 1H); 7.99-8.00 (m, 1H); 7.61 (d, J=8.9 Hz, 1H); 7.26 (dd, J=1.5, 8.9 Hz, 1H); 4.50-4.61 (m, 1H); 4.32-4.41 (m, 1H); 3.06 (s, 3H); 2.77-2.90 (m, 1H); 2.58-2.69 (m, 1H); 2.46-2.55 (overlapped m, 1H); 2.33-2.44 (m, 1H); 1.47-1.51 (overlapped m, 1H); 1.50 (s, 3H); 1.33-1.41 (m, 1H); 0.85-0.98 (m, 2H).
MS1 (ESI, m/z): 429.0 [M+H$^+$] for $C_{21}H_{24}N_4O_4S$; $t_R$=0.55 min.

Example 73: (R)—N-hydroxy-4-(5-((1-(hydroxymethyl)cyclobutyl)buta-1,3-diyn-1-yl)-2H-indazol-2-yl)-2-methyl-2-(methylsulfonyl)butanamide 73.i. (2R)-4-(5-((1-(((tert-butyldiphenylsilyl)oxy)methyl)cyclobutyl)buta-1,3-diyn-1-yl)-2H-indazol-2-yl)-2-methyl-2-(methylsulfonyl)-N—(((RS)-tetrahydro-2H-pyran-2-yl)oxy)butanamide Starting from the compound of Preparation J (0.1 g; 0.238 mmol) and the compound of Preparation AT (0.11 g; 0.253 mmol), and proceeding in analogy to Example 37, step 37.i, the title compound was obtained, after purification by CC (Hept-EA/MeOH), as a pink foam (0.16 g; 87% yield).

$^1$H NMR (500 MHz, d$_6$-DMSO) δ: 11.45 (s, 0.5H); 11.43 (s, 0.5H); 8.50 (d, J=0.4 Hz, 0.5H); 8.49 (d, J=0.4 Hz, 0.5H); 8.03-8.04 (m, 1H); 7.66-7.69 (m, 4H); 7.61-7.65 (m, 1H); 7.44-7.49 (m, 6H); 7.28 (dd, J=1.5, 9.0 Hz, 1H); 4.96 (s, 0.5H); 4.92 (s, 0.5H); 4.53-4.61 (m, 1H), 4.36-4.45 (m, 1H); 4.08-4.15 (m, 0.5H); 4.02-4.08 (m, 0.5H); 3.75 (s, 2H); 3.49-3.56 (m, 1.5H); 3.08 (s, 1.5H); 3.05 (s, 1.5H); 2.79-2.90 (m, 1H); 2.38-2.46 (m, 1H); 2.14-2.25 (m, 4H); 1.95-2.02 (m, 1H); 1.86-1.93 (m, 1H); 1.63-1.73 (m, 3H); 1.54 (s, 1.5H); 1.52 (s, 1.5H); 1.49-1.59 (overlappped m, 3H); 1.05 (s, 9H).

MS1 (ESI, m/z): 765.86 [M+H$^+$] for C$_{43}$H$_{51}$N$_3$O$_6$SSi; t$_R$=1.15 min.

73.ii. (2R)-4-(5-((1-(hydr oxymethyl)cyclobutyl) buta-1,3-diyn-1-yl)-2H-indazol-2-yl)-2-methyl-2- (methylsulfonyl)-N—(((RS)tetrahydro-2H-pyran-2- yl)oxy)butanamide To a stirred solution of intermediate 73.i (0.15 g; 0.2 mmol) in THF (0.4 mL) was added TBAF (1M; 1 mL; 1 mmol). The mixture was stirred at rt for 6 h and then concentrated to dryness. The residue was purified by CC (Hept-EA/MeOH) to afford the title compound as an off-white foam (0.1 g; 99% yield).

$^1$H NMR (500 MHz, d$_6$-DMSO) δ: 11.45 (s, 0.5H); 11.43 (s, 0.5H); 8.49 (s, 0.5H); 8.48 (s, 0.5H); 8.02 (s, 1H); 7.61-7.64 (m, 1H); 7.28 (dd, J=1.4, 8.8 Hz, 1H); 5.17 (t, J=5.8 Hz, 1H); 4.96 (s, 0.5H); 4.93 (s, 0.5H); 4.52-4.61 (m, 1H); 4.35-4.45 (m, 1H); 4.08-4.15 (m, 0.5H); 3.99-4.07 (m, 0.5H); 3.49-3.57 (overlapped m, 1H); 3.49 (d, J=5.8 Hz, 2H); 3.08 (s, 1.5H); 3.05 (s, 1.5H); 2.78-2.90 (m, 1H); 2.37-2.45 (m, 1H); 2.11-2.17 (m, 4H); 1.84-1.98 (m, 2H); 1.64-1.73 (m, 3H); 1.48-1.60 (overlapped m, 3H), 1.53 (s, 1.5H), 1.51 (s, 1.5H).

MS1 (ESI, m/z): 528.05 [M+H$^+$] for C$_{27}$H$_{33}$N$_3$O$_6$S; t$_R$=0.84 min.

73.iii. (R)—N-hydroxy-4-(5-((1-(hydroxymethyl) cyclobutyl)buta-1,3-diyn-1-yl)-2H-indazol-2-yl)-2- methyl-2-(methylsulfonyl)butanamide Starting from intermediate 73.ii (0.1 g; 0.131 mmol) and proceeding in analogy to Example 1, step 1.ii, the title compound was obtained, after purification by prep-HPLC (Method 2), as an off-white solid (0.056 g; 97% yield).

$^1$H NMR (500 MHz, d$_6$-DMSO) δ: 10.99-11.08 (m, 1H); 9.28 (s, 1H); 8.52 (s, 1H); 8.02-8.03 (m, 1H); 7.63 (d, J=8.9 Hz, 1H); 7.29 (dd, J=1.5, 8.9 Hz, 1H); 5.18 (t, J=5.8 Hz, 1H); 4.52-4.61 (m, 1H); 4.32-4.41 (m, 1H); 3.50 (d, J=5.8 Hz, 2H); 3.08 (s, 3H); 2.81-2.90 (m, 1H); 2.37-2.45 (m, 1H); 2.12-2.18 (m, 4H); 1.85-2.02 (m, 2H); 1.52 (s, 3H).

MS1 (ESI, m/z): 444 [M+H$^+$] for C$_{22}$H$_{25}$N$_3$O$_5$S; t$_R$=0.72 min.

Example 74: (R)-4-(5-(((1R,2R)-1-fluoro-2-(hy- droxymethyl)cyclopropyl)buta-1,3-diyn-1-yl)-2H- indazol-2-yl)-N-hydroxy-2-methyl-2-(methylsulfo- nyl)butanamide Starting from the compound of Preparation J (0.1 g; 0.238 mmol) and the compound of Preparation AU (0.12 g; 0.279 mmol), and proceeding successively in analogy to Example 37, step 37.i (87% yield), Example 73, step 73.ii (84% yield) and Example 1, step 1.ii (80% yield), the title compound was obtained, after precipitation in water, as a beige solid (0.06 g).

$^1$H NMR (500 MHz, d$_6$-DMSO) δ: 11.05 (d, J=1.0 Hz, 1H); 9.28 (d, J=1.5 Hz, 1H); 8.56 (s, 1H); 8.12 (s, 1H); 7.66 (d, J=8.9 Hz, 1H); 7.33 (dd, J=1.4, 8.9 Hz, 1H); 4.91 (t, J=4.6 Hz, 1H); 4.54-4.62 (m, 1H); 4.34-4.41 (m, 1H); 3.66-3.72 (m, 1H); 3.35-3.41 (m, 1H); 3.08 (s, 3H); 2.82-2.90 (m, 1H); 2.37-2.44 (m, 1H); 1.64-1.71 (m, 1H); 1.53 (s, 3H); 1.38-1.44 (m, 1H); 1.23-1.31 (m, 1H).

MS1 (ESI, m/z): 448.0 [M+H$^+$] for C$_{21}$H$_{22}$N$_3$O$_5$FS; t$_R$=0.69 min.

Example 75: (R)-4-(5-(5-(dimethylamino)penta-1,3- diyn-1-yl)-2H-indazol-2-yl)-N-hydroxy-2-methyl-2- (methylsulfonyl)butanamide Starting from the compound of Preparation J (0.1 g; 0.238 mmol) and the compound of Preparation AV (0.075 g; 0.358 mmol), and proceeding successively in analogy to Example 37, step 37.i (quant.) and Example 1, step 1.ii (41% yield), the title compound was obtained, after purification by prep-HPLC (Method 3), as a beige solid (0.042 g).

$^1$H NMR (500 MHz, d$_6$-DMSO) δ: 11.02 (m, 1H); 9.29 (m, 1H); 8.53 (s, 1H); 8.07 (m, 1H); 7.64 (d, J=8.9 Hz, 1H); 7.31 (dd, J=1.5, 8.9 Hz, 1H); 4.57 (m, 1H); 4.37 (m, 1H); 3.48 (s, 2H); 3.08 (s, 3H); 2.86 (m, 1H); 2.40 (m, 1H); 2.23 (s, 6H); 1.53 (s, 3H).

MS1 (ESI, m/z): 458.0 [M+H$^+$] for C$_{20}$H$_{24}$N$_4$O$_4$S; t$_R$=0.51 min.

Example 76: (R)—N-hydroxy-2-methyl-2-(methyl- sulfonyl)-4-(5-(piperidin-4-ylbuta-1,3-diyn-1-yl)- 2H-indazol-2-yl)butanamide Starting from the compound of Preparation J (0.08 g; 0.191 mmol) and the compound of Preparation AW (0.096 g; 0.286 mmol), and proceeding successively in analogy to Example 37, step 37.i (79% yield) and Example 13, step 13.ii (66% yield), the title compound was obtained, after purification by prep-HPLC (Method 3), as a beige solid (0.042 g).

$^1$H NMR (500 MHz, d$_6$-DMSO) δ: 8.51 (d, J=0.4 Hz, 1H); 8.03 (m, 1H); 7.62 (d, J=8.9 Hz, 1H); 7.29 (dd, J=1.5, 8.9 Hz, 1H); 4.56 (m, 1H); 4.38 (m, 1H); 3.07 (s, 3H); 2.88-2.93 (m, 2H); 2.84 (m, 1H); 2.74 (m, 1H); 2.54-2.60 (m, 2H); 2.39 (m, 1H); 1.75-1.82 (m, 2H); 1.44-1.56 (overlapped m, 2H); 1.51 (s, 3H).

MS1 (ESI, m/z): 443.0 [M+H$^+$] for C$_{22}$H$_{26}$N$_4$O$_4$S; t$_R$=0.55 min.

Example 77: (R)-4-(5-(((1R,2R)-2-fluoro-2-(hy- droxymethyl)cyclopropyl)buta-1,3-diyn-1-yl)-2H- indazol-2-yl)-N-hydroxy-2-methyl-2-(methylsulfo- nyl)butanamide Starting from the compound of Preparation J (0.1 g; 0.238 mmol) and the compound of Preparation AX (0.084 g; 0.358 mmol), and proceeding successively in analogy to Example 37, step 37.i (88% yield) and Example 1, step 1.ii (45% yield), the title compound was obtained, after purification by prep-HPLC (Method 3), as a beige solid (0.040 g).

$^1$H NMR (500 MHz, d$_6$-DMSO) δ: 11.04 (d, J=1.0 Hz, 1H); 9.28 (d, J=1.4 Hz, 1H); 8.52 (d, J=0.5 Hz, 1H); 8.04 (m, 1H); 7.63 (d, J=8.9 Hz, 1H); 7.29 (dd, J=1.5, 8.9 Hz, 1H); 5.25 (t, J=6.1 Hz, 1H); 4.57 (m, 1H); 4.36 (m, 1H); 3.59-3.74

(m, 2H); 3.07 (s, 3H); 2.85 (m, 1H); 2.40 (m, 1H); 1.96 (m, 1H); 1.52 (s, 3H); 1.32-1.43 (m, 2H).

MS1 (ESI, m/z): 448.0 [M+H$^+$] for $C_{21}H_{22}N_3O_5FS$; $t_R$=0.55 min.

Example 78: (R)—N-hydroxy-4-(5-41-(2-hydroxy-acetyl)piperidin-4-yl)buta-1,3-diyn-1-yl)-2H-indazol-2-yl)-2-methyl-2-(methylsulfonyl)butanamide Starting from the compound of Preparation J (0.1 g; 0.238 mmol) and the compound of Preparation AY (0.110 g; 0.374 mmol), and proceeding successively in analogy to Example 37, step 37.i (100% yield) and Example 1, step 1.ii (35% yield), the title compound was obtained, after purification by prep-HPLC (Method 2), as a white solid (0.044 g).

$^1$H NMR (500 MHz, d$_6$-DMSO) δ: 11.05 (br. s, 1H); 9.30 (br. s, 1H); 8.52 (d, J=0.6 Hz, 1H); 8.04 (s, 1H); 7.63 (d, J=8.9 Hz, 1H); 7.29 (dd, J=1.5, 8.9 Hz, 1H); 4.56 (overlapped m, 1H); 4.53 (t, J=5.5 Hz, 1H); 4.36 (m, 1H); 4.09 (dd, J=2.4, 5.3 Hz, 2H); 3.88 (m, 1H); 3.53 (m, 1H); 3.11-3.22 (m, 2H); 3.07 (s, 3H); 2.95 (m, 1H); 2.84 (m, 1H); 2.40 (m, 1H); 1.79-1.90 (m, 2H); 1.45-1.62 (overlapped m, 2H); 1.52 (s, 3H).

MS1 (ESI, m/z): 501.0 [M+H$^+$] for $C_{24}H_{28}N_4O_6S$; $t_R$=0.67 min.

Example 79: (R)-4-(5-((4-(1-aminocyclopropyl)phenyl)ethynyl)-2H-indazol-2-yl)-N-hydroxy-2-methyl-2-(methylsulfonyl)butanamide formate Starting from the compound of Preparation J (0.1 g; 0.238 mmol) and tert-butyl (1-(4-iodophenyl)cyclopropyl)carbamate (0.100 g; 0.27 mmol), and proceeding successively in analogy to Example 7, step 7.i (42% yield) and Example 13, step 13.ii (35% yield), the title compound was obtained, after purification by prep-HPLC (Method 2), as a white solid (0.044 g).

$^1$H NMR (500 MHz, d$_6$-DMSO) δ: 8.51 (d, J=0.5 Hz, 1H); 7.99 (m, 1H); 7.66 (d, J=8.9 Hz, 1H); 7.54 (d, J=8.5 Hz, 2H); 7.39 (d, J=8.5 Hz, 2H); 7.34 (dd, J=1.5, 8.9 Hz, 1H); 4.58 (m, 1H); 4.37 (m, 1H); 3.08 (s, 3H); 2.88 (m, 1H); 2.41 (m, 1H); 1.54 (s, 3H); 1.17-1.22 (m, 2H); 1.11-1.17 (m, 2H).

MS1 (ESI, m/z): 467.0 [M+H$^+$] for $C_{24}H_{26}N_4O_4S$; $t_R$=0.57 min.

Example 80: (R)—N-hydroxy-4-(5-(5-(3-hydroxyoxetan-3-yl)penta-1,3-diyn-1-yl)-2H-indazol-2-yl)-2-methyl-2-(methylsulfonyl)butanamide Starting from the compound of Preparation J (0.082 g; 0.195 mmol) and the compound of Preparation AZ (0.080 g; 0.332 mmol), and proceeding successively in analogy to Example 37, step 37.i (81% yield) and Example 1, step 1.ii (67% yield), the title compound was obtained, after purification by CC (DCM-MeOH gradient), as a beige solid (0.046 g).

$^1$H NMR (500 MHz, d$_6$-DMSO) δ: 11.04 (s, 1H); 9.28 (s, 1H); 8.52 (s, 1H); 8.05 (s, 1H); 7.63 (d, J=8.9 Hz, 1H); 7.30 (dd, J=1.5, 8.9 Hz, 1H); 6.08 (s, 1H); 4.57 (m, 1H); 4.45-4.48 (m, 2H); 4.41-4.44 (m, 2H); 4.36 (m, 1H); 3.07 (s, 3H); 2.86 (overlapped m, 1H); 2.87 (s, 2H); 2.40 (m, 1H); 1.52 (s, 3H).

MS1 (ESI, m/z): 446.0 [M+H$^+$] for $C_{21}H_{23}N_3O_6S$; $t_R$=0.62 min.

Example 81: (R)—N-hydroxy-4-(5-((1-(2-hydroxy-acetyl)azetidin-3-yl)buta-1,3-diyn-1-yl)-2H-indazol-2-yl)-2-methyl-2-(methylsulfonyl)butanamide Starting from the compound of Preparation J (0.07 g; 0.167 mmol) and the compound of Preparation BA (0.088 g; 0.334 mmol), and proceeding successively in analogy to Example 37, step 37.i (100% yield) and Example 1, step 1.ii (12% yield), the title compound was obtained, after purification by CC (DCM-MeOH gradient), as a yellowish solid (0.01 g).

$^1$H NMR (500 MHz, d$_6$-DMSO) δ: 11.04 (d, J=1.0 Hz, 1H); 9.28 (d, J=1.4 Hz, 1H); 8.53 (s, 1H); 8.07 (s, 1H); 7.64 (d, J=8.9 Hz, 1H); 7.30 (dd, J=1.5, 8.9 Hz, 1H); 5.01 (t, J=6.1 Hz, 1H); 4.58 (m, 1H); 4.48 (m, 1H); 4.37 (m, 1H); 4.17-4.22 (m, 2H); 3.92 (d, J=6.0 Hz, 2H); 3.86 (m, 1H); 3.75 (m, 1H); 3.07 (s, 3H); 2.86 (m, 1H); 2.41 (m, 1H); 1.52 (s, 3H)

MS1 (ESI, m/z): 473.0 [M+H$^+$] for $C_{22}H_{24}N_4O_6S$; $t_R$=0.61 min.

Example 82: (R)-4-(5-(6-amino-6-methylhepta-1,3-diyn-1-yl)-2H-indazol-2-yl)-N-hydroxy-2-methyl-2-(methylsulfonyl)butanamide Starting from the compound of Preparation J (0.085 g; 0.203 mmol) and the compound of Preparation BB (0.124 g; 0.384 mmol), and proceeding successively in analogy to Example 37, step 37.i (74% yield) and Example 13, step 13.ii (53% yield), the title compound was obtained, after purification by prep-HPLC (Method 3), as a white solid (0.03 g).

$^1$H NMR (500 MHz, d$_6$-DMSO) δ: 8.51 (d, J=0.6 Hz, 1H); 8.04 (m, 1H); 7.63 (d, J=8.9 Hz, 1H); 7.29 (dd, J=1.5, 8.9 Hz, 1H); 4.51-4.61 (m, 1H); 4.37 (m, 1H); 3.07 (s, 3H); 2.84 (m, 1H); 2.48 (s, 2H); 2.39 (m, 1H); 1.52 (s, 3H); 1.14 (s, 6H).

MS1 (ESI, m/z): 431.0 [M+H$^+$] for $C_{24}H_{26}N_4O_4S$; $t_R$=0.55 min.

Example 83: (R)-4-(5-((1-glycylpiperidin-4-yl)buta-1,3-diyn-1-yl)-2H-indazol-2-yl)-N-hydroxy-2-methyl-2-(methylsulfonyl)butanamide formate Starting from the compound of Preparation J (0.1 g; 0.238 mmol) and the compound of Preparation BC (0.094 g; 0.239 mmol), and proceeding successively in analogy to Example 7, step 7.i (53% yield) and Example 13, step 13.ii (11% yield), the title compound was obtained, after purification by prep-HPLC (Method 3), as a white solid (0.013 g). MS1 (ESI, m/z): 500.0 [M+H$^+$] for $C_{24}H_{29}N_5O_5S$; $t_R$=0.57 min.

Example 84: (R)-4-(5-((1-glycylazetidin-3-yl)buta-1,3-diyn-1-yl)-2H-indazol-2-yl)-N-hydroxy-2-methyl-2-(methylsulfonyl)butanamide Starting from the compound of Preparation J (0.09 g; 0.215 mmol) and the compound of Preparation BD (0.074 g; 0.232 mmol), and proceeding successively in analogy to Example 37, step 37.i and Example 13, step 13.ii, the title compound was obtained, after purification by prep-HPLC (Method 3), as a beige solid (0.037 g; 37% yield over the two steps).

$^1$H NMR (500 MHz, d$_6$-DMSO) δ: 8.52 (s, 1H); 8.06 (s, 1H); 7.63 (d, J=8.9 Hz, 1H); 7.29 (dd, J=1.5, 8.9 Hz, 1H); 4.55 (m, 1H); 4.32-4.43 (m, 2H); 4.11-4.21 (m, 2H); 3.84

(m, 1H); 3.75 (m, 1H); 3.09-3.19 (m, 2H); 3.07 (s, 3H); 2.83 (m, 1H); 2.38 (m, 1H); 1.51 (s, 3H).

MS1 (ESI, m/z): 472.0 [M+H$^+$] for $C_{22}H_{25}N_5O_5S$; $t_R$=0.53 min.

Example 85: (R)-4-(5-((1-(2-amino-2-methylpropanoyl)azetidin-3-yl)buta-1,3-diyn-1-yl)-2H-indazol-2-yl)-N-hydroxy-2-methyl-2-(methylsulfonyl)butanamide Starting from the compound of Preparation J (0.098 g; 0.233 mmol) and the compound of Preparation BE (0.178 g; 0.455 mmol), and proceeding successively in analogy to Example 37, step 37.i and Example 13, step 13.ii, the title compound was obtained, after purification by prep-HPLC (Method 3), as a beige solid (0.031 g; 27% yield over the two steps).

$^1$H NMR (500 MHz, d$_6$-DMSO) δ: 9.21 (br. s, 1H); 8.52 (s, 1H); 8.06 (d, J=1.0 Hz, 1H); 7.64 (d, J=8.9 Hz, 1H); 7.30 (dd, J=1.5, 8.9 Hz, 1H); 4.74 (m, 1H); 4.56 (m, 1H); 4.45 (m, 1H); 4.38 (m, 1H); 4.13 (m, 1H); 3.80 (m, 1H); 3.68 (m, 1H); 3.07 (s, 3H); 2.83 (m, 1H); 2.39 (m, 1H); 1.51 (s, 3H); 1.19 (s, 6H).

MS1 (ESI, m/z): 500.0 [M+H$^+$] for $C_{24}H_{29}N_5O_5S$; $t_R$=0.55 min.

Besides, the racemic mixtures of Reference Examples 1 to 7 can be separated into their enantiomers using, for example, chiral HPLC. Thus the following further invention compounds or salts would be obtained:

(R)—N-hydroxy-2-methylsulfonyl-2-methyl-4-{5-[4-(3 morpholin-4-yl-propoxy)-phenyl]-indazol-2-yl}-butanamide formate;

(R)—N-hydroxy-2-methylsulfonyl-2-methyl-4-{5-[4-(2-morpholin-4-yl-ethoxy)-phenyl]-indazol-2-yl}-butanamide formate;

(R)-4-{5-[2-fluoro-4-(2-morpholin-4-yl-ethoxy)-phenyl]-indazol-2-yl}-N-hydroxy-2-methylsulfonyl-2-methyl-butanamide formate;

(R)-4-(5-but-2-ynyloxy-indazol-2-yl)-N-hydroxy-2-methylsulfonyl-2-methyl-butanamide;

(R)—N-hydroxy-2-methylsulfonyl-2-methyl-4-(5-phenethyl-indazol-2-yl)-butanamide;

(R)—N-hydroxy-2-methylsulfonyl-2-methyl-4-[5-(4-oxazol-2-yl-phenyl)-indazol-2-yl]-butanamide formate; and (R)-4-(5-(2-fluoro-3-methoxyphenyl)-2H-indazol-2-yl)-N-hydroxy-2-methyl-2-(methylsulfonyl)butanamide.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA (2006).

Results:

All Example compounds, except the compound of Example 62, were tested against several Gram-positive and Gram-negative bacteria. Typical antibacterial test results are given in Table 1 hereafter (MICs in mg/L). *K. pneumoniae* A-651 and *Acinetobacter baumannii* T6474 are multiply-resistant strains (in particular quinolone-resistant), while *E. coli* ATCC25922 and *P. aeruginosa* ATCC27853 are quinolone-sensitive strains.

TABLE 1

| Example No. | MIC for E. coli ATCC25922 | MIC for P. aeruginosa ATCC27853 | MIC for A. Baumannii T6474 | MIC for K. Pneumoniae A-651 |
|---|---|---|---|---|
| RE1 | 0.5 | 4 | 4 | 1 |
| RE2 | 1 | 4 | 4 | 1 |
| RE3 | 1 | 8 | 8 | 2 |
| RE4 | 4 | 8 | 32 | 8 |
| RE5 | 0.5 | 8 | 0.25 | 2 |
| RE6 | 0.125 | 8 | 4 | 0.25 |
| RE7 | 0.125 | 2 | 0.5 | 0.125 |
| 1 | 0.063 | 2 | 1 | 0.063 |
| 2 | 0.125 | 4 | 1 | 0.5 |
| 3 | 0.063 | 2 | 0.5 | 0.125 |
| 4 | 0.125 | 4 | 2 | 0.5 |
| 5 | 0.063 | 4 | 2 | 0.063 |
| 6 | 0.125 | 4 | 2 | 0.5 |
| 7 | 0.25 | 2 | 0.5 | 0.125 |
| 8 | 0.25 | 4 | 0.125 | 0.5 |
| 9 | 0.063 | 2 | 0.25 | 0.063 |
| 10 | 0.5 | 2 | 2 | 0.5 |
| 11 | 0.063 | 8 | 2 | 0.063 |
| 12 | 0.063 | 2 | 1 | 0.125 |
| 13 | 0.125 | 0.5 | 32 | 0.25 |
| 14 | 0.25 | 2 | 16 | 0.25 |
| 15 | 2 | 2 | >32 | 2 |
| 16 | 0.125 | 1 | 0.5 | 0.125 |
| 17 | 0.063 | 16 | 1 | 0.063 |
| 18 | 0.125 | 0.5 | 4 | 0.125 |
| 19 | 0.063 | 2 | 0.5 | 0.125 |
| 20 | 0.25 | 0.5 | 0.5 | 0.125 |
| 21 | 0.125 | 1 | 0.5 | 0.25 |
| 22 | 0.125 | 2 | 1 | 0.5 |
| 23 | 0.25 | 4 | 1 | 0.25 |
| 24 | 0.5 | 0.5 | >32 | 1 |
| 25 | 0.063 | 0.5 | 0.5 | 0.063 |
| 26 | 0.5 | 1 | 8 | 0.5 |
| 27 | 0.063 | 0.5 | 0.25 | 0.125 |
| 28 | 0.5 | 1 | >32 | 0.5 |
| 29 | 0.25 | 1 | 0.5 | 0.25 |
| 30 | 1 | 4 | 2 | 2 |
| 31 | 1 | 2 | >32 | 1 |
| 32 | 0.5 | 1 | 32 | 0.5 |
| 33 | 0.063 | 0.5 | 2 | 0.125 |
| 34 | 0.063 | 0.5 | 1 | 0.125 |
| 35 | 0.125 | 4 | 0.25 | 0.5 |
| 36 | 0.063 | 0.25 | 2 | 0.125 |
| 37 | 0.063 | 0.25 | 2 | 0.063 |
| 38 | 0.5 | 1 | >32 | 1 |
| 39 | 0.125 | 1 | 0.25 | 0.125 |
| 40 | 0.125 | 1 | 1 | 0.25 |
| 41 | 0.125 | 1 | 0.125 | 0.063 |
| 42 | 0.063 | 0.25 | 0.125 | 0.063 |
| 43 | 1 | 2 | 2 | 1 |
| 44 | 0.125 | 1 | 0.25 | 0.25 |
| 45 | 0.25 | 1 | 8 | 1 |
| 46 | 4 | 4 | >32 | 8 |
| 47 | 0.25 | 1 | 1 | 0.5 |
| 48 | 2 | 2 | >32 | 4 |
| 49 | 4 | 4 | >32 | 4 |
| 50 | 0.5 | 2 | 2 | 1 |
| 51 | 1 | 0.5 | 1 | 0.5 |
| 52 | 0.125 | 2 | 1 | 0.5 |
| 53 | ≤0.063 | 0.5 | 2 | 0.125 |
| 54 | ≤0.063 | 0.5 | 4 | ≤0.063 |
| 55 | 2 | 2 | >32 | 4 |
| 56 | 0.25 | 0.5 | >32 | 0.5 |
| 57 | 0.125 | 0.5 | 8 | 0.25 |
| 58 | 2 | 2 | 8 | 4 |
| 59 | 4 | 8 | 8 | 8 |
| 60 | ≤0.063 | 0.5 | ≤0.063 | 0.125 |
| 61 | 2 | 1 | >8 | 4 |
| 63 | 2 | 8 | 8 | 4 |
| 64 | 0.125 | 0.25 | 4 | 0.5 |
| 65 | 0.125 | 0.5 | >32 | 0.125 |
| 66 | 1 | 2 | >32 | 4 |
| 67 | 0.125 | 0.25 | 32 | 0.125 |
| 68 | 1 | 1 | >32 | 1 |
| 69 | ≤0.063 | 0.25 | 2 | 0.125 |
| 70 | 1 | 2 | >32 | 1 |

TABLE 1-continued

| Example No. | MIC for E. coli ATCC25922 | MIC for P. aeruginosa ATCC27853 | MIC for A. Baumannii T6474 | MIC for K. Pneumoniae A-651 |
|---|---|---|---|---|
| 71 | 0.25 | 0.25 | 8 | 0.5 |
| 72 | 2 | 2 | >8 | 4 |
| 73 | 0.125 | 1 | 32 | 0.25 |
| 74 | 0.125 | 0.5 | 4 | 0.125 |
| 75 | 0.125 | 0.5 | >32 | 0.15 |
| 76 | 8 | 2 | >32 | 32 |
| 77 | 0.125 | 0.25 | 4 | 0.25 |
| 78 | 0.5 | 1 | 4 | 2 |
| 79 | 0.125 | 1 | 2 | 0.25 |
| 80 | 0.5 | 1 | 32 | 1 |
| 81 | 0.5 | 1 | 4 | 1 |
| 82 | 4 | 4 | >32 | 8 |
| 83 | 2 | 4 | 32 | 8 |
| 84 | 1 | 0.5 | >32 | 4 |
| 85 | 4 | 2 | >32 | 8 |
| Cipro | 0.5 | >32 | >8 | >32 |

The compounds of Examples 62 and 63 were tested against wild-type E. coli A-1261 in the absence of alkaline phosphatase or esterase, in the presence of an alkaline phosphatase and in the presence of an esterase. The corresponding antibacterial test results are given in Table 2 hereafter (MICs in mg/L).

TABLE 2

| | MIC for E. coli A-1261 | | |
|---|---|---|---|
| Example No. | In the absence of alkaline phosphatase or esterase | In the presence of an alkaline phosphatase (2 i.U./mL) | In the presence of an esterase (10 i.U./mL) |
| 62 | >16 | 1 | >16 |
| 63 | 0.25 | 0.5 | 0.063 |

The invention claimed is:
1. A compound of formula I

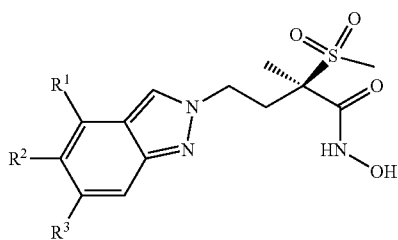

I wherein
$R^1$ represents H or halogen;
$R^2$ represents $(C_3-C_4)$alkynyloxy or the group M;
$R^3$ represents H or halogen;
M is one of the groups $M^A$, $M^B$, $M^C$ and $M^D$ represented hereafter

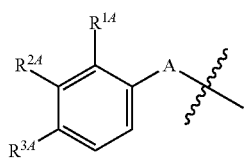

$M^A$

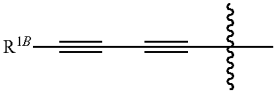

$M^B$

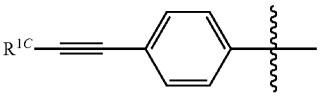

$M^C$

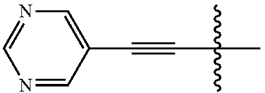

$M^D$ wherein A represents a bond, $CH_2CH_2$, CH=CH or C≡C;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$alkoxy$(C_2-C_3)$alkoxy, dihydroxy$(C_3-C_4)$alkoxy, $(C_1-C_3)$thioalkoxy, trifluoromethoxy, amino, di$(C_1-C_3)$alkylamino, 2-hydroxyacetamido, hydroxy$(C_1-C_4)$alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-(di$(C_1-C_3)$alkylamino)oxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl;
$R^{1B}$ represents 3-hydroxyoxetan-3-yl, 3-aminooxetan-3-yl, 3-hydroxythietan-3-yl, hydroxy$(C_1-C_3)$alkyl, dihydroxy$(C_2-C_4)$alkyl, amino$(C_1-C_4)$alkyl, (dimethylamino)methyl, 1-hydroxymethyl-cycloprop-1-yl, trans-2-(1,2-dihydroxyethyl)cycloprop-1-yl, 1-((phosphonooxy)methyl)cyclopropyl, 1-(((dimethylglycyl)oxy)methyl)cyclopropyl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, trans-2-aminomethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxy-oxetan-3-yl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, piperidin-4-yl, 1-(2-hydroxyacetyl)piperidin-4-yl, 1-(2-aminoacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl; and
$R^{1C}$ represents 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, 1-fluoro-2-(hydroxymethyl)cyclopropyl or 2-fluoro-2-(hydroxymethyl)cyclopropyl;
or a salt of the compound.

2. The compound of formula I according to claim 1, which is a compound of formula $I_{CE}$

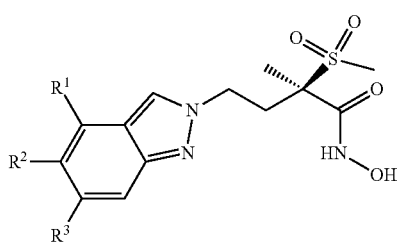

$I_{CE}$ wherein
$R^1$ represents H or halogen;
$R^2$ represents the group M;
$R^3$ represents H or halogen;
M is the one of the groups $M^A$, $M^B$, $M^C$ and $M^D$ represented hereafter

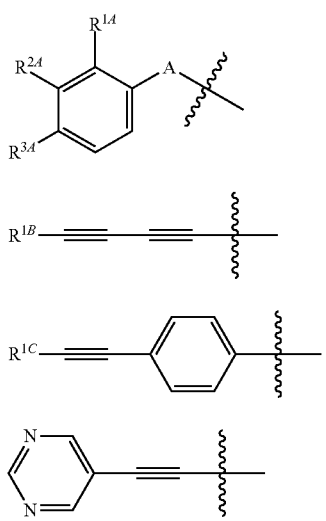

wherein A represents a bond, CH=CH or C≡C;
$R^{1A}$ represents H or halogen;
$R^{2A}$ represents H or halogen;
$R^{3A}$ represents H, $(C_1-C_3)$alkoxy, hydroxy$(C_1-C_4)$alkoxy, $(C_1-C_3)$alkoxy$(C_2-C_3)$alkoxy, $(C_1-C_3)$thioalkoxy, trifluoromethoxy, amino, di$(C_1-C_3)$alkylamino, 2-hydroxyacetamido, hydroxy$(C_1-C_4)$alkyl, 1-aminocyclopropyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-(di$(C_1-C_3)$alkylamino)oxetan-3-yl, morpholin-4-yl-$(C_1-C_2)$alkyl or [1,2,3]triazol-2-yl;
$R^{1B}$ represents 3-hydroxyoxetan-3-yl, 3-aminooxetan-3-yl, 3-hydroxythietan-3-yl, hydroxy$(C_1-C_3)$alkyl, 1,2-dihydroxyethyl, 1,2-dihydroxy-2-methylethyl, amino$(C_1-C_4)$alkyl, (dimethylamino)methyl, 1-hydroxymethyl-cycloprop-1-yl, trans-2-(1,2-dihydroxyethyl)cycloprop-1-yl, 1-((phosphonooxy)methyl)cyclopropyl, 1-(((dimethylglycyl)oxy)methyl)cyclopropyl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, trans-2-aminomethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethyl-bicyclo[1,1,1]pentan-1-yl, piperidin-4-yl, 1-(2-hydroxyacetyl)piperidin-4-yl, 1-(2-aminoacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl; and
$R^{1C}$ represents trans-2-hydroxymethyl-cycloprop-1-yl;
or a salt of the compound.

3. The compound of formula I according to claim 1, which is a compound of formula $I_P$

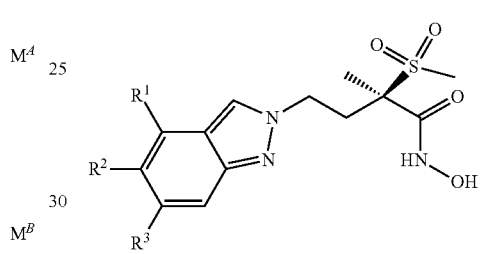

$I_P$ wherein
$R^1$ represents H or halogen;
$R^2$ represents $(C_3-C_4)$alkynyloxy or the group M;
$R^3$ represents H or halogen;
M is one of the groups $M^A$ and $M^B$ represented below

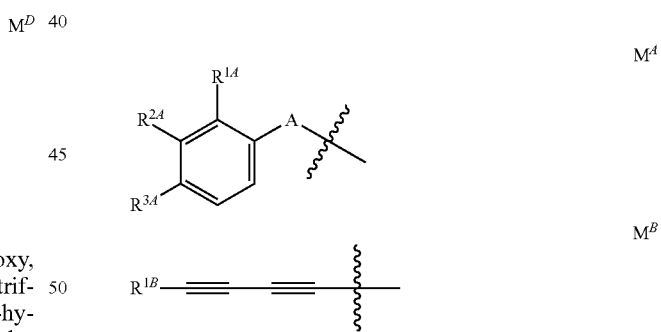

wherein A represents a bond, $CH_2CH_2$, CH=CH or C≡C;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$thioalkoxy, trifluoromethoxy, amino, di$(C_1-C_3)$alkylamino, hydroxy$(C_1-C_4)$alkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-(di$(C_1-C_3)$alkylamino)oxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl; and R$^{1B}$ represents 3-hydroxyoxetan-3-yl, 3-hydroxythietan-3-yl, hydroxy(C$_1$-C$_3$)alkyl, amino(C$_1$-C$_3$)alkyl, trans-2-hydroxymethyl-cycloprop-1-yl or 4-hydroxytetrahydro-2H-pyran-4-yl;
or a salt of the compound.

4. The compound of formula I according to claim 1, wherein R$^1$ represents H or fluorine, R$^3$ represents H or fluorine, R$^{1A}$, when present, represents H or fluorine and R$^{2A}$, when present, represents H or fluorine;
or a salt of the compound.

5. The compound of formula I according to claim 1, wherein
R$^2$ represents the group M$^A$;
or a salt of the compound.

6. The compound of formula I according to claim 5, wherein A represents a bond;
or a salt of the compound.

7. The compound of formula I according to claim 5, wherein A represents C≡C;
or a salt of the compound.

8. The compound of formula I according to claim 7, wherein R$^{1A}$ represents H or fluorine, R$^{2A}$ represents H and R$^{3A}$ represents hydroxy(C$_1$-C$_4$)alkoxy, 2-hydroxyacetamido, hydroxy(C$_1$-C$_4$)alkyl, 1-aminocyclopropyl, 1-hydroxymethyl-cycloprop-1-yl, trans-2-hydroxymethyl-cycloprop-1-yl, 1,2-dihydroxyethyl or 3-hydroxyoxetan-3-yl; or a salt of the compound.

9. The compound of formula I according to claim 1, wherein R$^2$ represents the group M$^B$;
or a salt of the compound.

10. The compound of formula I according to claim 9, wherein R$^{1B}$ represents 1,2-dihydroxyethyl, 3-hydroxyoxetan-3-yl, 3-hydroxythietan-3-yl, hydroxy(C$_1$-C$_3$)alkyl, amino(C$_1$-C$_3$)alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminocyclopropyl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxymethyl-oxetan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, piperidin-4-yl, 1-(2-hydroxyacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl;
or a salt of the compound.

11. The compound of formula I according to claim 1, wherein R$^2$ represents the group M$^C$;
or a salt of the compound.

12. The compound of formula I according to claim 11, wherein R$^{1C}$ represents trans-2-hydroxymethyl-cycloprop-1-yl;
or a salt of the compound.

13. The compound of formula I according to claim 1, wherein said compound is:
(R)-4-[5-(2-fluoro-4-methoxy-phenyl)-indazol-2-yl]-N-hydroxy-2-methylsulfonyl-2-methyl-butanamide;
(R)—N-hydroxy-2-methylsulfonyl-4-[5-(4-methoxy-phenyl)-indazol-2-yl]-2-methyl-butanamide;
(R)-4-[6-fluoro-5-(4-methoxy-phenyl)-indazol-2-yl]-N-hydroxy-2-methylsulfonyl-2-methyl-butanamide;
(R)-4-[4-fluoro-5-(4-methoxy-phenyl)-indazol-2-yl]-N-hydroxy-2-methylsulfonyl-2-methyl-butanamide;
(R)-4-[6-fluoro-5-(2-fluoro-4-methoxy-phenyl)-indazol-2-yl]-N-hydroxy-2-methylsulfonyl-2-methyl-butanamide;
(R)-4-[4-fluoro-5-(2-fluoro-4-methoxy-phenyl)-indazol-2-yl]-N-hydroxy-2-methylsulfonyl-2-methyl-butanamide;
(R)—N-hydroxy-2-methylsulfonyl-2-methyl-4-[5-(4-morpholin-4-ylmethyl-phenylethynyl)-indazol-2-yl]-butanamide;
(R)—N-hydroxy-2-methylsulfonyl-2-methyl-4-[5-(4-trifluoromethoxy-phenyl)-indazol-2-yl]-butanamide;
(R)-4-[5-(2-fluoro-4-methylsulfanyl-phenyl)-indazol-2-yl]-N-hydroxy-2-methylsulfonyl-2-methyl-butanamide;
(R)-4-{5-[4-(3-amino-oxetan-3-yl)-phenylethynyl]-indazol-2-yl}-N-hydroxy-2-methylsulfonyl-2-methyl-butanamide;
(R)-4-[5-(4-dimethylamino-phenyl)-indazol-2-yl]-N-hydroxy-2-methylsulfonyl-2-methyl-butanamide;
(R)—N-hydroxy-2-methylsulfonyl-2-methyl-4-[5-(4-[1,2,3]triazol-2-yl-phenyl)-indazol-2-yl]-butanamide;
(R)—N-hydroxy-4-(5-((3-hydroxythietan-3-yl)buta-1,3-diyn-1-yl)-2H-indazol-2-yl)-2-methyl-2-(methylsulfonyl)butanamide;
(R)-4-(4-fluoro-5-((4-(2-hydroxypropan-2-yl)phenyl)ethynyl)-2H-indazol-2-yl)-N-hydroxy-2-methyl-2-(methylsulfonyl)butanamide;
(R)—N-hydroxy-4-(5-((4-hydroxytetrahydro-2H-pyran-4-yl)buta-1,3-diyn-1-yl)-2H-indazol-2-yl)-2-methyl-2-(methyl sulfonyl)butanamide;
(R)—N-hydroxy-4-(5-((4-(1-(hydroxymethyl)cyclopropyl)phenyl)ethynyl)-2H-indazol-2-yl)-2-methyl-2-(methylsulfonyl)butanamide;
(R)—N-hydroxy-2-methylsulfonyl-2-methyl-4-[5-((E)-styryl)-indazol-2-yl]-butanamide;
(R)-4-{4-fluoro-5-[4-((1S*,2S*)-2-hydroxymethyl-cyclopropyl)-buta-1,3-diynyl]-indazol-2-yl}-N-hydroxy-2-methyl sulfonyl-2-methyl-butanamide;
(R)-4-[5-(4-amino-phenylethynyl)-indazol-2-yl]-N-hydroxy-2-methylsulfonyl-2-methyl-butanamide;
(R)—N-hydroxy-4-{5-[4-(3-hydroxy-oxetan-3-yl)-phenylethynyl]-indazol-2-yl}-2-methylsulfonyl-2-methyl-butanamide;
(R)—N-hydroxy-4-(5-((4-(hydroxymethyl)phenyl)ethynyl)-2H-indazol-2-yl)-2-methyl-2-(methylsulfonyl)butanamide;
(R)-4-[5-(3-fluoro-4-hydroxymethyl-phenylethynyl)-indazol-2-yl]-N-hydroxy-2-methylsulfonyl-2-methyl-butanamide;
(R)-4-[4-fluoro-5-(4-hydroxymethyl-phenylethynyl)-indazol-2-yl]-N-hydroxy-2-methylsulfonyl-2-methyl-butanamide;
(R)-4-(5-(5-amino-5-methylhexa-1,3-diyn-1-yl)-2H-indazol-2-yl)-N-hydroxy-2-methyl-2-(methylsulfonyl)butanamide;
(R)—N-hydroxy-4-{5-[4-(2-hydroxy-ethyl)-phenylethynyl]-indazol-2-yl}-2-methylsulfonyl-2-methyl-butanamide;
(2R)-4-{5-[4-((R)-1,2-dihydroxy-ethyl)-phenylethynyl]-indazol-2-yl}-N-hydroxy-2-methylsulfonyl-2-methyl-butanamide;
(R)—N-hydroxy-4-(5-((4-(2-hydroxypropan-2-yl)phenyl)ethynyl)-2H-indazol-2-yl)-2-methyl-2-(methylsulfonyl)butanamide;
(R)—N-hydroxy-4-(5-((3-hydroxyoxetan-3-yl)buta-1,3-diyn-1-yl)-2H-indazol-2-yl)-2-methyl-2-(methylsulfonyl)butanamide;

(R)-4-{4-fluoro-5-[4-(3-hydroxy-oxetan-3-yl)-phenyl-ethynyl]-indazol-2-yl}-N-hydroxy-2-methylsulfonyl-2-methyl-butanamide;
(R)-4-{5-[4-(3-dimethylamino-oxetan-3-yl)-phenylethynyl]-indazol-2-yl}-N-hydroxy-2-methylsulfonyl-2-methyl-butanamide;
(R)-4-{6-fluoro-5-[4-(3-hydroxy-oxetan-3-yl)-buta-1,3-diynyl]-indazol-2-yl}-N-hydroxy-2-methylsulfonyl-2-methyl-butanamide;
(R)—N-hydroxy-4-[5-(5-hydroxy-5-methyl-hexa-1,3-diynyl)-indazol-2-yl]-2-methylsulfonyl-2-methyl-butanamide;
(R)—N-hydroxy-4-(5-((4-((R)-1-hydroxyethyl)phenyl)ethynyl)-2H-indazol-2-yl)-2-methyl-2-(methylsulfonyl)butanamide;
(R)—N-hydroxy-4-(5-((4-((S)-1-hydroxyethyl)phenyl)ethynyl)-2H-indazol-2-yl)-2-methyl-2-(methylsulfonyl)butanamide;
(R)-4-[5-(2-fluoro-4-trifluoromethoxy-phenyl)-indazol-2-yl]-N-hydroxy-2-methylsulfonyl-2-methyl-butanamide;
(R)—N-hydroxy-4-(5-(((1S,2S)-2-(hydroxymethyl)cyclopropyl)buta-1,3-diyn-1-yl)-2H-indazol-2-yl)-2-methyl-2-(methylsulfonyl)butanamide;
(R)—N-hydroxy-4-(5-(((1R,2R)-2-(hydroxymethyl)cyclopropyl)buta-1,3-diyn-1-yl)-2H-indazol-2-yl)-2-methyl-2-(methylsulfonyl)butanamide;
(R)-4-{4-fluoro-5-[4-(3-hydroxy-oxetan-3-yl)-buta-1,3-diynyl]-indazol-2-yl}-N-hydroxy-2-methylsulfonyl-2-methyl-butanamide;
(R)-4-[5-(2-fluoro-4-hydroxymethyl-phenylethynyl)-indazol-2-yl]-N-hydroxy-2-methylsulfonyl-2-methyl-butanamide;
-4-(6-fluoro-5-((4-(3-hydroxyoxetan-3-yl)phenyl)ethynyl)-2H-indazol-2-yl)-N-hydroxy-2-methyl-2-(methylsulfonyl)butanamide;
(R)—N-hydroxy-4-(54(4-((1R,2R)-2-(hydroxymethyl)cyclopropyl)phenyl)ethynyl)-2H-indazol-2-yl)-2-methyl-2-(methylsulfonyl)butanamide;
(R)—N-hydroxy-4-(5-((4-((1S,2S)-2-(hydroxymethyl)cyclopropyl)phenyl)ethynyl)-2H-indazol-2-yl)-2-methyl-2-(methyl sulfonyl)butanamide;
(R)—N-hydroxy-4-(5-((4-(3-(hydroxymethyl)oxetan-3-yl)phenyl)ethynyl)-2H-indazol-2-yl)-2-methyl-2-(methylsulfonyl)butanamide;
(R)—N-hydroxy-4-(5-((4-(2-hydroxyethoxy)phenyl)ethynyl)-2H-indazol-2-yl)-2-methyl-2-(methylsulfonyl)butanamide;
(R)—N-hydroxy-2-methylsulfonyl-2-methyl-4-{5-[4-(3-morpholin-4-yl-propoxy)-phenyl]-indazol-2-yl}-butanamide;
(R)—N-hydroxy-2-methylsulfonyl-2-methyl-4-{5-[4-(2-morpholin-4-yl-ethoxy)-phenyl]-indazol-2-yl}-butanamide;
(R)-4-{5-[2-fluoro-4-(2-morpholin-4-yl-ethoxy)-phenyl]-indazol-2-yl}-N-hydroxy-2-methylsulfonyl-2-methyl-butanamide;
(R)-4-(5-but-2-ynyloxy-indazol-2-yl)-N-hydroxy-2-methylsulfonyl-2-methyl-butanamide;
(R)—N-hydroxy-2-methylsulfonyl-2-methyl-4-(5-phenethyl-indazol-2-yl)-butanamide;
(R)—N-hydroxy-2-methylsulfonyl-2-methyl-4-[5-(4-oxazol-2-yl-phenyl)-indazol-2-yl]-butanamide;
(R)-4-(5-(2-fluoro-3-methoxyphenyl)-2H-indazol-2-yl)-N-hydroxy-2-methyl-2-(methylsulfonyl)butanamide;
(R)-4-(5-((3-fluoro-4-(2-hydroxyacetamido)phenyl)ethynyl)-2H-indazol-2-yl)-N-hydroxy-2-methyl-2-(methylsulfonyl)butanamide;
(R)-4-(5-((R)-5,6-dihydroxy-5-methylhexa-1,3-diyn-1-yl)-2H-indazol-2-yl)-N-hydroxy-2-methyl-2-(methylsulfonyl)butanamide;
(R)—N-hydroxy-4-(5-((4-(2-hydroxyacetamido)phenyl)ethynyl)-2H-indazol-2-yl)-2-methyl-2-(methylsulfonyl)butanamide;
(R)-4-(5-((3-aminooxetan-3-yl)buta-1,3-diyn-1-yl)-2H-indazol-2-yl)-N-hydroxy-2-methyl-2-(methylsulfonyl)butanamide;
(R)—N-hydroxy-4-(5-(4-(2-hydroxyacetamido)phenyl)-2H-indazol-2-yl)-2-methyl-2-(methylsulfonyl)butanamide;
(R)-4-(5-(2-fluoro-4-(2-hydroxyethoxy)phenyl)-2H-indazol-2-yl)-N-hydroxy-2-methyl-2-(methylsulfonyl)butanamide;
(R)-4-(5-((4-((S)-1,2-dihydroxyethyl)phenyl)ethynyl)-2H-indazol-2-yl)-N-hydroxy-2-methyl-2-(methylsulfonyl)butanamide;
(R)—N-hydroxy-4-(5-(4-(2-methoxyethoxy)phenyl)-2H-indazol-2-yl)-2-methyl-2-(methylsulfonyl)butanamide;
(R)-4-(6-fluoro-5-(((1S,2S)-2-(hydroxymethyl)cyclopropyl)buta-1,3-diyn-1-yl)-2H-indazol-2-yl)-N-hydroxy-2-methyl-2-(methylsulfonyl)butanamide;
(R)-4-(4-fluoro-5-(((1S,2S)-2-(hydroxymethyl)cyclopropyl)buta-1,3-diyn-1-yl)-2H-indazol-2-yl)-N-hydroxy-2-methyl-2-(methylsulfonyl)butanamide;
(R)-4-(5-((S)-5,6-dihydroxyhexa-1,3-diyn-1-yl)-2H-indazol-2-yl)-N-hydroxy-2-methyl-2-(methylsulfonyl)butanamide;
(R)—N-hydroxy-4-(5-((1-(hydroxymethyl)cyclopropyl)buta-1,3-diyn-1-yl)-2H-indazol-2-yl)-2-methyl-2-(methyl sulfonyl)butanamide;
(R)—N-hydroxy-4-(5-((3-(hydroxymethyl)bicyclo[1.1.1]pentan-1-yl)buta-1,3-diyn-1-yl)-2H-indazol-2-yl)-2-methyl-2-(methylsulfonyl)butanamide;
(R)-4-(5-(4-((R)-2,3-dihydroxypropoxy)-2-fluorophenyl)-2H-indazol-2-yl)-N-hydroxy-2-methyl-2-(methylsulfonyl)butanamide;
(R)—N-hydroxy-2-methyl-2-(methylsulfonyl)-4-(5-(pyrimidin-5-ylethynyl)-2H-indazol-2-yl)butanamide;
(R)—N-hydroxy-4-(5-(4-(((1S*,2S*)-2-(hydroxymethyl)cyclopropyl)ethynyl)phenyl)-2H-indazol-2-yl)-2-methyl-2-(methylsulfonyl)butanamide;
(R)-4-(5-(((2 S*,5 S*)-5-aminotetrahydro-2H-pyran-2-yl)buta-1,3-diyn-1-yl)-2H-indazol-2-yl)-N-hydroxy-2-methyl-2-(methylsulfonyl)butanamide;
(R)-(1-(4-((2-(4-(hydroxyamino)-3-methyl-3-(methylsulfonyl)-4-oxobutyl)-2H-indazol-5-yl)ethynyl)phenyl)cyclopropyl)methyl dihydrogen phosphate;
(R)-(1-(4-((2-(4-(hydroxyamino)-3-methyl-3-(methylsulfonyl)-4-oxobutyl)-2H-indazol-5-yl)ethynyl)phenyl)cyclopropyl)methyl dimethylglycinate;
(R)-4-(5-(((1S,3R,4S)-3,4-dihydroxycyclopentyl)buta-1,3-diyn-1-yl)-2H-indazol-2-yl)-N-hydroxy-2-methyl-2-(methyl sulfonyl)butanamide;
(R)-4-(5-((1-aminocyclopropyl)buta-1,3-diyn-1-yl)-2H-indazol-2-yl)-N-hydroxy-2-methyl-2-(methylsulfonyl)butanamide;
(R)—N-hydroxy-4-(5-(5-((1S,3R)-1-hydroxy-3-(hydroxymethyl)cyclobutyl)penta-1,3-diyn-1-yl)-2H-indazol-2-yl)-2-methyl-2-(methyl sulfonyl)butanamide;
(R)—N-hydroxy-4-(5-(((1R,2R)-2-(hydroxymethyl)-1-methylcyclopropyl)buta-1,3-diyn-1-yl)-2H-indazol-2-yl)-2-methyl-2-(methyl sulfonyl)butanamide;

(R)—N-hydroxy-4-(5-((3-(hydroxymethyl)oxetan-3-yl) buta-1,3-diyn-1-yl)-2H-indazol-2-yl)-2-methyl-2-(methylsulfonyl)butanamide;

(R)—N-hydroxy-4-(5-(((1R,2S)-2-(hydroxymethyl)-2-methylcyclopropyl)buta-1,3-diyn-1-yl)-2H-indazol-2-yl)-2-methyl-2-(methylsulfonyl)butanamide;

(R)-4-(5-((3-(2-aminoacetamido)cyclopentyl)buta-1,3-diyn-1-yl)-2H-indazol-2-yl)-N-hydroxy-2-methyl-2-(methylsulfonyl)butanamide;

(R)-4-(5-(((1R,2R)-2-((S)-1,2-dihydroxyethyl)cyclopropyl)buta-1,3-diyn-1-yl)-2H-indazol-2-yl)-N-hydroxy-2-methyl-2-(methylsulfonyl)butanamide;

(R)-4-(5-(((1R,2R)-2-(aminomethyl)cyclopropyl)buta-1,3-diyn-1-yl)-2H-indazol-2-yl)-N-hydroxy-2-methyl-2-(methylsulfonyl)butanamide;

(R)—N-hydroxy-4-(5-((1-(hydroxymethyl)cyclobutyl) buta-1,3-diyn-1-yl)-2H-indazol-2-yl)-2-methyl-2-(methylsulfonyl)butanamide;

(R)-4-(5-(((1R,2R)-1-fluoro-2-(hydroxymethyl)cyclopropyl)buta-1,3-diyn-1-yl)-2H-indazol-2-yl)-N-hydroxy-2-methyl-2-(methylsulfonyl)butanamide;

(R)-4-(5-(5-(dimethylamino)penta-1,3-diyn-1-yl)-2H-indazol-2-yl)-N-hydroxy-2-methyl-2-(methylsulfonyl) butanamide;

(R)—N-hydroxy-2-methyl-2-(methylsulfonyl)-4-(5-(piperidin-4-ylbuta-1,3-diyn-1-yl)-2H-indazol-2-yl)butanamide;

(R)-4-(5-(((1R,2R)-2-fluoro-2-(hydroxymethyl)cyclopropyl)buta-1,3-diyn-1-yl)-2H-indazol-2-yl)-N-hydroxy-2-methyl-2-(methylsulfonyl)butanamide;

(R)—N-hydroxy-4-(5-((1-(2-hydroxyacetyl)piperidin-4-yl)buta-1,3-diyn-1-yl)-2H-indazol-2-yl)-2-methyl-2-(methylsulfonyl)butanamide;

(R)-4-(5-((4-(1-aminocyclopropyl)phenyl)ethynyl)-2H-indazol-2-yl)-N-hydroxy-2-methyl-2-(methylsulfonyl) butanamide;

(R)—N-hydroxy-4-(5-(5-(3-hydroxyoxetan-3-yl)penta-1,3-diyn-1-yl)-2H-indazol-2-yl)-2-methyl-2-(methylsulfonyl)butanamide;

(R)—N-hydroxy-4-(5-((1-(2-hydroxyacetyl)azetidin-3-yl)buta-1,3-diyn-1-yl)-2H-indazol-2-yl)-2-methyl-2-(methylsulfonyl)butanamide;

(R)-4-(5-(6-amino-6-methylhepta-1,3-diyn-1-yl)-2H-indazol-2-yl)-N-hydroxy-2-methyl-2-(methylsulfonyl) butanamide;

(R)-4-(5-((1-glycylpiperidin-4-yl)buta-1,3-diyn-1-yl)-2H-indazol-2-yl)-N-hydroxy-2-methyl-2-(methylsulfonyl)butanamide;

(R)-4-(5-((1-glycylazetidin-3-yl)buta-1,3-diyn-1-yl)-2H-indazol-2-yl)-N-hydroxy-2-methyl-2-(methylsulfonyl) butanamide; or (R)-4-(5-((1-(2-amino-2-methylpropanoyl)azetidin-3-yl) buta-1,3-diyn-1-yl)-2H-indazol-2-yl)-N-hydroxy-2-methyl-2-(methylsulfonyl)butanamide;

or a salt of the compound.

14. The compound of formula I according to claim 1, or a pharmaceutically acceptable salt thereof, wherein the compound is formulated as a medicament.

15. A pharmaceutical composition comprising, as active principle, the compound of formula I according to claim 1, or a pharmaceutically acceptable salt thereof, and at least one therapeutically inert excipient.

16. A method of treating a Gram-negative bacterial infection comprising administering the compound or salt thereof according to claim 1 to a subject in need thereof.

* * * * *